United States Patent [19]

Christensen et al.

[11] 4,342,757

[45] Aug. 3, 1982

[54] CEPHALOSPORIN ANTIBIOTIC COMPOSITIONS

[75] Inventors: Burton G. Christensen, Scotch Plains; Sandor Karady, Elizabeth; Lovji D. Cama, Edison; Meyer Sletzinger, North Plainfield, all of N.J.

[73] Assignee: Merck & Co., Inc., Rahway, N.J.

[21] Appl. No.: 145,070

[22] Filed: Apr. 30, 1980

Related U.S. Application Data

[62] Division of Ser. No. 149,364, Jun. 2, 1971, Pat. No. 4,297,488.

[30] Foreign Application Priority Data

Jun. 16, 1970 [GB] United Kingdom ............... 29158/70
Jul. 9, 1970 [GB] United Kingdom ............... 33415/70
Sep. 30, 1970 [GB] United Kingdom ............... 46556/70
Dec. 10, 1970 [GB] United Kingdom ............... 58731/70
Jan. 27, 1971 [GB] United Kingdom ............... 3296/71
Jan. 27, 1971 [GB] United Kingdom ............... 3297/71
Jan. 27, 1971 [GB] United Kingdom ............... 3298/71
Feb. 8, 1971 [GB] United Kingdom ............... 4179/71
Feb. 11, 1971 [GB] United Kingdom ............... 4479/71
Feb. 11, 1971 [GB] United Kingdom ............... 4480/71
Feb. 26, 1971 [GB] United Kingdom ............... 5588/71

[51] Int. Cl.$^3$ ................. C07D 501/20; A61K 31/545
[52] U.S. Cl. ..................................... 424/246; 544/21; 544/16
[58] Field of Search ................. 544/28, 30, 21, 16; 424/246

[56] References Cited

U.S. PATENT DOCUMENTS 4,123,612  10/1972  Gorman et al. ...................... 544/16
4,145,538  3/1979   Nagabajan ........................... 544/16

Primary Examiner—Nicholas S. Rizzo
Attorney, Agent, or Firm—Frank M. Mahon; Hesna J. Pfeiffer

[57] ABSTRACT

Process and intermediate products useful in the preparation of cephalosporin compounds having a substituent at the 7-position in place of hydrogen are provided. The new cephalosporin compounds are active against various gram-negative and gram-positive organisms.

3 Claims, No Drawings

CEPHALOSPORIN ANTIBIOTIC COMPOSITIONS

This is a division of application Ser. No. 149,364, filed June 2, 1971, now U.S. Pat. No. 4,297,488.

This invention relates to new antibiotics, new intermediate products useful in the preparation of these antibiotics, and processes for the preparation of these compounds. More particularly, it is concerned with new 7-aminocephalosporanic acid derivatives having a substituent at position 7, and with new intermediates and processes for their production.

The discovery of penicillin, which was found to be such an important and effective antibiotic, stimulated great interest in this field. Subsequently, various other antibiotics such as streptomycin, the tetracyclines, novobiocin, and the like were found which greatly increased the doctors' armamentarium for treating infections due to a variety of pathogens. Unfortunately, the use of these antibiotics gave rise to strains of pathogens resistant to these known antibiotics. In addition, the known antibiotics suffer from the disadvantage that they are only effective against certain types of microorganisms and are not effective against a broad range of pathogens. Accordingly, the search for other antibiotics has continued.

It is an object of this invention to provide new cephalosporins having antibiotic activity. A further object is to provide processes for the preparation of these new antibiotics. Another object is to provide new intermediates useful in preparing these new cephalosporins. Other objects will be apparent from the detailed description of this invention hereinafter provided.

The new cephalosporins of the present invention are compounds wherein the $\Delta^3$-cepham nucleus, namely a dehydrothiazine ring with a fused $\beta$-lactam, contains a substituent at the 7 position. Thus, these new cephalosporins which can be represented by the structural formula

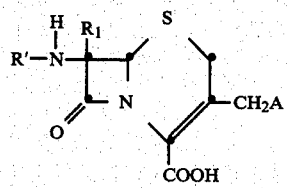

wherein R' represents an acyl group, A represents an organic radical or group, and $R_1$ represents a radical or group replacing hydrogen, and the derivatives thereof such as esters, amides and salts are valuable new antibiotic substances.

The acyl radical represented by R' can be a substituted or unsubstituted aliphatic, aromatic or heterocyclic, araliphatic or heterocyclylaliphatic carboxylic acid radical or a carbothioic acid radical such as the acyl radicals of the known cephalosporins and penicillins. These acyl radicals can be represented by the general formula

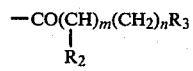

where $R_2$ is a radical of the group defined below, m and n represent 0–4 and $R_3$ represents R" or ZR", which are defined below.

One group of acyl radicals can be represented by the acyl group general formula

wherein R" represents a substituted or unsubstituted straight or branched chain alkyl, alkenyl or alkynyl group; aryl, aralkyl; cycloalkyl; or a heteroaryl or heteroaralkyl group. These groups can be unsubstituted or can be substituted by radicals such as alkyl, alkoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, $\beta,\beta$-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula $$-\overset{O}{\underset{\|}{C}}(CH_2)_nZR''$$

wherein n is 0–4, Z represents oxygen or sulfur, and R'' is defined as above. Representative members of the substituent $$-(CH_2)_nZR''$$

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, 6,8-bis(methylthio)octanoyl.

Alternatively, the acyl group can be a radical of the formula $$-\overset{O}{\underset{\|}{C}}-\underset{R'''}{\overset{}{C}}HR''$$

wherein R'' is defined as above and R''' is a radical such as amino, hydroxy, azido, carbamoyl, guanidino, acyloxy, halo, sulfamino, tetrazolyl, sulfo, carboxy, carbalkoxy, and the like. Representative members of the substituent $$-\underset{R'''}{\overset{}{C}}HR''$$

that might be mentioned are α-aminobenzyl, α-amino-2-thenyl, α-methylaminobenzyl, α-amino-γ-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(−)-α-hydroxybenzyl, α-carboxybenzyl, α-amino-3-thenyl, α-amino-2-thenyl, D(−)-α-amino-3-chloro-4-hydroxybenzyl, D(−)-α-amino-3-thenyl, 1-aminocyclohexyl, α-(5-tetrazolyl)benzyl, α-sulfaminobenzyl, α-sulfamino-3-thenyl, α-(N-methylsulfamino)benzyl, D(−)-α-guanidino-2-thenyl, D(−)-α-guanidinobenzyl, α-guanylureidobenzyl, α-hydroxybenzyl, α-azidobenzyl, α-fluorobenzyl, 4-(5-methoxy-1,3-oxadiazole)-aminomethyl, 4-(5-methoxy-1,3-oxadiazole)-hydroxymethyl, 4-(5-methoxy-1,3-oxadiazole)-carboxymethyl, 4-(5-methoxy-1,3-sulfadiazole)-aminomethyl, 4-(5-methoxy-1,3-sulfadiazole)-hydroxymethyl, 4-(5-methoxy-1,3-sulfadiazole)-carboxymethyl, 2-(5-chlorothienyl)-aminomethyl, 2-(5-chlorothienyl)-hydroxymethyl, 2-(5-chlorothienyl)-carboxymethyl, 3-(1,2-thiazole)-aminomethyl, 3-(1,2-thiazole)-hydroxymethyl, 3-(1,2-thiazole)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-sulfobenzyl, and α-phosphonobenzyl.

Alternatively, the group $$\underset{R'-N-}{\overset{H}{}}$$

can be a sulfonamido group such as phenylsulfonamido, ethylsulfonamido, benzylsulfonamido, 2,5-dimethylsulfonamido, 4-chlorosulfonamido, 4-chlorophenylsulfonamido, 4-methoxysulfonamido, and the like.

The acyl substituents of the general formula $$R_{11}R_{10}CHCO$$

wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino, guanidinomethyl, carboxamidomethyl, aminomethyl, nitro, methoxy or methyl. Examples of these preferred substituents that might be mentioned are phenacetyl, 3-bromophenylacetyl, p-aminomethylphenylacetyl, 4-carboxylmethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

The substituent A in formula I above can be hydrogen, hydroxy, halo, mercapto, acyloxy, acylthio, substituted hydroxy, substituted mercapto, a quaternary ammonium group, azido, amino or a N-substituted amino group. Alternatively, $CH_2A$ can be replaced by a formyl group.

Thus, $CH_2A$ can be a halomethyl such as chloromethyl, bromomethyl or fluoromethyl.

When A is a substituted hydroxy or substituted mercapto group, it can be shown by the formula $-CH_2ZR_5$ where Z is oxygen or sulfur, and $R_5$ is an acyl group; a straight chain or branched chain loweralkyl, alkenyl or alkynyl group; an aryl group; an aralkyl group; or a heterocyclic group such as heteroaryl or heteroalkyl. These groups can be unsubstituted or can be substituted by radicals such as alkyl, alkoxy, halo, cyano, carboxy, carbamoyl, azido, sulfo, amino, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the groups thus represented that might be mentioned are methoxymethyl, n-propoxymethyl, methylthiomethyl, acetoxymethyl, propionyloxymethyl, benzoyloxymethyl, (p-chlorobenzoyl)oxymethyl, (p-methylbenzoyl)oxymethyl, pivaloyloxymethyl, (1-adamantyl)carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, (N-p-sulfophenylcarbamoyl)oxymethyl, p-carboxymethylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N,N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

Alternatively, when $CH_2A$ is hydroxymethyl, the cephalosporin can also exist as the lactone which is formed by internal esterification with the carboxy group.

The substituent $CH_2A$ can also be a group of the general formula $-CH_2Y_1$ wherein $Y_1$ represents amino or substituted amino including nitrogen heterocycles and substituted heterocyclic groups. Examples of such groups that might be mentioned are aminomethyl, acetamidomethyl, carbamoylaminomethyl, N,N-dimethylaminomethyl, N-(2-chloroethyl)aminomethyl, 5-cyanotriazol-1-ylmethyl, 4-methoxycarbonyltriazol-1-ylmethyl.

When A is amino the cephalosporin compound can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The preferred groups representing A are hydrogen, halo, azido, cyano, hydroxy, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5 or 6 membered hetero ring containing one or more nitrogen, oxygen or sulfur atoms. The acyl group can be a loweralkanoyl group of 2-6 carbon atoms, carbamoyl, or thiocarbamoyl and N-alkyl or N,N-dialkyl derivatives thereof. The alkyl group of the foregoing substituents contains 1-6 carbon atoms and may be further substituted radicals such as alkoxy, halo, amino, cyano, carboxy, sulfo, and the like.

The substituent $R_1$ in formula I above can be hydroxy, mercapto or substituted hydroxy and mercapto groups; a hydrocarbyl or substituted hydrocarbyl group; cyano, or a carbonyl or thiocarbonyl containing substituent bonded by said carbonyl or thiocarbonyl radical; a nitrogen bonded group; halo; or phosphono or a substituted phosphono group.

The oxy or thio substituent represented by $R_1$ in formula I can be hydroxy or mercapto or a substituted hydroxy or mercapto group such as $-XR'_1$ wherein X is oxygen or sulfur and $R'_1$ is a hydrocarbyl group, preferably a straight or branched loweralkyl group of 1-6 carbon atoms, a straight or branched chain loweralkenyl or loweralkynyl group of 3-6 carbon atoms, a monocyclic aryl group such as phenyl, or an aralkyl group such as benzyl. These alkyl, alkenyl, alkynyl, aryl or aralkyl groups can be substituted with groups such as hydroxy, halo, nitro, amino, carboxy, sulfo, and the like. Other specific substituents represented by $R_1$ that might be mentioned are groups of the formula $-OCN$, $-SCN$, $-ONR_3R_4$, $-SNR_3R_4$, $-OAc$, $-SAc$, $-SO_3H$, $-SO_3R_2$, $-SO_2NH_2$, $OCD_3$, $-SO_2NR_3R_4$, $-SO_2R_2$, $-SO_2NR_3R_4$, $-OCOOR_2$, $-SOR_2$, $-OCOSR_2$, $-OCONR_3R_4$, and the like wherein Ac represents an acyl group such as a loweralkanoyl, $R_3$ and $R_4$ represent hydrogen, loweralkyl, acyl and loweralkoxy, and $R_2$ represents loweralkyl, haloloweralkyl, aryl, aralkyl and substituted derivatives of such groups.

When $R_1$ is hydrocarbyl or substituted hydrocarbyl it can be loweralkyl, loweralkenyl, loweralkynyl, aralkyl, cycloalkyl, a monocyclic aryl group, or a monocyclic heterocyclic group which can also be substituted with one or more groups such as halo, hydroxy, alkoxy, amino, nitro, sulfonyl, sulfamoyl, acyloxy, carbamoyloxy, carboxy, carboxamido and N-substituted carboxamido.

$R_1$ in formula I above represents cyano or a group of the general formula —CX′R″ wherein X′ is oxygen or sulfur, and R″ is hydrogen, halo, hydroxy, mercapto, amino, substituted amino, an aliphatic radical, an aromatic radical, an aliphatic-oxy radical or an aromatic-oxy radical. Examples of these substituents that might be mentioned are —COOH, —CSSH, —COR$_2$, —COOR$_2$, —COSR$_2$, —CSSR$_2$, —CONH$_2$, —CSNH$_2$, —CSR$_2$, —CONHR$_2$, —CSNH, —CONR$_3$R$_4$ and —CSNR$_3$R$_4$ wherein R$_2$ represents a straight or branched chain alkyl group of 1–6 carbon atoms and R$_3$ and R$_4$ represent hydrogen or R$_2$.

$R_1$ in formula I above represents a nitrogen bonded group such as amino and substituted amino groups, nitro, azido, nitroso, isocyanoto, isothiocyanato and hydroxyamino. Specific examples of nitrogen bonded groups that might be mentioned are —NH$_2$, —NHR$_2$, —NHC(O)$_n$R$_2$, —NHC(S)$_n$R$_2$, —NR$_2$R$_3$, —NHNH$_2$, —NHNR$_2$R$_3$,

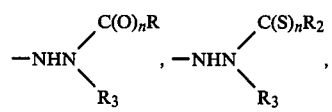

—NNR$_2$, —NR$_3$OH, —NHCNHNH$_2$, —NHCNHNR$_2$R$_3$, —NO$_2$, —NO, —NCO, N$_3$ and —NCS, wherein R$_2$ represents a straight or branched chain loweralkyl group of 1 to 6 carbon atoms, R$_3$ represents R$_2$ or hydrogen, and n represents the integer 1 or 2.

The substituent R$_1$ in formula I represents phosphono or a metal or amine salt thereof, or a substituted phosphono group of the formula

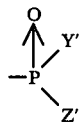

where Y′ and Z′ are the same or different and represent —OR$_2$, —NR$_3$R$_4$,

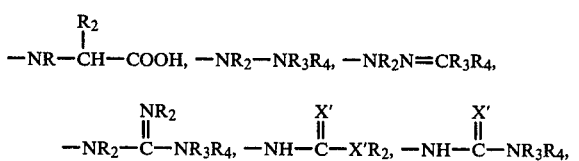

—NC≡X′, —OCOR$_2$ and —N$_3$, where R$_2$ represents hydrogen or a hydrocarbyl radical, R$_3$ and R$_4$ represent hydrogen, hydrocarbyl, alkoxy or an acyl radical, and X′ represents oxygen or sulfur.

In accordance with the nomenclature of cephalosporin compounds used in the art, the compound obtained by hydrolysis of cephalosporin C, which can be represented by the structural formula

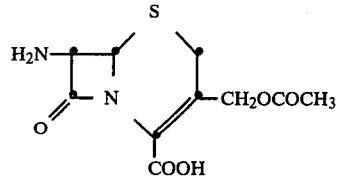

is called 7-aminocephalosporanic acid or 7-ACA.

The term "decephalosporanic acid" used herein to described certain products, pursuant to its usage in this art, represents the basic heterocyclic nucleus having the structural formula

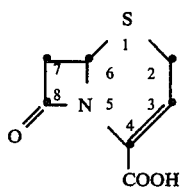

Thus, a compound of the formula

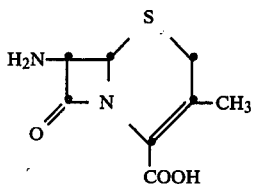

is called 3-methyl-7-aminodecephalosporanic acid using this system of nomenclature.

The cephalosporin compounds with which this invention is concerned are also conveniently designated as "cepham" compounds containing the basic fused-ring betalactam thiazine structure

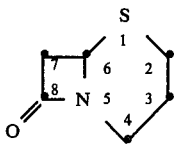

which is known as cepham. Thus, the cephalosporin compounds are called "cephem" referring to the basic structure with a single olefin band. For example, in this system of nomenclature cephalosporin C having the structural formula

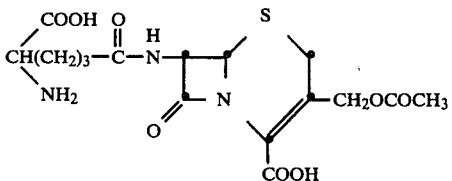

is named 7-(5′-aminoadipamido)-3-acetoxymethyl-3-cepham-4-carboxylic acid.

In accordance with the present invention, it is now found that the new cephalosporins of this invention can be prepared by processes which can be depicted as follows

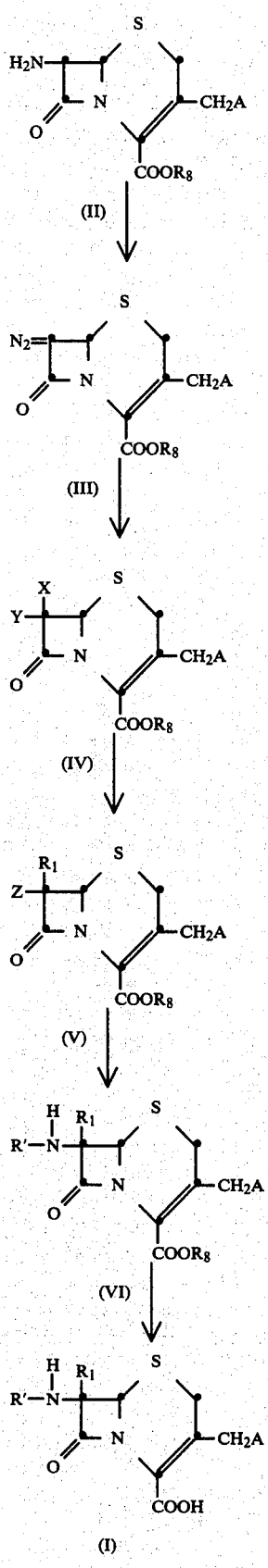

where R', $R_1$ and A are as defined above.

In the foregoing flowsheet the starting compound is a derivative of 7-aminocephalosporanic acid (II), hereinafter also called 7-ACA, wherein the carboxy group is preferably blocked, for example by forming a suitable ester. Thus, 7-ACA or analogs thereof having a different substituent at 3 can be esterified in accordance with methods well known in this art to obtain, for example, the esters wherein $R_8$ represents an alkyl or substituted alkyl group such as methyl, t-butyl, pivaloyloxymethyl, acetoxymethyl and the like, a haloalkyl such as trichloroethyl, an alkenyl group such as allyl, an alkynyl group such as propargyl, an aralkyl group such as benzyl, benzhydryl, o-nitrobenzyl, 3,5-dinitrobenzyl or p-methoxybenzyl, an aryl group such as phenacyl, an organicmetallic group for example a silyl group such as trimethylsily, or a stannyl group such as tributyltin, phenacyl or trichloroethoxycarbonyl. The ester (II) is converted to the corresponding 7-diazocephalosporanic acid ester or 3-$CH_2$A-7-diazocephalosporanic acid ester (III) by reaction with nitrite. The 7-diazo ester (III) is converted by reaction with a pseudo halogen compound or compounds, or a compound which acts as a pseudo halogen, to form intermediate product (IV) wherein X represents halogen from the group consisting of bromine, chlorine and iodine or another leaving group, and Y is a nitrogenous substituent or $R_1$. Intermediate compound (IV) is then converted to compound (V) wherein $R_1$ represents a substituent other than hydrogen and Z represents a nitrogenous group which is readily convertible to amino or acylamino. Compound (V) is then converted to the desired cephalosporin ester (VI) which can be reacted to obtain the corresponding cephalosporin acid or a salt thereof. Also, the substituent at position 3 of the $\Delta^3$-cepham nucleus can be converted to the other substituents of the formula —$CH_2$A in accordance with methods known in this art and those described herein. The processes for carrying out the various steps of the foregoing flowsheet will be more readily understood from the detailed descriptions of methods which can be used to carry out these processes which follows.

The starting material in the foregoing process can be 7-ACA or a 3-$CH_2$A-7-aminodecephalosporanic acid which is first reacted to block or protect the carboxy group. Examples of particularly suitable 3-$CH_2$A-7-aminodecephalosporanic acids that might be mentioned are those wherein A represents hydrogen, hydroxy, azido, halo, a tertiary amine, isothiouronium, a loweralkoxy or loweralkylthio group, an acyloxy or acylthio group, or a heterocyclic oxy or heterocyclic thio substituent. When A is halo it can be fluoro, chloro or bromo. When A represents a loweralkoxy or loweralkylthio group it may be a group such as methoxy, methylthio, tertiary butyloxy, tertiary butylthio, and the like. When A represents an acyloxy or acylthio group it may be a group such as acetoxy, benzoyloxy, cinnamoyloxy, p-sulfocinnamoyloxy, isobutyryloxy, pivaloyloxy, adamantoyloxy, carbamoyloxy, n-methylcarbamoyloxy, N-p-sulfophenylcarbamoyloxy, N-p-carboxymethylphenylcarbamoyloxy, N-chloroethylcarbamoyloxy, N,N-diethyldithiocarbamoyloxy, N,N-dimethyl-piperidinodithiocarbamoyloxy, mesyloxy, sulfamoyloxy and 1R:2S-1,2-epoxypropylphosphonyloxy. When A is a heterocyclic oxy or heterocyclic thio group it may be a group such as 5-methyl-1,3,4-thiadiazolyl-2-thio and 4-carboxamido-1,3,4-thiadiazolyl-2-thio. When A represents a tertiary amine it can be pyridinium and the like.

The diazotization of the 7-amino ester is carried out in accordance with processes well known in this art. Thus, it is conveniently effected in aqueous or aqueous-organic solvent medium, for example by reaction with sodium nitrite in the presence of acid or by reaction with an organic nitrite. Organic solvents suitable for carrying out this reaction are those which do not contain an active hydrogen. Examples of such solvents that might be mentioned are methylene chloride, ether, benzene, toluene, chloroform, and the like. The reaction is preferably carried out at temperatures between about 0° and 50° C.; usually it is most conveniently effected at room temperature. The isolation of the desired diazo compound is readily accomplished in accordance with methods known in the art.

Thus, in accordance with one specific embodiment of this invention, the new cephalosporins are obtained by the following processes:

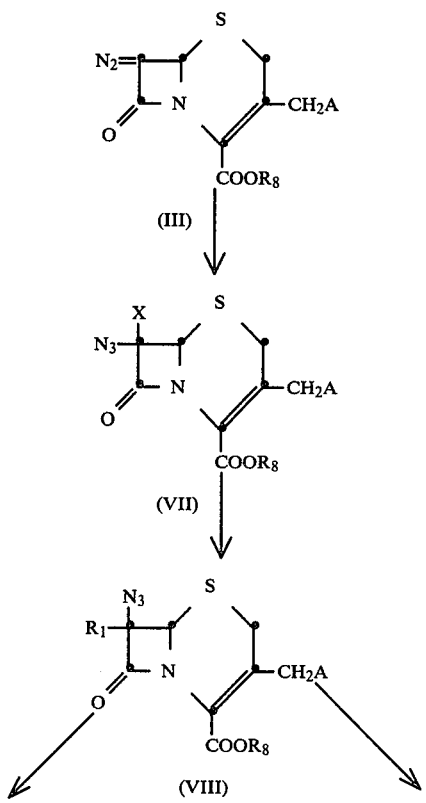

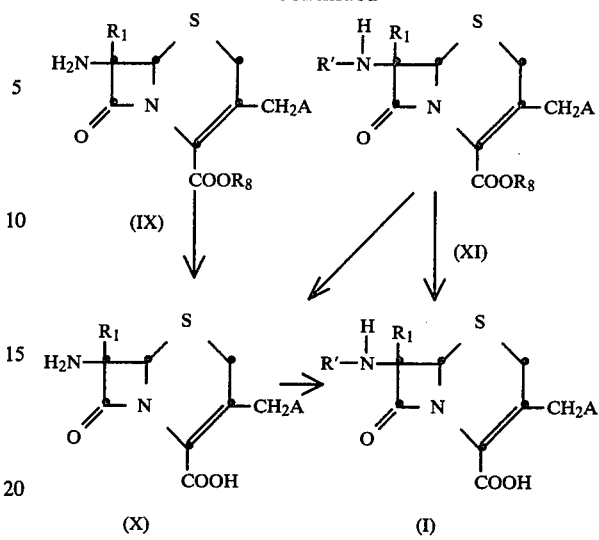

where the substituents are as defined above.

In the above process the 7-diazocephalosporanic acid ester (III) is reacted with a halo azide from the group consisting of bromine, chlorine or iodine azide, preferably in the presence of a tertiary amine azide, to produce the intermediate 7-halo-7-azidocephalosporanic acid ester (VII) which on reaction with a suitable nucleophilic reagent is converted to the desired 7-$R_1$-7-azidocephalosporanic acid ester (VIII). This intermediate product is reduced and acylated in one step to form the substituted cephalosporanic ester (XI) which can then be cleaved to remove the blocking group and obtain the cephalosporanic acid or a salt thereof (X). Alternatively, as shown in the flowsheet, the 7-$R_1$-7-azidocephalosporanic acid ester (VIII) is reduced to the 7-$R_1$-7-aminocephalosporanic acid ester (IX) which can be acylated to produce the 7-$R_1$-7-acylaminocephalosporanic acid ester (XI), or the ester group of compound (IX) can be cleaved to obtain the free acid (X) which can be acylated to form the desired substituted cephalosporin or a salt thereof. The step of cleaving the blocking group is readily effected in accordance with methods known in this art. For example, an aralkyl group such as the benzyl ester is removed by reduction, a silyl ester can be removed by hydrolysis to form the free acid or a salt thereof and a benzhydryl group is readily cleaved by reaction with trifluoroacetic acid in the presence of anisole. In this process other esters which are readily cleaved to form the free acid such as trichloroethyl, phthalimidomethyl, succinimidomethyl, p-methoxybenzyl, o-nitrobenzyl, phenacyl and t-butyl and the like can be used. Also, as is discussed above, the 3-substituent on the $\Delta^3$-cepham nucleus can be varied following the procedures known in this art to obtain the substituted cephalosporins of formula I.

The step of producing the halo azide intermediate is carried out by reacting the diazo compound with a halo azide at a temperature between about 0° and 50° C. for sufficient time to complete the formation of the desired compound. The reaction is preferably carried out in a suitable organic solvent medium which is inert to the reactants. Various solvents which do not contain an active hydrogen such as methylene chloride, chloroform, benzene, toluene, ether and the like, or mixtures thereof provide suitable mediums for carrying out the reaction. Generally, it is preferred to effect the reaction in the presence of a second azide such as lithium azide or a tertiary ammonium azide, for example triethylammonium azide, since under these conditions the formation of the undesired 7-dibromo compound is avoided. The halo azide is used in an amount in slight excess of stoichemetric requirements. The amount of second azide is not critical and it is generally desirable to use an excess in order to obtain maximum yields of the desired halo azido compound under optimum conditions. After completion of the formation of the halo azide the product is recovered and can be purified further, for example by chromatography, in accordance with processes well known in this art.

The next step of the process comprising the replacement of the halo substituent by a nucleophilic group is effected by reacting the halo azide with a substance capable of furnishing a group to replace the halo. This reaction is preferably carried out in the presence of a suitable non-reactant solvent such as methylene chloride, chloroform, benzene, toluene, ether, petroleum ether and the like; again it is desirable to avoid using any solvents containing an active hydrogen. Thus, in accordance with a specific embodiment of this invention, the nucleophilic displacement reagent can be an alcohol such as methanol, ethanol, phenol, benzyl alcohol, a substituted alcohol such as 2-bromoethanol, 2-methoxyethanol, glycol amide, an ester of glycolic acid and the like which results in the displacement of the halo group and the introduction of a methoxy, ethoxy, phenoxy, benzyloxy, 2-bromoethoxy, methoxy, 2-methoxyethoxy, carbonylmethoxy or esterified carbonylmethoxy substituent, respectively. The reaction is preferably carried out in the presence of a heavy metal cation such as a silver salt.

When the reaction is carried out by reacting a salt of an organic acid, preferably a heavy metal salt such as a silver salt, the corresponding 7-acyloxy compound is obtained. For example, reaction of the halo azide with silver acetate, silver benzoate, silver t-butylacetate, silver phenylacetate the corresponding 7-acetoxy, 7-benzoyloxy, 7-t-butylacetoxy and the 7-phenylacetoxy intermediate compound is obtained. The acyl groups of these various acyloxy compounds can then be cleaved to obtain the corresponding 7-hydroxy compound. Alternatively, in this process of preparing the 7-acyloxy compounds the reaction can be carried out by using a salt of the appropriate acid and carrying out the reaction in the presence of a heavy metal salt such as silver oxide or silver tetrafluoroborate.

In the next step of the above-described process the 7-azido-7-$R_1$ compound is then reduced to afford the corresponding 7-amino-7-$R_1$ compound. Various methods of carrying out this reduction can be employed, but it is generally preferred to carry out the reduction of the azido to the amino group by catalytic hydrogenation employing a noble metal catalyst such as platinum, palladium or oxides thereof. These processes are carried out in accordance with procedures well known in this art. Alternatively, the reduction can be effected in the presence of a suitable acylating agent to produce the desired 7-acylamino-7-$R_1$ compound. The 7-amino compound can be reacted with suitable acylating agents using procedures well known in this art to obtain the desired 7-acylamido compounds. Thus, in the above-described process where the substituent R is a halo group, for example chlorine, bromine or iodine, the 7-azido-7-halo compound can be reduced to the corresponding amine compound and the latter compound can then be acylated to obtain the 7-acylamino-7-halo product. Alternatively, as discussed above, the reduction and acylation steps can be combined to produce the 7-acylamido compound without separating and acylating the 7-acylamido intermediate.

Those 7-amidocephalosporanate products wherein the substituent in position 7 of the cepham nucleus is bonded to the 7-carbon via a nitrogen atom are conveniently synthesized from their corresponding 7-halo-7-azido precursors. According to this method of preparation a 7-halo-7-azidocephalosporanate is converted to the corresponding 7,7-diazidocephalosporanate via treatment with an alkali metal azide and this intermediate is then subjected to reduction via hydrogenation in the presence of a suitable catalyst as, for example, a palladium-on-charcoal catalyst. The resulting 7-amino-7-azidocephalosporanate is then acylated by treatment with an acyl halide, carboxylic acid anhydride or sulfonyl halide and the 7-amido-7-azidocephalosporanate thus obtained is again subjected to reduction and then converted to the free acid by conventional means to afford the desired product. The following equation, wherein the acylating agent employed is an acyl halide, illustrates this method of preparation; however, it is to be understood that any other acylating agent can be substituted therefor in an otherwise analogous reaction to afford the desired 7-amido- or 7-sulfonamidocephalosporanic acid product:

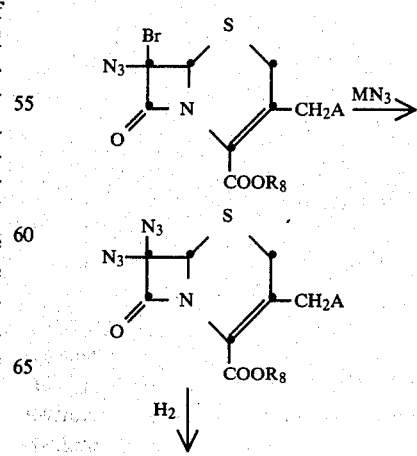

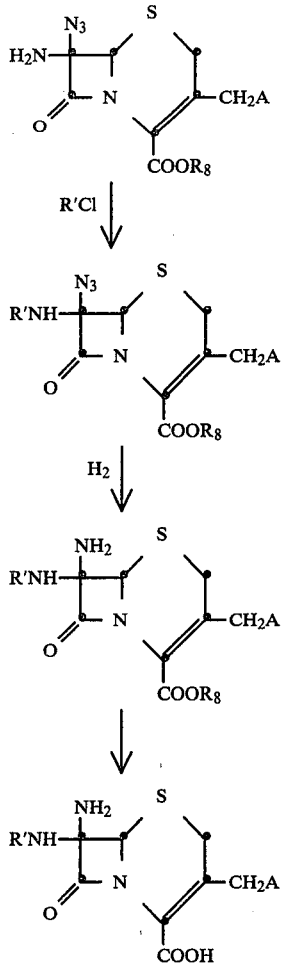

The 7-amido-7-aminocephalosporanic acids of this invention are intermediates which will react at the amino nitrogen atom with a wide variety of reagents to afford the N-substituted and N,N-disubstituted derivatives thereof. Thus, for example, a 7-amido-7-aminocephalosporanic acid will react with one or more equivalents of an aldehyde such as formaldehyde, acetaldehyde or propionaldehyde and the like or an aralkaldehyde such as benzaldehyde and the like to afford the corresponding 7-amido-7-N-alkyl(or aralkyl)cephalosporanic acid.

In addition to the reaction with aldehydes a 7-amido-7-aminocephalosporanic acid can be treated with an acylating and sulfonating agent such as an acyl halide, carboxylic acid anhydride, alkanesulfonyl halide or pyridine-sulfur trioxide complex to afford the corresponding 7-amido-7-acylamido(or 7-sulfonamido)cephalosporanic acid product.

Those 7-amido-7-aminocephalosporanic acids wherein the 7-amino radical is substituted by ureido or an N,N-dialkylureido are conveniently obtained by treating the former with the appropriate carbamoyl halide or N,N-dialkylcarbamoyl halide. Similarly, the 7-amido-7-guanidinocephalosporanic acid derivatives are obtained by simply treating the 7-amido-7-aminocephalosporanic acid precursor with N-amidino-3,5-dimethylpyrazole.

The 7-amido(7-amidinoureido)cephalosporanic acid derivatives are obtained by first treating the 7-amido-7-aminocephalosporanic acid precursor with phosgene to afford an intermediate which, upon treatment with guanidine, yields the desired product.

Alternatively, in accordance with a further embodiment of this invention the 7-aminocephalosporins are also obtained using a benzhydryl ester of the 7-azido-7-halo compound of formula VII as the starting material. This compound is reacted with t-butyl carbamate to produce the corresponding 7-t-butylcarbonylamino compound. Reduction of this intermediate product with hydrogen in the presence of platinum oxide affords the 7-amino-7-t-butylcarbamoylaminobenzhydryl ester. The latter compound is then acylated to produce the benzhydryl-7-acylamido-7-t-butylcarbamoylamino compound which on treatment with trifluoroacetic acid in the presence of anisole affords the 7-aminocephalosporin.

The 7-amido-7-phosphono compounds and the 7-amido-7-phosphinyl products of this invention and their corresponding salt and ester derivatives are obtained by treating a 7-azido-7-halocephalosporanate compound with an appropriate phosphite, phosphonamidic acid or diamidophosphorous acid in the presence of a metal salt, i.e. a silver salt such as silver oxide or silver tetrafluoroborate and the like. The 7-azido-7-phosphono (or 7-phosphinyl) compound thus obtained is then reduced to the corresponding 7-amino-7-phosphono (or 7-phosphinyl)cephalosporanate and subjected to acylation via treatment with an acyl halide, carboxylic acid anhydride or sulfinyl halide to afford the corresponding 7-amido-7-phosphono (or phosphinyl) compound and this intermediate can then be isolated and purified or, if desired, the said ester may be converted to the corresponding free acid as described above. Also, upon treatment with a base, the said acid can be converted to its corresponding 7-amido-7-phosphono (or phosphinyl) salt.

When the halo azide compound is reacted with carbon dioxide or carbon disulfide in the presence of phenyllithium, the corresponding 7-azido-7-carboxy or 7-azido-7-thiocarboxy compound is obtained. These carboxy or thiocarboxy compounds can be converted to the corresponding haloformyl compound by reaction with halogenating agents pursuant to processes well known in this art. For example, the 7-carboxy-7-azido compound by reaction with thionyl chloride is converted to the 7-chloroformyl-7-azido compound which can be reduced to the 7-amino-7-chloroformyl compound and acylated to produce the desired cephalosporanic acid or decephalosporanic acid compounds. Further, the 7-haloformyl compound on reaction with an alcohol such as methanol, phenol or benzyl alcohol is converted to the corresponding 7-methoxycarbonyl, 7-phenoxycarbonyl, or 7-benzyloxycarbonyl compound. Upon reacting the 7-haloformyl compound with an amine such as dimethylamine, dibenzylamine, diphenylamine, monoethylamine, monobenzylamine, monophenylamine, phenethylamine, hydrazine or a substituted hydrazine is converted to the corresponding 7-carboxamido compound. The 7-carboxycephalosporanic and decephalosporanic acid compounds are also obtained by oxidizing the corresponding 7-formyl compounds with argentic oxide. The 7-formyl compounds are prepared by treating the 7-hydroxymethyl substituted products with phosphoric acid at pH 2–3 to obtain the 7-hydroxy compound and then oxidizing these latter products with chromium trioxide pyridine complex.

The new cephalosporanic and decephalosporanic acids wherein $R_1$ is a hydrocarbyl group are prepared by reactions shown in the following flowsheet:

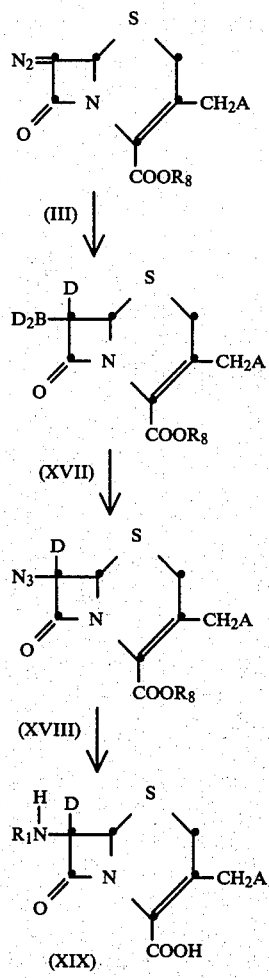

where D is a hydrocarbyl and $R_1$ and A are as defined above.

In accordance with the foregoing flowsheet, the diazocephalosporin compound is reacted with a trihydrocarbyl boron compound at low temperatures, i.e. $-50°$ C. to $-100°$ C., for sufficient time to produce the 7-dihydrocarbylboron-7-hydrocarbon intermediate (XVII). Upon reacting this intermediate with a halogen azide such as bromine azide at room temperature, the 7-hydrocarbyl-7-azido compound (XVIII) is obtained. The latter compound is then reduced catalytically, acylated and the ester group is cleaved in accordance with the procedures described above to produce the desired 7-hydrocarbyl-7-acylamidocephalosporanic or decephalosporanic acid (XIX) or a salt thereof.

In carrying out the first step of this procedure, the hydrocarbyl group of the boron compound can be a lower-alkyl group of 1 to 6 carbon atoms, a loweralkenyl group of 2 to 6 carbon atoms, a loweralkynyl group of 2 to 6 carbon atoms, an aralkyl group such as benzyl, or an aryl group such as phenyl. Thus, using these trisubstituted boron compounds, the corresponding 7-alkyl, alkenyl, alkynyl, aralkyl or arylcephalosporanic acid compounds are obtained.

Thus, in accordance with a specific embodiment of this invention, new cephalosporins having a 7-carboxy or substituted carboxy substituent are obtained by the following processes:

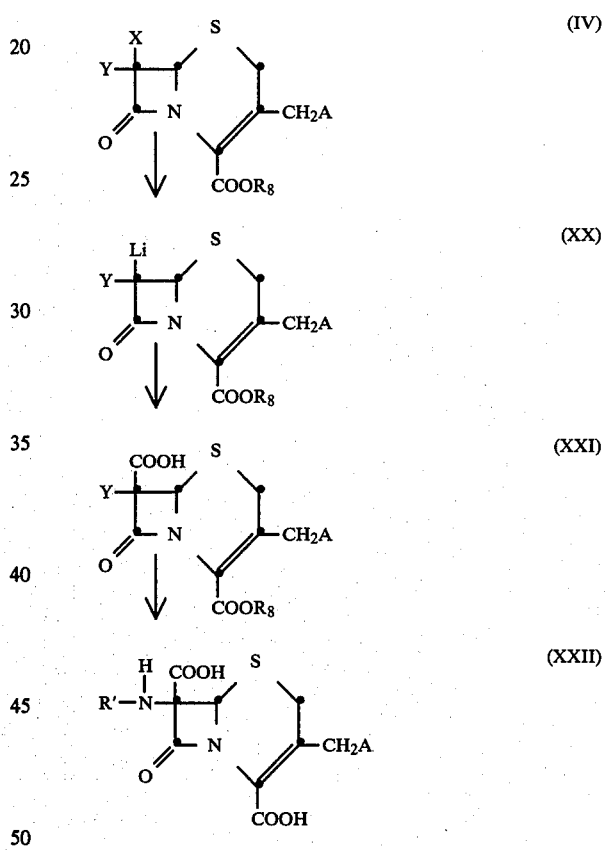

Thus, pursuant to one of the foregoing processes, the intermediate product (IV) obtained as described above is reacted with a hydrocarbyl lithium compound of the formula $R_{10}Li$ where $R_{10}$ represents a hydrocarbyl group such as loweralkyl or aryl, for example n-butyl lithium, to form the 7-lithium compound (XX) which is reacted with carbon dioxide to produce the 7-α-carboxy compound (XXI). This intermediate is converted to the carboxy 7-cephalosporin (XXII) using methods shown above, or the carboxy substituent can be converted to a carboxylic acid derivative such as an ester, an amide, a hydrazide, an azide or a hydroxamic acid using procedures known in the art. Alternatively, when the 7-lithium compound is reacted with carbon disulfide in place of carbon dioxide, the corresponding 7-dithiocarboxy (—CSSH) compound is obtained.

The 7-cyanocephalosporins are prepared by reacting the 7-halo-7-azido intermediate of formula VII above with tetrabutylammonium cyanide to obtain the 7-cyano-7-azido compound. This intermediate product is then reduced to the 7-cyano-7-amino compound, the latter product is acylated, and the acylated ester is cleaved to obtain the desired 7-cyano-7-acylamido cephalosporin using the procedures described above.

The 7-formyl cephalosporins are prepared by converting a 7-hydroxymethyl-7-acylamido-cephalosporanic acid or a corresponding 3-CH$_2$A decephalosporanic acid with an oxidizing agent such as pyridine-chromium trioxide to produce the 7-formyl compound. This latter cephalosporin compound is converted to the corresponding 7-carboxy product by mild oxidizing agents such as argentic oxide.

The 7-halo-substituted cephalosporins of this invention are prepared by subjecting the 7-halo-7-azido intermediates of formula VII above to reduction to afford the corresponding 7-halo-7-amino compound and this intermediate is acylated to afford the corresponding 7-acylamido-7-halocephalosporin compound. The resulting ester is then cleaved and converted to its corresponding carboxylate salt by conventional means as, for example, by treatment with trifluoroacetic acid and an aqueous solution of a base.

In another embodiment of this invention, the novel 7-hydrocarbyloxy and 7-hydrocarbylthiocephalosporins can be obtained by the following sequence:

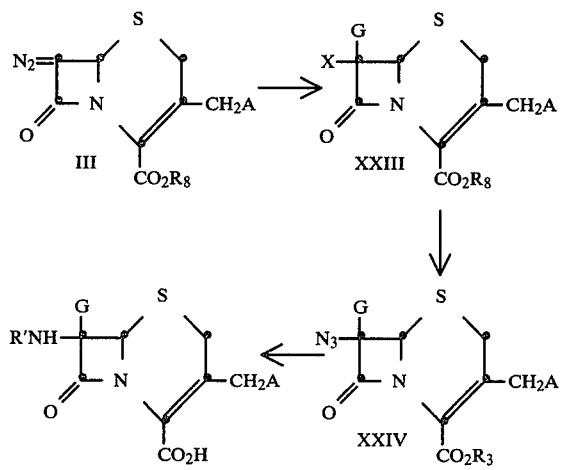

where R$_8$ and A are the same as defined above and G represents hydrocarbyloxy or hydrocarbylthio.

In accordance with the above flowsheet, the starting compound, an ester of a 7-diazo compound defined as in III above, is reacted with a hypohalite of an alcohol or a thiol, or with an alcohol in the presence of a positive halogen such as a N-halo-amide, for example, N-bromoacetamide, N-bromosuccinimide, N-bromophthalimide and the like, that react as though they were the corresponding hypohalite. The resultant 7-halo-7-hydrocarbyloxy or hydrocarbylthio ester (XXIII) is frequently a mixture of epimers at 7, which are readily separable by chromatography. However, when only one epimer is obtained, it may be equilibrated to a mixture of epimers by treatment with an inorganic halide in a polar solvent. A lithium salt of the appropriate halide in dimethylformamide is particularly useful for epimerizing these intermediates. The 7-halo-7-hydrocarbyloxy or hydrocarbylthio product can then be reacted with an azide, such as lithium azide, to form the 7-hydrocarbyloxy or hydrocarbylthio-7-azidocephalosporanate ester (XXIV). This latter compound can then be reduced either with hydrogen or an inorganic reducing agent to form the intermediate 7-hydrocarbyloxy or hydrocarbylthio-7-amino ester (XXV) (R'=H). This latter compound can be acylated to produce the substituted cephalosporin ester. Alternatively, the reduction of the azido intermediate can be done in the presence of an acylating agent to produce these esters directly. These compounds can then be converted to the desired cephalosporin of formula XXV or salts thereof in accordance with procedures described above.

The various processes described above can result in the production of a particular epimer at 7, or in a mixture of epimers at 7; i.e., a 7α-halo-7β-R$_1$ or a 7β-halo-7α-R$_1$ compound. When a mixture of epimers is obtained, these can be readily separated in accordance with methods, such as chromatography, which are well known in this art. In some cases, when only one epimer is obtained it can be equilabrated to produce a mixture of epimers by procedures known in the art.

Pursuant to a further embodiment of this invention, novel products are also obtained by a new process whereby the acyl group of a 7-acylamidocephalosporin compound is replaced by a different acyl substituent. In accordance with this new process, the 7-acylamidocephalosprin compound is reacted with an acylating agent to obtain an intermediate 7-diacylamidocephalosporin compound containing two different acyl substituents, and the original acyl group is then cleaved to obtain a new 7-acylamidocephalosporin compound. This process is illustrated in the following flowsheet:

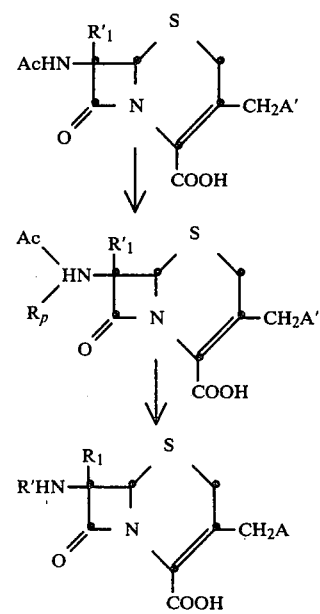

wherein Ac represents an acyl group, A', R'$_1$ and R$_p$ represent, respectively, substituents defined as A, R$_1$ and R', respectively, or are reconvertible thereto by the removal of any protecting or blocking group.

In the process described in the foregoing flowsheet, the reactions can be carried out with the free acid, although in general it is found preferable to block or protect the carboxy group by the formation of a suitable ester which can be readily removed at the end of the process.

The first step of this process comprises reacting the cephalosporin compound, or a derivative thereof wherein the carboxyl group is blocked, with an acylating agent, preferably an acyl halide, in the presence of a silyl group to produce the 7-diacylamido compound. This product is then reacted to remove the original acyl substituent and produce the cephalosporin compound having the new 7-acylamido substituent.

The first step of producing the diacylated product is best effected by intimately contacting the cephalosporin compound with an acylating agent in a suitable solvent medium in the presence of a tri-substituted silyl derivative of a negatively-substituted amide. The temperature at which the reaction is carried out is not particularly critical and temperatures from about −20° C. to about 100° C. are generally satisfactory, although we prefer to carry out the reaction at temperatures from about 25° to 40° C. Various solvents which do not contain an active hydrogen such as chloroform, acetonitrile, methylene chloride, dioxane, benzene, halobenzene, carbon tetrachloride, and diethylether are most suitable as mediums in the reaction.

Various trihydrocarbylsilyl compounds in which the hydrocarbyl substituent is a loweralkyl (1 to 6 carbon atoms), an aryl such as phenyl, or an aralkyl group such as benzyl can be utilized in the process of this invention. These compounds are readily prepared by reacting equimolecular amounts of a trihydrocarbylsilyl halide with a negatively-substituted amide or imide. However, it is generally preferred to use a triloweralkylsilyl derivative, and in particular the trimethylsilyl derivative since this product is inexpensive and readily available. Negatively-substituted amides and imides that might be mentioned are succinamide, phthalimide, cyanoacetamide, trifluoroacetamide, benzamide, p-nitrobenzamide, trichloroacetamide, a sulfonamide, and the like. Examples of triloweralkylsilyl derivatives that are especially useful and might be mentioned are N-trimethylsilyltrifluoroacetamide, N-trimethylsilylphthalamide.

Generally, it is preferred to carry out the foregoing reactions with a cephalosporin compound wherein the carboxy group is blocked or protected since maximum yields of the desired product are obtained with such derivatives. For this purpose, the carboxy substituent is blocked by forming a suitable ester such as a benzyl, benzhydryl, p-nitrophenyl, trimethylsilyl, trichloroethoxy, p-methoxybenzyl, phthalimidomethyl, or succinimidomethyl ester which are readily removed by processes well known in this art. In addition, it is generally preferred to block or protect any amino groups present in the starting cephalosporin compound since maximum yields of the desired products are obtained with such derivatives. For this purpose, the groups are preferably blocked with substituents that are readily removed. Such groups are well known in the art. For example, the amino group is most conveniently blocked by a group such as trichloroethoxycarbonyl, t-butoxycarbonyl, benzoylmethoxycarbonyl, trimethylsilyl, p-methoxybenzyloxy, o-nitrophenylthio, and the like.

The step of cleaving the original acyl group can be effected in several ways, namely, by prolonging the reaction time, by the addition of an alcohol such as a loweralkanol or a loweralkylthiol, or by hydrolysis in an aqueous solution containing a small amount of an acid or a base. Thus, in some cases cleavage is effected by the addition of a loweralkanol or loweralkylthiol containing from 1 to 6 carbon atoms, an aralkanol such as benzyl alcohol, or the corresponding thiol. The cleavage affords the desired monoacylated cephalosporin compound or can also result in the production of a mixture of the monacylated compounds. In the latter case the desired monoacylated cephalosporin compound is recovered by separation procedures such as chromatography which are well known in this art.

The process of this embodiment of our invention is particularly suitable for replacing the aminoadipoyl group of 7-(aminoadipoylamido) side chain of cephalosporins such as those obtained by fermentation and derivatives thereof having other substituents at the 3 position. Thus, in accordance with a specific embodiment of this process, a cephalosporin compound such as cephalosprin C or 7-(D-5'-amino-5'-carboxyvaleramido)-3-carbamoyloxymethyl-7-methoxy-3-cephem-4-carboxylic acid or derivatives thereof, is reacted with an acylating agent in the presence of a tri-substituted silyl radical to obtain the 7-diacylamido derivative having two different acyl groups. The diacylated product can be selectively cleaved to remove the α-aminoadipoyl group and obtain the desired different 7-acylamidocephalosporin compound. Although the cephalosporin compound per se can be transesterified by our process, we have found that the process is facilitated and maximum yields of the new 7-acylamido compound are obtained under optimum conditions when the amino and the carboxy substituents of the cephalosprin compound are blocked or protected in carrying out our process. The various blocking or protecting groups mentioned above are suitable for this purpose. Thus, for example, in replacing the α-aminoadipoyl side chain of the cephalosporins mentioned above with another acyl group, pursuant to this preferred embodiment of this invention, both the carboxy group at the 4-position and the carboxy group of the aminoadipoyl substituent are blocked and the amino group is similarly protected. The resulting blocked derivative is reacted with an acylating agent, preferably an acid halide such as the chloride, in the presence of the tri-substituted silyl derivative of the negatively-substituted amide or imide to produce the 7-diacylamido derivative. During this acylation reaction some cleavage of the α-aminoadipoyl group occurs, but most of the product is obtained in the form of the diacylated derivative.

When the protecting group of the amino substituent of the aminoadipoyl moiety such as a trichloroethoxycarbonyl or a t-butoxycarbonyl group, is removed by suitable means, a selective cleavage of the aminoadipoyl group occurs. This removal of the protecting group of the amino function apparently results in an internal cyclization of the aminoadipoyl group resulting in cleavage of the grup as the α-carboxylic ester of the formula

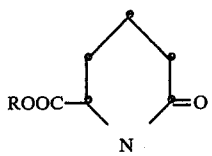

Our present evidence indicates that this is the mechanism of this cleavage, however we do not wish to be bound by this explanation of how the cleavage occurs since subsequent studies may establish that the product is cleaved and extruded in some other manner. This explanation of how the cleavage occurs is presented to provide a better understanding of our invention.

The cleavage of the protective groups on the amino and carboxy functions is accomplished in accordance with procedures well known in this art. Thus, for example, the trichloroethoxy carbonyl group is removed by reaction with zinc and acetic acid, and the t-butoxycarbonyl and benzhydryl groups are removed by reaction with trifluoroacetic acid.

In accordance with a further aspect of our invention, new 7-diacylamido compounds obtained by our process are not only useful as intermediates in the preparation of monoacylated cephalosporins but are useful antimicrobial products active against various pathogenic microorganisms.

A more complete understanding of the processes of this invention is provided by illustrative embodiments which follow. Thus, 7-(D-5'-amino-5'-carboxyvaleramido)-3-carbamoyloxymethyl-7-methoxy-3-cephem-4-carboxylic acid is converted to the corresponding 7-(2-thienylacetamido) compound in accordance with the processes of the following sequence of reactions:

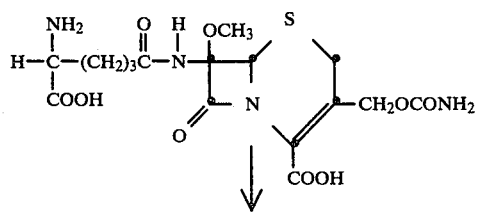

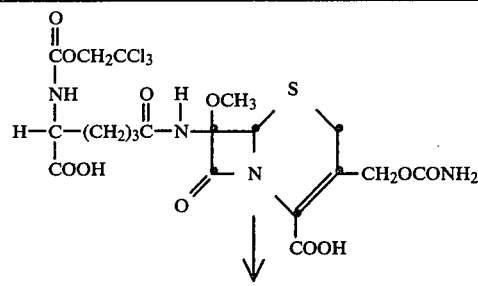

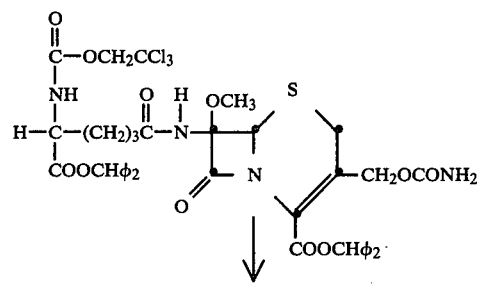

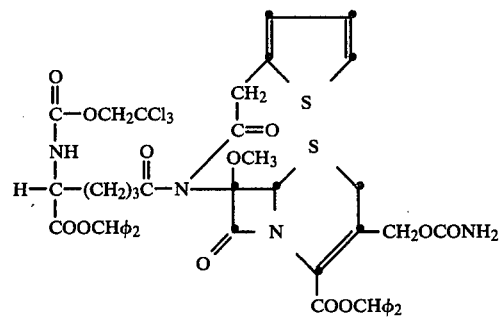

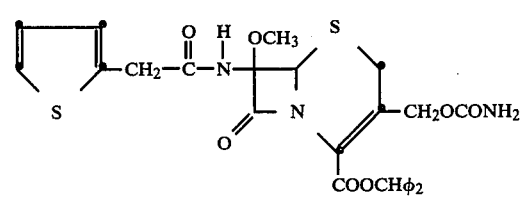

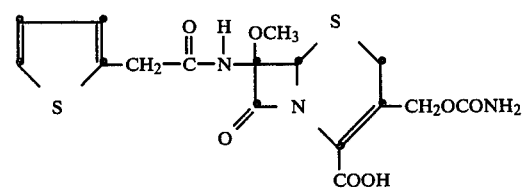

In the foregoing process the starting compound is acylated by reaction with trichloroethoxycarbonyl chloride to produce the N-trichloroethoxycarbonyl derivative which, upon alkylation with diphenyldiazomethane, is converted to the dibenzhydryl ester. Reaction of the resulting cephalosporin compound with trimethylsilyltrifluoroacetamide and 2-thienylacetyl chloride affords the 7-[(D-5'-trichloroethoxycarbonylamino-5'-carboxyvaleryl)-(2-thienylacetaylamino)] compound. This aminoadipoyl group is then cleaved by reaction with zinc in the presence of acid to obtain the benzhydryl ester of 3-carbamoyloxymethyl-7-(2-thienylacetamidodecephalosporanic acid, which is further deblocked to remove the benzhydryl group and form the free acid. This product can be converted to a salt in accordance with methods known in this art.

Other acylating agents such as those defined in $R_1$ above can be used in place of the 2-thienylacetylchloride shown in the foregoing flowsheet to produce the corresponding 7-acylamido cephem compounds. In using such acylating agents it is necessary to avoid the use of acylating agents containing substituents which would be affected during the reactions. Thus, amino, carboxy or hydroxy substituents of the acylating agent should be blocked or protected by groups such as those mentioned above and then subsequently removed. Examples of other specific acylating agents that might be mentioned are phenylacetylchloride, 2-furylacetylchloride, thiophenoxyacetylchloride, α-azidophenylacetylchloride, and the like. Alternatively, other acylating agents such as the anhydrides or mixed anhydrides can be utilized in place of the acid halides. This method of transacylation is indeed a valuable advance in this art since it provides a means of preparing cephalosporins containing different 7-acylamido substituents in place of the aminoadipoylamido group and thereby avoids the need for first converting known cephalosporins to the corresponding 7-aminocephalosporanic acid compound and then acylating this product. In addition to using cephalosporins produced by fermentation as starting materials in this process, derivatives of such cephalosporins containing other substituents at 3 in place of the carbamoyloxymethyl or the acetoxymethyl substituent such as 3-substituents of the general formula $CH_2A$ defined above can be utilized. Alternatively, other 3-substituted cephalosporins can be prepared, for example, from the 3-acetoxymethyl-7-acylamidocephalosporins, in accordance with methods well known in this art.

Thus, examples of other cephalosporins having a 7-methoxy or 7-hydrogen substituent which can be prepared by the above-described processes that might be mentioned are shown in the following table:

| 7-acylamido substituent | 3-substituent |
| --- | --- |
| ![thienyl-CH2CONH-] | $-CH_3$ |
| ![furyl-CH2CONH-] | $-CH_2N^+$(pyridyl) |
| $\phi-S-CH_2-CONH-$ | $-CH_2OCON(CH_3)(H)$ |
| ![fluorofuryl-CH2CONH-] | $-CH_2OCONH_2$ |

| 7-acylamido substituent | 3-substituent |
| --- | --- |
| ![tetrazolyl-N-CH2CONH-] | $-CH_2N(CH_3)_2$ |
| $CH_3(CH_2)_3SCH_2-CONH-$ | $-CH_2OCH_3$ |
| ![methylthienyl-CH2CONH-] | $-CH_2OCON(CH_2-CH_2Cl)(H)$ |

An alternative route for the preparation of the 7-$R_1$-7-amino compounds of formula IX above comprises reacting a 7-amino compound of formula II above with an aromatic aldehyde to form an imino adduct, treating this imino adduct with a defined reagent yielding a 7-$R_1$ Schiff's base adduct and then regenerating the amino moiety. This process is not a part of this invention but is disclosed and claimed in a co-pending application, Great Britain Ser. No. 13,008, filed Mar. 16, 1972.

More specifically, this alternative route can be used to prepare compounds having the following formula:

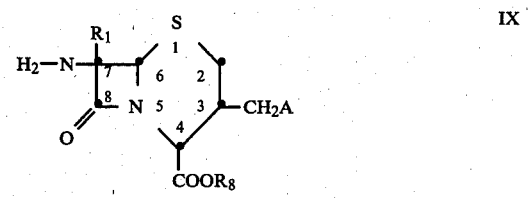

wherein A and $R_8$ are as previously defined, and $R_1$ is lower alkyl, lower alkoxy, lower alkylthio, lower alkanoyl, lower haloalkoxy, lower haloalkylthio, halo, lower haloalkyl, lower alkanoyloxy, (α-hydroxy) lower alkyl, (α-hydroxy) lower alkenyl, β-substituted ethylene derivatives, allyl, benzyl, cyano, nitroso, carbamoyl, carboloweralkoxy, sulfo, sulfonoyl, loweralkylsulfo, phospho, nitro, carboxy, and dithiocarboxy.

The starting material is the 7-$NH_2$ compound of formula II above which is reacted with an aromatic aldehyde, preferably one having at least one o- or p-electronegative substituent, selected from the group consisting of nitro, methyl sulfonyl, cyano, carboxyl, derivatives, and the like. The preferred reactant is p-nitrobenzaldehyde.

The starting material and the aromatic aldehyde are mixed together in approximately equimolar amounts in an inert solvent. Suitable solvents are dioxane, acetonitrile, dimethylformamide, dimethylsulfoxide, benzene, toluene, and the like. The aldehyde can be employed in a molecular excess if desired. The reaction proceeds readily at temperatures ranging from ambient to reflux temperature of the solvent. Since this condensation is an equilibrium reaction and since water is one of the products of the reaction, water is removed from active participation in further reactions by any of a number of usual methods, including azeotropic distillation, molecular sieves, or borate esters. The particular method is dependent upon the exact parameters of the reaction. The reaction is terminated by evaporation of the solvent. The imino derivative is then recovered and used in the next step.

The latter involves the substitution of the $R_1$ group at the carbon atom adjacent to the imino nitrogen. This reaction takes place in the presence of an inert solvent, such as those listed above, and in the additional presence of an organic or inorganic base. It is preferred to use organic bases, such as tertiary amines or pyridine. A specific tertiary amine which is preferred is diisopropylethylamine, although any tertiary lower alkylamine can be used. Inorganic bases, such as NaH, NaOH, KOH, carbonate, or bicarbonate salts, etc. can also be employed. For instance, the reaction can be conducted in "soft glass" which contains enough soluble inorganic base to catalyze the reaction.

The specific reactant which is employed in the reaction with the imino compound to result in the chosen $R_1$ group obviously depends on the $R_1$ group desired.

The following is of value in defining each reactant in terms of the final $R_1$ group.

| Reactant | $R_1$ |
|---|---|
| 1. lower alkyl sulfate or halide | loweralkyl |
| 2. loweralkanoyl halide | loweralkanoyl |
| 3. loweralkyl peroxide | loweralkoxy |
| 4. haloloweralkyl peroxide | lowerhaloalkoxy |
| 5. loweralkyl disulfide | loweralkylthio |
| 6. haloloweralkyl disulfide | lowerhaloalkylthio |
| 7. tertbutylhypohalite or perhalomethylhypohalite | halo |
| 8. haloloweralkane | haloloweralkyl |
| 9. loweralkanoyl peroxide | loweralkanoyloxy |
| 10. formaldehyde or loweralkyl-aldehyde | (α-hydroxy) loweralkyl |
| 11. reactive loweralkyl ketone | (α-hydroxy) branched-loweralkyl |
| 12. reactive ethylene derivatives | (β-substituted) ethyl |
| 13. allyl halide | allyl |
| 14. benzyl halide | benzyl |
| 15. cyanogen bromide | cyano |
| 16. nitrosyl halide | nitroso |
| 17. carbamoyl halide | carbamoyl |
| 18. loweralkylhalo formate | carboloweralkoxy |
| 19. sulfuryl chloride | sulfo |
| 20. sulfamoylchloride | sulfamoyl |
| 21. loweralkylsulfonyl halide | loweralkylsulfo |
| 22. phosphorus oxychloride | phospho |
| 23. acetonecyanhydrinnitrate | nitro |
| 24. carbondioxide | carboxy |
| 25. carbondisulfide | dithiocarboxy |

"(α-Hydroxy)loweralkyl" is used to mean a group of the formula

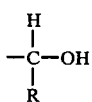

wherein R is hydrogen or alkyl having 1-6 carbon atoms.

"Reactive loweralkyl ketone" is used to mean a ketone of the formula

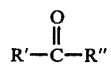

wherein one of R' or R" is a halogenated loweralkyl group, the halogen-substituted carbon being adjacent to the carbonyl function; or one of R' or R" is an alkyl carbonyl group. The carbonyl being adjacent to the carbonyl of the ketone; the other of R' or R" is loweralkyl. Thus, to illustrate, one type of "reactive loweralkyl ketone" is:

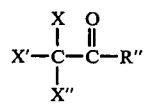

wherein X is halo, X" is halo or hydrogen, and X' is halo, hydrogen, or loweralkyl; and R" is loweralkyl.

The other type is

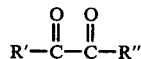

R" is hydrogen or loweralkyl, and wherein R" is loweralkyl, haloloweralkyl, loweralkoxy, or lowerhaloalkoxy.

"(α-Hydroxy)branchedloweralkyl" means a group of the formula

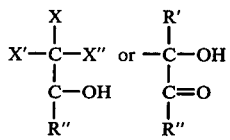

wherein X, X', X", R', and R" are as defined above.

"Reactive ethylene derivative" is used to mean an ethylenically unsaturated compound which is activated by the presence of one or more strong electron withdrawing groups. For example, compounds of the formula $CH_2=CHY$ where Y is

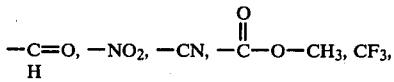

and the like are included.

The term "(β-substituted)ethyl" is employed to mean the following group

wherein Y is the same as defined as above.

Following the reaction between the imino compound and the reactant to form the novel 7-R' compounds, the imino moiety is regenerated to amino.

This regeneration is effected by aminolysis or hydrazinolysis, in the presence of a catalytic amount of acid. Preferably, aniline hydrochloride is employed which serves both as a source of amine and acid. When hydrazine or hydrazine derivatives such as phenylhydrazine, 2,4-dinitrophenylhydrazine, and the like are used, acid is added. Other hydrazines or amines can be employed. Preferred media are the loweralkanols, such as methanol, ethanol, and the like. The usual acids or bases can be employed. For instance, hydrochloric p-toluene sulfonic acid or aniline can be used. The only limitation is that no undesired hydrolysis or ring damage occur.

The 7-$R_1$-7-aminocephalosporanic acid and 7-$R_1$-7-aminodecephalosporanic acid esters of formula IX above prepared in this way can then be converted to the cephalosporin compounds following the procedures described above.

The step of acylating the 7-amino compounds of formula IX above is effected by reacting the amine compound with the acyl acid in the presence of an activating agent such as dicyclohexyldiimide, with the acyl anhydride, with an acyl halide such as the acid chloride, or with an activated ester of the acid such as the p-nitrophenyl ester. In the process of reductively acylating the 7-azido compounds of formula VIII above, the reductive acylation is preferably effected in the presence of the acyl anhydride.

The following examples are given for the purpose of illustration and not by way of limitation.

EXAMPLE 1

A. Benzyl 7-diazocephalosporanate

A mixture of 10 g. sodium nitrite, 4.5 g. benzyl 7-aminocephalosporanate p-toluenesulfonic acid salt, 300 ml. methylene chloride and 300 ml. water/ice is shaken in a separatory funnel. p-Toluenesulfonic acid monohydrate (1.6 g.) is added in three portions during 20 minutes. The separatory funnel is shaken vigorously during this time. The methylene chloride layer is separated, dried over sodium sulfate and evaporated under reduced pressure to 40 ml.

B. Benzyl 7-azido-7-bromocephalosporanate

To the solution of benzyl 7-diazocephalosporanate in 40 ml. of methylene chloride is added 40 ml. of nitromethane, and the resulting solution is cooled in an ice bath. To this solution is added 80 ml. of triethylammonium azide in methylene chloride prepared as described below. To this reaction mixture is then added 40 ml. of methylene chloride containing bromine azide prepared as described below with good stirring. After the gas evolution ceases, 200 ml. of 0.1 N sodium thiosulfate is added and the mixture is shaken vigorously. The organic layer is then separated and 200 ml. of water added. To this mixture is then added solid sodium bicarbonate in small portions until the aqueous phase remains at pH 7 after shaking. The organic layer is then separated, dried with magnesium sulfate and evaporated under reduced pressure to afford 4.8 g. of crude benzyl 7-azido-7-bromocephalosporanate in the form of a brown oil. The product is purified further by chromatography on 120 g. of silica gel using hexane/benzene in 1:1 and 1:3 ratio to elute the product. The fractions containing clean product are combined and evaporated to give benzyl 7-azido-7-bromocephalosporanate. IR (liq. film): 4.7$\mu$ (azide), 5.60$\mu$ ($\beta$-lactam carbonyl), 5.75$\mu$ (esters). NMR$_{CDCl_3}^{TMS}$ (100 MHz):

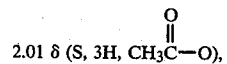
2.01 $\delta$ (S, 3H, $CH_3C-O$), 3.42$\delta$ (AB, 2H, S—$CH_2$—), 4.68 and 4.71$\delta$ (singlets, C-6 hydrogens). Thin layer chromatography Rf of 0.70 on silica gel G using 1% methanol in chloroform.

The solution of triethylammonium azide is prepared by mixing 6.0 g. of sodium azide, 20 ml. of water and 50 ml. of methylene chloride, cooling this reaction mixture to 0° C. and adding 6 ml. of concentrated sulfuric acid. The resulting reaction mixture is allowed to stir for 10 minutes, the layers are separated and the aqueous layer washed with a small amount of methylene chloride which is added to the previously separated methylene chloride phase. After drying with calcium chloride, the methylene chloride solution is neutralized to pH 7 with triethylamine and the final volume is adjusted to 100 ml. with methylene chloride.

The solution of bromine azide is prepared by cooling a mixture consisting of 26 g. of sodium azide, 80 ml. of methylene chloride and 6.4 g. of bromine to 0° C., adding 20 ml. of concentrated hydrochloric acid, allowing the reaction mixture to stir in an ice bath for 3 hours, separating the organic phase, washing the aqueous phase with a small quantity of methylene chloride which is added to the separated organic phase, and adjusting the volume to 100 ml. with methylene chloride.

C. Benzyl 7-azido-7-methoxycephalosporanate

A solution of benzyl 7-azido-7-bromocephalosporanate in methanol is treated with one equivalent of dry silver fluoroborate. A buff colored precipitate forms rapidly. The mixture is stirred at 22° C. for 2¾ hours. The solid is removed by filtration and the filtrate is evaporated to afford crude benzyl 7-azido-7-methoxycephalosporanate. The crude product is chromatographed on silica gel using 2% chloroform in benzene. The desired product has NMR$_{CDCl_3}^{TMS}$ (Partial, 100 MHz

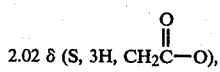
2.02 $\delta$ (S, 3H, $CH_2C-O$), 3.60$\delta$ (S, 3H, $OCH_3$). IR (liq. film): strong absorption at 4.70$\mu$ (azide), 5.60$\mu$ ($\beta$-lactam), 6.76$\mu$ (esters). Thin layer chromatography Rf of 0.65 on silica gel G with 1% methanol in chloroform.

D. Benzyl 7-acetamido-7-methoxycephalosporanate

A mixture of 70.5 mg. benzyl 7-azido-7-methoxycephalosporanate, 69.5 mg. of platinum oxide and 5.0 ml. acetic anhydride is hydrogenated at atmospheric pressure for 16 hours. The solvent is evaporated under reduced pressure, and the crude product is chromatographed on 12 g. silica gel using chloroform and chloroform with 1–5% methanol. Crude benzyl 7-acetamido-7-methoxycephalosporanate elutes with 1% methanol in chloroform. The product has IR (liq. film) 3.0μ (NH), 5.60μ (β-lactam carbonyl). 5.75μ (esters), 5.93 and 6.60μ (amide) and no absorption at 4.7μ (azide). NMR$_{CDCl_3}^{TMS}$ (partial, 100 MHz):

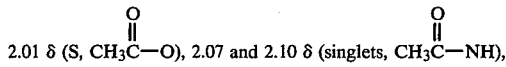

2.01 δ (S, CH₃C—O), 2.07 and 2.10 δ (singlets, CH₃C—NH), 3.50δ (singlet, OCH₃), 5.20δ (singlet, C-6 hydrogen). Thin layer chromatography Rf of 0.40 on silica gel G with 5% methanol in chloroform.

E. Potassium 7-acetamido-7-methoxycephalosporanate

A solution of benzyl 7-acetamido-7-methoxycephalosporanate (25 mg.) in 3 ml. of 1:1 aqueous methanol is hydrogenated using 25 mg. of 10% Pd/C catalyst at 40 p.s.i. of hydrogen for 1 hour. The mixture is filtered and the pH of the filtrate adjusted to 8 with potassium bicarbonate. The aqueous solution is lyophilized to give potassium 7-acetamido-7-methoxycephalosporanate.

EXAMPLE 2

A. Benzhydryl 7-aminocephalosporanate

To a slurry of 6.8 g. (0.025 mole) of 7-aminocephalosporanic acid in 300 ml. of peroxide-free dioxane at room temperature is added with stirring 4.3 g. (0.022 mole) of p-toluenesulfonic acid monohydrate. The clear solution is concentrated in vacuo and flushed twice with dioxane.

The residue is dissolved in 300 ml. of dioxane at room temperature, and a solution of 10 g. (0.05 mole) of diphenyldiazomethane in 25 ml. of dioxane is added dropwise over 15 minutes. The wine-colored solution is stirred for an additional 30 minutes, then 25 ml. MEOH is added to destroy the excess φ₂CN₂. The mixture is concentrated in vacuo and the residue partitioned between 200 cc. CH₂Cl₂ and 200 ml. water containing 10 g. K₂HPO₄ (pH 8.5). The organic phase is washed with water, dried over Na₂SO₄ and concentrated in vacuo to yield an oil.

The oil is stirred with 100 ml. of ether for 1 hour. The precipitate is filtered, washed with ether and dried to constant weight 4.7 g. (43%). m.p.=126°-128° C. Analysis calculated: C, 63.0; H, 5.01; N, 6.37. Found: C, 62.7; H, 5.18; N, 5.18. IR in CHCl₃ is 5.6μ (β-lactam C=O) and 5.8μ (ester C=O). NMR in CDCl₃ is 1.85 δ(singlet, NH₂);

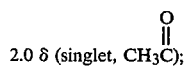

3.45 δ(doublet, CH₂S); 4.8 δ(singlet, CH₂OAC); 4.7 δ(doublet, C₆H); 4.9 δ(doublet, C₇H);

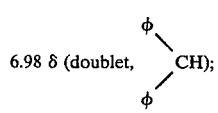

and 7.4 δ(singlet, phenyl).

B. Benzhydryl 7-diazocephalosporanate

To a stirring mixture of 1.6 g. of NaNO₂, 30 ml. of water and 40 ml. of CH₂Cl₂ at 0° C. is added 880 mg. (0.002 mole) of ester followed by the addition of a solution of 760 mg. (0.004 mole) of p-toluenesulfonic acid in 5 ml. water over a few minutes. The mixture is stirred at 0° C. for 20 minutes, then the organic phase is cut away, washed with 1×10 cc. ice water, dried over Na₂SO₄ at 0° C., filtered and concentrated in vacuo at room temperature to yield 900 mg. of a glass. IR is 4.8μ (strong N=N), 5.6μ (β-lactam C=O) and 5.8μ (ester C-O). NMR in CDCl₃ is

3.4 δ(doublet, CH₂S); 4.8 δ(singlet, CH₂OAC); 5.6 δ(singlet, C₆H);

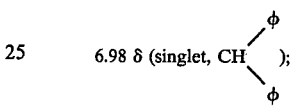

and 7.4 δ(singlet, phenyl).

C. Benzhydryl 7-bromo-7-azidocephalosporanate

To a solution of 900 mg. of benzhydryl 7-diazocephalosporanate in 20 ml. CH₂Cl₂ and 10 ml. CH₃NO₂ at 0°-10° C. is added all at once the Et₃N⁺NH₃⁻ followed by the BrN₃ solution, then 50 ml. of water is added followed by the addition of solid NaHCO₃ to pH 8.

The organic layer is separated and extracted with 2×20 ml. water, dried over Na₂SO₄ and concentrated in vacuo to yield 900 mg. (83%).

The NMR fits the structure. Thin layer chromatography on silica gel with CHCl₃ shows a major spot at Rf 0.2. Chromatography of 900 mg. crude product on 25 g. silica gel with CHCl₃ gives 400 mg. (39%) single spot material as an oil.

IR in CHCl₃ is 4.72μ (N₃), 5.56μ (β-lactam C=O) and 5.75μ (ester C=O). NMR in CDCl₃ is

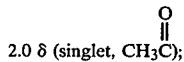

3.38 δ(CH₂S); 4.7 δ(singlet C₆HO); 4.94 δ(CH₂—O)

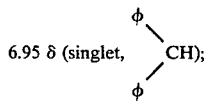

and 7.4 δ(singlet, phenyl).

Preparation of BrN₃ Solution

To 8 ml. of CH₂Cl₂ at 0° C. is added 2.66 g. (0.04 mole) of NaN₃ followed by 0.65 g. (0.0042 mole) of bromine. To this stirring mixture at 0° C. is added dropwise 2 ml. of concentrated hydrochloric acid. The mixture is stirred for 3 hours at 0° C.

The organic layer is decanted and the aqueous layer extracted with 1×5 ml. of CH₂Cl₂. The combined organic phase is stored at −10° C.

Preparation of Et₃N$_H$⁺N₃⁻ Solution

To a slurry of 1.5 g. of NaN₃ in 5 ml. water and 10 ml. CH₂Cl₂ at −10° C. is added dropwise at −10° C. to 0° C. 4 ml. of 50% H₂SO₄. The organic phase is poured off the aqueous paste, and the aqueous extract washed with 1×5 cc. CH₂Cl₂. The combined organic phase is dried over CaCl₂. The decanted HN₃ solution is brought to pH 7 with Et₃N and stored at −10° C.

D. Benzhydryl 7-methoxy-7-azidocephalosporanate

To a solution of 400 mg. (0.00072 mole) of bromoazide in 30 ml. methanol is added 150 mg. (0.0008 mole) of AgBF₄. The mixture is stirred in the dark for 2½ hours.

The mixture is concentrated in vacuo and the residue taken up in 50 ml. of CH₂Cl₂ filtered. The filtrate is extracted twice with saturated NaHCO₃ solution, twice with water, dried over anhydrous MgSO₄ and concentrated in vacuo to yield 300 mg. (83%) of crystals. m.p.=145°-148° C.

IR in CHCl₃ is 4.72μ (N₃ band), 5.6μ (β-lactam) and 5.75μ (ester C=O). NMR is

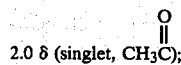

2.0 δ (singlet, CH₃C);

3.4 δ(CH₂S); 3.6 δ(singlet, OCH₃); 4.88 δ(singlet, C₆H); 4.9 δ(CH₂O);

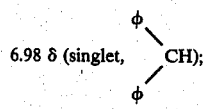

6.98 δ (singlet, CH);

and 7.4 δ(singlet, phenyl).

Analysis calculated: C, 58.4; H, 4.45, N, 11.3; S, 6.5. Found: C, 58.56; H, 4.65; N, 11.30; S, 5.70.

EXAMPLE 3

A. Benzhydryl 7-methoxy-7-aminocephalosporanate 1.0 g. of benzhydryl 7-azido-7-methoxycephalosporanate is dissolved in 100 ml. of dioxane. 1.0 g. of platinum oxide is added and the reaction mixture stirred under hydrogen at atmospheric pressure for 1 hour. Another 1.0 g. quantity of platinum oxide is added and the reaction mixture is again placed under hydrogen and stirred for 3 hours until the azide is completely reacted as determined by infrared analysis of aliquots. The solvent is removed under reduced pressure and the residue taken up in 50 ml. of chloroform and filtered through silica gel G in chloroform in a 60 ml. sintered glass funnel. The material is eluted with chloroform until 200 ml. of chloroform has been collected. The chloroform is removed under reduced pressure affording 0.632 g. of benzhydryl 7-methoxy-7-aminocephalosporanate, which is acylated directly without further purification. The starting compound is prepared using the procedures described in Example 1 starting with the benzhydryl ester of 7-aminocephalosporanic acid.

B. Benzhydryl 7-methoxy-7-(2-thienylacetamido)cephalosporanate 0.632 g. of benzhydryl 7-methoxy-7-aminocephalosporanate is taken up in 25 ml. of methylene chloride and cooled to 0° C. 0.6 ml. of 2-thienyl acetyl chloride is added dropwise over 30 seconds followed by 0.6 ml. of pyridine 60 seconds later. The reaction mixture is stirred at 0° C. for 15 minutes and poured into crushed ice. The mixture is agitated and the organic layer separated and washed once with 20 ml. of water, once with 20 ml. of 5% sodium bicarbonate and once again with 20 ml. of water. The methylene chloride is dried and evaporated to dryness affording 1.417 g. of crude product. This material is placed on a column of 60 g. of silica gel under benzene and the column is eluted with benzene, taking 100 ml. fractions followed by 300 ml. of methylene chloride/benzene (1:1) in 3 fractions, and 500 ml. of methylene chloride in 5 fractions. The product is removed from the column by eluting with 400 ml. of chloroform in 4 fractions, affording 0.592 g. This material is taken up in 25 ml. of methylene chloride and stirred at room temperature with 20 ml. of a solution of 0.120 g. of sodium bicarbonate in water for ½ hour. The layers are separated and the organic layer washed with water, dried and evaporated to dryness, affording 0.420 g. of benzhydryl 7-methoxy-7-(2-thienylacetamido)cephalosporanate, which shows 1 spot on a thin layer chromatographic plate.

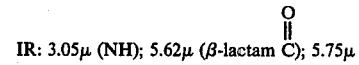

IR: 3.05μ (NH); 5.62μ (β-lactam C); 5.75μ (ester C—O); 5.92μ (amide C). NMR:

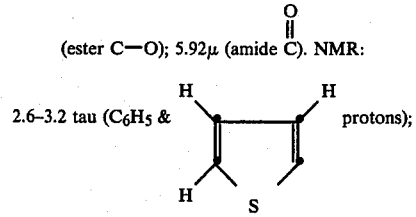

2.6–3.2 tau (C₆H₅ & protons);

4.94 tau (S, 6H); 5.05 tau g(CH₂—OAc);

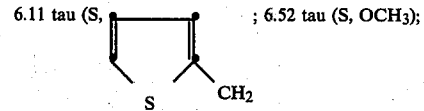

6.11 tau (S, ; 6.52 tau (S, OCH₃);

6.64 tau(—CH₂—S); 7.99 tau (S, CH₃—C=O).

C. Sodium 7-methoxy-7-(2-thienylacetamido)cephalosporanate 0.420 g. of benzhydryl 7-methoxy-7-(2-thienylacetamido)cephalosporanate is dissolved in 3.5 ml. of anisole and treated with 10 ml. of trifluoroacetic acid at room temperature for 10 minutes. The trifluoroacetic acid and anisole are removed under reduced pressure maintaining the temperature below 40° C., and the residue is taken up in 25 ml. of chloroform and treated with 20 ml. of water containing 0.120 g. of sodium bicarbonate. The mixture is stirred for ½ hour at room temperature and the organic phase is separated and washed with water. The combined aqueous phase is washed twice with methylene chloride and lyophilized affording 0.382 g. of sodium 7-methoxy-7-(2-thienylacetamido)cephalosporanate as a brownish solid. IR: 5.65μ (β-lactam), 5.91μ (amide carbonyl). NMR (DMSOD₆): 2.65 tau (singlet) and 3.06 tau (doublet) (thienyl protons); 5.04 tau (singlet, 6H);

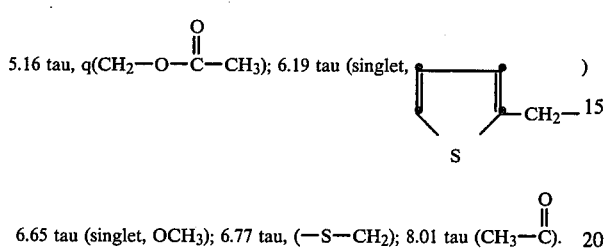

5.16 tau, q(CH₂—O—C(=O)—CH₃); 6.19 tau (singlet, ); 6.65 tau (singlet, OCH₃); 6.77 tau, (—S—CH₂); 8.01 tau (CH₃—C(=O)).

EXAMPLE 4

7-Methoxy-7-(2-thienylacetamido)-3-desacetoxy-3-pyridiniumcephalosporanic acid thiocyanate 0.100 g. of sodium 7-methoxy-7-(2-thienylacetamido)cephalosporanate is dissolved in 100 μl of water containing 50 μl of pyridine, 5 μl of 85% phosphoric acid and 0.475 g. potassium thiocyanate. The reaction mixture is stirred at 60° C. for 5 hours and cooled to room temperature. The reaction mixture is diluted with water to a total volume of 20 ml. and extracted 5 times with 5 ml. portions of chloroform. Chloroform is removed from the aqueous phase by evaporation under vacuum and the aqueous phase is then cooled to 0° C. and acidified to pH 2. The mixture is allowed to stand at 0° C. for 2 hours and the precipitated solid removed by filtration and dried to give 0.015 g. of 7-methoxy-7-(2-thienylacetamido)-3-desacetoxy-3-pyridiniumcephalosporanic acid thiocyanate as a pale yellow solid. IR: 4.83μ (CNS⁻), 5.62μ (β-lactam). Rf 0.61 (BAW 3:1:1, on paper).

EXAMPLE 5

A. Benzhydryl 7-methoxy-7-(2-thianaphthene-2-acetamido)cephalosporanate 330 mg. (1.57 mm.) of benzothiophene-2-acetyl chloride is added in 1 portion to a solution of 330 mg. (0.75 mm.) benzhydryl 7-amino-7-methoxycephalosporanate in 10 ml. of methylene chloride at 0° C. 330 μl of dry pyridine is added after 1 minute and the homogeneous reaction mixture stirred for 15 minutes at room temperature and poured onto 10 ml. of water. The organic layer is washed once with 3 ml. of cold aqueous 5% sodium bicarbonate and once with 3 ml. of cold water and dried over sodium sulfate. The solvent is removed in vacuo at room temperature and the crude product chromatographed on a 2.1 cm. (outside diameter) column containing 30 g. of silica gel under methylene chloride. All less polar contaminants, including the azide from the previous step, are eluted with 400 ml. of methylene chloride. The eluant is then changed to chloroform to remove the product. All fractions containing the product are combined and washed with 5% sodium bicarbonate and water. The solution is dried over sodium sulfate and evaporated to dryness in vacuo affording 301 mg. of benzhydryl 7-methoxy-7-(2-thianaphthene-2-acetamido)cephalosporanate as a gold oil. IR: 6.65μ (β-lactam), 5.78μ (ester), 5.95μ (amide).

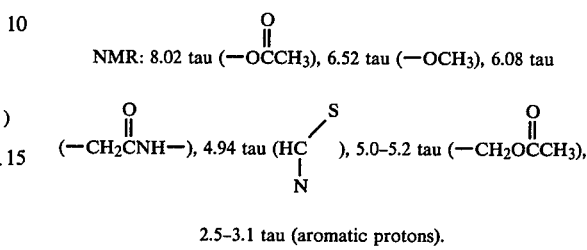

NMR: 8.02 tau (—OC(=O)CH₃), 6.52 tau (—OCH₃), 6.08 tau (—CH₂CNH—), 4.94 tau (HC(S)(N)), 5.0-5.2 tau (—CH₂OC(=O)CH₃), 2.5-3.1 tau (aromatic protons).

TLC: silica gel G, 5% EtOAc/CH₂Cl₂ Rf=0.37.

B. Sodium 7-methoxy-7-(2-thianaphthene-2-acetamido)cephalosporanate 2.0 ml. of anisole and 5.9 ml. of trifluroacetic acid are combined and added to 300 mg. of the benzhydryl 7-methoxy-7-(2-thianaphthene-2-acetamido)cephalosporanate, and the reaction mixture is stirred for 10 minutes at room temperature. Excess anisole and trifluoroacetic acid are removed in vacuo and residual anisole and trifluoroacetic acid are removed by placing the flask directly onto a high vacuum pump for 15 minutes. The residual dark oil is taken up in 15 ml. of a benzene/ethyl ether mixture (1:1). A small amount of insoluble gum is dissolved by the addition of 5 ml. of a 5% sodium bicarbonate solution in water. The organic layer is washed with water and the combined aqueous layers are lyophilized to give 185 mg. of sodium 7-methoxy-7-(2-thianaphthene-2-acetamido)cephalosporanate as a pale yellow powder. NMR: 6.18 tau (—CH₂CNH—), 8.13 tau (—O=C—CH₃), 6.52 tau (—OCH₃).

EXAMPLE 6

Benzhydryl 7-amino-7-methoxycephalosporanate 500 mg. of platinum oxide is added to a solution of 500 mg. (1.07 mm.) of benzhydryl 7-azido-7-methoxycephalosporanate in 50 ml. of p-dioxane in a 250 ml. round bottom flask. The reaction vessel is placed under hydrogen at room temperature and atmospheric pressure with vigorous magnetic stirring. After 1 hour, 500 mg. of fresh platinum oxide is added and the reaction continued under the same conditions for an additional 3 hours. The dioxane is removed in vacuo at room temperature and the residue taken up in 5 ml. of chloroform. The catalyst is removed by passing the mixture through 15 g. of silica gel G packed in a sintered glass funnel. The product is eluted with 400 ml. of chloroform using a vacuum. The chloroform is evaporated in vacuo affording 300 mg. of benzhydryl 7-amino-7-methoxycephalosporanate as a yellow oil.

EXAMPLE 7

A.
7-Methoxy-7-(p-guanidinophenylacetamido)cephalosporanic acid benzhydryl ester hydrochloride To a solution of 250 mg. of 7-amino-7-methoxycephalosporanic acid benzhydryl ester, dissolved in 1.5 ml. of dry dimethylformamide, is added in 1 portion with cooling and stirring 0.15 g. of p-guanidinophenyl acetyl chloride and 0.15 ml. of pyridine. The reaction mixture is stirred at 5° C. for 5 minutes and at room temperature for 10 minutes. The solution is diluted with 15 ml. of methylene chloride and extracted 3 times with 15 ml. of water. The methylene chloride solution is dried and evaporated to dryness in vacuo and the residue is chromatographed through 20 g. of silica gel. Elution with chloroform, followed by an ethanol/chloroform mixture (1:1), affords 100 mg. of 7-methoxy-7-(p-guanidinophenylacetamido)cephalosporanic acid benzhydryl ester hydrochloride. Thin layer chromatography on silica gel using 1:1 ethanol/chloroform shows a single spot with a Rf of 0.6. IR: 6.5$\mu$ (lactam), 5.8$\mu$ (ester).

B.
7-Methoxy-7-(p-guanidinophenylacetamido)cephalosporanic acid

A solution of 88 mg. of the above ester and 0.7 ml. of anisole dissolved in 1.8 ml. of trifluoroacetic acid is kept at room temperature for 10 minutes. The solution is evaporated on the high vacuum pump for 5 minutes and the residue is triturated with ether until it solidifies. After decanting the ether, the solid is stirred with 50 ml. of water and filtered. The clear filtrate is lyophilized, affording 40 mg. of 7-methoxy-7-(p-guanidinophenylacetamido)cephalosporanic acid. Circular paper chromatography using butanol-acetic acid in water (3:1:1) shows 1 spot of Rf 0.25 which gives a positive Sakaguchi test and bioactivity against *B. subtilis*. IR: 5.7$\mu$ (ester, shoulder), 5.65$\mu$ (lactam).

EXAMPLE 8

Sodium 7-methoxy-7-(2-furylacetamido)cephalosporanate

Benzhydryl 7-methoxy-7-azidocephalosporanate, 1.00 g., is hydrogenated in 100 ml. dioxane for 1 hour with 1 g. PtO$_2$, then for 3 more hours with another gram of PtO$_2$. The solvent is removed in vacuo at a temperature below 30° C. The residue is taken up in chloroform and filtered through a bed of about 1 inch of silica gel (thin layer chromatography grade), washing copiously with chloroform; total volume about 500 ml. Removal of the chloroform in vacuo affords benzhydryl 7-methoxy-7-aminocephalosporanate.

Methylene chloride, 40 ml., is added, and then at 0° C., first 0.7 ml. of furylacetyl chloride and then 1 ml. of pyridine are added. After 25 minutes of stirring at 0° C. water is added and stirring continued for a few more minutes. The layers are separated and the organic portion washed successively with 1% aqueous H$_3$PO$_4$, water, and saturated aqueous sodium bicarbonate. After drying the methylene chloride solution with MgSO$_4$, filtering and evaporating the solvent, benzhydryl 7-methoxy-7-(2-furylacetamido)cephalosporanate is obtained. It is purified by chromatography on 60 g. neutral silica gel (Brinkmann's 70-325 mesh ASTM), and eluted with 4:1 chloroform-ethyl acetate. Its Rf on the column is 0.69-0.45, and on TLC in the same system is found to be 0.69-0.57, single spot. Its IR spectrum (CHCl$_3$ solution) has bands at 3.0$\mu$ (N-H), 5.61$\mu$ ($\beta$-lactam), 5.76$\mu$ (esters) and 5.9$\mu$ (amide). The NMR spectrum in CDCl$_3$ has bands at 8.05 tau (3H, singlet, —COCH$_3$), 6.65, 6.70 tau (2H, S—CH$_2$—), 6.55 tau (3H, singlet, —OCH$_3$), 6.32 tau (2H, singlet, furyl—CH$_2$—), 4.85 5.05, 5.15, 5.35 tau (2H, AB qt., J=14 Hz, —CH$_2$OAc), 4.97 tau (1H, singlet, C$_6$—H), 3.72 tau (2H, m, furyl $\beta$-H), 3.09 tau (1H, singlet, —CH$\phi_2$), 2.7 tau (6H, m, phenyl and furyl $\alpha$—H).

This compound, 0.57 g., is treated at 0° C. for 5 minutes with 0.8 ml. anisole and 4.0 ml. trifluoroacetic acid. The TFA and anisole are removed below 30° C. in vacuo, and 2 ml. more anisole is added and evaporated as before. The residue is taken up in a few ml. water containing 0.1 g. NaHCO$_3$ and lyophilized to a powder, which is washed copiously with ether and dried to afford 0.45 g. of sodium 7-methoxy-7-(2-furylacetamido)cephalosporanate. Its IR spectrum (CHCl$_3$ solution) has bands at ca. 3.1$\mu$ (broad, N—H), 5.67$\mu$ ($\beta$-lactam), 5.75$\mu$ (ester), 5.92$\mu$ (amide) and 6.18$\mu$ (COONa). Its NMR spectrum in D$_2$O has bands at 7.92 tau (3H, —COCH$_3$), 6.60, 6.66 tau (2H, S—CH$_2$—), 6.47 tau (3H, —OCH$_3$), 6.20 tau (2H, furyl-CH$_2$—), 5.38 tau (HDO), 5.13 tau (2H, —CH$_2$OAc), 4.88 tau (1H, C$_6$—H), 3.63 tau (2H, furyl $\beta$—H), 2.53 tau (1H, furyl $\alpha$-H). The UV spectrum in pH 7 buffer has $\lambda$max. 263 nm, E%=141. Its Rf on TLC (silica gel, acetone-AcOH 9:1) is 0.68.

EXAMPLE 9

A. Benzhydryl 7-methoxy-7-tetrazolylacetamidocephalosporanate

To a solution of 1.17 g. benzhydryl 7-amino-7-methoxycephalosporanate in 100 ml. methylene chloride cooled at 0°-5° C. in an ice bath is added 1.78 ml. of pyridine with stirring followed by a cooled solution of 1.17 g. tetrazolylacetyl chloride in 100 ml. methylene chloride. The mixture is allowed to react for 10 minutes at 0°-5° C. It is then shaken with 200 ml. of pH 2 phosphate buffer. The methylene chloride layer is dried and evaporated. The crude product, 1.2 g., is eluted through 48 g. of silica gel, using chloroform as an eluant. The desired product is eluted with 2% methanol/chloroform yielding 450 mg. of benzhydryl 7-methoxy-7-tetrazolylacetamidocephalosporanate. NMR: 8.0 tau (acetyl singlet), 6.53 tau (SCH$_2$), 4.84 tau (6H, singlet), 3.0 tau (singlet, CH of benzhydryl), 2.6 tau (singlet, aromatic), 1.1 tau (tetrazole H). TLC on silica gel in 5% methanol/chloroform Rf=0.28.

B.
Sodium-7-methoxy-7-tetrazolylacetamidocephalosporanate

A mixture of 680 mg. of benzhydryl 7-methoxy-7-tetrazolylacetamidocephalosporanate, 4.4 ml. anisole and 12.2 ml. trifluoroacetic acid is stirred at room temperature for 8 minutes. The excess acid is evaporated under reduced pressure and the residue is flushed twice with carbon tetrachloride and then thrice with hexane. The solid residue is dissolved in ethylacetate, adjusted to pH 5.8 with sodium bicarbonate solution, extracted with water and freeze dried to yield 420 mg. of sodium 7-methoxy-7-tetrazolylacetamidocephalosporanate. UV $\lambda_{max.}^{H2O}$ 265 E% 104.

EXAMPLE 10

Sodium 7-methoxy-7-[1(1H)-tetrazolylacetamido]-3-(5-methyl-1,3,4-thiadiazolethiomethyl)cepham-4-carboxylate A mixture of 420 mg. sodium 7-methoxy-7-tetrazolylacetamidocephalosporanate, 168 mg. 2-methyl-5-mercapto-1,3,4-thiadiazole and 16.8 ml. phosphate buffer (pH 6.4) is heated on the steam bath for ½ hour. The reaction mixture is adjusted to pH 4.85 and extracted with 25 ml. ethylacetate. The aqueous layer is adjusted to pH 1.8 with 2.5 N hydrochloric acid solution and extracted with ethylacetate. Ethylacetate is removed under reduced pressure and the residue is flushed thrice with ethanol to remove traces of ethylacetate. Then it is taken into ethanol and water, adjusted to pH 6.5 with sodium bicarbonate solution, treated with charcoal and filtered. Ethanol is evaporated and the aqueous layer is freeze dried to yield 210 mg. of sodium 7-methoxy-7-[1(1H)-tetrazolylacetamido]-3-(5-methyl-1,3,4-thiadiazolethiomethyl)cephem-4-carboxylate. UV $\lambda_{max.}^{H2O}$ 273 E% 155. NMR: 7.28 tau (singlet, methyl of thiadiazole), 6.42 tau (singlet of methoxy group), 0.74 tau (singlet, tetrazole H).

EXAMPLE 11

A. Benzhydryl 7-aminodesacetoxycephalosporanate

To a mixture of 11.0 g. (0.0514 mole) of 7-aminodesacetoxycephalosporanic acid in 1.5 liter of water in a 5 liter 3-necked flask fitted with mechanical stirrer and dropping funnel is added 3.5 g. of boron trifluoride in 80 ml. of dioxane. The mixture is stirred for 1 hour (pH 2.2), 1.5 liter acetone is added, and the mixture is stirred for 10 minutes (pH 2.4).

Diphenyldiazomethane (31.4 g., 0.162 mole) in 85 ml. acetone is added dropwise with good stirring during 4 hours, during which time the slurry becomes thinner. The mixture is filtered and the solid is air dried and washed well with chloroform to afford 3.8 g. recovered starting material.

This 3.8 g. of starting material is recycled using 750 ml. water, 1.2 g. of BF$_3$ in 30 ml. dioxane, 750 ml. of acetone and 11 g. Ph$_2$CN$_2$ in 30 ml. acetone as described above.

Filtrates from both reactions are evaporated under reduced pressure to remove acetone. The aqueous residues are extracted with chloroform (3×250 ml. and 3×150 ml.). Drying of the chloroform extracts with magnesium sulfate and evaporating affords about 45 g. of crude product, which is chromatographed on 125 g. silica gel using chloroform and chloroform-methanol (1–3%) mixtures as eluant. Fractions 3–8 are triturated individually with ether. Crystals are obtained from fractions 4–7: crop 1, m.p. 133°–143° C., 5.58 g.; crop 2, m.p. 95°–125° C., 0.52 g.

Filtrates and adjacent fractions from above chromatography are combined and rechromatographed as before. Fractions 4–12 are triturated with ether. Fraction 9 is crystallized well to give crop 3, m.p. 133°–142° C., 1.47 g.

Combined yield of benzhydryl 7-aminodesacetoxycephalosporanate is 7.57 g. Starting material is recovered from the aqueous phase by concentrating in vacuo to remove water and adjusting pH to 3.7. Starting material is precipitated on stirring. After filtering, washing the precipitate with water and acetone, and drying, 3.19 g. of recovered starting material is obtained.

Benzhydryl 7-amino-3-desacetoxycephalosporanate, m.p. 146°–150° C. is characterized by IR, NMR and elemental analysis. Calculated for $C_{21}H_{20}N_2O_3S$: C, 66.30; H, 5.30; N, 7.36. Found: C, 66.24; H, 5.55; N, 7.07.

The 7-aminodesacetoxycephalosporanic acid used as the starting material is prepared by the hydrogenolysis of 7-aminocephalosporanic acid using palladium-on-barium sulfate catalyst in accordance with procedures known in this art.

D. Benzhydryl 7-azido-7-bromo-3-desacetoxycephalosporanate

A mixture of 7.57 g. benzhydryl 7-aminodesacetoxycephalosporanate, 2.74 g. sodium nitrite, 14.7 ml. 2 N sulfuric acid, 400 ml. water and 400 ml. methylene chloride is stirred for 1 hour in a stoppered, ice cold flask. The layers are separated while cold. The aqueous layer is washed with methylene chloride and the combined $CH_2Cl_2$ layers are dried with magnesium sulfate and evaporated under reduced pressure at $\leq 30°$ C. to about 125 ml. of solution of the benzhydryl 7-diazocephalosporanate.

During the time the above reaction mixture is stirring, triethylammonium azide and bromine azide are prepared. A mixture of 11.7 g. sodium azide, 9.7 ml. concentrated sulfuric acid diluted to 40 ml. with water, and 190 ml. of methylene chloride are stirred for 30 minutes in a closed system in an ice bath. The layers are separated while cold, and the aqueous residue is washed with 10 ml. of cold methylene chloride. The $CH_2Cl_2$ layers are combined, dried with MgSO$_4$ while kept in an ice bath, and divided into two equal parts. To one is added 4.9 ml. triethylamine; to the other 4.93 g. N-bromosuccinimide. Both solutions are stored in an ice bath until use.

The 7-diazo compound in about 125 ml. of methylene chloride in a 500 ml. round bottomed flask protected with calcium chloride tube and stirred magnetically is cooled in a solid $CO_2$/acetone bath to $-40°$ C. (internal temperature). The bath temperature is kept at $-40°$ C. to $-50°$ C. during reaction. The triethylammonium azide solution is added all at once. The bromine azide solution is added during 5 minutes at $-30°$ C. to $-25°$ C. The flask is removed from the bath and allowed to come to 0° C. during 20 minutes.

10 g. of disodium hydrogen phosphate in 300 ml. water is mixed with the reaction mixture and the layers separated. The methylene chloride layer is dried with magnesium sulfate and evaporated to give 10.3 g. crude product, which is chromatographed on 125 g. of silica gel using benzene as eluant. Fractions are collected when the yellow color approaches the bottom of the column: fraction 1, 3.8 g.; fraction 2, 1.3 g.; total yield=5.1 g. Both fractions crystallize immediately.

An analytical sample of benzhydryl 7-azido-7-bromo-3-desacetoxycephalosporanate, m.p. 122° C. is characterized by IR, NMR and elemental analysis. Calculated for $C_{19}H_{17}N_4O_3S$: C, 51.97; H, 3.53; N, 11.54. Found: C, 52.23; H, 3.59; N, 11.63.

C. Benzhydryl 7-azido-7-methoxy-3-desacetoxycephalosporanate

A solution of 5.1 g. (10.5 mmoles) of benzhydryl 7-azido-7-bromo-3-desacetoxycephalosporanate in 50 ml. methylene chloride and 200 ml. methanol is prepared. Pyridine (0.844 ml., 10.5 mmole) and 2.084 g. silver fluoroborate (10.7 mmole) in 10 ml. methanol are added and the reaction mixture is stirred at 22° C. for 16 ½ hours. The mixture is filtered and the filtrate is evaporated under reduced pressure. The residue is chromatographed on 125 g. of silica gel using benzene as eluant. Fraction 1 is collected when yellow color nears bottom of the column. Fractions 2–9 are combined and triturated with methanol. The methoxy azide crystallizes, m.p. 115°–117° C., 3.156 g. and is characterized by IR, NMR and elemental analysis. Calculated for $C_{22}H_{20}N_4O_4S$: C, 60.54; H, 4.62; N, 12.84. Found: C, 60.42; H, 4.36; N, 12.93.

D. Benzhydryl 7-(D-α-azidophenylacetamido)-7-methoxy-3-desacetoxycephalosporanate A mixture of 1.51 g. of benzhydryl 7-azido-7-methoxy-3-desacetoxycephalosporanate, 150 ml. dioxane and 1.5 g. platinum oxide is stirred under hydrogen for 1 hour. Another 1.5 g. catalyst is added and the mixture is hydrogenated for another hour. The reaction mixture is evaporated under diminished pressure (≦35° C.). The residue is taken up in chloroform and passed through silica gel-diatomaceous earth (1:1) in a 120 ml. sintered funnel. About 500 ml. of eluant is collected. The filtrate is evaporated and the process is repeated in a 60 ml. sintered funnel.

The filtrate (about 500 ml.) is evaporated under reduced pressure and the residue is dried with nitrogen to give about 2 g. of benzhydryl 7-amino-7-methoxydesacetoxycephalosporanate.

The benzhydryl 7-amino-7-methoxydesacetoxycephalosporanate is taken up in 50 ml. of methylene chloride and stirred magnetically in an ice bath. To the solution is added 1.65 g. D-α-azidophenylacetyl chloride. After 3 minutes 1.4 ml. of pyridine is added.

The solution is stirred in an ice bath for 25 minutes, poured into 50 ml. ice water and the layers separated. The methylene chloride layer is washed with 40 ml. of dilute aqueous sodium bicarbonate and 50 ml. of water and dried overnight in a refrigerator with magnesium sulfate. The mixture is filtered, evaporated and dried to give 2.0 g. of product. The product is chromatographed on 100 g. of silica gel using benzene and benzene/chloroform mixtures as eluant. Fractions 16–20 (benzene/chloroform 1:3) contain the product, benzhydryl 7-(D-α-azidophenylacetamido)-7-methoxy-3-desacetoxycephalosporanate (834 mg.), which is characterized by IR and NMR.

E. 7-(D-α-azidophenylacetamido)-7-methoxy-3-desacetoxycephalosporanic acid

A solution of 708.4 mg. of benzhydryl 7-(D-α-azidophenylacetamido)-7-methoxy-3-desacetoxycephalosporanate in 2 ml. anisole is cooled in an ice bath and 8 ml. of trifluoroacetic acid added. The reaction solution is kept at 0° C. for 10 minutes with occasional swirling. The solution is evaporated under reduced pressure and flushed and evaporated twice with anisole. The residue is taken up in 30 ml. methylene chloride and extracted with 3×5 ml. saturated aqueous sodium bicarbonate solution. The combined aqueous phase is washed with 2×5 ml. of methylene chloride and the pH adjusted to 1.8 with 2.5 N HCl and then extracted with 4×10 ml. ethylacetate. The extracts are dried with magnesium sulfate and evaporated under reduced pressure at ≦45° C., then put directly onto a pump. The product obtained, (487.4 mg.), is characterized by IR and NMR.

EXAMPLE 12

7-(D-α-aminophenylacetamido)-7-methoxy-3-desacetoxycephalosporanic acid

To an ice-cooled solution of 487.4 mg. of 7-(D-α-azidophenylacetamido)-7-methoxy-3-desacetoxycephalosporanic acid in 6 ml. acetic acid and 9 ml. water is added 3.1 g. of powdered zinc. The mixture is stirred in an ice bath for 10 minutes and then filtered. The solid is washed with 40 ml. of water. The combined aqueous filtrates are saturated with hydrogen sulfide. After filtration the filtrate is lyophilized to afford 0.5 g. crude product. This crude product is dissolved in water and relyophilized twice to give 400 mg. of product, which is characterized by IR, NMR, electrophoresis mobility, reaction with ninhydrin and UV (λmax. 262.5 mμ, ε=5770).

EXAMPLE 13

A. Benzhydryl 7-(D-α-azido-2-phenylacetamido)-7-methoxycephalosporanate

To a solution of 1 g. of benzhydryl 7-amino-7-methoxycephalosporanate in 25 ml. of methylene chloride at 0° C. is added 1.1 g. of D-α-azidophenylacetyl chloride in 15 ml. of methylene chloride followed by 1 ml. of pyridine. After 15 minutes stirring at 0° C., the mixture is extracted with 2×5 ml. of cold water, 3×5 ml. of 1% aqueous phosphoric acid, 3×5 ml. of saturated aqueous sodium bicarbonate solution and 2×5 ml. of water. The methylene chloride solution is dried over magnesium sulfate, filtered, and concentrated under reduced pressure to afford 1.1 g. of benzhydryl 7-(D-α-azido-2-phenylacetamido)-7-methoxycephalosporanate in the form of an oil. This product is chromatographed on 60 g. of neutral silica gel and the product eluted with chloroform. Evaporation of the solvent affords 600 mg. of product whose Rf on the column is 0.069–0.047, and on TLC (silica gel, CHCl₃) is 0.25, single spot. Its IR spectrum (CHCl₃ solution) has bands at 3.0μ (N—H), 4.74μ (azide), 5.62μ (β-lactam), 5.76μ (ester) and 5.88μ (amide). The NMR spectrum in CDCl₃ has bands at 8.05 tau (3H, singlet, —COCH₃), 6.65 tau (doublet, 2H, S—CH₂—), 6.55 tau (3H, singlet, —OCH₃), 4.85, 5.05, 5.15, 5.35 tau (2H, AB qt., J-14 Hz, —CH₂OAc), 4.97 tau (1H, singlet, C$_\phi$—H), 4.89 tau (1H, singlet, $\phi$(N₃)C—H), 3.09 tau (1H, singlet, —CH$\phi_2$), 2.65, 2.75 tau (15H, phenyls).

D. 7-(D-α-azido-2-phenylacetamido)-7-methoxycephalosporanic acid

The product obtained in A above (600 mg.) is treated for 5 minutes at 0° C. with 1 ml. of anisole and 5 ml. of trifluoroacetic acid. The resulting reaction mixture is evaporated at 30° C. at 0.1 mm. pressure and then twice treated with anisole and evaporated again. The residue so obtained is dissolved in 25 ml. of methylene chloride and extracted with 4×3 ml. of saturated aqueous sodium bicarbonate. The aqueous solution is washed once with 5 ml. of methylene chloride, adjusted to pH 1.8 with 5% phosphoric acid and extracted with 3×10 ml. of ethylacetate. The ethylacetate solution is dried with magnesium sulfate and evaporated to yield 370 mg. of 7-(D-α-azido-2-phenylacetamido)-7-methoxycephalosporanic acid. IR spectrum (CHCl₃): 3–4μ (COOH), 4.74μ (azide), 5.62μ (β-lactam), 5.75μ (ester), 5.85μ (amide), ca. 8μ (acid C=O). NMR spectrum (CDCl₃): 7.92 tau (3H, singlet, —COCH₃), 6.65 tau (2H, doublet, S—CH₂—), 6.51 tau (3H, singlet, —OCH₃), 4.96 tau (2H, doublet, —CH₂OAc), 4.92 tau (1H, singlet, C₆—H), 4.83 tau (1H, singlet, $\phi$(N₃)C—H), 2.55 tau (5H, phenyl).

C. 7-(D-α-amino-2-phenylacetamido)-7-methoxycephalosporanic acid

To a solution of 620 mg. of 7-(D-α-azido-2-phenylacetamido)-7-methoxycephalosporanic acid in 6.2 ml. of acetic acid and 9 ml. of water is added 3.1 g. of powdered zinc and the solution stirred for 6 minutes at 0° C. The zinc is filtered off and washed with 60 ml. of cold water. The combined filtrates are saturated at 0° C. with hydrogen sulfide and through diatomaceous earth. The filtrate is washed with 3×50 ml. of ethylacetate and the aqueous solution is warmed under reduced pressure to remove dissolved ethylacetate and finally lyophilized to afford 480 mg. of 7-(D-α-amino-2-phenylacetamido)-7-methoxycephalosporanic acid as a white powder. This product contains 1 equivalent of acetic acid and 2 equivalents of water and 2% ammonia as the acetate or antibiotic salt. Spinco analysis shows 1.58 micromoles/mg. phenylglycine (84% of theory). TGA finds 17.8% weight loss to 110° C. (99% of theory). Titration: inflections at pH 5.7 and 8.7, pH ½=7.0, EW 476 (theory for acetate dihydrate=515). Electrophoresis at pH 7 shows a single spot as a monoanion. Calculated for C₁₉H₂₁N₃O₇.2H₂O.AcOH+2% NH₃: C, 46.2; H, 5.7; N, 8.8; S, 5.6. Found: C, 47.41; H, 4.99; N, 9.48; S, 6.36. Distillation from alkali and titration of the distillate finds 2% NH₃. UV (pH 7 buffer): $\lambda_{max.}$=263, E%= 116 (ε=6170). The NMR spectrum (100 MHz, D₂O) has bands at 7.65 tau (AcOH, ca. 1 equivalent), 7.61 tau (singlet, —COCH₃), 6.17 tau (singlet, —OCH₃), 6.02, 6.19, 6.45, 6.62 tau (AB qt., J=Hz, S—CH₂—), 2.13 tau (singlet, phenyl); HOD at 5 tau obscures the other protons. IR spectrum (Nujol): 2.8–4.5μ (NH₃⁺), 5.65μ (β-lactam), 5.85μ (ester), 6.2–6.3μ (COO⁻).

EXAMPLE 14

A. Benzhydryl 7-(2-carboxy-2-phenylacetamido)-7-methoxycephalosporanate

To a solution of 0.5 g. of benzhydryl 7-amino-7-methoxycephalosporanate in 15 ml. of methylene chloride is added the monobenzhydryl phenylmalonyl chloride (prepared as described below) followed by 0.5 ml. of pyridine. The resulting reaction mixture is stirred for 30 minutes and then 12 ml. of water is added. The aqueous mixture is stirred for 5 minutes and the layers separated. The methylene chloride portion is washed with 2.5 N HCl, water, twice with aqueous sodium bicarbonate and saturated sodium chloride. The solvent layer is then dried over magnesium sulfate, filtered and evaporated below 25° C. under reduced pressure to afford 0.695 g. of benzhydryl 7-(2-carboxy-2-phenylacetamido)-7-methoxycephalosporanate. This is chromatographed on 50 g. of neutral silica gel and eluted with chloroform to afford 400 mg. of product as a tan glass. IR: 3.03μ (NH), 5.62μ (β-lactam), 5.78μ (ester), 5.88μ (amide). NMR (CCl₄): 8.18 tau (3H, singlet, acetyl), 7.0 tau (2H, S—CH₂—), 6.80, 6.73 tau (3H, doublet, diastereomeric OCH₃'s), 5.2 tau (4H, multiplet, —CH₂O—, C₆ proton, malonyl CH), 3.17 tau (2H, CH$\phi_2$), 2.8 tau (20H, aromatic), 2.0 tau (1H, amide NH).

The monobenzhydryl phenylmalonyl chloride used above is prepared as follows: To a solution of 19.25 g. of phenylmalonic acid in 165 ml. of ethylacetate is added a solution of 25 g. of diphenyldiazomethane in 100 ml. of ethylacetate over 15 minutes at 15°–20° C. The solution is stirred 10 minutes more and 500 ml. of water is added, and sufficient 50% sodium hydroxide is added at 15° C. to make the reaction mixture alkaline. The solvent layer of the mixture is separated, extracted twice with aqueous sodium bicarbonate solution. The combined aqueous solutions are washed twice with ethylacetate, cooled, acidified with hydrochloric acid and extracted 3 times with ethylacetate. The ethylacetate extractions are washed twice with water, once with saturated sodium chloride solution and then dried over magnesium sulfate. The solvent is then evaporated at a temperature below 25° C. under reduced pressure to an oil which is crystallized from 200 ml. of 1:3 ether in petroleum ether to afford 20.9 g. of monobenzhydryl phenylmalonate, m.p. 119.5°–122° C. To a slurry of 0.7 g. of this monoester in 2.5 ml. of water is added 2.10 ml. of 0.962 N sodium hydroxide. The solution is stirred for 3 minutes, filtered and freeze dried to obtain the sodium salt of the monoester. To this sodium salt is added 5 ml. of benzene and the slurry is treated at 0° C. with 1.5 ml. of oxalyl chloride. After 10 minutes at 0° C. and 5 minutes at 25°

C. the mixture is evaporated at a temperature below 25° C. under reduced pressure and the residue is twice concentrated from carbon tetrachloride. Under a dry atmosphere, the product in 5 ml. of carbon tetrachloride is filtered and concentrated to afford the monobenzhydryl phenylmalonyl chloride.

B. Disodium 7-(2-carboxy-2-phenylacetamido)-7-methoxycephalosporanate

Benzhydryl 7-(2-carboxy-2-phenylacetamido)-7-methoxycephalosporanate (400 mg.) is treated at 0° C. for 2 minutes with 1.2 ml. of anisole and 6 ml. of trifluoroacetic acid. The resulting reaction product is then frozen, stripped at low temperature and high vacuum, diluted with anisole and stripped once again at 25° C. The residue comprising the free acid is taken up in 20 ml. of 1 molar sodium bicarbonate solution, washed 4 times with small amounts of methylene chloride, acidified with HCl, saturated with NaCl and extracted with 4×10 ml. of ethylacetate. The solvent extractions are washed twice with saturated sodium chloride, dried with magnesium sulfate, filtered and evaporated under reduced pressure to afford 218 mg. of 7-(2-carboxy-2-phenylacetamido)-7-methoxycephalosporanic acid as a yellow syrup. This is dissolved in 5 ml. of water containing 79 mg. of sodium bicarbonate and freeze dried. The freeze dried residue is dissolved in 5 ml. of water, filtered, and lyophilized again to afford 182 mg. of disodium 7-(2-carboxy-2-phenylacetamido)-7-methoxycephalosporanate. The product so obtained is combined with 550 mg. of the same product obtained from a second run and dissolved in 10 ml. of water. The resulting solution is filtered and lyophilized to give 647 mg. of product. UV (pH 7): λmax. 265 nm., ε=6300. NMR (D$_2$O): 7.90 tau (3H, singlet, acetyl), 6.70, 6.54 tau (2H, 2 AB quartets, diastereomeric S—CH$_2$—), 6.50, 6.38 tau (3H,2 singlets, diastereomeric OCH$_3$'s), 5.22 tau (2H, broad s, —CH$_2$O—), 4.85 tau (1H, singlet, C$_6$ proton), 2.55 tau (5H, singlet, aromatic). The large HOD peaks covers the malonyl proton adsorption. On electrophoresis at pH 7, the product moves as a dianion, single spot. The pH of a 10% aqueous solution is 8.8. Calculated for $C_{20}H_{18}N_2SO_4Na_2 + Na_2CO_3 + 0.4$ NaHCO$_3$+H$_2$O: C, 38.59; H, 3.09; N, 4.21; S, 4.81; ash (as Na) 15.19. Found: C, 38.99; H, 3.10; N, 4.17; S, 4.91; ash (as Na) 15.3.

EXAMPLE 15

A. Benzhydryl 7-azido-7-benzyloxycephalosporanate

A mixture of 2.4 g. of benzhydryl 7-azido-7-bromocephalosporanate prepared as described in Example 2C and 1.5 g. of silver tetrafluoroborate in 10 ml. of benzyl alcohol is stirred at room temperature for 3 hours. The mixture is diluted with 300 ml. of ether and the silver salts removed by filtration. The filtrate is washed with aqueous sodium bicarbonate, dried over sodium sulfate and evaporated under reduced pressure. The excess benzyl alcohol is removed on a high vacuum pump with magnetic stirring for 18 hours and the residue chromatographed on silica gel. Elution with hexane followed by increasing concentrations of methylene chloride in hexane and evaporation of the fractions containing the product affords benzhydryl 7-azido-7-benzyloxycephalosporanate.

B. Benzhydryl 7-benzyloxy-7-phenylacetamidocephalosporanate

A solution of 1.2 g. of the benzhydryl 7-azido-7-benzyloxycephalosporanate in 25 ml. of dry ethylacetate is hydrogenated in the presence of 1.2 g. of 10% palladium-on-charcoal catalyst for 18 hours at room temperature. The catalyst is removed by filtration and phenylacetic anhydride (1.0 g.) is added to the filtered solution and the mixture kept for 45 minutes at room temperature. The resulting reaction mixture is diluted with 200 ml. of ether, 200 ml. of pH 7 phosphate buffer is added, and the mixture stirred vigorously for ½ hour. The ether layer is separated, washed with water, dried and evaporated under reduced pressure. The residue is chromatographed on 50 g. of silica gel and eluted with 5% ethylacetate in methylene chloride which, on evaporation, affords benzhydryl 7-benzyloxy-7-phenylacetamidocephalosporanate.

C. Sodium 7-benzyloxy-7-phenylacetamidocephalosporanate

A solution of 0.5 g. of benzhydryl 7-benzyloxy-7-phenylacetamidocephalosporanate in 3.5 ml. of anisole is treated with 10 ml. of trifluoroacetic acid at room temperature for 10 minutes. The trifluoroacetic acid and anisole are removed under reduced pressure at a temperature below 40° C. and the residue is taken up in 25 ml. of chloroform and treated with 20 ml. of water containing 0.15 g. of sodium bicarbonate. The mixture is stirred for ½ hour at room temperature and the organic phase is separated and washed with water. The combined aqueous phase is washed twice with methylene chloride and the water layer and washes combined and lyophilized affording sodium 7-benzyloxy-7-phenylacetamidocephalosporanate.

EXAMPLE 16

A. Benzhydryl 7-azido-7-methylmercaptocephalosporanate

To a solution of 2 g. of benzhydryl 7-diazocephalosporanate prepared as described in Example 2B in 100 ml. of methylene chloride at −75° C. under an atmosphere of nitrogen is added a solution of 1 ml. of methylsulfenyl chloride in 10 ml. of methylene chloride with vigorous stirring. Nitrogen is immediately evolved. After the addition of the reagent over a period of about 10 minutes, the mixture is brought to −5° C. gradually in about ½ hour. Saturated sodium bicarbonate is added an the organic layer is separated and washed with water. After drying over sodium sulfate the solvent is removed at room temperature under reduced pressure affording benzhydryl 7-chloro-7-methylmercaptocephalosporanate. This product is stirred with a 20 ml. solution of trimethylammoniumazide in methylene chloride at 0°-5° C. under nitrogen for 1½ hours. The solution is then washed with cold saturated sodium bicarbonate solution, water, and dried over sodium sulfate. Evaporation of the solvent affords the crude benzhydryl 7-azido-7-methylmercaptocephalosporanate.

B. Benzhydryl 7-methylmercapto-7-phenylacetamidocephalosporanate

A solution of 1.2 g. of the benzhydryl 7-azido-7-methylmercaptocephalosporanate in 25 ml. of dry ethylacetate containing 0.8 ml. of diisopropylethylamine is hydrogenated in the presence of 1.2 g. of 10% palladium-on-charcoal catalyst for 18 hours at room temperature. Phenylacetic anhydride (0.1 g.) is added and the mixture kept for 45 minutes at room temperature. The mixture is diluted with 200 ml. of ether, 200 ml. of pH 7 phosphate buffer is added, and the mixture stirred vigorously for ½ hour. The ether layer is separated, washed with water, dried and evaporated to afford benzhydryl 7-methylmercapto-7-phenylacetamidocephalosporanate

C. Sodium 7-methylmercapto-7-phenylacetamidocephalosporanate

A solution of 0.4 g. of benzhydryl 7-methylmercapto-7-phenylacetamidocephalosporanate in 3.5 ml. of anisole is treated with 10 ml. of trifluoroacetic acid at room temperature for 10 minutes. The trifluoroacetic acid and anisole are removed under reduced pressure, maintaining the temperature below 40° C., and the residue is taken up in 25 ml. of chloroform and treated with 20 ml. of water containing 0.12 g. of sodium bicarbonate. The mixture is stirred for ½ hour at room temperature and the organic phase is separated and washed with water. The combined aqueous phase is washed twice with methylene chloride and then lyophilized to give sodium 7-methylmercapto-7-phenylacetamidocephalosporanate.

EXAMPLE 17

A. Benzhydryl 7-azido-7-ethoxycephalosporanate

To a solution of 217 mg. benzhydryl 7-azido-7-bromocephalosporanate in 15 ml. of absolute ethanol is added 31.6 μl. of pyridine and 78 mg. of silver fluoroborate and the mixture stirred at room temperature for 2 hours, protected from light and moisture. The mixture is evaporated to dryness in vacuo and the residue chromatographed on 20 g. of silica gel. Elution with chloroform affords 121 mg. of benzhydryl 7-azido-7-ethoxycephalosporanate, m.p. 144.5°–145° C.

B. Benzhydryl 7-ethoxy-7-thienylacetamidocephalosporanate

A solution of 320 mg. of benzhydryl 7-azido-7-ethoxycephalosporanate in 30 ml. of dioxane is stirred with 320 mg. of platinum oxide at room temperature under an atmosphere of hydrogen for 1 hour. An additional 320 mg. of catalyst is introduced and the hydrogenation continued for 5 hours. The mixture is evaporated under vacuum to dryness and the residue taken up in chloroform and filtered through 2 inches of silica gel and evaporated, leaving benzhydryl 7-amino-7-ethoxycephalosporanate as a yellow oil. This is dissolved in methylene chloride and to the cooled solution is added with stirring 0.2 ml. of thienylacetyl chloride and 0.2 ml. of dry pyridine. The mixture is stirred for 15 minutes at 0° C. and then poured over ice and the methylene chloride layer separated, washed with aqueous sodium bicarbonate solution, dried and evaporated. The residue is chromatographed on 20 g. of silica gel. Elution with chloroform affords 120 mg. of benzhydryl 7-ethoxy-7-thienylacetamidocephalosporanate. TLC 2% MeOH in CH$_2$Cl$_2$ Rf 0.73. IR: 5.65μ (lactam); 5.85, 5.95; 6.0 (amide). NMR: 8.82 tau (CH$_2$CH$_3$),

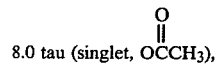
8.0 tau (singlet, OCCH$_3$), 6.64–6.67 tau (doublet, SCH$_2$), 6.14 tau (singlet, thienyl CH$_2$), 4.96 tau (singlet, 6H).

C. Sodium 7-ethoxy-7-thienylacetamidocephalosporanate

A solution of 0.9 g. of benzhydryl 7-ethoxy-7-thienylacetamidocephalosporanate in 6.35 ml. anisole and 17.1 ml. of trifluoroacetic acid is kept at room temperature for 5 minutes and then evaporated under high vacuum. The residue is stirred with water and methylene chloride and the pH adjusted to 5.8 by the addition of sodium bicarbonate solution. The aqueous layer is evaporated and acidified to pH 2 and the gummy precipitate filtered off. This is dissolved in butylacetate, filtered and the filtrate stirred with water with the addition of sodium bicarbonate solution to pH 6.5. The aqueous extract is evaporated and freezedried, leaving 0.2 g. of sodium 7-ethoxy-7-thienylacetamidocephalosporanate. Circular paper chromatography in butanole-thanol-water (4:1:5) gives a spot of Rf 0.55. Analysis calculated: C, 46.74; H, 4.14; N, 6.00. Found: C, 47.73; H, 4.09; N, 5.73.

EXAMPLE 18

A. Benzhydryl 7-(dl-α-fluorophenylacetamido)-7-methoxycephalosporanate

To a solution of 0.9 g. of benzhydryl 7-amino-7-methoxycephalosporanate in 45 ml. of methylene chloride at 0° C. is added with stirring 0.96 ml. of dl-α-fluorophenylacetyl chloride. After 1 minute 0.96 ml. of pyridine is added and the mixture stirred for 15 minutes. The reaction mixture is then poured over ice, shaken and the methylene chloride layer is removed. The aqueous layer is extracted twice with methylene chloride. The combined aqueous layers are washed with aqueous sodium bicarbonate, then with water and dried over sodium. The solvent is evaporated to afford 1.2 g. of benzhydryl 7-(dl-α-fluorophenylacetamido)-7-methoxycephalosporanate. The product in methylene chloride solution is chromatographed over 90 g. of silica gel. The silica gel column is developed successively with 1,000 ml. of methylenechloride, 500 ml. of methylene chloride containing 5% chloroform, and then 300 ml. each of ethylene chloride containing 10%, 25% and 50% chloroform, respectively. The pooled fractions of the 50% chloroform eluates are evaporated under reduced pressure to afford 370 mg. of product. Analysis calculated: C, 63.56; H, 4.83; N, 4.63. Found: C, 62.71; H, 5.02; N, 4.38. TLC in 5% ethylacetate in methylene chloride shows two spots at Rf 0.406 and 0.54.

B. Sodium 7-(dl-α-fluorophenylacetamido)-7-methoxycephalosporanate

To a solution of 360 mg. of benzhydryl 7-(dl-α-fluorophenylacetamido)-7-methoxycephalosporanate in 2.44 ml. of anisole is added 6.9 ml. of trifluoroacetic acid and the reaction allowed to proceed for 15 minutes. The mixture is evaporated under reduced pressure and the residue taken up in a mixture of water and methylene chloride. The pH of the mixture is adjusted to 6.8 and the aqueous layer freeze-dried to afford sodium 7-(dl-α-fluorophenylacetamido)-7-methoxycephalosporanate, Rf in butanol-ethanol-water (4:1:5) 0.41 and 0.60.

EXAMPLE 19

A. 3-Methyl-7β-trichloroethoxycarboxamidodecephalosporanic acid

To a solution of 21.4 g. of 3-methyl-7-aminodecephalosporanic acid in 250 ml. of water adjusted to pH 8.7 with 15% sodium hydroxide solution is added 21.2 g. of trichloroethoxycarbonyl chloride over a half hour period while keeping the temperature at 20° C. and maintaining the pH at 8.7 by means of a pH stat. The reaction mixture is allowed to stir for another half hour at this temperature and then adjusted to pH 2 and extracted into ethylacetate using three extractions. The ethylacetate layer is washed twice with water, dried over anhydrous sodium sulfate, and evaporated under reduced pressure to give 3-methyl-7β-trichloroethoxycarboxamidodecephalosporanic acid.

The 3-methyl-7-aminodecephalosporanic acid used as the starting material in this example is produced by the catalytic reduction of cephalosporin C followed by hydrolytic removal of the 5-amino adipoyl side chain as described in U.S. Pat. No. 3,129,224.

B. p-Methoxybenzyl 3-methyl-7β-trichloroethoxycarboxamidodecephalosporanate

3-Methyl-7β-trichloroethoxycarboxamidodecephalosporanic acid (22.38 g.) and triethylamine (14 ml.) are stirred in 200 ml. of acetone for 45 minutes and p-methoxybenzyl bromide (10.1 g.) is added to this mixture and stirring continued for an additional 20 minutes at room temperature. The entire reaction mixture is then chilled in an ice bath and the precipitated triethylamine hydrobromide is removed by filtration. The filtrate is evaporated under reduced pressure and the residue is extracted by shaking with a mixture of ether and aqueous sodium hydrogen phosphate. The ethereal layer is dried over anhydrous sodium sulfate and concentrated under reduced pressure to give p-methoxybenzyl 3-methyl-7β-trichloroethoxycarboxamidodecephalosporanate.

C. p-Methoxybenzyl 3-methyl-7-aminodecephalosporanate

The trichloroethoxycarbonyl protecting group is removed by adding an ethylacetate solution (50 ml.) containing p-methoxybenzyl 3-methyl-7β-trichloroethoxycarboxamidodecephalosporanate (10 g.) to a vigorously stirred slurry of 5 g. of zinc dust in 50 ml. of 90% acetic acid in an ice water bath over 5–10 minutes. The temperature is kept at 25°–30° C. After 2 hours the solids are removed by filtration and washed with 100 ml. of ethylacetate. The combined filtrate is diluted with 200 ml. water, the layers separated and the organic layer washed with 100 ml. water. The organic layers are washed with cold sodium bicarbonate solution, dried and concentrated under reduced pressure. The residue is chromatographed on silica gel (40 g.) using $CHCl_3$:MeOH mixtures as eluants to give p-methoxybenzyl 3-methyl-7-aminodecephalosporanate.

D. p-Methoxybenzyl 3-methyl-7-diazodecephalosporanate

To a stirring mixture of 1.6 g. of sodium nitrite, 30 ml. of water and 40 ml. of methylene chloride at 0° C. is added 0.8 g. of p-methoxybenzyl 3-methyl-7-aminodecephalosporanate followed by the addition of a solution of 0.75 g. of p-toluenesulfonic acid in 5 ml. of water over a few minutes. The mixture is stirred at 0° C. for 20 minutes and the organic phase is separated, washed with ice water, dried over anhydrous sodium sulfate, filtered and concentrated under reduced pressure at room temperature to afford p-methoxybenzyl 3-methyl-7-diazodecephalosporanate.

E. Sodium 3-methyl-7-methoxy-7-(2-thienylacetamido)decephalosporanate

Following the procedures described in Examples 2C, 2D, 3A, 3B and 3C, p-methoxybenzyl 3-methyl-7-diazodecephalosporanate is converted to sodium 3-methyl-7-methoxy-7-(2-thienylacetamido)decephalosporanate.

EXAMPLE 20

A. o-Nitrobenzyl 3-methyl-7β-trichloroethoxycarboxamidodecephalosporanate

When p-methoxybenzyl bromide in Example 19B is replaced by an equivalent amount of o-nitrobenzyl bromide and the resulting reaction product is recovered using the described processes, the corresponding o-nitrobenzyl ester is obtained.

D. o-Nitrobenzyl 3-methyl-7-aminodecephalosporanate

The trichloroethoxycarbonyl protecting group is removed and the product is recovered using the procedures described in Example 19C to afford o-nitrobenzyl 3-methyl-7-aminodecephalosporanate.

C. o-Nitrobenzyl 3-methyl-7-diazodecephalosporanate

Diazotization of the product of B above and recovery of the diazo product is carried out using the procedures described in Example 19D.

D. o-Nitrobenzyl 3-methyl-7-azido-7-bromodecephalosporanate

When o-nitrobenzyl 3-methyl-7-diazodecephalosporanate is reacted with triethylammonium azide and bromine azide, the resulting reaction product is recovered in accordance with the procedures described in Example 2C to afford o-nitrobenzyl 3-methyl-7-azido-7-bromodecephalosporanate.

E. o-Nitrobenzyl 3-methyl-7-azido-7-methoxydecephalosporanate

The product of D above is reacted with methanol in the presence of silver fluoroborate and the resulting reaction product is recovered as described in Example 1C to obtain the title compound.

F. o-Nitrobenzyl 3-methyl-7-(2-furylacetamido)-7-methoxydecephalosporanate o-Nitrobenzyl 3-methyl-7-azido-7-methoxydecephalosporanate is hydrogenated and the resulting 7-amino compound is reacted with furylacetyl chloride and is recovered in accordance with procedures described in Example 8 to obtain o-nitrobenzyl 3-methyl-7-(2-furylacetamido)-7-methoxydecephalosporanate.

G. Sodium 3-methyl-7-(2-furylacetamido)-7-methoxydecephalosporanate

A 0.5% solution of o-nitrobenzyl 3-methyl-7-(2-furylacetamido)-7-methoxydecephalosporanate in dioxane is placed in a pyrex reaction vessel, thoroughly de-gassed and purged with helium. The solution is then irradiated with 3000 nM light until the ester group is removed as evidenced by TLC. After evaporating the solvent under reduced pressure, the residue is taken up in 15 ml. of methylene chloride and stirred for ½ hour with a solution of one equivalent of sodium bicarbonate in 10 ml. of water. The aqueous layer is lyophilized to give a mixture containing sodium 3-methyl-7-(2-furylacetamido)-7-methoxydecephalosporanate.

EXAMPLE 21

A. 3-Benzoylthiomethyl-7β-t-butoxycarboxamidodecephalosporanic acid

A solution of 35 g. of 3-benzoylthiomethyl-7-aminodecephalosporanic acid in 250 ml. of water is adjusted to pH 8.7 with 15% sodium hydroxide solution and maintained at this pH throughout the reaction by means of a pH stat. To this solution at 20° C. is added t-butoxychloroformate over a half hour period. After continuing the stirring for another half hour, the reaction mixture is adjusted to pH 2 and extracted into ethylacetate using three extractions. The ethylacetate solution is washed twice with water and dried over anhydrous sodium sulfate. After filtration the solvent is removed under reduced pressure to afford 3-benzoylthiomethyl-7β-t-butoxycarboxamidodecephalosporanic acid.

The starting compound is a known derivative of 7-aminocephalosporanic acid described in Belgian Pat. No. 650,444.

B. Phenacyl 3-benzoylthiomethyl-7β-t-butoxycarboxamidodecephalosporanate

3-Benzoylthiomethyl-7β-t-butoxycarboxamidodecephalosporanic acid (35.0 g.) and triethylamine (23 ml.) are stirred in 200 ml. of acetone for 45 minutes and 15.9 g. of α-bromoacetophenone is added to the mixture and stirring continued for an additional 20 minutes at room temperature. The entire reaction mixture is then chilled in an ice bath and the triethylamine hydrobromide is removed by filtration. The filtrate is evaporated under reduced pressure and the residue is extracted by shaking with a mixture of ether and aqueous sodium hydrogen phosphate. The ethereal layer is dried over anhydrous sodium sulfate and concentrated under reduced pressure to give phenacyl 3-benzoylthiomethyl-7β-butoxycarboxamidodecephalosporanate.

C. Phenacyl 3-benzoylthiomethyl-7-aminodecephalosporanate

Phenacyl 3-benzoylthiomethyl-7β-t-butoxycarboxamidodecephalosporanate (10 g.) is dissolved in 35 ml. of anisole and 100 ml. of trifluoroacetic acid at room temperature for 10 minutes. The solvents are removed under reduced pressure, maintaining the temperature below 40° C. The residue is taken up in water and neutralized with solid sodium bicarbonate. Chloroform is added and the chloroform layer is separated, washed with water and dried. The organic extract is concentrated under reduced pressure to give phenacyl 3-benzoylthiomethyl-7-aminodecephalosporanate.

D. Phenacyl 3-benzoylthiomethyl-7-diazodecephalosporanate

A mixture of 10 g. of sodium nitrite, 4.5 g. of phenacyl 3-benzoylthiomethyl-7-aminodecephalosporanate, 300 ml. of methylene chloride and 300 ml. of a mixture of water and ice is shaken in a separatory funnel. p-Toluenesulfonic acid monohydrate (0.27 g.) is added in three portions during 20 minutes. The mixture is shaken vigorously and the methylene chloride layer is separated, dried over sodium sulfate and evaporated under reduced pressure to 40 ml. The solution of phenacyl 3-benzoylthiomethyl-7-diazodecephalosporanate is used in the next step without isolation of the intermediate product.

E. Sodium 3-benzoylthiomethyl-7-(2-furylacetamido)-7-methoxydecephalosporanate Following the procedures described in Example 1B and 1C using phenacyl 3-benzoylthiomethyl-7-diazodecephalosporanate in place of benzyl 7-diazodecephalosporanate, the diazo compound is converted to phenacyl 3-benzoylthiomethyl-7-azido-7-methoxydecephalosporanate. The latter product is then converted to sodium 3-benzoylthiomethyl-7-(2-furylacetamido)-7-methoxydecephalosporanate following the procedures described in Example 8.

EXAMPLE 22

A. Trimethylsilyl 3-carbamoyloxymethyl-7-aminodecephalosporanate

A mixture of 0.5 g. of 3-carbamoyloxymethyl-7-aminodecephalosporanic acid, 2 ml. of hexamethyldisilazane and 8 ml. of chloroform is stirred overnight at reflux temperature protected from moisture. The solvent and excess hexamethyldisilazane are removed at reduced pressure, leaving a residue containing trimethylsilyl 3-carbamoyloxymethyl-7-aminodecephalosporanate.

B. Trimethylsilyl 3-carbamoyloxymethyl-7-diazodecephalosporanate

A mixture of trimethylsilyl 3-carbamoyloxymethyl-7-aminodecephalosporanate, 0.05 ml. of trifluoroacetic acid and 5 ml. of chloroform is stirred at 0° C. and 0.2 ml. of isoamylnitrite is added. After stirring for 1 hour at 0° C. the resulting reaction mixture containing the trimethylsilyl 3-carbamoyloxymethyl-7-diazodecephalosporanate is used directly in the next step.

C. 3-Carbamoyloxymethyl-7-azido-7-bromodecephalosporanic acid

To the solution obtained in B above is added at 0° C. 5 ml. of nitromethane. This is followed in rapid succession by 1 ml. of a methylene chloride solution of trimethylammonium azide and 1.5 ml. of a methylene chloride solution of bromine azide, both of which are in considerable excess of the amount required. The bromine size is decolorized rapidly and nitrogen is evolved. After about 5–10 minutes 20 ml. of 0.1 N sodium thiosulfate is added and the layers are separated. The aqueous phase is adjusted to pH 2 by the addition of a few drops of hydrochloric acid and is extracted twice with methylene chloride. The combined extractions are washed with water, dried over anhydrous sodium sulfate and concentrated under reduced pressure to afford 3-carbamoyloxymethyl-7-azido-7-bromodecephalosporanic acid.

The 3-carbamoyloxymethyl-7-aminodecephalosporanic acid used as the starting material in this example can be prepared by the following procedures:

7-Aminocephalosporanic acid is reacted with t-butoxycarbonylazide to produce the 7β-(t-butoxycarbonyl) derivative in accordance with known methods. This derivative is then intimately contacted with citrus acetylesterase in aqueous phosphate buffer at pH 6.5–7 for 15 hours and 3-hydroxymethyl 7β-(t-butoxycarbonyl)aminodecephalosporanic acid is recovered from the resulting reaction mixture.

To 0.2 g. of 3-hydroxymethyl 7β-(t-butoxycarbonyl)aminodecephalosporanic acid suspended in 5 ml. of acetonitrile, cooled to 0° C. and maintained under nitrogen atmosphere is added 0.15 ml. of chlorosulfonyl isocyanate. The reaction mixture is stirred for 70 minutes and then evaporated under diminished pressure to dryness. The resulting residue is taken up in 10 ml. of ethylacetate and 10 ml. of 0.1 N phosphate buffer. The pH of the aqueous layer is adjusted to about 1.6 and the mixture stirred for 2½ hours at room temperature. The pH is then adjusted to about 8 with aqueous tripotassium phosphate solution, and the aqueous phase is separated. The organic phase is reextracted with 10 ml. of phosphate buffer at pH 8. The combined aqueous phase is adjusted to pH 2.1 with hydrochloric acid and extracted twice with ethylacetate. The ethylacetate extractions are dried over sodium sulfate and evaporated under diminished pressure to afford 0.055 g. of residue. This residue is washed with ether to afford 3-carbamoyloxymethyl-7β-(t-butoxycarbonyl)aminodecephalosporanic acid which is recovered as a yellow solid.

3-Carbamoyloxymethyl-7β-(t-butoxycarbonyl)aminodecephalosporanic acid (0.5 g.) in 3.5 ml. of anisole is stirred with 2 ml. of trifluoroacetic acid at 0° C. for 5 minutes. The resulting reaction mixture is evaporated under reduced pressure to afford 3-carbamoyloxymethyl-7-aminodecephalosporanic acid which is purified further by crystallization from aqueous isopropanol.

EXAMPLE 23

Benzyl 3-picolinoylthiomethyl-7-diazodecephalosporanate

Following the procedures described in Example 1A, benzyl 3-picolinoylthiomethyl-7-aminodecephalosporanate, obtained by the esterification of the free acid with benzyl chloride, is converted to the corresponding diazo compound, benzyl 3-picolinoylthiomethyl-7-diazodecephalosporanate.

The 3-picolinoylthiomethyl-7-aminodecephalosporanic acid is obtained by reacting 3-hydroxymethyl-7-aminodedephalosporanic acid with thiopicolinic acid following procedures described in British Patent Specification No. 1,101,423.

EXAMPLE 24

Benzhydryl 3-pyridiniummethyl-7-diazodecephalosporanate

Following the procedures described in Example 2A and 2B, 3-pyridiniummethyl-7-aminodecephalosporanic acid is converted to the benzhydryl ester which, on reaction with nitrite, is converted to the desired benzhydryl 3-pyridiniummethyl-7-diazodecephalosporanate.

The starting compound is prepared by treating cephalosporin C with pyridine followed by acid hydrolysis as described in U.S. Pat. No. 3,117,126.

EXAMPLE 25

Benzhydryl 3-N-(2-chlorethyl)carbamoyloxymethyl-7-diazodecephalosporanate

Following the procedures described in Example 2A, 3-N-(2-chloroethyl)carbamoyloxymethyl-7-aminodecephalosporanic acid is converted to the benzhydryl ester which is then diazotized following the procedures described in Example 2B to obtain the desired 7-diazodecephalosporanate.

The substituted aminodecephalosporanic acid used as the starting material in this example can be prepared by subjecting the 7-t-butyloxycarboxy-7-ACA to enzymatic hydrolysis to obtain the desacetyl compound which is reacted with β-chloroethyl-isocyanate in dimethylformamide to afford the 3-N-(2-chloroethyl)carbamoyloxymethyldecephalosporin which is hydrolyzed to obtain 3-N-(2-chlorethyl)carbamoyloxymethyl-7-aminodecephalosporanic acid.

EXAMPLE 26

3-Hydroxymethyl-7-diazodecephalosporanic acid lactone

A mixture of 10 g. of sodium nitrite, 4 g. of 3-hydroxymethyl-7-aminodecephalosporanic acid lactone, 300 ml. of methylene chloride and 300 ml. of water and ice is shaken in a separatory funnel. p-Toluenesulfonic acid monohydrate (1.6 g.) is added in 3 portions during 20 minutes. The reaction mixture is shaken vigorously during the addition of the sulfonic acid. The methylene chloride layer is separated, dried over sodium sulfate and evaporated under reduced pressure to afford the desired 3-hydroxymethyl-7-diazodecephalosporanic acid lactone.

The 3-hydroxymethyl-7-aminodecephalosporanic acid lactone is obtained by acid hydrolysis of cephalosporin C in accordance with procedures known in this art.

EXAMPLE 27 t-Butyl-7-diazocephalosporanate

To a stirring mixture of 1.6 g. of sodium nitrite, 30 ml. of water and 40 ml. of methylene chloride at 0° C. is added 0.8 g. of t-butyl-7-aminocephalosporanate followed by the addition of a solution of 0.8 g. of p-toluenesulfonic acid in 5 ml. of water; the acid being added in small portions over a period of about 10 minutes. The resulting mixture is stirred at 0° C. for 20 minutes and the organic phase is then separated, washed with 1×10 ml. of ice water, dried over anhydrous sodium sulfate at 0° C., filtered and concentrated under reduced pressure at room temperature to afford the t-butyl-7-diazocephalosporanate.

EXAMPLE 28

Benzhydryl 3-n-amyloxymethyl-7-diazodecephalosporanate

To a slurry of 6.8 g. of 3-n-amyloxymethyl-7-aminodecephalosporanic acid in 300 ml. of dioxane at room temperature is added with stirring 4.3 g. of p-toluenesulfonic acid monohydrate. The resulting solution is concentrated under reduced pressure and flushed twice with dioxane. The residue is dissolved in 300 ml. of dioxane at room temperature, and a solution of 10 g. of diphenyldiazomethane in 25 ml. of dioxane is added dropwise over 15 minutes. The solution is stirred for an additional 30 minutes and then 25 ml. of methanol is added to destroy the excess diphenyldiazomethane. The mixture is concentrated under reduced pressure and the residue partitioned between 200 ml. of methylene chloride and 200 ml. of water containing 10 g. of dipotassium sulfate (pH 8.5). The organic phase is washed with water, dried over sodium sulfate and concentrated under reduced pressure to afford the desired benzhydryl 3-n-amyloxymethyl-7-aminodecephalosporanate.

To a stirring mixture of 1.6 g. of sodium nitrite, 30 ml. of water and 40 ml. of methylene chloride at 0° C. is added 0.8 g. of the ester prepared above followed by the addition of a solution of 0.8 g. of p-toluenesulfonic acid in 5 ml. of water over a few minutes. The mixture is stirred at 0° C. for 20 minutes and the organic phase is separated, washed with a small amount of ice water, dried over anhydrous sodium sulfate at 0° C., filtered and concentrated under reduced pressure at room temperature to afford the benzhydryl 3-n-amyloxymethyl-7-diazodecephalosporanate.

EXAMPLES 29–32

The p-methoxybenzyl 3-methyl-7-diazodecephalosporanate obtained in Example 19D, the phenacyl 3-benzoylthiomethyl-7-diazodecephalosporanate, prepared as in Example 21D, the benzyl 3-picolinoylthiomethyl-7-diazodecephalosporanate of Example 23, the benzhydryl 3-pyridiniummethyl-7-diazodecephalosporanate of Example 24, the benzhydryl 3-N-(2-chloroethyl)carbamoyloxymethyl-7-diazodecephalosporanate of Example 25, and the benzhydryl 3-n-amyloxymethyl-7-diazodecephalosporanate of Example 28 are each reacted with trimethylammonium azide and bromine azide, and the resulting reaction product is isolated following the procedure described in Example 2C to afford the following products:

| Example No. | Product |
| --- | --- |
| 29 | p-Methoxybenzyl 3-methyl-7-azido-7-bromodecephalosporanate |
| 30 | Phenacyl 3-benzoylthiomethyl-7-azido-7-bromodecephalosporanate |
| 31 | Benzyl 3-picolinoylthiomethyl-7-azido-7-bromodecephalosporanate |
| 32 | Benzhydryl 3-pyridiniummethyl-7-azido-7-bromodecephalosporanate |

EXAMPLE 33

A. p-Methoxybenzyl 3-methyl-7-azido-7-chlorodecephalosporanate p-Methoxybenzyl 3-methyl-7-diazodecephalosporanate (0.9 g.) is dissolved in a mixture of 10 ml. of methylene chloride and 10 ml. of nitromethane. To this cooled solution at 0°–10° C. is added a solution of triethylammonium azide prepared as described in Example 2C and a methylene chloride solution of chlorineazide (0.31 N, 15 ml.) and then 50 ml. of water. The resulting reaction mixture is adjusted to pH 8 by the addition of solid sodium bicarbonate. The mixture is allowed to stand and the organic layer is separated, extracted with 2×20 ml. of water, dried over anhydrous sodium sulfate and concentrated under reduced pressure to afford p-methoxybenzyl 3-methyl-7-azido-7-chlorodecephalosporanate.

B. When an equivalent amount of benzyl 7-diazocephalosporanate, benzhydryl 7-diazocephalosporanate, phenacyl 3-benzoylthiomethyl-7-diazodecephalosporanate, trimethylsilyl 3-carbamoyloxymethyl-7-diazodecephalosporanate, benzyl 3-picolinoylthiomethyl-7-diazodecephalosporanate, benzhydryl 3-pyridiniummethyl-7-diazodecephalosporanate, benzhydryl 3-N-(2-chloroethyl)carbamoyloxymethyl-7-diazodecephalosporanate; t-butyl-7-diazocephalosporanate or benzhydryl 3-n-amyloxymethyl-7-diazodecephalosporanate is substituted for the p-methoxybenzyl 3-methyl-7-diazodecephalosporanate in the process of Example 33A, the following compounds are obtained:

Benzyl 7-azido-7-chlorocephalosporanate
Benzhydryl 7-azido-7-chlorocephalosporanate
Phenacyl 3-benzoylthiomethyl-7-azido-7-chlorodecephalosporanate
Trimethylsilyl 3-carbamoyloxymethyl-7-azido-7-chlorodecephalosporanate
Benzyl 3-picolinoylthiomethyl-7-azido-7-chlorodecephalosporanate
Benzhydryl 3-pyridiniummethyl-7-azido-7-chlorodecephalosporanate
Benzhydryl 3-N-(2-chloroethyl)carbamoyloxymethyl-7-azido-7-chlorodecephalosporanate
t-Butyl-7-azido-7-chlorocephalosporanate
Benzhydryl 3-n-amyloxymethyl-7-azido-7-chlorodecephalosporanate.

EXAMPLE 34

A. Benzhydryl 7-azido-7-(2-bromoethoxy)cephalosporanate

A solution of 543 mg. benzhydryl 7-azido-7-bromocephalosporanate in 25 ml. dry acetonitrile is treated with 195 mg. silver fluoroborate and 150 mg. 2-bromoethanol. The mixture is stirred for 24 hours at room temperature, filtered, and evaporated at 30° C./0.1 mm. The residue is chromatographed on silica gel, eluting with chloroform to afford pure benzhydryl 7-azido-7-(2-bromoethoxy)cephalosporanate.

B. Benzhydryl 7-(2-thienylacetamido)-7-(2-bromoethoxy)cephalosporanate

Benzhydryl 7-azido-7-(2-bromoethoxy)cephalosporanate (587 mg.) is hydrogenated at 40 psi for 3 hours using 1 g. platinum oxide in 50 ml. dioxane containing 500 mg. thienylacetic anhydride. After filtration of the catalyst, the solution is treated for 15 minutes with 0.5 ml. water to hydrolyze excess anhydride, then vacuum stripped. The crude product is taken up in 25 ml. ethylacetate, washed with aqueous sodium bicarbonate, dried over magnesium sulfate, filtered, evaporated, and chromatographed on silica gel using 4:1 chloroform-ethylacetate to elute pure benzhydryl 7-(2-thienylacetamido)-7-(2-bromoethoxy)cephalosporanate.

C. Benzhydryl 7-(2-thienylacetamido)-7-(2-triphenylphosphonioethoxy)cephalosporanate bromide Benzhydryl 7-(2-thienylacetamido)-7-(2-bromoethoxy)cephalosporanate (673 mg.) is refluxed in 15 ml. benzene with 262 mg. triphenylphosphine overnight. Crude benzhydryl 7-(2-thienylacetamido)-7-(2-triphenylphosphonoethoxy)cephalosporanate bromide is obtained on evaporation of the benzene and is used directly for the next step.

D. Benzhydryl 7-(2-thienylacetamido)-7-hydroxycephalosporanate

The sample of benzhydryl 7-(2-thienylacetamido)-7-(2-triphenylphosphonoethoxy)cephalosporanate bromide obtained from the previous step (ca. 1 mmole) is stirred under nitrogen at −30° C. in 50 ml. of ether. An equivalent amount of phenyllithium in ether is slowly added over 30 minutes. The reaction mixture is then allowed to warm with stirring, over about ½ hour, to 0° C. The reaction mixture is quenched with 50 ml. of 0.1 M aqueous pH 7 phosphate buffer at 0° C. The ether layer is separated and the aqueous phase washed twice more with ether. The combined organic portions are dried over magnesium sulfate, filtered, evaporated and chromatographed on silica gel, eluting with B 3% methanol in chloroform, to afford benzhydryl 7-(2-thienylacetamido)-7-hydroxycephalosporanate after evaporation of the solvent under reduced pressure.

E. Sodium 7-(2-thienylacetamido)-7-hydroxycephalosporanate

Benzhydryl 7-(2-thienylacetamido)-7-hydroxycephalosporanate (566 mg.) is dissolved in 0.8 g. anisole and cooled to 0° C. Trifluoroacetic acid (4 ml.) precooled to 0° C. is added and the reaction allowed to proceed for 2 minutes at 0° C. Vacuum of 0.1 mm. is immediately applied and the reaction mixture allowed to warm to room temperature without external heating. Anisole is then distilled out at 30° C./0.1 mm. A few ml. anisole is added to the residue and evaporated at 30° C./0.1 mm. to insure total removal of trifluoroacetic acid. The product is treated with 5 ml. of water containing 84 mg. of sodium bicarbonate and lyophilized. The resulting powder is washed thoroughly with ether and dried, affording sodium 7-(2-thienylacetamido)-7-hydroxycephalosporanate.

EXAMPLES 35–39

When Example 34, step B above is carried out using phenylacetic anhydride, acetic anhydride, benzothiophene-2-acetic anhydride, furylacetic anhydride or tetraazolylacetic anhydride in place of thienylacetic anhydride, the corresponding benzhydryl 7-acylamido-7-(2-bromoethoxy)cephalosporanate is obtained. These intermediate products, when treated by the procedures described in C, D and E above, afford respectively:

| Example No. | Product |
|---|---|
| 35 | Sodium 7-benzylamido-7-hydroxycephalosporanate |
| 36 | Sodium 7-acetamido-7-hydroxycephalosporanate |
| 37 | Sodium 7-(2-thianaphthene-2-acetamido)-7-hydroxycephalosporanate |
| 38 | Sodium 7-(2-furylacetamido)-7-hydroxycephalosporanate |
| 39 | Sodium 7-tetraazolylacetamido-7-hydroxycephalosporanate |

EXAMPLE 40

A. Benzhydryl 7-(2-thienylacetamido)-7-(aminocarbonyloxy)cephalosporanate

Benzhydryl 7-(2-thienylacetamido)-7-hydroxycephalosporanate (566 mg.) is dissolved in 30 ml. of ether and treated at 0° C. with 80 mg. aminocarbonyl chloride and 0.3 ml. pyridine. After 15 minutes, the solution is washed successively with water, dilute aqueous phosphoric acid (buffered to pH 2), water, and aqueous sodium bicarbonate. After drying over magnesium sulfate, filtration and evaporation of the solvent, the residue is essentially pure benzhydryl 7-(2-thienylacetamido)-7-(aminocarbonyloxyl)cephalosporanate.

B. Sodium 7-(2-thienylacetamido)-7-(aminocarbonyloxy)cephalosporanate

Benzhydryl 7-(2-thienylacetamido)-7-(aminocarbonyloxy)cephalosporanate is deblocked following the procedures described in Example 34E above to afford sodium 7-(2-thienylacetamido)-7-(aminocarbonyloxy)cephalosporanate.

EXAMPLE 41

A. Benzhydryl 7-(2-thienylacetamido)-7-(methoxycarbonyloxy)cephalosporanate

To benzhydryl 7-(2-thienylacetamido)-7-hydroxycephalosporanate in 30 ml. of ether is added 95 mg. of methyl chlorocarbonate and 0.3 ml. of pyridine. After 15 minutes the reaction mixture is worked up as described in Example 40A to afford benzhydryl 7-(2-thienylacetamido)-7-(methoxycarbonyloxy)cephalosporanate.

B. Sodium 7-(2-thienylacetamido)-7-(methoxycarbonyloxy)cephalosporanate

Benzhydryl 7-(2-thienylacetamido)-7-(methoxycarbonyloxy)cephalosporanate is deblocked following the procedures described in Example 34E above to afford sodium 7-(2-thienylacetamido)-7-(methoxycarbonyloxy)cephalosporanate.

EXAMPLE 42

A. Benzhydryl 7-(2-thienylacetamido)-7-(aminosulfonyloxy)cephalosporanate

To benzhydryl 7-(2-thienylacetamido)-7-hydroxycephalosporanate in 30 ml. of ether is added 116 mg. of aminosulfonyl chloride and 0.3 ml. of pyridine. After 15 minutes the reaction mixture is worked up as described in Example 40A to afford benzhydryl 7-(2-thienylacetamido)-7-(aminosulfonyloxy)cephalosporanate.

B. Sodium 7-(2-thienylacetamido)-7-(aminosulfonyloxy)cephalosporanate

Benzhydryl 7-(2-thienylacetamido)-7-(aminosulfonyloxy)cephalosporanate is deblocked following the procedures described in Example 34E above to afford sodium 7-(2-thienylacetamido)-7-(aminosulfonyloxy)cephalosporanate.

EXAMPLE 43

A. 7-(p-Nitrobenzylideneamino)cephalosporanic acid benzhydryl ester

7-Aminocephalosporanic acid benzhydryl ester (438 mg.) is refluxed 1 hour in 50 ml. benzene with 151 mg. p-nitrobenzaldehyde in an azeotropic drying apparatus. The solvent is vacuum distilled away, leaving 571 mg. crystalline product. If desired, it can be recrystallized from benzenecylohexane (1:2) to obtain the product in pure form.

B. Benzhydryl 7-(p-nitrobenzylideneamino)-7-acetoxycephalosporanate

Benzhydryl 7-(p-nitrobenzylideneamino)cephalosporanate (571 mg.) is stirred at 0° C. under nitrogen in 10 ml. acetonitrile. Acetyl peroxide (118 mg.) is introduced, followed by 129 mg. diisopropylethylamine, which is added in acetonitrile over a 5 minute period.

The reaction mixture is aged 5 minutes at room temperature and evaporated under reduced pressure. The residue is taken up in 25 ml. of benzene and washed successively with water, dilute phosphoric acid (buffered at pH 2) water and aqueous sodium bicarbonate. The solution is dried over magnesium sulfate, filtered, evaporated and chromatographed on silica gel, using 4:1 chloroform-ethylacetate to elute the product. Evaporation of the solvent affords benzhydryl 7-(p-nitrobenzylideneamino)-7-acetoxycephalosporanate.

C. Benzhydryl 7-amino-7-acetoxycephalosporanate hydrochloride

Benzhydryl 7-(p-nitrobenzylideneamino)-7-acetoxycephalosporanate (629 mg.) and 260 mg. aniline hydrochloride are stirred together for 1 hour at 25° C. in 10 ml. methanol. The methanol is removed at 0.1 mm. pressure and 30° C. and the residue covered with ether to crystallize for 1 hour. The solid is triturated with ether, filtered, and washed with ether several times. It consists of benzhydryl 7-amino-7-acetoxycephalosporanate hydrochloride and aniline hydrochloride mixed together and is used immediately in the next step.

D. Benzhydryl 7-(2-thienylacetamido)-7-acetoxycephalosporanate

The mixture of benzhydryl 7-amino-7-acetoxycephalosporanate hydrochloride and aniline hydrochloride obtained in the previous experiment is stirred vigorously at −10° C. in 25 ml. methylene chloride. Thienylacetyl chloride (0.5 g.) is added, and then 0.5 g. triethylamine is slowly introduced. This liberates the free 7-amino compound which is instantly acylated. The reaction mixture is slowly allowed to warm to room temperature. Excess acid chloride is hydrolyzed by shaking with water, and the methylene chloride layer is then washed successively with dilute phosphoric acid (buffered to pH 2), water and dilute aqueous sodium bicarbonate. After drying over magnesium sulfate, the solution is filtered and evaporated, affording a mixture of the product and N-phenyl thienylacetamide. Chromatography over silica gel and elution with 4:1 chloroform-ethylacetate affords the title compound.

E. Sodium 7-(2-thienylacetamido)-7-acetoxycephalosporanate

Benzhydryl 7-(2-thienylacetamido)-7-acetoxycephalosporanate (620 mg.) is dissolved in 0.8 ml. anisole and cooled to 0° C. Trifluoroacetic acid (4 ml.) precooled to 0° C. is added and the reaction allowed to proceed for 2 minutes at 0° C. Vacuum of 0.1 mm. is immediately applied and the reaction mixture allowed to warm to room temperature. Anisole is then distilled at 30° C./0.1 mm. A few ml. anisole is added to the residue and pulled off at 30° C./0.1 mm. to insure total removal of trifluoroacetic acid. The product is treated with 5 ml. water containing 84 mg. of sodium bicarbonate and lyophilized. The resulting powder is washed thoroughly with ether and dried, affording the title compound.

EXAMPLE 44

A. p-Methoxybenzyl 7-azido-7-bromocephalosporanate

A mixture of p-methoxybenzyl 7-aminocephalosporanate (3.9 g.) in 250 ml. methylene chloride and sodium nitrite (1.4 g.) in 250 ml. of water is stirred under nitrogen with ice cooling and 7.5 ml. of 2 N sulfuric acid is added all at once. The mixture is stirred at 3° C. for 1 hour and the organic phase is separated and rapidly dried over sodium sulfate and concentrated to 50 ml. in vacuo. To this solution of p-methoxybenzyl-7-diazocephalosporanate cooled to −40° C. is rapidly added 50 ml. of triethylammonium azide solution and 50 ml. of bromine azide solution prepared as described below. The solution is allowed to warm to 0° C., then washed with 200 ml. of 2% sodium hydrogen phosphate solution. The orgaic phase is dried over sodium sulfate and evaporated. The residue is rapidly chromatographed on a 4.5 cm. × 15 cm. column of silica gel using 20% methylene chloride 80% benzene as eluant, affording p-methoxybenzyl 7-azido-7-bromocephalosporanate.

Preparation of Triethylammonium Azide Solution

To a slurry of 6 g. of sodium azide in 10 ml. of water and 100 ml. of methylene chloride at −10° C. is added 10 ml. of 50% $H_2SO_4$. The organic phase is decanted from the aqueous paste and dried over anhydrous magnesium sulfate. To 50 ml. of this hydrazoic acid solution is added 2.25 ml. of triethylamine. The resulting pH is 7.

Preparation of Bromine Azide Solution

To 50 ml. of the above hydrazoic acid solution is added 2 g. of N-bromosuccinimide with stirring and ice cooling. After 10 minutes at 0° C. the reaction is complete and the solution is used immediately for reaction with 7-diazocephalosporanates.

The p-methoxybenzyl 7-aminocephalosporanate used as the starting material is prepared from 7-aminocephalosporanic acid using the procedures described in Example 19A, B and C for the preparation of p-methoxybenzyl 3-methyl-7-aminodecephalosporanate.

B. p-Methoxybenzyl 7-azido-7-(2-methoxyethoxy)cephalosporanate

To a solution of 4.8 g. of p-methoxybenzyl 7-azido-7-bromocephalosporanate in 20 ml. of 2-methoxyethanol is added 1.95 g. of silver tetrafluoroborate and 0.8 ml. of pyridine. After stirring for 3 hours at room temperature, the 2-methoxyethanol is removed under vacuum. The residue is taken up in methylene chloride, filtered, and the filtrate washed with water, dried and evaporated. The residue is chromatographed on 140 g. of silica gel. Elution with 2% methanol in chloroform gives substantially pure p-methoxybenzyl 7-azido-7-(2-methoxyethoxy)cephalosporanate.

C. p-Methoxybenzyl 7-amino-7-(2-methoxyethoxy)cephalosporanate p-Methoxybenzyl 7-azido-7-(2-methoxyethoxy)cephalosporanate (2 g.) and platinum oxide (2 g.) in 200 ml. of dioxane are vigorously stirred under an atmosphere of hydrogen for 1 hour. Fresh catalyst (2 g.) is added and the hydrogenation continued for 2 hours. The dioxane is evaporated under reduced pressure and the catalyst adsorbed onto 30 g. of silica gel in 50 ml. of chloroform and filtered. The cake is washed with 500 ml. of chloroform and the combined filtrate and washings evaporated giving p-methoxybenzyl 7-amino-7-(2-methoxyethoxy)cephalosporanate as a viscous oil.

D. p-Methoxybenzyl 7-(D-α-azidophenylacetamido)-7-(2-methoxyethoxy)-cephalosporanate To an ice-cooled solution of 0.9 g. of p-methoxybenzyl 7-amino-7-(2-methoxyethoxy)cephalosporanate in 20 ml. of methylene chloride is added 0.8 g. of D-α-azidophenylacetyl chloride and 0.7 ml. of dry pyridine. The solution is stirred at 2° C. for 20 minutes, then poured into 20 ml. of water. The mixture is acidified to pH 2 with dilute sulfuric acid and the organic phase is separated, washed with water, dried and evaporated. The residue is chromatographed on 50 g. silica gel. Elution with chloroform-ethylacetate yields p-methoxybenzyl 7-(D-α-azidophenylacetamido)-7-(2-methoxyethoxy)cephalosporanate.

E. 7-(D-α-Azodiphenylacetamido)-7-(2-methoxyethoxy)-cephalosporanic acid

A solution of 420 mg. of p-methoxybenzyl 7-(D-α-azidophenylacetamido)-7-(2-methoxyethoxy)cephalosporanate, 300 mg. of anisole and 3 ml. of trifluoroacetic acid in 10 ml. of benzene is stirred for 2 hours at room temperature. The reaction mixture is evaporated and the residue is taken up in ethylacetate and extracted with sodium bicarbonate solution. The aqueous extract is cooled to 0° C., overlayered with ethylacetate and acidified to pH 2.1 with dilute sulfuric acid. The ethylacetate layer is separated, dried over anhydrous sodium sulfate and evaporated, affording 7-(D-α-azidophenylacetamido)-7-(2-methoxyethoxy)cephalosporanic acid.

F. 7-(D-α-aminophenylacetamido)-7-(2-methoxyethoxy)-cephalosporanic acid

To an ice-cooled solution of 240 mg. of 7-(D-α-azidophenylacetamido)-7-(2-methoxyethoxy)cephalosporanic acid in 3 ml. of acetic acid and 2 ml. of water is added 1.5 g. of powdered zinc. The mixture is stirred for 15 minutes, then filtered. The residue is washed with 10 ml. of water and the combined filtrate and washings are evaporated to dryness. The residue is taken up in 2 ml. of water and poured onto a 2×40 cm. column of ion retardation resin. The column is eluted with water and the ninhydrin positive fractions lyophilized, giving 7-(D-α-aminophenylacetamido)-7-(2-methoxyethoxy)-cephalosporanic acid as a yellow powder.

EXAMPLE 45

A. p-Methoxybenzyl 7-(2-methoxyethoxy)-7-(2-thienylacetamido)cephalosporanate Following the procedure described in Example 3B, an equivalent quantity of p-methoxybenzyl 7-amino-7-(2-methoxyethoxy)cephalosporanate is reacted with 2-thienylchloride and the resulting reaction product is worked up in the same manner to afford p-methoxybenzyl 7-(2-methoxyethoxy)-7-(2-thienylacetamido)cephalosporanate.

B. Sodium 7-(2-methoxyethoxy)-7-(2-thienylacetamido)cephalosporanate

A solution of 0.4 g. of p-methoxybenzyl 7-(2-methoxyethoxy)-7-(2-thienylacetamido)cephalosporanate is dissolved in 3.5 ml. of anisole and treated with 10 ml. of trifluoroacetic acid at room temperature for 10 minutes. The trifluoroacetic acid and anisole are removed under reduced pressure maintaining the temperature below 40° C., and the residue is taken up in 25 ml. of chloroform and treated with 20 ml. of water containing 0.120 g. of sodium bicarbonate. The mixture is stirred for ½ hour at room temperature and the organic phase is separated and washed with water. The combined aqueous phase is washed twice with methylene chloride and lyophilized affording sodium 7-(2-methoxyethoxy)-7-(2-thienylacetamido)cephalosporanate.

EXAMPLES 46–50

In similar manner as described in Example 45, p-methoxybenzyl 7-amino-7-(2-methoxyethoxy)cephalosporanate is reacted with 2-thianaphthene-2-acetyl chloride, p-guanidinophenylacetyl chloride hydrochloride, furylacetyl chloride, phenylacetyl chloride, or tetraazolylacetyl chloride, and the resulting ester is cleaved to obtain

| Example | Product |
|---|---|
| 46 | Sodium 7-(2-methoxyethoxy)-7-(2-thianaphthene-2-acetamido)cephalosporanate |
| 47 | 7-(2-methoxyethoxy)-7-(p-guanidinophenylacetamido)cephalosporanic acid |
| 48 | Sodium 7-(2-methoxyethoxy)-7-(2-furylacetamido)cephalosporanate |
| 49 | Sodium 7-(2-methoxyethoxy)-7-phenylacetamidocephalosporanate |
| 50 | Sodium 7-(2-methoxyethoxy)-7-tetraazolylacetamidocephalosporanate |

EXAMPLE 51

A. Benzhydryl 7-azido-7-(t-butoxycarbonylaminoacetoxy)cephalosporanate

A mixture of 3.1 g. of benzhydryl 7-azido-7-bromocephalosporanate, 1.1 g. of silver fluoroborate, 2 g. of t-butoxycarbonylglycine and 0.45 ml. of pyridine in 10 ml. of dioxane is stirred under the exclusion of moisture and light for 3 hours at room temperature. The mixture is diluted with 100 ml. of ether and filtered and the filtrate is washed successively with 2% aqueous phosphoric acid, water and 5% aqueous sodium bicarbonate solution. The ethereal phase is dried over anhydrous sodium sulfate and evaporated and the residue is chromatographed on 140 g. of silica gel. Elution with 2% methanol in chloroform gives benzhydryl 7-azido-7-(t-butoxycarbonylaminoacetoxy)cephalosporanate.

B. Benzhydryl 7-amino-7-(t-butoxycarbonylaminoacetoxy)cephalosporanate

A solution of 3 g. of benzhydryl 7-azido-7-(t-butoxycarbonylaminoacetoxy)cephalosporanate in 300 ml. of dry dioxane is hydrogenated in the presence of 3 g. Pt oxide for 1 hour at room temperature. Fresh catalyst (3 g.) is added and the hydrogenation continued for 3 hours. The dioxane is evaporated under reduced pressure and the residue taken up in chloroform and filtered through 20 g. of silica gel packed in a fritted glass funnel. The cake is washed with 500 ml. of chloroform and the combined washings and filtrate are evaporated, leaving benzhydryl 7-amino-7-(t-butoxycarbonylaminoacetoxy)cephalosporanate.

C. Benzhydryl 7-(t-butoxycarbonylaminoacetoxy)-7-(2-furylacetamido)cephalosporanate To a cooled solution of 2 g. of benzhydryl 7-amino-7-(t-butoxycarbonylaminoacetoxy)cephalosporanate in 30 ml. of methylene chloride is added 1.5 ml. of 2-furylacetyl chloride and 1.5 ml. of dry pyridine. The mixture is stirred at 0° C. for 15 minutes, then poured over ice. The methylene chloride layer is separated, washed successively with 2% phosphoric acid, water and 2% sodium bicarbonate solution, dried and evaporated. The residue is chromatographed on 80 g. of silica gel. Elution with chloroformethylacetate mixtures yields substantially pure benzhydryl 7-(t-butoxycarbonylaminoacetoxy)-7-(2-furylacetamido)cephalosporanate.

D. 7-aminoacetoxy-7-(2-furylacetamido)cephalosporanic acid trifluoroacetate salt A solution of 400 mg. of benzhydryl 7-(t-butoxycarbonylaminoacetoxy)-7-(2-furylacetamido)cephalosporanate in 3 ml. of anisole and 3 ml. of trifluoroacetic acid is kept at room temperature for 5 minutes, then the excess trifluoroacetic acid is pumped off under high vacuum for 5 minutes. The residue is triturated with ether and the resulting powder filtered off and washed with ether. The residue is dissolved in 200 ml. of water and filtered through 50 mg. of charcoal layered on diatomaceous earth. The filtrate is lyophilized affording 7-aminoacetoxy-7-(2-furylacetamido)cephalosporanic acid trifluoroacetate salt as a light powder.

The zwitterionic inner salt is obtained by neutralizing an aqueous solution to pH 6.5 followed by concentration to a small volume and precipitation with alcohol.

EXAMPLE 52

When the process of Example 51 is repeated using tetraazolylacetyl chloride, 2-thienylacetyl chloride or phenylacetyl chloride in place of 2-furylacetyl chloride, the corresponding 7-tetraazolylacetamido, 7-(2-thienylacetamido), or 7-phenylacetamido-7-aminoacetoxycephalosporanic acid trifluoroacetate salt is obtained.

EXAMPLE 53

A. Benzhydryl 7-azido-7-benzyloxycephalosporanate

A mixture of 4.6 g. of benzhydryl 7-azido-7-bromocephalosporanate, 1.6 g. of silver fluoroborate and 0.66 ml. of dry pyridine in 15 ml. of benzyl alcohol is stirred at room temperature for 2½ hours. The mixture is diluted with 300 ml. of ether and filtered. The filtrate is washed with 2% phosphoric acid and with water, then dried over sodium sulfate and evaporated. The excess benzyl alcohol is removed on a high vacuum pump with magnetic stirring for 18 hours and the residue chromatographed on 200 g. of silica gel. Elution with hexane followed by increasing concentrations of methylene chloride in hexane affords benzhydryl 7-azido-7-benzyloxycephalosporanate.

B. Benzhydryl 7-amino-7-benzyloxycephalosporanate

A solution of 3 g. of benzhydryl 7-azido-7-benzyloxycephalosporanate in 300 ml. of dry dioxane is hydrogenated in the presence of 3 g. of platinum oxide at room temperature at atmospheric pressure for 1 hour. Fresh catalyst (3 g.) is added and the hydrogenation continued for 2 hours. The dioxane is removed under reduced pressure and the residue taken up in chloroform and filtered through 20 g. of silica gel packed in a fritted glass funnel. The cake is washed with 500 ml. of chloroform and the combined filtrate and washings are evaporated, leaving benzhydryl 7-amino-7-benzyloxycephalosporanate as a yellow resin.

C. Benzhydryl 7-benzyloxy-7-(2-thienylacetamido)cephalosporanate

To a cooled solution of 1.2 g. of benzhydryl 7-amino-7-benzyloxycephalosporanate in 15 ml. of methylene chloride is added with stirring 0.8 ml. of 2-thienylacetyl chloride and 0.8 ml. of pyridine. The mixture is stirred for 15 minutes at 2° C. and then poured over ice. The organic phase is separated and washed successively with 2% phosphoric acid, water and 2% sodium bicarbonate solution, then dried over anhydrous sodium sulfate and evaporated. The residue is chromatographed on 50 g. of silica gel with 5% ethylacetate in methylene chloride as eluant, giving benzhydryl 7-benzyloxy-7-(2-thienylacetamido)cephalosporanate.

D. Sodium 7-benzyloxy-7-(2-thienylacetamido)cephalosporanate

A solution of 0.9 g. of benzhydryl 7-benzyloxy-7-(2-thienylacetamido)cephalosporanate in 3 ml. of anisole and 7 ml. of trifluoroacetic acid is stirred at room temperature for 5 minutes and the excess anisole and trifluoroacetic acid rapidly removed on the vacuum pump. The residue is taken up in a mixture of 25 ml. of methylene chloride and 25 ml. of water and rapidly stirred while sodium bicarbonate is added to bring the pH to 6.5. The aqueous layer is separated, washed once with ether and lyophilized, giving sodium 7-benzyloxy-7-(2-thienylacetamido)cephalosporanate as a light powder.

EXAMPLE 54

Sodium 7-hydroxy-7-(2-thienylacetamido)cephalosporanate

A solution of sodium 7-benzyloxy-7-(2-thienylacetamido)cephalosporanate (300 mg.) in 10 ml. of water is hydrogenated at 40 PSIG and room temperature in the presence of 0.39 g. of 10% palladium-on-charcoal for 6 hours. Fresh catalyst (0.3 g.) is added and the hydrogenation continued for 18 hours. The catalyst is filtered and the filtrate lyophilized, leaving sodium 7-hydroxy-7-(2-thienylacetamido)cephalosporanate.

EXAMPLE 55

Following the procedures described in Example 53 using furylacetyl chloride, p-guanidinophenylacetyl chloride hydrochloride, tetraazolylacetyl chloride, or phenylacetyl chloride in place of 2-thienylacetyl chloride, there are obtained, respectively, sodium 7-benzyloxy-7-(2-furylacetamido)cephalosporanate,
7-benzyloxy-7-(p-guanidinophenylacetamido)cephalosporanic acid,
sodium 7-benzyloxy-7-tetraazolylacetamidocephalosporanate, and
sodium 7-benzyloxy-7-phenylacetamido-cephalosporanate.

EXAMPLE 56

Following the procedures described in Example 54, the 7-benzyloxycephalosporins are converted to the corresponding 7-hydroxycephalosporins.

EXAMPLE 57

A. Benzhydryl 7-azido-7-(L-2-benzhydryloxycarbonyl-2-t-butoxycarbonylaminoethoxy)cephalosporanate The benzhydryl ester of N-t-butoxycarbonyl-L-serine is prepared by the addition of a solution of diphenyldiazomethane (2.5 g.) in 10 ml. of dioxane to a solution of N-t-butoxycarbonyl-L-serine (2.5 g.) in 5 ml. of dioxane. To the resulting solution is added benzhydryl 7-azido-7-bromo-cephalosporanate (4.5 g.), silver fluoroborate (1.6 g.) and pyridine (0.65 ml.). The mixture is stirred for 3 hours at room temperature, then diluted with 100 ml. of ether and filtered. The filtrate is washed successively with pH 2 phosphoric acid buffer, water and sodium bicarbonate solution and then dried over anhydrous sodium sulfate and evaporated. The residue is chromatographed on 200 g. of silica gel. Elution with chloroform-ethylacetate mixture affords the product as a tan gum.

B. Benzhydryl 7-amino-7-(L-2-benzhydryloxycarbonyl-2-t-butoxycarbonylaminoethoxy)cephalosporanate A solution of 3 g. of benzhydryl 7-azido-7-(L-2-benzhydryloxycarbonyl-2-t-butoxycarbonylaminoethoxy) cephalosporanate in 300 ml. of dry dioxane is hydrogenated in the presence of 3 g. of platinum oxide at room temperature and atmospheric pressure for 1 hour. Fresh catalyst (3 g.) is added and the hydrogenation continued for 2 hours. The dioxane is removed under reduced pressure and the residue taken in chloroform and filtered through 20 g. of silica gel packed in a fritted glass funnel. The cake is washed with chloroform and the combined washings and filtrate are evaporated, leaving benzhydryl 7-amino-7-(L-2-benzhydryloxycarbonyl-2-t-butoxycarbonylaminoethoxy)cephalosporanate.

C. Benzhydryl 7-(α-benzhydryloxycarbonylphenylacetamido)-7-(L-2-benzhydryloxycarbonyl-2-t-butoxycarbonylaminoethoxy)-cephalosporanate α-Benzhydryloxycarbonylphenylacetyl chloride (377 mg.) is added in one portion to a cooled solution of 450 mg. of benzhydryl 7-amino-7-(L-2-benzhydryloxycarbonyl2-t-butoxycarbonylaminoethoxy)cephalosporanate and 0.2 ml. of dry pyridine in 10 ml. of methylene chloride. The solution is stirred for 20 minutes at 0° C., then poured into 20 ml. of pH 2 phosphoric acid buffer. The organic phase is washed with water and sodium bicarbonate solution, dried over anhydrous sodium sulfate and evaporated. The residue is chromatographed on 30 g. of silica gel. Elution with chloroform yields benzhydryl 7-(α-benzhydryloxycarbonylphenylacetamido)-7-(L-2-benzhydryloxycarbonyl-2-t-butoxycarbonylaminoethoxy)cephalosporanate.

D. Disodium 7-(L-2-carboxy-2-aminoethoxy)-7-(α-carboxyphenylacetamido)cephalosporanate 2 ml. of anisole and 6 ml. of trifluoroacetic acid are added to 200 mg. of benzhydryl 7-(α-benzhydryloxycarbonylphenylacetamido)-7-(L-2-benzhydryloxycarbonyl-2-t-butoxycarbonylaminoethoxy)cephalosporanate and the mixture is stirred at room temperature for 8 minutes. Excess anisole and trifluoroacetic acid are rapidly evaporated on a vacuum pump. The residue is taken up in 20 ml. of methylene chloride and 20 ml. of water and the mixture vigorously stirred as the pH is adjusted to 7 by the addition of sodium bicarbonate solution. The aqueous phase is separated, washed once with ether and lyophilized, giving the disodium salt of 7-(L-2-carboxy-2-aminoethoxy)-7-(α-carboxyphenylacetamido)cephalosporanate.

In a similar manner starting with N-t-butoxycarbonyl-D-serine in place of N-t-butoxycarbonyl-L-serine, 7-(D-2-carboxy-2aminoethoxy)-7-(α-carboxyphenylacetamido)cephalosporanate is obtained.

EXAMPLE 58

When benzhydryl 7-amino-7-(L-2-benzhydryloxycarbonyl-2-t-butoxycarbonylaminoethoxy)cephalosporanate is acylated with phenylacetyl chloride, 2-thienylacetyl chloride or furylacetyl chloride in accordance with the procedures described in the foregoing examples, the corresponding 7-phenylacetamido, 7-(2-thienylacetamido) and 7-(2-furylacetamido) analogs are obtained.

EXAMPLE 59

A. Benzhydryl 7-azido-7-(carbamoylmethoxy)cephalosporanate

To a solution of 3.1 g. of benzhydryl 7-azido-7-bromocephalosporanate and 2 g. of glycolamide in 10 ml. of dioxane is added 1.1 g. of silver fluoroborate and 0.45 ml. of pyridine. The mixture is stirred for 2 hours at room temperature, then diluted with 100 ml. of ether and filtered. The filtrate is washed successively with 2% aqueous phosphoric acid, water and sodium bicarbonate solution, then dried over anhydrous sodium sulfate and evaporated. The residue is chromatographed on 120 g. of silica gel. Elution with 2% methanol in chloroform affords substantially pure benzhydryl 7-azido-7-(carbamoylmethoxy)cephalosporanate.

B. Benzhydryl 7-amino-7-(carbamoylmethoxy)cephalosporanate

A solution of 3 g. of benzhydryl 7-azido-7-(carbamoylmethoxy)cephalosporanate in 300 ml. of dry dioxane is vigorously stirred with 3 g. of platinum oxide under one atmosphere of hydrogen at room temperature for 1 hour. Fresh catalyst (3 g.) is added and the hydrogenation continued for 2 hours. The dioxane is removed under reduced pressure and the residue is taken up in chloroform and filtered through 20 g. of silica gel packed in a sintered glass funnel. The silica gel is washed with chloroform and the combined filtrate and washes are evaporated, leaving benzhydryl 7-amino-7-(carbamoylmethoxy)cephalosporanate.

C. Benzhydryl 7-carbamoylmethoxy-7-(2-thienylacetamido)cephalosporanate

To a cooled solution of 1.5 g. of benzhydryl 7-amino-7-(carbamoylmethoxy)cephalosporanate in 20 ml. of methylene chloride is added 1.0 g. of thienylacetyl chloride and 1.0 ml. of dry pyridine. The mixture is stirred for 15 minutes at 0°-2° C. and then poured into 100 ml. of pH 2 phosphoric acid buffer. The methylene chloride phase is washed with water and sodium bicarbonate solution, dried over anhydrous sodium sulfate and evaporated. The product is chromatographed over 50 g. of silica gel with 5% ethylacetate-chloroform as eluant, affording benzhydryl 7-carbamoylmethoxy-7-(2-thienylacetamido) cephalosporanate.

D. Sodium 7-carbamoylmethoxy-7-(2-thienylacetamido)cephalosporanate

A mixture of 0.5 g. of benzhydryl 7-carbamoylmethoxy-7-(2-thienylacetamido)cephalosporanate in 3 ml. of anisole and 7 ml. of trifluoroacetic acid is stirred at 0° C. for 10 minutes. Excess anisole and trifluoroacetic acid are rapidly evaporated on a vacuum pump. The residue is taken up in 40 ml. of water and 40 ml. of methylene chloride and the mixture vigorously stirred as the pH is adjusted to 6.5 by the addition of sodium bicarbonate. The aqueous phase is separated, washed once with ether and lyophilized, giving sodium 7-carbamoylmethoxy-7-(2-thienylacetamido)cephalosporanate.

EXAMPLE 60

When benzhydryl 7-amino-7-(carbamoylmethoxy)cephalosporanate is acylated with phenylacetyl chloride, furylacetyl chloride or tetraazolylacetyl chloride in place of 2-thienylacetyl chloride, the corresponding sodium 7-phenylacetamido, 7-(2-furylacetamido) and 7-tetraazolylacetamido-7-(carbamoylmethoxy)cephalosporins are obtained.

EXAMPLE 61

A. Benzhydryl 7-azido-7-(benzhydryloxycarbonylmethoxy)cephalosporanate

A solution of the benzhydryl ester of glycolic acid is prepared by the addition of a solution of 2.5 g. of diphenyldiazomethane in 10 ml. of dioxane to a solution of 0.7 g. of glycolic acid in 5 ml. of dioxane. To this is added 4.5 g. of benzhydryl 7-azido-7-bromocephalosporanate, 1.6 g. of dry silver fluoroborate and 0.65 ml. of dry pyridine. The mixture is stirred for 3 hours at room temperature, then diluted with ether and filtered. The filtrate is washed with water, dried over anhydrous sodium sulfate an evaporated. The residue is chromatographed over 160 g. of silica gel, affording benzhydryl 7-azido-7-(benzhydryloxycarbonylmethoxy)cephalosporanate.

B. Benzhydryl 7-amino-7-(benzhydryloxycarbonylmethoxy)cephalosporanate

A solution of 3 g. of benzhydryl 7-azido-7-(benzhydryloxycarbonylmethoxy)cephalosporanate in 300 ml. of dry dioxane is vigorously stirred with 3 g. of platinum oxide under one atmosphere of hydrogen at room temperature for 1 hour. Fresh catalyst (3 g.) is added and the hydrogenation continued for 2 hours. The dioxane is removed under reduced pressure and the residue taken up in chloroform and filtered through 20 g. of silica gel packed in a sintered glass funnel. The silica gel is washed with 300 ml. of chloroform and the filtrate and washings combined and evaporated, leaving benzhydryl 7-amino-7-(benzhydryloxycarbonylmethoxy)cephalosporanate as a heavy oil.

C. Benzhydryl 7-(benzhydryloxycarbonylmethoxy)cephalosporanate

To a cooled solution of 0.4 g. of benzhydryl 7-amino-7-(benzhydryloxycarbonylmethoxy)cephalosporanate in 5 ml. of methylene chloride is added 0.25 g. of thienylacetyl chloride and 0.25 ml. of pyridine. The mixture is stirred for 15 minutes at 0°-3° C. and then poured over ice. The organic phase is washed successively with 2% phosphoric acid, water and aqueous sodium bicarbonate solution and finally dried over anhydrous sodium sulfate and evaporated. The residue is chromatographed over 25 g. of silica gel of the product eluted with 5% ethylacetate in methylene chloride, affording benzhydryl 7(benzhydryloxycarbonylmethoxy)-7-(2-thienylacetamido)cephalosporanate.

D. Disodium 7-(carboxymethoxy)-7-(2-thienylacetamido)cephalosporanate

To a solution of 0.4 g. of benzhydryl 7-(benzhydryloxycarbonylmethoxy)-7-(2-thienylacetamido)cephalosporanate in 3 ml. of anisole is added 5 ml. of trifluoroacetic acid. The mixture is kept for 8 minutes, then the excess anisole and trifluoroacetic acid are rapidly evaporated on a vacuum pump. The residue is stirred in a mixture of 20 ml. of methylene chloride and 20 ml. of water and the pH adjusted to 6.5 (glass electrode) with sodium bicarbonate. The aqueous phase is separated and extracted once with ether and then lyophilized, affording the disodium salt of 7-(carboxymethoxy)-7-(2-thienylacetamido)cephalosporanate.

EXAMPLE 62

When benzhydryl 7-amino-7-(benzhydryloxycarbonylmethoxy)cephalosporanate is reacted with 2-thianaphthene-2-acetyl chloride or monobenzhydryl phenylmalonyl chloride in place of thienyl chloride and the resulting reaction product is recovered and then deblocked following the procedures of Example 61, sodium 7-(2-carboxymethoxy)-7-(2-thianaphthene-2-acetamido)cephalosporanate and sodium 7-(2-carboxymethoxy)-7-(2-carboxy-2-phenylacetamido)cephalosporanate are obtained.

EXAMPLE 63

A. Benzhydryl 7-acetoxy-7-azidocephalosporanate

A mixture of 2.2 g. of benzhydryl 7-azido-7-bromocephalosporanate and 0.8 g. of silver acetate in 10 ml. of acetic acid is stirred at room temperature for 3 hours. The acetic acid is removed under reduced pressure and the residue taken up in methylene chloride and filtered. The filtrate is washed with sodium bicarbonate solution, then dried over sodium sulfate and evaporated. The residue is chromatographed over 80 g. of silica gel. Elution with chloroform yields benzhydryl 7-acetoxy-7-azidocephalosporanate.

B. Benzhydryl 7-amino-7-acetoxycephalosporanate 2 g. of benzhydryl 7-acetoxy-7-azidocephalosporanate in 200 ml. of dry dioxane is hydrogenated at room temperature and atmospheric pressure in the presence of 2 g. of platinum oxide for 1 hour. Fresh catalyst (2 g.)

is added and the hydrogenation continued for 2 hours. The solvent is evaporated and the residue is dissolved in ether and shaken with 10 ml. of powdered anhydrous magnesium sulfate and filtered through diatomaceous earth in a fritted glass funnel. The filtrate is evaporated, leaving benzhydryl 7-amino-7-acetoxycephalosporanate.

C. Benzhydryl 7-acetoxy-7-(2-thienylacetamido)cephalosporanate

To a cooled solution of 1.2 g. of benzhydryl 7-amino-7-acetoxycephalosporanate in 20 ml. of methylene chloride is added 0.8 ml. of thienylacetyl chloride and 0.8 ml. of pyridine. The mixture is stirred at 0° C. for 15 minutes then poured over ice. The organic phase is washed successively with 2% phosphoric acid solution, water and 2% sodium bicarbonate solution, dried over anhydrous sodium sulfate and evaporated. The residue is chromatographed on 50 g. of silica gel. Elution with chloroform yields benzhydryl 7-acetoxy-7-(2-thienylacetamido)cephalosporanate.

D. Sodium 7-acetoxy-7-(2-theinylacetamido)cephalosporanate

A solution of 2 g. of benzhydryl 7acetoxy-7-(2-thienylacetamido)cephalosporanate in 8 ml. of anisole and 16 ml. of trifluroroacetic acid is stirred at room temperature for 5 minutes. The excess anisole and trifluoroacetic acid are rapidly removed on the vacuum pump and the residue is taken up in 50 ml. of methylene chloride and extracted twice with sodium bicarbonate solution. The aqueous extract is cooled and overlayered with ethylacetate and the pH adjusted to 2.1 with dilute sulfuric acid. The ethylacetate layer is vigorously stirred with water as the pH is adjusted to 6.5 (glass electrode). Evaporation of the aqueous extract gives the sodium salt of 7-acetoxy-7-(2-thienylacetamido)cephalosporanate.

EXAMPLE 64

Sodium 3-hydroxymethyl-7-hydroxy-7-(2-thienylacetamido)-decephalosporanate 1.8 g. of sodium 7-acetoxy-7-(2-thienylacetamido)cephalosporanate is dissolved in 50 ml. of citrus acetylesterase solution heated in a water bath at 30° C. The pH is maintained at 6.6 by the addition of N sodium hydroxide solution under the control of a pH stat. After 8 hours 15 g. of sodium chloride is added, the solution is overlayered with 100 ml. of ethylacetate and the pH taken to 2.1 with hydrochloric acid. The mixture is centrifuged and the supernatant ethylacetate separated. The ethylacetate extract is vigorously stirred with water as the pH is taken to 7 with sodium bicarbonate solution. The aqueous phase is separated and lyophilized, giving sodium 3-hydroxymethyl-7-hydroxy-7-(2-thienylacetamido)decephalosporanate.

EXAMPLE 65

3-Carbamoyloxymethyl-7-carbamoyloxy-7-(2-thienylacetamido)decephalosporanic acid To 0.4 g. of sodium 3-hydroxymethyl-7-hydroxy-7(2-thienylacetamido)decephalosporanate suspended in 10 ml. of acetonitrile cooled to 0° C. is added 0.6 ml. of chlorosulfonyl isocyanate. The reaction mixture is stirred for 2 hours and then evaporated to dryness. The residue is taken up in a mixture of 20 ml. of ethylacetate and 20 ml. of phosphate buffer and the pH adjusted to 1.6. The mixture is stirred for 3 hours at room temperature and the pH adjusted to 8 and the aqueous phase separated. The organic phase is extracted with pH 8 phosphate buffer. The combined aqueous phase is taken to pH 2 with hydrochloric acid and extracted twice with ethylacetate. The ethylacetate extract is dried over anhydrous sodium sulfate and evaporated and the residue washed with ether to give 3-carbamoyloxymethyl-7-carbamoyloxy-7-(2-thienylacetamido)decephalosporanic acid as a yellow solid.

Following the same procedures and using other acylating agents in place of thienylacetyl chloride, other 7-acylamido analogs of the products of Examples 63, 64 and 65 are obtained.

EXAMPLE 66

A. Benzhydryl 7-azido-7-phenoxycephalosporanate

To a solution of 2.3 g. of benzhydryl 7-azido-7-bromocephalosporanate in 10 ml. of benzene is added 6 g. of phenol followed by 0.82 g. of dry silver fluoroborate and 0.33 ml. of dry pyridine. The mixture is stirred at 23° C. for 6 hours, then filtered, and the residue washed with benzene. The combined filtrate and washings is washed with pH 2 phosphoric acid buffer and with aqueous sodium bicarbonate and then dried over sodium sulfate and evaporated. The residue is placed on a high vacuum pump overnight to remove excess phenol, then chromatographed on 100 g. of silica gel. Elution with methylene chloride gives benzhydryl 7-azido-7-phenoxycephalosporanate as a viscous oil.

B. Benzhydryl 7amino-7-phenoxycephalosporanate

A solution of 3 g. of benzhydryl 7-azido-7-phenoxycephalosporanate in 300 ml. of dry dioxane is hydrogenated in the presence of 3 g. of platinum oxide at room temperature and atmospheric pressure for 1 hour. Fresh catalyst (3 g.) is added and the hydrogenation continued for 2 hours. The dioxane is removed under reduced pressure and the residue is taken up in chloroform and filtered through 20 g. of silica gel packed in a fritted glass funnel. The cake is washed with 500 ml. of chloroform and the combined washings and filtrate are evaporated, leaving benzhydryl 7-amino-7-phenoxycephalosporanate.

C. Benzhydryl 7-phenoxy-7-(5-thiazolylacetamido)cephalosporanate

A solution of 2.3 g. of benzhydryl 7-amino-7-phenoxycephalosporanate in 25 ml. of methanol is cooled in an ice bath and to it is added with magnetic stirring 1.8 ml. of dry pyridine followed immediately by a solution of 1.5 g. of 5-thiazolylacetyl chloride in 4 ml. of methylene chloride. The mixture is stirred at 2° C. for 15 minutes, then extracted with pH 2 phosphoric acid buffer and water. The organic phase is dried over anhydrous sodium sulfate and evaporated. The residue is chromatographed on 100 g. of silica gel. Elution with chloroform gives benzhydryl 7-phenoxy-7-(5-thiazolylacetamido)-cephalosporanate.

D. 7-Phenoxy-7-(5-thiazolylacetamido)cephalosporanic acid

A solution of 2 g. of benzhydryl 7-phenoxy-7-(5-thiazolylacetamido)cephalosporanate in 8 ml. of anisole and 16 ml. of trifluoroacetic acid is stirred at room temperature for 5 minutes. The excess anisole and trifluoroacetic acid are rapidly removed under high vacuum and the residue taken up in 50 ml. of methylene chloride and extracted twice with sodium bicarbonate solution. The aqueous extract is cooled and overlayered with ethylacetate and the pH adjusted to 2.1 with dilute sulfuric acid. The ethylacetate layer is dried over sodium sulfate and evaporated, leaving 7-phenoxy-7-(5-thiazolylacetamido)cephalosporanic acid.

EXAMPLE 67

A. Benzhydryl 7-chloro-7-(t-butoxycarbonylthio)cephalosporanate t-Butoxycarbonylsulfenyl chloride is prepared by the addition of t-butanol to chlorocarbonylsulfenyl chloride in 1:1 molar ratio at 30° C. 10 MMoles of t-butoxycarbonylsulfenyl chloride is dissolved in 50 ml. $CH_2Cl_2$ and added dropwise to a solution of 10 mmoles of benzhydryl 7-diazocephalosporanate in 50 ml. $CH_2Cl_2$ cooled to $-40°$ C. in a dry ice bath. The addition is carried out over 15 minutes and at the end the temperature is allowed to rise to $-10°$ C. to $-5°$ C. gradually. Saturated sodium bicarbonate is added and the organic layer separated and washed with water. After drying over sodium sulfate the solvent is removed in vacuo. The crude product is evaluated by IR (loss of diazo 2100 cm$^{-1}$, presence of β-lactam 1790 cm$^{-1}$, presence of ester bands 1745 cm$^{-1}$). It is purified further by TLC to give benzhydryl 7-chloro-7-(t-butoxycarbonylthio)cephalosporanate in purer form.

B. Benzhydryl 7-azido-7-(t-butoxycarbonylthio)cephalosporanate

To a solution of 5 mmoles lithium azide in 5 ml. of DMF is added 5 mmoles benzhydryl 7-chloro-7-(t-butoxycarbonylthio)cephalosporanate. The solution is heated at 40° C. to 70° C. for from 3-6 minutes, then quenched into ice water. The DMF-water solution is extracted with 2×25 ml. CHCl$_3$ washed with saturated sodium bicarbonate solution, 2×50 ml. H$_2$O and the organic layer is dried over Na$_2$SO$_4$. Evaporation of the solvent gives the crude product as a mixture of isomers which can be purified further by conventional chromatography on silica gel. The two isomers are evaluated by IR (presence of β-lactam 1790 cm$^{-1}$, presence of azide band 2100 cm$^{-1}$, ester bands 1745 cm$^{-1}$).

C. Benzhydryl 7-(2-thienylacetamido)-7-(t-butoxycarbonylthio)cephalosporanate

The mixture of isomers of 7-azido compound prepared above (5 mmoles) is reduced with 3 g. Bolhoffer catalyst (10% Pd/C) at 40 psi at room temperature in 50 ml. ethylacetate in the presence of 5 mmoles of pyridine and 5 mmoles of thienylacetic anhydride. At the end of 1 hour the catalyst is filtered and the ethylacetate extracted with 2×20 ml. 1 N HCl and 2×50 ml. with 10% sodium bicarbonate, 2×50 ml. H$_2$O. The ethylacetate is dried over Na$_2$SO$_4$ and the solvent removed in vacuo. The crude product, a mixture of isomers, is evaluated by IR (presence of β-lactam 1790 cm$^{-1}$, loss of azide 2100 cm$^{-1}$, appearance of new amide bands 1680 cm$^{-1}$).

D. 7-Thienylacetamido-7-mercaptocephalosporanic acid

5 Mmoles thienylacetamido benzhydryl ester prepared above is dissolved in 10 ml. of anisole and cooled to 0° C. To this is added 20 ml. of trifluoroacetic acid. The solution is kept at 0° C. and stirred for 1-3 hours. The excess trifluoroacetic acid and anisole are removed by evaporation with a vacuum pump. The product is evaluated by IR (appearance of carboxyl 1710 cm$^{-1}$, β-lactam 1790 cm$^{-1}$ loss of ester band). The compound absorbs in the UV spectrum λmax. 260-265 ε (8000).

EXAMPLE 68

A. Benzhydryl 7-chloro-7-(carbamoylthio)cephalosporanate

Carbamoylsulfenyl chloride (10 mmoles) formed by the action of 20 mmole of ammonia on chlorocarbonylsulfenyl chloride at $-70°$ C. in 50 ml. CH$_2$Cl$_2$ is added dropwise to a solution of 10 mmoles of benzhydryl 7-diazocephalosporanate at $-40°$ C. At the end of the addition the temperature is permitted to rise slowly to $-5°$ C. Saturated sodium bicarbonate solution (50 ml.) is added and the organic layer separated, washed with water and dried over sodium sulfate. The solvent is removed in vacuo to yield a gum. The crude product is evaluated by IR (absence of diazo 2100 cm$^{-1}$, presence of β-lactam, new carbamoyl absorption 1680 cm$^{-1}$). The crude product can be purified by preparative TLC.

B. Benzhydryl 7-azido-7-(carbamoylthio)cephalosporanate

The reaction is carried out in the same manner as in the preparation of benzhydryl 7-azido-7-(t-butoxycarbonylthio)cephalosporanate. The crude product, a mixture of isomers, is evaluated by IR (new azide band 2100 cm$^{-1}$, β-lactam 1790 cm$^{-1}$ and carbamoyl group 1680 cm$^{-1}$).

C. Benzhydryl 7-thienylacetamido-7-(carbamoylthio)cephalosporanate

Reduction-acylation is carried out in the same manner as that for benzhydryl 7-azido-7-(t-butoxycarbonylthio)cephalosporanate. The crude product is evaluated by IR (loss of azide 2100 cm$^{-1}$, presence of β-lactam, new amide at 1680 cm$^{-1}$). It may be purified further by preparative TLC or column chromatography.

D. 7-Thienylacetamido-7-(carbamoylthio)cephalosporanic acid

Removal of the benzhydryl ester is accomplished in the same manner as for the 7-thienylacetamido-7-butoxycarbonylthiocephalosporanate. The crude product is evaluated by IR (ester band disappears at 1740 cm$^{-1}$, acid band appears at 1710 cm$^{-1}$) and UV spectrum λmax. 260–265 ε (8000).

EXAMPLE 69

A. Benzhydryl 7-bromo-7-methylthiocephalosporanate

10 Mmoles of benzhydryl 7-diazocephalosporanate dissolved in 100 ml. methylene chloride is cooled to −40° C. under N$_2$. To this is added 12 mmoles methylsulfenyl bromide in 100 ml. CH$_2$Cl$_2$ dropwise with vigorous stirring. Nitrogen evolution is immediate. After addition of the reagent (15 minutes) at −40° C. the mixture is allowed to warm gradually to −5° C. Saturated sodium bicarbonate solution is added and the organic layer separated and washed with water. After drying over sodium sulfate the solvent is removed at room temperature in vacuo. The crude product is evaluated by IR (Loss of diazo 2100 cm$^{-1}$, presence of β-lactam 1790 cm$^{-1}$) and positive Beilstein test for halogen. The crude product can be further purified by preparative TLC or column chromatography.

B. Benzhydryl 7-azido-7-methylthiocephalosporanate

10 Mmoles of the 7-bromo-7-methylthio compound are heated for 4 minutes at 68° C. in 60 ml. DMF which contains 10 mmoles lithium azide. The solution is diluted with 300 ml. water and extracted 2×50 ml. chloroform. The chloroform layer is washed 3×100 ml. water and dried over anhydrous sodium sulfate. The crude product is evaluated by IR (azide 2100 cm$^{-1}$, β-lactam 1790 cm$^{-1}$) and negative Beilstein test. The crude product is further purified by preparative TLC or column chromatography.

C. Benzhydryl 7-(2-thienylacetamido)-7-methylthiocephalosporanate

10 Mmoles of 7-azido-7-methylthio compound are dissolved in 50 ml. ethylacetate and 10 mmoles of thienylacetic anhydride, 0.1 ml. pyridine and 800 mg. Bolhoffer catalyst are added. The mixture is hydrogenated at room temperature for 1 hour. The catalyst is removed by filtration and the residue evaporated to a glass in vacuo. Infrared analysis of the crude product shows no azide left 2100 cm$^{-1}$, appearance of a new amide 1680 cm$^{-1}$ and β-lactam 1790 cm$^{-1}$. The crude product can be purified further by preparative TLC or column chromatography.

D. 7-Thienylacetamido-7-methylthiocephalosporanic acid

1 Mmole of the 7-(2-thienylacetamido)-7-methylthio compound (mixture of isomers) is dissolved in 10 ml. of anisole and cooled to 0° C. To the solution is added 15 ml. trifluoroacetic acid cooled to 0° C. and the mixture is aged at room temperature for 1 hour. The excess trifluoroacetic acid and anisole are removed by evaporation in vacuo and the residue flushed twice with chloroform and evaporated to dryness. The crude product is evaluated by IR (loss of ester at 1740 cm$^{-1}$ and the appearance of carboxyl at 1710 cm$^{-1}$) and UV λmax. 260–262 ε (8000).

EXAMPLE 70

7-(2-Thienylacetamido)-7-acetylthiocephalosporanic acid

10 Mmoles of 7-(2-thienylacetamido)-7-mercapto compound are dissolved in 50 ml. pyridine at 0° C. and 10 mmoles of acetyl chloride added dropwise over 5 minutes. The mixture is quenched in ice water and the pH adjusted to 8 with sodium hydroxide. The pyridine is removed by extraction with ether and the aqueous layer lyophilized. The crude product is evaluated by IR (new carbonyl 1740 cm$^{-1}$, β-lactam 1790 cm$^{-1}$) and UV spectrum λmax. 260–265 ε (8000).

EXAMPLE 71

7-(2-Thienylacetamido)-7-methylsulfinylcephalosporanic acid

10 Mmoles of the 7-(2-thienylacetamido)-7-Methylthio compound is dissolved in 50 ml. tetrahydrofuran at 0° C. and treated with 10 mmoles of peracetic acid. The solution is stirred at 0° C. for 30 minutes. Sodium thiosulfate solution is added until a negative test with KI paper. 100 ml. of saturated sodium chloride is added and the organic layer separated and dried over sodium sulfate. The solvent is removed in vacuo and the product evaluated by IR analysis (β-lactam 1790, sulfinyl bands 1060 cm$^{-1}$, 1150 cm$^{-1}$) and UV spectrum λmax. 260–265.

EXAMPLE 72

Sodium 3-hydroxymethyl-7-acetamido-7-methoxydecephalosporanate

Treatment of 7-acetamido-7-methoxycephalosporanic acid in aqueous solution at pH 6 with acetylesterase obtained from orange peels results in the formation of 3-hydroxymethyl-7-acetamido-7-methoxydecephalosporanic acid which is recovered as the sodium salt in accordance with procedures known in this art.

EXAMPLE 73

Following the procedure described in Example 72 above with other 7-oxy and 7-thio substituted cephalosporins prepared as described in the foregoing examples, the following 3-hydroxymethyldecephalosporanic acids are prepared:

Sodium 3-hydroxymethyl-7-methoxy-7-(2-thienylacetamido)decephalosporanate
Sodium 3-hydroxymethyl-7-methoxy-7-(2-thianaphthene)decephalosporanate
Sodium 3-hydroxymethyl-7-methoxy-7-(p-guanidinophenylacetamido)decephalosporanate
Sodium 3-hydroxymethyl-7-methoxy-7-(2-furylacetamido)decephalosporanate
Sodium 3-hydroxymethyl-7-methoxy-7-tetraazolylacetamidodecephalosporanate
Sodium 3-hydroxymethyl-7-methoxy-7-(D-α-amino-2-phenylacetamido)decephalosporanate
Sodium 3-hydroxymethyl-7-methoxy-7-(2-carboxy-2-phenylacetamido)decephalosporanate
Sodium 3-hydroxymethyl-7-benzyloxy-7-phenylacetamidodecephalosporanate Sodium 3-hydroxymethyl-7-ethoxy-7-(2-thienylacetamido)decephalosporanate Sodium 3-hydroxymethyl-7-methylthio-7-phenylacetamidodecephalosporanate Sodium 3-hydroxymethyl-7-mercapto-7-(2-thienylacetamido)decephalosporanate Sodium 3-hydroxymethyl-7-carbamoylthio-7-(2-thienylacetamido)decephalosporanate Sodium 3-hydroxymethyl-7-(2-thienylacetamido)-7-(aminocarbonyloxy)decephalosporanate Sodium 3-hydroxymethyl-7-(2-thienylacetamido)-7-(methoxycarbonyloxy)decephalosporanate Sodium 3-hydroxymethyl-7-(2-thienylacetamido)-7-(aminosulfonyloxy)decephalosporanate

EXAMPLE 74

Sodium 3-(N,N-dimethylcarbamoyloxymethyl)-7-methoxy-7-(2-thienylacetamido)decephalosporanate An excess of phosgene is bubbled into a stirred solution of 0.5 g. of 3-hydroxymethyl-7-methoxy-7-(2-thienylacetamido)cephalosporanic acid in 100 ml. of methylene chloride and the resulting mixture is allowed to stand overnight at room temperature. The excess phosgene is removed by bubbling dry nitrogen through the solution for 3 hours and the resulting solution is evaporated under reduced pressure.

To a solution of 0.45 g. of the residue in 50 ml. of methylene chloride cooled in an ice bath is added 0.2 g. of dimethylamine. The mixture is stirred for an hour at room temperature and the excess amine hydrochloride is removed by filtration. To the resulting filtrate is added a solution of 0.1 g. of sodium bicarbonate in 20 ml. of water. The mixture is stirred for 1 hour at room temperature and the aqueous layer is separated, washed twice with methylene chloride, and then freeze dried to afford a mixture containing sodium 3-(N,N-dimethylcarbamoyloxymethyl)-7-methoxy-7-(2-thienylacetamido)decephalosporanate.

In the same way the other 3-hydroxymethyldecephalosporanic acid compounds obtained as described in Example 73 are converted to the corresponding 3-(N,N-dimethylcarbamoyloxymethyl)decephalosporanic acid salts.

EXAMPLE 75

Following the procedures described in Example 74 using an equivalent amount of piperidine, pyrrolidine or morpholine in place of dimethylamine, the following products are obtained:

Sodium 3-(piperidinocarbonyloxymethyl)-7-methoxy-7-(2-thienylacetamido)decephalosporanate Sodium 3-(pyrrolidinylcarbonyloxymethyl)-7-methoxy-7-(2-thienylacetamido)decephalosporanate Sodium 3-(morpholinocarbonyloxymethyl)-7-methoxy-7-(2-thienylacetamido)decephalosporanate Sodium 3-(piperidinocarbonyloxymethyl)-7-methoxy-7-methylthio-7-(2-thienylacetamido)decephalosporanate

EXAMPLE 76

Sodium 3-(N-methylcarbamoyloxymethyl)-7-methoxy-7-(2-thienylacetamido)decephalosporanate Sodium 3-hydroxymethyl-7-methoxy-7-(2-thienylacetamido)decephalosporanate (250 mg.) is suspended in dimethylformamide (5 ml.). To this mixture is added with agitation 0.2 ml. of trimethylamine and 0.7 ml. of methylisocyanate, and the resulting reaction mixture is allowed to stand for ½ hour and then evaporated to dryness under reduced pressure. The resulting residue is taken up in 10 ml. of ethylacetate and 10 ml. of 0.1 N phosphate buffer. The pH of the aqueous layer is adjusted to pH 1.6 and the mixture stirred for 2 hours at room temperature. The pH is then adjusted to about 8 with aqueous tripotassium phosphate, and the aqueous phase is separated. The organic phase is reextracted with 10 ml. of pH 8 phosphate buffer. The combined aqueous phase is adjusted to pH 2.1 with hydrochloric acid and extracted twice with ethylacetate. The ethylacetate extracts are treated with 10 ml. of water containing 0.15 g. of sodium bicarbonate. Separation and freeze drying of the aqueous phase affords sodium 3-(N-methylcarbamoyloxymethyl)-7-methoxy-7-(2-thienylacetamido)decephalosporanate.

In the same manner, the 3-hydroxymethylcephalosporanates prepared as described in Example 73 are converted to the corresponding 3-(N-methylcarbamoyloxymethyl) compounds.

EXAMPLES 77-86

Following the procedure of Example 76 using other isocyanates, the new 3-hydroxymethyl-7-oxy substituted decephalosporanic compounds are converted to the corresponding N-substituted 3-carbamoyloxymethyl compounds in accordance with the following equation:

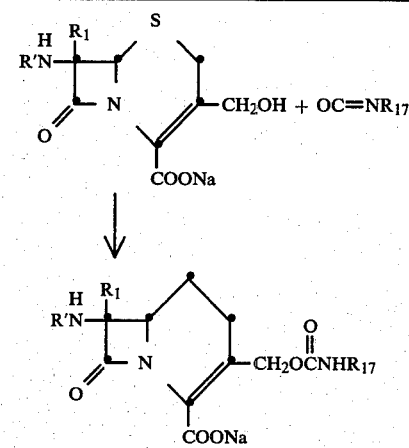

| Example | OC=NR$_{17}$ | R$_{17}$ |
|---|---|---|
| 77 | OC=NCH$_2$CH$_2$Cl | —CH$_2$CH$_2$Cl |
| 78 | OC=NCH$_2$Cl | —CH$_2$Cl |
| 79 | OC=NC(CH$_3$)$_3$ | —C(CH$_3$)$_3$ |
| 80 | OC=NC$_2$H$_5$ | —C$_2$H$_5$ |
| 81 | OC=NC(CH$_3$)$_2$CH$_2$Cl | —C(CH$_3$)$_2$CHCl |
| 82 | OC=NCOOC$_2$H$_5$ | —COOC$_2$H$_5$ |

-continued

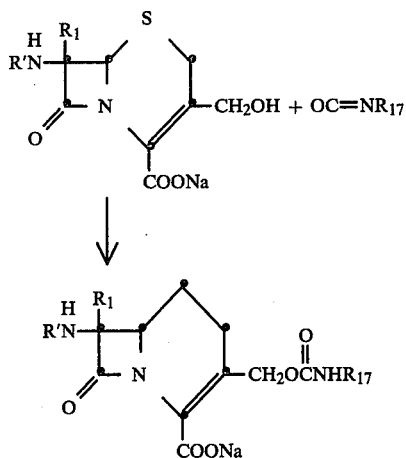

| Example | OC=NR$_{17}$ | R$_{17}$ |
|---|---|---|
| 83 | OC=NSO$_2$—⟨furyl⟩—CH$_3$ | —SO$_2$—⟨furyl⟩—CH$_3$ |
| 84 | OC=N—⟨furyl⟩ | ⟨furyl⟩ |
| 85 | OC=NCH—(⟨furyl⟩)$_2$ | —CH—(⟨furyl⟩)$_2$ |
| 86 | OC=N—⟨furyl⟩—SO$_3$— | —⟨furyl⟩—SO$_3$— | wherein R' and R$_1$ represent the specific substituents shown in Example 73.

EXAMPLE 87

3-Pyridiniummethyl-7-methoxy-7-(2-furylacetamido)-decephalosporanic acid

A solution of 1 g. of sodium 7-methoxy-7-(2-furylacetamido)cephalosporanate in 5 ml. of water is brought to pH 2.5 with dilute HCl. Pyridine (8 ml.) is added and the solution is heated at 70° C. for 3½ hours. The resulting reaction mixture is lyophilized and the residue is dissolved in water and passed through a polystyrene trimethylbenzylammonium anion exchange resin (43% water). The resulting resin adsorbate is eluted with water and selected fractions are lyophilized to afford substantially pure 3-pyridiniummethyl-7-methoxy-7-(2-furylacetamido)decephalosporanic acid.

When an equivalent amount of trimethylamine or triethylamine is substituted for the pyridine in the foregoing process and otherwise following the described procedure, the corresponding 3-(trimethylammonium-methyl) and 3-(triethylammoniummethyl) compounds are obtained.

Similarly, when 3-fluoropyridine, 4-trifluoromethyl-pyridine, 3-carboxypyridine, 4-carbamoylpyridine, 4-(N-methylcarbamoyl)pyridine, 4-(N,N-dimethylcarbamoyl)pyridine, 3-(carboxymethyl)pyridine, 2-methyl-pyridine, 3-(hydroxymethyl)pyridine, 3-sulfopyridine or 3-cyanopyridine are substituted for the pyridine in the described procedure, the corresponding 3- or 4-substituted pyridiniummethyl compounds are obtained.

EXAMPLE 88

3-Thiouroniummethyl-7-methoxy-7-phenylacetamidodecephalosporanate

A solution of 1 g. of 7-methoxy-7-phenylacetamidocephalosporanic acid and 1 g. of thiourea in 25 ml. of water is maintained at 37° C. for 5 days. Acetone (200 ml.) is added and the mixture is cooled in an ice bath. The cooled solution is filtered to recover the precipitated product which is then fractionated through a polystyrene trimethylbenzylammonium anion exchange resin (43% water). Selected fractions are lyophilized and the crude product is then recrystallized from a mixture of methanol and water to afford 3-thiouroniummethyl-7-methoxy-7-phenylacetamidodecephalosporanate.

Upon substituting an equivalent amount of N-methylthiourea, N-ethylthiourea, N,N-dimethylthiourea or N,N-dipropylthiourea in the foregoing process in place of thiourea in the foreoing process and following the procedure described therein, the corresponding N-substituted isothiouronium compounds are obtained.

EXAMPLE 89

3-(Ethylthiomethyl)-7-methoxy-7-(2-thienylacetamido)decephalosporanic acid

A mixture of 7-methoxy-7-(2-thienylacetamido)cephalosporanic acid (0.65 g.) and ethanethiol (0.37 ml.) in 10 ml. of 50% aqueous acetone is stirred at room temperature and a 10% aqueous sodium hydroxide solution (2 ml.) is added with stirring. The resulting reaction mixture is then heated in a sealed glass tube for 100 hours and the resulting mixture is concentrated under reduced pressure. The residue is dissolved in water and fractionated through a polystyrene trimethylbenzylammonium anion exchange resin (43% water). Selected fractions are combined and lyophilized to afford 3-(ethylthiomethyl)-7-methoxy-7-(2-thienylacetamido)-decephalosporanic acid.

Upon substituting an equivalent amount of methanethiol, propanethiol, pyridine-2-thiol, pyridine-3-thiol, pyridine-4-thiol, benzothiazole-2-thiol, 4-methylpyrimidine-2-thiol or 2-methyl-3,4-thiadiazole-5-thiol for the ethanethiol in the foregoing process and otherwise following the described procedure, there is thus obtained the 3-(methylthiolmethyl), 3-(propylthiomethyl), 3-(2-pyridylthiomethyl), 3-(3-pyridylthiomethyl), 3-(4-pyridylthiomethyl), 3-(2-benzothiazolylthiomethyl), 3-(4-methylpyrimidin-2-ylthiomethyl), and 3-(2-methyl-3,4-thiadiazol-5-ylthiomethyl) substituted 7-methoxy-7-(2-thienylacetamido)decephalosporanic acids, respectively.

EXAMPLE 90

3-(N,N-dimethylthiocarbamoylthiomethyl)-7-methoxy-7-tetraazolylacetamidodecephalosporanic acid A solution of 7-methoxy-7-tetraazolylacetamidocephalosporanic acid (6.8 g.) and sodium N,N-dimethyldithiocarbamate (2.8 g.) in 60 ml. of water is heated to 50° C. for 24 hours. The product is lyophilized and then fractionated through a polystyrene trimethylbenzylammonium anion exchange resin (43% water). Selected fractions are then lyophilized to afford 3-(N,N-dimethylthiocarbamoylthiomethyl)-7-methoxy-7-tetraazolylacetamidodecephalosporanic acid.

Upon substituting an equivalent amount of the following reactants: sodium N-methyldithiocarbamate, sodium N,N-diethyldithiocarbamate, sodium N,N-di-n-propyldithiocarbamate, sodium N-methyl-N-(2-dimethylaminoethyl)-dithiocarbamate, sodium N-ethyl-n-(2-diethylaminoethyl)dithiocarbamate, sodium N-(2-di-n-propylaminoethyl)dithiocarbamate, sodium N-methyl-N-(2-morpholinoethyl)eithiocarbamate, sodium N-methyl-N-(3-diethylaminopropyl)dithiocarbamate, sodium N-phenyl-N-(2-methylaminoethyl)dithiocarbamate, sodium N,N-tetramethylenedithiocarbamate, sodium N,N-pentamethylenedithiocarbamate, sodium N,N-bis-(2-hydroxyethyl)dithiocarbamate or the sodium salt of 4-methyl-piperazinodithiocarboxylate for the sodium dimethyldithiocarbamate in the foregoing process, but otherwise following the described procedure, there is thus obtained the corresponding 3-(N-methylthiocarbamoylthiomethyl), 3-(N,N-diethylthiocarbamoylthiomethyl), 3-(N,N-di-n-propylthiocarbamoylthiomethyl), 3-[N-methyl-N-(2-dimethylaminoethyl)thiocarbamoylthiomethyl], 3-[N-ethyl-N-(2-diethylaminoethyl)thiocarbamoylthiomethyl], 3-[N-(2-di-n-propylaminoethyl)thiocarbamoylthiomethyl], 3-[N-methyl-N-(2-morpholinoethyl)thiocarbamoylthiomethyl], 3-[N-methyl-N-(3-diethylaminopropyl)thiocarbamoylthiomethyl], 3-[N-phenyl-N-(2-methylaminoethyl)thiocarbamoylthiomethyl], 3-(N,N-tetramethylene)thiocarbamoylthiomethyl, 3-(N,N-pentamethylene)thiocarbamoylthiomethyl, 3-[N,N-bis-(2-hydroxyethyl)thiocarbamoylthiomethyl], and 3-(4-methylpiperazino)thiocarbamoylthiomethyl 7-methoxy-7-tetraazolylacetamidodecephalosporanic acids.

In the same way other 7-substituted cephalosporins produced as described in the foregoing examples are converted to the corresponding 3-substituted compounds as described above.

EXAMPLE 91

3-(Benzoylthiomethyl)-7-methoxy-7-(2-carboxy-3-phenylacetamido)decephalosporanic acid A mixture of 7-methoxy-7-(2-carboxy-2-phenylacetamido)cephalosporanic acid (0.654 g.), sodium bicarbonate (0.504 g.) and thiobenzoic acid (0.414 g.) in 5.0 ml. of water is heated at 50° C. overnight under a nitrogen atmosphere. The product is precipitated by the addition of acetone and crystallized from a mixture of alcohol and water to afford 3-(benzoylthiomethyl)-7-methoxy-7-(2-carboxy-3-phenylacetamido)-decephalosporanic acid.

Upon substituting an equivalent amount of potassium ethyl xanthate, potassium n-propyl xanthate, potassium isopropyl xanthate, potassium n-butyl xanthate, potassium n-hexyl xanthate, potassium cyclopentyl xanthate and potassium cyclohexyl xanthate for the thiobenzoic acid in the foregoing process and otherwise following the described procedure, the corresponding 3-(ethoxythiocarbonylthiomethyl), 3-(n-propoxythiocarbonylthiomethyl), 3-(isopropoxythiocarbonylthiomethyl), 3-(n-butoxythiocarbonylthiomethyl), 3-(n-hexyloxythiocarbonylthiomethyl), 3-(cyclopentyloxythiocarbonylthiomethyl), and 3-(cyclohexyloxythiocarbonylthiomethyl) 7-methoxy-7-(2-carboxy-2-phenylacetamido)-decephalosporanic acids are obtained.

In like manner, the other 7-substituted cephalosporins produced as described in the foregoing examples can be converted to the corresponding 3-substituted compounds.

EXAMPLE 92

3-(Toluene-p-sulfonylmethyl)-7-methoxy-7-(2-thienylacetamido)decephalosporanic acid A mixture of 7-methoxy-7-(2-thienylacetamido)cephalosporanic acid (0.654 g.) and sodium toluene-p-sulfinate (1.0 g.) in 5.0 ml. of water is heated at 50° C. for 24 hours. The mixture is concentrated in vacuo and crystallized from a mixture of methanol and water to afford 3-(toluene-p-sulfonylmethyl)-7-methoxy-7-(2-thienylacetamido)decephalosporanic acid.

EXAMPLE 93

3-(Azidomethyl)-7-methoxy-7-(2-furylacetamido)-decephalosporanic acid

A mixture of 7-methoxy-7-(2-furylacetamido)cephalosporanic acid (2.0 g.) and sodium azide (1.0 g.) are dissolved in 10 ml. water and heated at 50° C. overnight. The mixture is then lyophilized to afford crude 3-(azidomethyl)-7-methoxy-7-(2-furylacetamido)-decephalosporanic acid.

Alternatively, in lieu of treating 7-methoxy-7-(2-furylacetamido)cephalosporanic acid with sodium azide, it is possible to substitute 3-(carbamoyloxymethyl)-7-(2-furylacetamido)-7-methoxydecephalosporanic acid therefor in an otherwise analogous process to afford an identical product. The following example illustrates this method of preparation:

3-(Carbamoyloxymethyl)-7-(2-furylacetamido)-7-methoxydecephalosporanic acid (100 mg.) in a 0.5 M phosphate buffer solution (5 ml., obtained by adding 3.5 g. of sodium dihydrogen phosphate and 3.4 g. of disodium phosphate in 100 ml. of water followed by the addition of sufficient hydrochloric acid to bring the pH to 5) is heated in the presence of sodium azide (20 mg.) at 95° C. for 8 minutes. Preparative thin layer chromatography gives 20 mg. of 3-(azidomethyl)-7-methoxy-7-(2-furylacetamido)decephalosporanic acid as indicated by infrared and nuclear magnetic resonance identification. Treatment of this material with trifluoroacetic acid (1.0 ml.) at 0° C. for 5 minutes followed by quenching in a large volume of ether and evaporation of the solvent affords 15 mg. of 3-(azidomethyl)-7-methoxy-7-(2-furylacetamido)decephalosporanic acid.

EXAMPLE 94

3-(2,4-Dihydroxybenzyl)-7-methylthio-7-phenylacetamidodecephalosporanic acid

A mixture of 7-methylthio-7-phenylacetamidocephalosporanic acid (0.654 g.), resorcinol (1.1 g.) and water (10 ml.) are heated at 50° C. for 2 days. The reaction mixture is then lyophilized to afford 3-(2,4-dihydroxybenzyl)-7-methylthio-7-phenylacetamidodecephalosporanic acid.

EXAMPLE 95

3-(N-methylindol-3-yl)-7-benzyloxy-7-phenylacetamidodecephalosporanic acid

A solution of N-methylindole (0.655 g.) in acetone (5 ml.) is added to a solution of 7-benzyloxy-7-phenylacetamidocephalosporanic acid (0.654 g.) in water (5 ml.) at 50° C. The mixture is heated for 48 hours and the solvent is then removed in vacuo and the residue triturated with ether to afford 3-(N-methylindol-3-yl)-7-benzyloxy-7-phenylacetamidodecephalosporanic acid.

EXAMPLE 96

3-Methyl-7-methoxy-7-(2-thienylacetamido)decephalosporanic acid

A 10% palladium-on-charcoal catalyst is suspended in water (80 ml.) and treated with hydrogen. The catalyst is then filtered and suspended again in water (50 ml.) and to this mixture (2.67 g.) is added sodium 7-methoxy-7-(2-thienylacetamido)cephalosporanate (1.0 g.) in water (10 ml.). The resulting mixture is shaken for 22 hours at room temperature.

The catalyst is removed by filtration and washed once with water (50 ml.). The combined wash and filtrate is then concentrated to dryness to afford 3-methyl-7-methoxy-7-(2-thienylacetamido)decephalosporanic acid.

EXAMPLE 97

3-(Amidinothiomethyl)-7-methoxy-7-(2-thienylacetamido)decephalosporanic acid

7-Methoxy-7-(2-thienylacetamido)cephalosporanic acid (100 mg.) is heated for 8 minutes with thiourea (26 mg.) at 95° C. in a 0.5 M phosphate buffer solution (5 ml., obtained by adding 3.5 g. of sodium dihydrogen phosphate and 3.4 g. of disodium phosphate in 100 ml. of water followed by the addition of sufficient hydrochloric acid to bring the pH to 5). Electrophoresis of the solution at pH 7 shows the thiouronium compound as a non-mobile entity. The mixture is purified by absorption on a polystyrene nuclear sulfonic acid cation exchange resin on the hydrogen cycle (Dowex 50) to remove the phosphate buffer. Elution is carried out using a 0.1 N pyridine solution. The pH is adjusted to 8 with 1 N sodium hydroxide and evaporated under vacuum to remove residual pyridine. Lyophilization gives the title compound.

EXAMPLE 98

3-(4-Methylthiazol-2-ylmercaptomethyl)-7-methylthio-7-(2-thienylacetamido)decephalosporanic acid 7-Methylthio-7-(2-thienylacetamido)cephalosporanic acid (100 mg.) in 5 ml. of a pH 7 buffer (a 0.5 M solution of a mixture of 3.5 g. sodium dihydrogen phosphate and 3.4 g. of disodium phosphate in 100 ml. of water) containing 2-mercapto-4-methylthiazole (50 mg.) is heated at 95° C. for 8 minutes. The resulting reaction mixture contains the title compound.

EXAMPLE 99

3-(1,3,4-Thiadiazol-2-ylmercaptomethyl)-7-methoxy-7-(2-thienylacetamido)decephalosporanic acid By reacting 2-mercapto-1,3,4-thiadiazole instead of 2-mercapto-4-methylthiazole and 7-methoxy-7-(2-thienylacetamido)cephalosporanic acid and otherwise following the procedure described in Example 98, there is thus obtained the title compound.

EXAMPLE 100

3-(Thiocyanatomethyl)-7-methoxy-7-(2-furylacetamido)decephalosporanic acid

7-Methoxy-7-(2-furylacetamido)cephalosporanic acid (100 mg.) is added to a 0.5 M buffer solution (5 ml.) consisting of 3.5 g. sodium dihydrogen phosphate and 3.4 g. disodium phosphate in 100 ml. of water and the pH of the mixture is brought to pH 5 by the addition of hydrochloric acid. Sodium thiocyanate (20 mg.) is added and the mixture is heated at 95° C. for 8 minutes. There is thus obtained the title compound.

EXAMPLE 101

3-(Chloromethyl)-7-methoxy-7-(2-thienylacetamido)-decephalosporanic acid trifluoroacetate The benzhydryl ester of 7-methoxy-7-(2-thienylacetamido)cephalosporanic acid (1 mmole) is dissolved in methylene chloride (5 ml.) and the mixture is cooled to 0° C. Collidine (1 mmole) is added, followed by the dropwise addition of a solution of phosphorous pentachloride (0.6 mmole) in methylene chloride (5 ml.). The mixture is then stirred for an hour in an ice bath at 0° C. and the resulting solution is extracted with sodium bicarbonate, dilute hydrochloric acid and a saturated solution of sodium chloride. The mixture is evaporated to dryness and then isolated by chromatography on a cooled silica gel column using chloroform as the eluant. The product thus obtained is the benzhydryl ester of 3-(chloromethyl)-7-(2-thienylacetamido)-decephalosporanic acid.

A solution of this benzhydryl ester (1 mmole) in anisole (13 ml.) is poured into 6.5 ml. of cold (0° C.) trifluoroacetic acid with stirring. After 5 minutes the solution is poured, with stirring, into an ether solution (1800 ml.) maintained at 0° C. The solid precipitate which results is then collected and dried to afford the title compound.

EXAMPLE 102

Sodium 3-[N-(2-chloroethyl)carbamoyloxymethyl]-7-methoxy-7-(2-thienylacetamido)decephalosporanate A suspension of 100 mg. of 3-hydroxymethyl-7-(2-thienylacetamido)decephalosporanic acid potassium salt in 3 ml. dry DMF is placed under $N_2$ and agitated by ultrasonic waves. 0.1 Ml. of triethylamine and 0.16 ml. β-chloroethylisocyanate are added. After 2 hours the solution is diluted with ethyl ether and centrifuged. The ether is decanted and the oily residue washed with more ether. After recentrifuging the ether is again decanted off. The solid residue is dissolved in water and the pH adjusted to 2 with concentrated HCl. The product is extracted with ethylacetate which has been washed with 5% NaHCO₃ solution. The ethylacetate is dried with MgSO₄, filtered and evaporated. The residue is redissolved in ethylacetate and washed with an aqueous solution of 16 mg. NaHCO₃, the pH of the aqueous solution is adjusted to 7.6 with NaHCO₃ and the mixture is stirred for ½ hour. The layers are separated and the water solution washed with EtOAc and then freeze dried overnight.

The 61 mg. of crude material so obtained is dissolved in methanol and all insoluble material filtered out. The methanol is evaporated and a small amount of ethyl ether added to start solidification. Yield: 55 mg., one spot on TLC, Rf of 0.54 in butanol:ethanol:water (4:1:5) upper layer.

EXAMPLE 103

Disodium 3-[N-(4-sulfophenyl)carbamoyloxymethyl]-7-methoxy-7-(2-thienylacetamido)decephalosporanate A suspension of 200 mg. of 3-(hydroxymethyl)-7-methoxy-7-(2-thienylacetamido)decephalosporanic acid potassium salt in 5 ml. dry DMF is placed under N₂ and agitated by ultrasonic waves. 0.096 ml. of triethylamine is added and then 94.4 mg. p-chlorosulfonyl-phenylisocyanate in 1 ml. DMF is added. After 5 minutes the solution is diluted with ethyl ether and centrifuged. The ether is decanted and the green solid residue is washed with more ether. After recentrifuging the ether is again decanted off. The remaining solid is dissolved in 30 ml. of water containing 50 mg. NaHCO₃. After stirring for ½ hour the pH is adjusted to 7.1 with dilute HCl. The solution is freeze dried overnight to give 295 mg. crude material which is dissolved in warm MeOH and filtered from insoluble material. A small amount of isopropanol is added and the first precipitate is filtered off and discarded. More isopropanol is then added and two crops of good material obtained in 39 mg. and 74 mg. yield of the title compound. Electrophoresis in 10% acetic acid shows a single spot.

EXAMPLE 104

A. Benzhydryl 7β-bromo-7-α-methoxycephalosporanate

To a solution of 1.8 g. of benzhydryl 7-diazocephalosporanate in 20 ml. of methylene chloride is added a cold solution of 560 mg. of N-bromoacetamide in 20 ml. of methanol. The mixture is stirred at room temperature for 30 minutes and the solvents are rapidly removed under waterpump vacuum. The gummy residue is taken up in methylene chloride and washed with sodium bicarbonate solution, and the organic phase is dried over anhydrous magnesium sulfate and evaporated. The residual oil is chromatographed in 60 g. of silica gel. Elution with methylene chloride gives benzhydryl 7-β-bromo-7-α-methoxycephalosporanate.

B. Benzhydryl 7-α-azido-7-β-methoxycephalosporanate

A solution of benzhydryl 7-β-bromo-7-α-methoxycephalosporanate (700 mg.) and lithium azide (435 mg.) in 5 ml. of dimethyl formamide is stirred at 30°–35° C. for 6 hours. The DMF is evaporated under high vacuum and the residue is taken up in methylene chloride and extracted four times with water. The methylene chloride phase is dried over anhydrous sodium sulfate and evaporated. The residual oil is chromatographed in 20 g. of silica gel. Elution with hexane-methylene chloride gives benzhydryl 7-α-azido-7-β-methoxycephalosporanate.

C. Benzhydryl 7-α-amino-7-β-methoxycephalosporanate

Benzhydryl 7-α-azido-7-β-methoxycephalosporanate (2 g.) and platinum oxide (2 g.) in 200 ml. of dioxane are vigorously stirred under an atmosphere of hydrogen for 2 hours. The dioxane is evaporated under reduced pressure and the residue is taken up in chloroform and filtered through 20 g. of silica gel packed in a fritted glass funnel. The cake is washed with 500 ml. of chloroform and the combined filtrate and washings are evaporated, leaving benzhydryl 7-α-amino-7-β-methoxycephalosporanate.

D. Benzhydryl 7-β-methoxy-7-α-(2-thienylacetamido)cephalosporanate

To an ice-cooled solution of 0.9 g. of benzhydryl 7-α-amino-7-β-methoxycephalosporanate in 20 ml. of methylene chloride is added 0.5 ml. of dry pyridine followed by 0.15 ml. of thienylacetyl chloride in 5 ml. of cold methylene chloride. The mixture is stirred in an ice-bath for 10 minutes, then washed successively with pH 2 phosphoric acid buffer, water and sodium bicarbonate solution. The methylene chloride phase is dried over anhydrous sodium sulfate and evaporated and the residue is chromatographed on 20 g. of silica gel. Elution with chloroform yields benzhydryl 7-β-methoxy-7-α-(2-thienylacetamido)cephalosporanate.

E. Sodium 7-β-methoxy-7-α-(2-thienylacetamido)cephalosporanate

A solution of 0.8 g. of benzhydryl 7-β-methoxy-7-α-(2-thienylacetamido)cephalosporanate in 3 ml. of anisole and 7 ml. of trifluoroacetic acid is stirred at room temperature for 5 minutes and the excess anisole and trifluoroacetic acid are then rapidly pumped off on a vacuum pump. The residue is taken up in a mixture of methylene chloride and water and rapidly stirred while sodium bicarbonate is added to bring the pH to 6.5. The aqueous layer is separated, washed with ether and lyophilized, affording sodium 7-β-methoxy-7-α-(2-thienylacetamido)cephalosporanate.

F. Epimerization of benzhydryl 7-β-bromo-7-α-methoxycephalosporanate

A solution of 250 mg. of benzhydryl 7-β-bromo-7-α-methoxycephalosporanate and 0.2 g. of lithium bromide in 1.5 ml. of dimethylformamide is stirred at room temperature overnight. The DMF is removed on the vacuum pump and the residue is taken up in chloroform and washed with water. The chloroform is evaporated, leaving an equilibrium mixture containing predominantly benzhydryl 7-α-bromo-7-β-methoxycephalosporanate. This is separated from the starting epimer by chromatography on silica gel.

G. Benzhydryl 7-β-azido-7-α-methoxycephalosporanate

This is prepared as in B starting with benzhydryl α-bromo-7-β-methoxycephalosporanate. The product is identical in all respects with benzhydryl 7-β-azido-7-α-methoxycephalosporanate previously prepared by the action of silver fluoroborate in methanol on benzhydryl 7-azido-7-bromocephalosporanate.

EXAMPLE 105

Pivaloyloxymethyl 3-carbamoyloxy-7-α-methoxy-7-(2-thienylacetamido)-decephalosporanate A mixture of 0.90 g. of sodium 3-carbamoyloxy-7-α-methoxy-7-(2-thienylacetamido)decephalosporanate, 0.30 g. of chloromethyl pivalate, and 5 ml. of dry dimethylformamide is shaken overnight at room temperature. The reaction mixture is then poured onto 25 ml. of pH 6 phosphate buffer and extracted with 3×10 ml. of chloroform. The combined extracts are washed with 4×10 ml. of water and 10 ml. of saturated brine, and dried over anhydrous magnesium sulfate. Evaporation of the solvent in vacuo leaves a gum which is washed by decantation with petroleum ether to afford pivaloyloxymethyl 3-carbamoyloxy-7-α-methoxy-7-(2-thienylacetamido)decephalosporanate.

EXAMPLE 106

A. Benzhydryl 7-(p-nitrobenzylideneamino)-7-trifluoromethoxycephalosporanate Benzhydryl 7-(p-nitrobenzylideneamino)cephalosporanate (571 mg.) is stirred at 0° C. under nitrogen in 10 ml. of acetonitrile. Bis(trifluoromethyl)peroxide (170 mg.) is added, and then over a 1 hour period 387 mg. diisopropylethylamine in 5 ml. acetonitrile.

The reaction mixture is evaporated in vacuo, taken up in 25 ml. benzene, filtered, and washed successively with water, dilute phosphoric acid (buffered at pH 2), water and aqueous bicarbonate. The solution is dried with MgSO₄, filtered and evaporated, providing benzhydryl 7-(p-nitrobenzylideneamino)-7-trifluoromethoxycephalosporanate as a mixture of epimers at C-7. These are separated by chromatography on silica gel, eluting with 4:1 chloroform-ethylacetate.

B. Benzhydryl 7-β-amino-7-α-trifluoromethoxycephalosporanate hydrochloride

The 7β-(p-nitrobenzylideneamino)-7β-trifluoromethoxy isomer (655 mg.) and 260 mg. aniline hydrochloride are stirred together for 5 hours at 25° C. in 10 ml. methanol. The methanol is removed at 0.1 mm. pressure and 30° C., and the residue covered with ether to crystallize for 1 hour. The solid is triturated with ether, filtered, and washed with ether several times. It consists of the title compound and aniline hydrochloride mixed together, and is used immediately for the next step.

The other epimer is converted to the epimeric compound in the same manner.

C. Benzhydryl 7β-(2-thienylacetamido)-7α-trifluoromethoxycephalosporanate

The mixture of product and aniline hydrochloride obtained as described in B above is stirred vigorously at −10° C. in 25 ml. methylene chloride. Thienylacetyl chloride (0.5 g.) is added, and then 0.5 g. triethylamine is slowly introduced. This liberates the free amine, benzhydryl 7β-amino-7α-trifluoromethoxycephalosporanate, which is instantly acylated. The reaction mixture is slowly allowed to warm to room temperature. Excess acid chloride is hydrolyzed by shaking with water, and the methylene chloride layer is then washed successively with dilute phosphoric acid (buffered to pH 2), water, and dilute bicarbonate. After drying with MgSO₄, the solution is filtered and evaporated, affording a mixture of the product and N-phenyl thienylacetamide. Pure product is obtained by silica gel chromatography, eluting with 4:1 chloroform-ethylacetate.

The other epimer at C-7 is converted to the epimeric compound using the same procedures.

D. Sodium 7β-(2-thienylacetamido)-7α-trifluoromethoxycephalosporanate

Benzhydryl 7β-(2-thienylacetamido)-7α-trifluoromethoxycephalosporanate (646 mg.) is dissolved in 0.8 ml. anisole and cooled to 0° C. Trifluoroacetic acid (4 ml.) precooled to 0° C. is added and the reaction allowed to proceed for 2 minutes at 0° C. Vacuum of 0.1 mm. is immediately applied and the reaction mixture allowed to warm to room temperature. Anisole is then distilled at 30° C./0.1 mm. A few ml. anisole is added to the residue and pulled off at 30° C./0.1 mm. to insure total removal of trifluoroacetic acid. The product is treated with 5 ml. water containing 84 mg. NaHCO₃ and lyophilized. The resulting powder is washed thoroughly with ether and dried, affording the title compound.

The sodium salt of the other epimer at C-7 is obtained in the same manner.

EXAMPLE 107

7-(D-α-sulfoaminophenylacetamido)-7-methoxycephalosporanic acid disodium salt

A suspension of 10 mmoles of 7-(D-α-aminophenylacetamido)-7-methoxycephalosporanic acid in 100 ml. of methylene chloride containing 12 mmoles of triethylamine is stirred and cooled in an ice bath. 12 Mmoles of trimethylamine sulfur trioxide is added in small portions over 5 minutes. After ½ hour the mixture is filtered and concentrated to 10% of the original volume. The solution is diluted with an equal volume of acetone and 30 mmoles of sodium 2-ethylhexanoate in butanol is added. A solid is formed upon chilling and scratching and is collected by filtration. The disodium salt of 7-(D-α-sulfoaminophenylacetamido)-7-methoxycephalosporanic acid can be recrystallized from isopropanol-water if desired.

EXAMPLE 108

Disodium 7α-cyano-7(2-carboxyphenylacetamido)cephalosporanate

A. Benzhydryl 7α-cyano-7-azidocephalosporanate

To a solution of benzhydryl-7-bromo-7-azidocephalosporanate (0.543 g. 0.001 mole) in 10 ml of $CH_3CN$ is added a solution of 0.350 g of tetrabutyl ammonium cyanide in 15 ml of $CH_3CN$. The reaction mixture is stirred at room temperature overnight, diluted with $CH_2Cl_2$ and washed with water, dried and evaporated. Chromatography on silica gel gives the benzhydryl 7α-cyano-7-azidocephalosporanate and the benzhydryl 7β-cyano-7-azidocephalosporanate.

The tetrabutyl ammonium cyanide is prepared as follows:

1 G of tetrabutylammonium iodide is dissolved in 10 ml of a 20% aqueous NaCN solution. The aqueous phase is discarded. The organic phase is treated with 3 further 5 ml quantities of the NaCN solution. The organic phase is dried over $MgSO_4$ and evaporated to give tetrabutylammonium cyanide.

B. Benzhydryl 7α-cyano-7-aminocephalosporanate 0.500 G of benzhydryl 7α-cyano-7-azidocephalosporanate is dissolved in 50 ml of ethyl acetate, 0.500 g of 10% Pd on carbon catalyst is added and the mixture is stirred under $H_2$ overnight. The catalyst is filtered off, the filtrate is evaporated and the residue is chromatographed on silica gel to separate starting material from product.

C. Benzhydryl 7α-cyano-7-(2-benzhydryloxycarbonylphenylacetamido)cephalosporanate 0.473 G of the benzhydryl-7α-cyano-7-aminocephalosporante is dissolved in 25 ml of $CH_2Cl_2$ and cooled to 0° C. 2-Benzhydryloxycarbonylphenylacetyl chloride 0.400 g is then added followed 1 minute later with 0.200 g of pyridine. The reaction mixture is stirred at 0° C. of 25 minutes and poured onto crushed ice. The mixture is agitated and the organic phase is separated and washed once with 5% $NaHCO_3$ solution, once with pH 2 phosphate buffer and once with water. The organic phase is dried over sodium sulfate and evaporated to give the crude product. Chromatography over silica gen gives the purified product.

D. Disodium 7α-cyano-7-(2-carboxyphenylacetamido)cephalosporanate

Benzhydryl 7α-cyano-7-(2-benzhydryloxycarbonylphenylacetamido)cephalosporanate 0.350 g is dissolved in 3 ml of anisole and treated with 10 ml of trifluoroacetic acid at room temperature for 10 minutes. The trifluoroacetic acid and the anisole are removed under reduced pressure below 40° C. and the residue is taken up in 25 ml of methylisobutyl ketone and treated with 0.300 g of $NaHCO_3$ in 30 ml of $H_2O$. The mixture is stirred for ½ hour, the organic phase is separated and the aqueous phase washed twice with methylene chloride and then lyophilized. The solid product is purified by crystallization from MeOH/isopropanol.

EXAMPLE 109

A. Benzhydryl 7-azido-7-carboxycephalosporanate

Benzhydryl 7-azido-7-bromocephalosporanate (5.43 g., 0.01 mole) is dissolved in 20 ml. of dry ether and cooled to −20° C., and 10 ml. of 1 M phenyl lithium solution is added slowly with vigorous stirring. After 1 hour at room temperature the mixture is poured onto pulverized dry ice. The residue is extracted with water and acidified to yield benzhydryl 7-azido-7-carboxycephalosporanate.

B. Benzhydryl 7-azido-7-chloroformylcephalosporanate

Benzhydryl 7-azido-7-carboxycephalosporanate (4.0 g.) is added to 15 ml. of thionyl chloride and the mixture stirred in an ice bath for 1 hour. The excess thionyl chloride is removed in vacuo and the residue flushed with dry acetone to give crude benzhydryl 7-azido-7-chloroformylcephalosporanate.

C. Benzhydryl 7-azido-7-carbomethoxycephalosporanate

Benzhydryl 7-azido-7-chloroformylcephalosporanate (2.63 g., 0.005 m.) is dissolved in methylene chloride (15 ml.) at 5° C. Pyridine (40 mg.) and methanol (1.0 ml.) are added slowly. The solvent is removed in vacuo and the product isolated by chromatography on silica gel.

D. Benzhydryl 7-amino-7-carbomethoxycephalosporanate 1.0 g. of benzhydryl 7-azido-7-carbomethoxycelphalosporanate is dissolved in 100 ml. of dioxane. 1.0 g. of platinum oxide is added and the reaction mixture stirred under hydrogen at atmospheric pressure for 1 hour. Another 1.0 g. quantity of platinum oxide is added, and the reaction mixture is again placed under hydrogen and stirred for 3 hours until the azide is completely reacted as determined by infrared analysis of aliquots. The solvent is removed under reduced pressure and the residue taken up in 50 ml. of chloroform and filtered through silica gel G in chloroform in a 60 ml. sintered glass funnel. The material is eluted with chloroform until 200 ml. of chloroform has been collected. The chloroform is removed under reduced pressure affording 0.632 g. of benzhydryl-7-amino-7-carbomethoxycephalosporanate, which is acylated directly without further purification.

E. Benzhydryl 7-carbomethoxy-7-(2-thienylacetamido)-cephalosporanate 0.632 g. of benzhydryl 7-amino-7-carbomethoxycephalosporanate is taken up in 25 ml. of methylene chloride and cooled to 0° C. 0.6 ml. (0.038 m.) of 2-thienyl acetyl chloride is added dropwise over 30 seconds followed by 0.6 ml. (0.01 m.) of pyridine 60 seconds later. The reaction mixture is stirred at 0° C. for 15 minutes and poured into crushed ice. The mixture is agitated and the organic layer separated and washed once with 20 ml. of water, once with 20 ml. of 5% sodium bicarbonate and once again with 20 ml. of water. The methylene chloride is dried and evaporated to dryness affording 1.417 g. of crude product. This material is placed on a column of 60 g. of silica gel under benzene and the column is eluted with benzene taking 100 ml. fractions followed by 300 ml. of methylene chloride/benzene (1:1) in 3 fractions, and 500 ml. of methylene chloride in 5 fractions. The product is removed from the column by eluting with 400 ml. of chloroform in 4 fractions, affording 0.592 g. This material is taken up in 25 ml. of methylene chloride and stirred at room temperature with 20 ml. of solution of 0.120 g. of 0.120 g. of sodium bicarbonate in water for ½ hour. The layers are separated and the organic layer washed with water, dried annd evaporated to dryness, affording 0.420 g. of benzhydryl 7-carbomethoxy-7-(2-thienylacetamido)cephalosporanate.

F. Sodium 7-carbomethoxy-7-(2-thienylacetamido)cephalosporanate 0.420 g. of benzhydryl 7-carbomethoxy-7-(2-thienylacetamido)cephalosporanate is dissolved in 3.5 ml. of anisole and treated with 10 ml. of trifluoroacetic acid at room temperature for 10 minutes. The trifluoroacetic acid and anisole are removed under reduced pressure maintaining the temperature below 40° C., and the residue is taken up in 25 ml. of chloroform and treated with 20 ml. of water containing 0.120 g. of sodium bicarbonate. The mixture is stirred for ½ hour at room temperature, and the organic phase is separated and washd with water. The combined aqueous phase is washed twice with methylene chloride and lyophilized to afford 0.382 g. of sodium 7-carbomethoxy-7-(2-thienylacetamido)cephalosporanate as a brownish solid.

EXAMPLE 110

3-Pyridiniummethyl-7-carbomethoxy-7-(2-thienylacetamido)decephalosporanic acid 1.3 g. of sodium 7-carbomethoxy-7-(2-thienylacetamido)cephalosporanate is dissolved in 3 cc. of a buffer solution made up by dissolving 30 g. of potassium iodide in 20 ml. of water containing 5 ml. of pyridine and adjusting the pH to 6.5 with dilute acetic acid. The resulting reaction mixture is stirred at 80° C. for 2 hours and then cooled to room temperature. The solution is then freeze dried, dissolved in 40 ml. of 25% acetic acid, filtered and the filtered solution subjected to electrophoresis to obtain 3-pyridiniummethyl-7-carbomethoxy-7-(2-thienylacetamido)-decephalosporanic acid.

EXAMPLE 111

Sodium 7-dimethylcarboxamido-7-(thiophene-2-acetamido)-cephalosporanate

Following the procedure described in Example 107C above, benzhydryl 7-azido-7-chloroformylcephalosporanate is reacted with dimethylamine in place of methanol to produce the corresponding 7-dimethylcarboxamide compound which is converted to sodium 7-dimethylcarboxamido-7-(thiophene-2-acetamido)-cephalosporanate using the procedures described in Example 109 above.

EXAMPLE 112

Sodium 7-hydrazinocarboxyl-7-(2-furylacetamido)cephalosporanate

When benzhydryl 7-azido-7-chloroformylcephalosporanate is reacted with hydrazine in place of methanol using the procedures described in Example 109C above, the corresponding 7-hydrazinocarboxycephalosporanate is obtained. This product is reduced to the corresponding 7-amino compound as described in Example 109D above, and the benzhydryl 7-amino-7-hydrazinocarboxylcephalosporanate obtained is reacted with furylacetyl chloride as described in Example 107E above to obtain benzhydryl 7-(2-furylacetamido)-7-hydrazinocarboxylcephalosporanate. This product is converted to sodium 7-hydrazinocarboxyl-7-(2-furylacetamido)cephalosporanate using the procedures described in Example 109F above.

EXAMPLE 113

Sodium 7-(2-furylacetamido)-7-thiocarboxymethylcephalosporanate

When benzhydryl 7-azido-7-bromocephalosporanate is reacted with carbon disulfide in place of carbon dioxide as described in Example 109A above, benzhydryl 7-azido-7-dithiocarboxycephalosporanate is obtained. This product is converted to sodium 7-(2-furylacetamido)-7-thiocarboxymethylcephalosporanate using the procedures shown in Examples 107–110 above.

EXAMPLE 114

Sodium 7α-formyl-7-(2-thienylacetamido)cephalosporanate

To a solution of 200 mg. of sodium 7α-hydroxymethyl-7-(2-thienylacetamido)cephalosporanate is added phosphoric acid to a pH of 2–3. The solution is immediately extracted with ethylacetate in three portions. The combined organic layers are washed successively with water and saturated sodium chloride solution, and finally dried over anhydrous magnesium sulfate. Concentration of the solution under reduced pressure at or below room temperature affords 7α-hydroxy-7-(2-thienylacetamido)cephalosporanic acid (158 mg.) as a gum which hardens to a glass. A solution of this material in 4 ml. of a mixture of 1:1 methylene chloride and alcohol-free chloroform is added at once at room temperature with vigorous agitation to a solution prepared by the addition of 225 mg. of anhydrous chromium trioxide to a mixture of 0.375 ml. of pyridine and 6 ml. of methylene chloride. After 5 minutes of agitation the reaction mixture is diluted with 15 ml. of ethylacetate and treated with 4 ml. of 2% hydrochloric acid. The phases are mixed well and filtered with pressure through diatomaceous earth. The phases are separated and the aqueous layer extracted with ethylacetate. The combined organic layers are washed with water and dried over anhydrous magnesium sulfate. Concentration under reduced pressure at room temperature affords 82 mg. of 7α-formyl-7-(2-thienylacetamido) cephalosporanic acid as a non-crystalline foam. The solid sodium salt is obtained by dissolving the product in one equivalent of aqueous sodium hydroxide followed by removal of the water by lyophilization.

EXAMPLE 115

Sodium 7α-carboxy-7-(2-thienylacetamido)cephalosporanate

Argentic oxide is prepared by adding 10% potassium hydroxide to an aqueous solution of equimolar quantities of silver nitrate and potassium permanganate. The silver (II) oxide which precipitates is recovered by filtration and washed with water until free of base and permanganate.

To a suspension of 250 mg. of this silver (II) oxide in 1.5 ml. of tetrahydrofuran-water (4:1) is added a solution of 100 mg. of 7α-formyl-7-(2-thienylacetamido) cephalosporanic acid in 1.5 ml. of tetrahydrofuran. This mixture is stirred at room temperature until thin layer chromatographic analysis indicates that the formyl compound is completely reacted. The reaction mixture is filtered and the filtrate treated with 2% hydrochloric acid to a pH of 2. Ethylacetate and water are added to the acidified filtrate and mixed. The separated organic layer is washed, dried and concentrated under reduced pressure below room temperature. The free acid thus obtained is converted to the sodium salt as in Example 114.

EXAMPLE 116

Sodium 7-Methyl-7-(2-Thienylacetamido)cephalosporate

A. Benzhydryl 7-dimethylboron-7-methylcephalosporanate

A solution of 0.228 g. of benzhydryl 7-diazocephalosporanate in 5 ml. of methylene chloride, prepared as described above, is diluted to about 10 ml. with tetrahydrofuran and cooled to about −78° C. in a dry ice bath. To this cooled solution is added 3.5 ml. of trimethylboron solution with stirring over a period of 10 minutes. The resulting reaction mixture is allowed to stir for another 10 minutes at −78° C. An infrared spectrum of a small aliquot of this solution at this point shows no diazo band. The reaction mixture containing the benzhydryl 7-dimethylboron-7-methylcephalosporanate is allowed to warm up to room temperature. Evaporation of the solvent affords the product in solid form.

The trimethylboron solution used in this example is prepared as follows: Methyl magnesium iodide is prepared from 1.44 g. of magnesium and 8.5 g. of methyl iodide in 40 ml. of ether, and the resulting Grignard solution is diluted to 50 ml. with additional ether. 5 ml. of this solution is placed in a 3 neck-round bottom flask equipped with dropping funnel, magnetic stirrer and a nitrogen inlet tube. The flask is connected to a gas inlet tube fitted with a 2 neck flask containing 5 ml. of ether, cooled to −78° C. in a dry ice bath and both flasks are placed under a nitrogen atmosphere; the nitrogen gas being passed into the first flask and bubbled into the ether in the second flask. 0.2 ml. of boron trifluoride etherate diluted to 2 ml. with ether is added dropwise to the first flask and the trimethylboron formed is collected in the second flask. The flow of nitrogen is continued until much of the ether in the first flask is flushed into the second flask to give about 9 ml. of trimethylboron solution.

B. Benzhydryl 7azido-7-methylcephalosporanate

To the methylene chloride solution of benzhydryl 7-dimethylboron-7-methylcephalosporanate prepared as described in A above is added a solution of bromine azide in methylene chloride prepared as described below. The resulting reaction mixture turns orange and is allowed to stir overnight at room temperature. It is then poured into cold N/10 sodium thiosulfate solution. The organic phase is separated, washed with an equal quantity of aqueous 5% sodium bicarbonate solution and then with water. The washed organic phase is then dried over sodium sulfate and evaporated to give benzhydryl 7-azido-7-methylcephalosporanate.

The solution of bromine azide is prepared as follows:

To a solution of 2.4 gm. of sodium azide in 4 ml. of water is added 40 ml. of methylene chloride and the mixture cooled to 0° C. To this cooled mixture is added dropwise 4 ml. of 50% aqueous sulfuric acid (vol./vol.) over 5 minutes and the mixture is allowed to stir another 5 minutes. The aqueous layer is frozen by cooling in a solid carbon dioxide bath and the organic phase is decanted off and dried over anhydrous sodium sulfate. To this solution of the hydrazoic acid is added 2 g. of N-bromosuccinamide and the mixture is stirred for 15 minutes at 0° C. until all the N-bromosuccinamide is dissolved.

C. Benzhydryl 7-amino-7-methylcephalosporanate 1.0 g. of benzhydryl 7-azido-7-methyl-cephalosporanate is dissolved in 100 ml. of dioxane. 1.0 g. of platinum oxide is added and the reaction mixture stirred under hydrogen at atmospheric pressure for 1 hour. Another 1.0 g. quantity of platinum oxide is added, and the reaction mixture is again placed under hydrogen and stirred for 3 hours until the azide is completely reacted as determined by infrared analysis of aliquots. The solvent is removed under reduced pressure and the residue taken up in 50 ml. of chloroform and filtered through silica gel G in chloroform in a 60 ml. sintered glass funnel. The material is eluted with chloroform until 200 ml. of chloroform has been collected. The chloroform is removed under reduced pressure affording 0.632 g. of benzhydryl 7-amino-7-methylcephalosporanate, which is acylated directly without further purification.

D. Benzhydryl 7-methyl-7-(2-thienylacetamido)cephalosporanate 0.632 g. of benzhydryl 7-methyl-7-aminocephalosporanate is taken up in 25 ml. of methylene chloride and cooled to 0° C. 0.6 ml. (0.038 m.) of 2-thienyl acetyl chloride is added dropwise over 30 seconds followed by 0.6 ml. (0.01 m.) of pyridine 60 seconds later. The reaction mixture is stirred at 0° C. for 15 minutes and poured into crushed ice. The mixture is agitated and the organic layer separated and washed once with 20 ml. of water, once with 20 ml. of 5% sodium bicarbonate and once again with 20 ml. of water. The methylene chloride is dried and evaporated to dryness affording 1.417 g. of crude product. This material is placed on a column of 60 g. of silica gel under benzene and the column is eluted with benzene taking 100 ml. fractions followed by 300 ml. of methylene chloride/benzene (1:1) in 3 fractions, and 500 ml. of methylene chloride in 5 fractions. The product is removed from the column by eluting with 400 ml. of chloroform in 4 fractions, affording 0.592 g. This material is taken up in 25 ml. of methylene chloride and stirred at room temperature with 20 ml. of a solution of 0.120 g. of sodium bicarbonate in water for ½ hour. The layers are separated and the organic layer washed with water, dried and evaporated to dryness, affording 0.420 g. of benzhydryl 7-methyl-7-(2-thienylacetamido)cephalosporanate.

E. Sodium 7-methyl-7-(2-thienylacetamino)cephalosporanate 0.420 g. of benzhydryl 7-methyl-7-(2-thienylacetamido)cephalosporanate is dissolved in 3.5 ml. of anisole and treated with 10 ml. of trifluoroacetic acid at room temperature for 10 minutes. The trifluoroacetic acid and anisole are removed under reduced pressure maintaining the temperature below 40° C., and the residue is taken up in 25 ml. of chloroform and treated with 20 ml. of water, containing 0.120 g. of sodium bicarbonate. The mixture is stirred for ½ hour at room temperature and the organic phase is separated and washed with water. The combined aqueous phase is washed twice with methylene chloride and lyophilized to afford 0.382 g. of sodium 7-methyl-7-(2-thienylacetamido)cephalosporanate as a brownish solid.

EXAMPLE 117

3-Pyridiniummethyl-7-methyl-7-(2-thienylacetamido)-decephalosporanic acid 1.3 g. of sodium 7-methyl-7-(2-thienylacetamido)-cephalosporanate is dissolved in 3 cc of a buffer solution made up by dissolving 30 g. of potassium iodide in 20 ml. of water containing 5 ml. of pyridine and adjusting the pH to 6.5 with dilute acetic acid. The resulting reaction mixture is stirred at 80° C. for 2 hours and then cooled to room temperature. The solution is then freeze dried, dissolved in 40 ml. of 25% acetic acid, filtered and the filtered solution subjected to electrophoresis to obtain 3-pyridiniummethyl-7-methyl-7-(2-thienylacetamido)decephalosporanic acid.

EXAMPLE 118

A. Benzhydryl 7-difluoromethylenecephalosporanate

Benzhydryl 7-diazocephalosporanate (4.5 g., 0.01 mole) in 10 ml. of dry dioxane is added to a solution of 4.1 g. of 0.05 mole thiocarbonyl fluoride and allowed to stand at room temperature until the reddish color of the diazo compound disappears. The reaction mixture is heated at reflux for 45 minutes and the solvent removed in vacuo. The product is chromatographed on silica gel using chloroform: methanol as the eluant to afford benzhydryl 7-difluoromethylenecephalosporanate.

B. Benzhydryl 7-trifluoromethyl-7-bromocephalosporanate

Benzhydryl 7-difluoromethylenecephalosporanate (2.35 g., 0.005 mole) and finely powdered silver monofluoride (1.90 g., 0.015 mole) in 50 ml. of benzene are vigorously stirred. Bromine (0.80 g., 0.005 mole) is added dropwise. Benzhydryl 7-trifluoromethyl-7-bromocephalosporanate is isolated by chromatography on silica gel.

C. Benzhydryl 7-trifluoromethyl-7-aminocephalosporanate

Benzhydryl 7-trifluoromethyl-7-bromocephalosporanate (1.14 g., 0.002 mole) is dissolved in 20 ml. of dry ether and cooled to −20° C. To this cooled solution is slowly added 0.4 ml. of 5 M ethereal methyllithium solution with vigorous stirring. After ½ hour, 66 mg. of 0-methylhydroxylamine is added. The mixture is kept at −10° C. for ½ hour and allowed to warm to room temperature before heating at reflux for 2 hours. The ether is removed in vacuo and the benzhydryl 7-trifluoromethyl-7-aminocephalosporanate is isolated by chromatography on silica gel.

D. Benzhydryl 7-(2-thiopheneacetamido)-7-trifluoromethylcephalosporanate

The benzhydryl 7-trifluoromethyl-7-aminocephalosporanate prepared as described in C above is acylated by reaction with 2-thiopheneacetylchloride using the processes described in Example IF above to afford benzhydryl 7-(2-thiopheneacetamido)-7-trifluoromethylcephalosporanate.

E. Sodium 7-(2-thiopheneacetamido)-7-trifluoromethylcephalosporanate

Benzhydryl 7-(2-thiopheneacetamido)-7-trifluoromethylcephalosporanate is dissolved in 3.5 ml. of anisole and treated with 10 ml. of trifluoroacetic acid at room temperature for 10 minutes. The trifluoroacetic acid and anisole are removed under reduced pressure maintaining the temperature below 40° C., and the residue is taken up in 25 ml. of chloroform and treated with 20 ml. of water, containing 0.120 g. of sodium bicarbonate. The mixture is stirred for ½ hour at room temperature and the organic phase is separated and washed with water. The combined aqueous phase is washed twice with methylene chloride and lyophilized affording 0.382 g. of sodium 7-(2-thiopheneacetamido)-7-trifluoromethylcephalosporanate.

EXAMPLE 119

A. Benzhydryl 7-ethynyl-7-azidocephalosporanate

A stirring solution of 0.900 g of benzhydryl 7-diazocephalosporanate in 10 ml each of methylene chloride and ether is cooled to −78° C. under a nitrogen atmosphere and is treated dropwise with a solution of triethynylboron. The addition is halted periodically, and the progress of the reaction is ascertained by infrared analysis of small aliquots. When the diazo compound has completely reacted, the remaining triethynylboron solution is discarded. Bromine azide in methylene chloride, 25 ml of a 0.28 N solution, is then added over a period of 20 min. The cooling bath is removed and the mixture is stirred for a further 60 min. at room temperature.

The reaction mixture is poured onto a solution of 20 ml. of 0.1 N sodium thiosulfate and 20 ml of 0.5 M pH 7 phosphate buffer and agitated. The organic phase is separated, washed with water and saturated brine, dried over anhydrous magnesium sulfate, and evaporated in vacuo. The residue is chromatographed on silica gel using benzene as eluant to afford benzhydryl 7α-ethynyl-7-azidocephalosporanate and benzhydryl 7β-ethynyl-7-azidocephalosporanate.

The triethynylboron solution used above is prepared as follows: A solution of 5.42 g of boron trifluoride in 20 ml of ether is stirred at 078° C. under a nitrogen atmosphere while 2.88 g of sodium acetylide in 20 ml of xylene is added over a period of 90 min. The reaction mixture, which is a white solid suspended in a clear liquid, is rapidly transferred to a drybox and filtered into a dry ice jacketed dropping funnel. This solution is used immediately. At no point is the temperature of the triethynylboron allowed to exceed −60° C.

B. Benzhydryl 7α-ethynyl-7-aminocephalosporanate

To a stirring solution of 0.028 g of anhydrous cobalt (II) bromide in 20 ml of absolute ethanol is added 0.061 g of 2,2'-bipyridine. After all the bipyridine has dissolved, a solution of 0.315 g of benzhydryl 7α-ethynyl-7-azidocephalosporanate in 5 ml of absolute ethanol is added followed by 0.073 g of sodium borohydride. The reaction mixture is stirred for 15 min. at room temperature, and is then quenched by the addition of cold aqueous acetic acid. The mixture is diluted with 25 ml of water and extracted with three 20 ml portions of ether. The combined extracts are washed with pH 7 phosphate buffer and saturated brine, and dried over anhydrous magnesium sulfate. Evaporation of the solvent under reduced pressure gives benzhydryl 7α-ethynyl-7-aminocephalosporanate. This material is acylated without further purification.

C. Benzhydryl 7α-ethynyl-7-(2-thienylacetamido)cephalosporanate

An ice cold, stirring solution of 0.274 g of benzhydryl 7α-ethynyl-7-aminocephalosporanate in 10 ml of methylene chloride is treated with 0.25 ml of 2-thienylacetyl chloride over a period of 30 sec., followed 1 minute later by 0.25 ml of pyridine. The reaction mixture is stirred for a further 15 min. at 0° C., and is then poured onto cracked ice. The methylene chloride phase is separated, washed with 10 ml of water, 2×40 ml of pH 2 phosphate buffer, 10 ml of water, and dried over anhydrous magnesium sulfate. Evaporation of the solvent leaves a yellow gum which is chromatographed on 15 g of silica gel. The column is eluted with 75 ml of benzene, 150 ml of 1:1 benzene-methylene chloride, 150 ml of methylene chloride, and 300 ml of chloroform. Evaporation of the chloroform fraction under reduced pressure affords an oil which is taken up in 10 ml of methylene chloride and stirred for 30 min with a solution of 0.050 g of sodium bicarbonate in 5 ml of water. The methylene chloride phase is separated, washed with 5 ml of water, dried over anhydrous magnesium sulfate, and evaporated to give benzhydryl 7α-ethynyl-7-(2-thienylacetamido)cephalosporanate.

D. Sodium 7α-ethynyl-7-(2-thienylacetamido)cephalosporanate

Benzhydryl 7α-ethynyl-7-(2-thienylacetamido)cephalosporanate, 0.179 g, is dissolved in 1.5 ml of anisole and treated with 4.5 ml of trifluoroacetic acid. After having been kept at room temperature for 10 min, the solution is evaporated in vacuo to remove excess reagents. The residue is dissolved in 10 ml of methylene chloride and is stirred for 30 min with a solution of 0.045 g of sodium bicarbonate in 7.5 ml of water. The phases are separated; the organic layer is extracted with 4 ml of water; and the combined aqueous solutions are washed with 3×4 ml of methylene chloride and lyophilized to give a powder. The crude product is partially dissolved in anhydrous methanol and filtered. Evaporation of the solvent from the filtrate affords sodium 7α-ethynyl-7-(2-thienylacetamido)cephalosporanate.

Following the procedures described in steps B, C, and D, benzhydryl 7β-ethynyl-7-azidocephalosporanate can be converted to sodium 7β-ethynyl-7-(2-thienylacetamido)cephalosporanate. The acetoxymethyl group of this compound and of the 7β-ethynyl compound can be converted to other 3-substituted cephalosporins as described in the foregoing examples. The acetoxy group can be displaced by nitrogen bases and with other compounds of greater nucleophilicity than the oxygen nucleophile. Other 3-substituted compounds, such as 3-hydroxymethyl, can also be prepared and further derivitized to produce new compounds. The corresponding 3-desacetyl derivatives can also be prepared by utilizing benzhydryl 7-diazodesacetoxycephalosporanate in step A of the sequence depicted above. Similarly, other 7-acylamido compounds can be prepared using the procedures described in other examples.

EXAMPLE 120

7α-Phenyl-7-[2-(4-pyridylthio)acetamido]cephalosporanic Acid

A. Benzhydryl 7-phenyl-7-azidocephalosporanate

A stirring solution of 1.350 g of benzhydryl 7-diazocephalosporanate in 15 ml each of methylene chloride and ether is cooled to −78° C. under a nitrogen atmosphere and is treated dropwise over a period of 20 min with a solution of 0.727 g of triphenylboron in 20 ml of ether. The mixture is stirred an additional 10 min at −78° C., at which time the diazo compound is completely reacted as determined by infrared analysis of a small aliquot. Bromine azide in methylene chloride, 45 ml of a 0.28 N solution, is then added over a period of 30 min. The cooling bath is removed and the mixture is stirred for a further 2 hrs. at room temperature.

The reaction mixture is poured into a solution of 30 ml of 0.1 N thiosulfate and 30 ml of 0.5 M pH 7 phosphate buffer and agitated. The organic phase is separated, washed with water and saturated brine, dried over anhydrous magnesium sulfate, and evaporated. The crude product is chromatographed on silica gel using benzene as eluant to afford benzhydryl 7α-phenyl-7-azidocephalosporanate and benzhydryl 7β-phenyl-7-azidocephalosporanate.

B. Benzhydryl 7α-phenyl-7-aminocephalosporanate

A mixture of 0.450 g of benzhydryl 7α-phenyl-7-azidocephalosporanate and 0.450 g of platinum oxide in 45 ml of dioxane is stirred under hydrogen at atmospheric pressure for one hour. After purging the system with nitrogen, an additional 0.450 g of platinum oxide is added, and the reaction mixture is again placed under hydrogen and stirred for 2 hrs. At this time the azide is completely reacted as evidenced by infrared analysis of an aliquot. The solvent is evaporated at reduced pressure and the residue taken up in 25 ml of chloroform and filtered through a packed pad of silica gel G and diatomaceous earth in a 60 ml sintered glass funnel. The product is eluted with chloroform until 200 ml of solution has been collected. Evaporation of the solvent under reduced pressure gives benzhydryl 7α-phenyl-7-aminocephalosporanate, which is acylated directly without further purification.

C. Benzhydryl 7α-phenyl-7-[2-(4-pyridylthio)acetamido]cephalosporanate

To a stirring solution of 0.395 g of benzhydryl 7α-phenyl-7-aminocephalosporanate in 15 ml of dry methylene chloride is added 0.130 g of (4-pyridylthio)acetic acid, followed by 5 ml of dimethylforamide to effect solution. Dicyclohexylcarbodiimide, 0.159 g, is then added, and the mixture is stirred at room temperature and under a nitrogen atmosphere for 18 hrs. The precipitate of dicyclohexylurea is removed by filtration and the filtrate evaporated under high vacuum. The residue is dissolved in 25 ml of chloroform and washed with water, 2% sodium bicarbonate, water, and saturated brine. The chloroform is dried over anhydrous magnesium sulfate and evaporated under reduced pressure to give the crude product. This material is chromatographed on 20 g of silica gel using an ethyl acetate in benzene gradient as eluant to afford benzhydryl 7α-phenyl-7-[2(4-pyridylthio)acetamido]cephalosporanate.

D. 7α-Phenyl-7-[2(4-pyridylthio)acetamido]cephalosporanic-acid

To a stirring solution of 0.330 g of benzhydryl 7α-phenyl-7-[2(4-pyridylthio)acetamido]cephalosporanate in 2.5 ml of anisole is added 7 ml of trifluoroacetic acid. The reaction mixture is stirred for 10 min at room temperature. Excess anisole and trifluoroacetic acid are removed under high vacuum, and the residue is taken up in 20 ml of chloroform and layered with 20 ml of water containing 0.100 g of sodium bicarbonate. The mixture is stirred for 30 min at room temperature, and the organic phase is separated and washed with water. The combined aqueous phase is washed with methylene chloride, layered with ethyl acetate, and acidified to pH 3 with 2 N hydrochloric acid. The ethyl acetate phase is separated, dried over anhydrous sodium sulfate, and evaporated to afford 7α-phenyl-7-[2-(4-pyridylthio)acetamido]cephalosporanic acid.

Following the procedures described in steps B-D, benzhydryl 7β-phenyl-7-azidocephalosporanate is converted to 7β-phenyl-7-[2-(4-pyridylthio)acetamido]-cephalosporanic acid.

The acetoxymethyl group of both 7β- and 7β-phenyl-7-[2(4-pyridylthio)acetamido]cephalosporanate can be converted to other 3-substituents using the procedures of the foregoing examples. The acetoxy group can be displaced by nitrogen bases and other compounds of greater nucleophilicity than the oxygen nucleophile. The 3-acetoxymethyl can be catalytically reduced in the presence of hydrogen to produce the 3-methyl derivatives. Other 3-substituted compounds, such as 3-hydroxymethyl, can also be made and converted to other useful compounds. Also, the benzhydryl 7α-phenyl-7-aminocephalosporanate can be acylated with other acylating agents such as phenyl acetyl chloride, thienylacetylchloride, furylacetylchloride, and the like to produce the corresponding 7-acylamido compounds using the procedures described in the other examples hereof.

EXAMPLE 121

7α-Ethyl-7-(D-2-amino-α-phenylacetamido)cephalosporanic acid

A. Benzhydryl 7-ethyl-7-azidocephalosporanate

A solution of 1.350 g of benzhydryl 7-diazocephalosporanate in 15 ml each of methylene chloride and ether is cooled to −78° C. under a nitrogen atmosphere and stirred while 0.295 g of triethylboron in 15 ml of ether is added dropwise over a period of 15 min. The mixture is stirred an additional 5 min. at −78° C., at which time the diazo compound is completely reacted as determined by infrared analysis of a small aliquot. Bromine azide in methylene chloride, 45 ml of a 0.28 N solution, is then added dropwise over a period of 30 min. The cooling bath is removed and the mixture is stirred for an additional 2 hours at room temperature. The reaction mixture is poured into a solution of 30 ml each of 0.1 N sodium thiosulfate and 0.5 M pH 7 phosphate buffer and agitated. The organic phase is separated, washed with water and saturated brine, dried over anhydrous magnesium sulfate, and evaporated. The residue is chromatographed on silica gel using benzene as eluant to give benzhydryl 7α-ethyl-7-azido-cephalosporanate and benzhydryl 7β-ethyl-7-azidocephalosporanate.

B. Benzhydryl 7α-ethyl-7-aminocephalosporanate

A solution of 0.520 g of benzhydryl 7α-ethyl-7-azidocephalosporanate in 50 ml of dioxane is treated with 0.520 g of platinum oxide, and the mixture is stirred under hydrogen at atmospheric pressure for one hour. After purging the mixture with nitrogen, an additional 0.520 g of platinum oxide is added. The mixture is again placed under hydrogen and stirred for 2 hours, at which time the azide is completely reacted as determined by infrared analysis of an aliquot. The dioxane is removed under reduced pressure and the residue taken up in 30 ml of chloroform and filtered through a packed pad of silica gel G and diatomaceous earth in a 60 ml sintered glass funnel. The product is eluted with chloroform until 200 ml of solution has been collected. Evaporation of the solvent under reduced pressure gives benzhydryl 7α-ethyl-7-aminocephalosporanate.

C. Benzhydryl 7α-ethyl-7-(D-2-azido-2-phenylacetamido) cephalosporanate

To a stirring solution of 0.418 g of benzhydryl 7α-ethyl-7-aminocephalosporanate in 20 ml of dry methylene chloride at 0° C. is added rapidly 0.350 g of D-α-azidophenylacetic acid, followed by 0.30 ml of pyridine 60 seconds later. The reaction mixture is stirred for 30 min. at 0° C. and then poured onto 40 ml of water. The mixture is agitated, and the methylene chloride phase is separated and washed successively with water, dilute sodium bicarbonate, water, and saturated brine. After having been dried over anhydrous magnesium sulfate, the methylene chloride is removed under reduced pressure to yield the crude product. This material is chromatographed on 40 g of silica gel using a chloroform in benzene gradient as eluant to afford benzhydryl 7α-ethyl-7-(D-2-azido-2-phenylacetamido)cephalosporanate.

D. 7α-Ethyl-7-(D-2-azido-2-phenylacetamido)cephalosporanic acid

A solution of 0.388 g of benzhydryl 7α-ethyl-7-(D-2-azido-2-phenylacetamido)cephalosporanate in 1.0 ml of anisole is cooled in an ice bath and treated with 4.0 ml of trifluoroacetic acid. The reaction mixture is kept at 0° for 10 min. with occasional swirling, and then evaporated in vacuo to remove excess anisole and trifluoroacetic acid. The residue is taken up in 20 ml of methylene chloride and extracted with three 5 ml portions of saturated sodium bicarbonate solution. The combined aqueous extracts are washed with two 5 ml portions of methylene chloride, acidified to pH 2 with 2.5 N hydrochloric acid, and extracted with four 10 ml portions of ethyl acetate. The organic extracts are combined and dried over anhydrous magnesium sulfate. Evaporation of the solvent under reduced pressure leaves 7α-ethyl-7-(D-2-azido-2-phenylacetamido)cephalosporanic acid.

E. 7α-Ethyl-7-(D-2-amino-2-phenylacetamido)cephalosporanic acid 0.291 g of 7α-ethyl-7-(D-2-azido-2-phenylacetamido)cephalosporanic acid is taken up in 3.0 ml of acetic acid and 4.5 ml of water, cooled in an ice bath, stirred, and treated with 1.550 g of zinc dust. The mixture is stirred for 10 min. and then filtered through sintered glass. The zinc is washed with 20 ml of water. The filtrate and washings are combined, saturated with hydrogen sulfide, and filtered through a pad of diatomaceous earth. Lyophilization of the filtrate affords crude 7α-ethyl-7-(D-2-amino-2-phenylacetamido)cephalosporanic acid. This material is freed of acetic acid by repetitive dissolution in water and lyophilization.

In an analogous manner, 7β-ethyl-7-azidocephalosporanate can be converted to 7β-ethyl-7-(D-2-amino-2-phenylacetamido)cephalosporanic acid by procedures C–E. Substitution of L-α-azidophenylacetic acid and DL-α-azidophenylacetic acid in Step C and subsequent transformations gives 7α-ethyl-7-(L-2-amino-2-phenylacetamido) cephalosporanic acid, 7β-ethyl-7-(L-2-amino-2-phenylacetamido)cephalosporanic acid, 7α-ethyl-7-(DL-2-amino-2-phenylacetamido)-cephalosphoranic acid, and 7β-ethyl-7-(DL-2-amino-2-phenylacetamido)-cephalosphoranic acid. Similarly using other acylating agents in C above affords analogous 7-acylamido compounds.

The acetoxymethyl group of these compounds can be converted to other 3-substituents in the usual manner. The acetoxy group can be displaced by nitrogen bases and other compounds of greater nucleophilicity than the oxygen nucleophile. Other 3-substituted compounds, such as 3-hydroxymethyl, can also be prepared and converted to other derivatives. In addition, the 3-acetoxymethyl group can be catalytically reduced in the presence of hydrogen to afford the 3-methyl cephalosporins.

EXAMPLE 122

A. Benzhydryl 7-benzyl-7-azidocephalosporanate

To a solution of 0.900 g (0.002 m) of benzhydryl 7-diazocephalosporanate in 10 ml of $CH_2Cl_2$ and 10 ml of ether, cooled to −78° C. under a $N_2$ atmosphere is added dropwise over 15 minutes, 10 ml of a 0.02 M tribenzyl boron solution in ether.

A check on a small aliquot shows the absence of the diazo compound by ir. The reaction mixture is stirred a further 5 minutes at −78° C. and is then treated with 40 ml of a 0.3 N solution of $BrN_3$ in methylene chloride. The reaction mixture is stirred at −78° C. for 15 minutes and then allowed to come to room temperature over 45 minutes and stirred another 20 minutes at room temperature. The reaction mixture is poured into ice cold 5% $NaHCO_3$ solution, agitated and the organic phase is separated and washed once with N/10 thiosulfate (30 ml) and then with water, dried and evaporated. The residue is chromatographed on 30 g of silica gel to give benzhydryl 7α-benzyl-7-azidocephalosporanate and benzhydryl 7β-benzyl-7-azidocephalosporanate.

B. Benzhydryl 7α-benzyl-7-aminocephalosporanate 0.500 g of benzhydryl 7-azido-7α-benzylcephalosporanate is dissolved in 25 ml of ethyl acetate and 0.500 g of $PtO_2$ is added and the mixture is stirred overnight under $H_2$. The catalyst is filtered off, the filtrate is evaporated and the residue is chromatographed on silica gel (15 g) to give the product.

C. Benzhydryl 7α-benzyl-7-(p-carboxymethylphenylacetamido) cephalosporanate 0.400 g of benzhydryl 7α-benzyl-7-aminocephalosporanate is dissolved in 25 ml of $CH_2Cl_2$ and cooled to 0° C. 0.400 g of p-phenylenediacetyl chloride is added followed 60 seconds layer by 0.400 g of pyridine. The reaction mixture is agitated, the organic phase is separated and washed once with pH 2 phosphate buffer and then with water. The organic phase is dried and evaporated. The crude product so obtained is purified by chromatography over silica gel.

D. Disodium 7α-benzyl-7-(p-carboxymethylphenylacetamido) cephalosporanate 0.325 g of benzhydryl 7α-benzyl-7-(p-carboxymethylphenylacetamido)-cephalosporanate is dissolved in 3 ml of anisole and treated with 10 ml of trifluoroacetic acid at room temperature for 10 minutes. The trifluoroacetic acid and the anisole are evaporated under reduced pressure below 40°. The residue is taken up in 25 ml of ethyl acetate (freed of any acetic acid) and treated with 20 ml of $H_2O$ containing 0.120 g of $NaHCO_3$. The mixture is stirred for ½ hour and the organic phase is separated and washed with water. The combined aqueous phase is washed twice with ethyl acetate and then freeze dried to give the product which is further purified by recrystallization from MeOH/iPrOH.

Reaction of benzhydryl 7β-benzyl-7-azidocephalosporanate in the above sequence gives 7β-benzyl-7-(p-carboxymethylphenylacetamido)cephalosporanate.

When other acylating agents such as phenylacetyl chloride, 2-thienylacetyl chloride, 2-furylacetyl chloride are used in Step C hereof the corresponding 7-acylamido compounds are obtained in accordance with the procedures of the examples hereof. The cephalosporins obtained are converted to other 3-substituted products such as the 3-methyl, 3-hydroxy methyl, and 3-pyridinummethyl compounds in accordance with methods well known in this art and described in the foregoing examples.

EXAMPLE 123

7α-Vinyl-7-(phenylacetamido)cephalosporanic acid

A. Benzhydryl-7-vinyl-7-azidocephalosporanate 0.900 g (0.002 m) of benzhydryl-7-diazocephalosporanate is dissolved in 10 ml $CH_2Cl_2$ and 10 ml $Et_2O$, cooled to −78° C., under $N_2$ and treated dropwise over 15 minutes with 10 ml of a 0.02 M trivinyl boron solution in ether. A check on a small aliquot shows the absence of the diazo compound by ir. The reaction mixture is stirred at −78° C. for a further 5 minutes and then treated with 40 ml of a 0.3 N solution of $BrN_3$ in $CH_2Cl_2$. The reaction mixture is stirred at −78° C. for 15 minutes and allowed to come to room temperature over 45 minutes and then stirred another 20 minutes at room temperature.

The reaction mixture is poured into ice cold 5% $NaHCO_3$ solution, agitated and the organic phase is separated, washed once with 0.1 N sodium thiosulfate solution (30 ml) and then with water, dried and evaporated. The residue is chromatographed on 30 g of silica gel to give benzhydryl 7α-vinyl-7-azidocephalosporanate and benzhydryl 7α-vinyl-7-azidocephalosporanate.

B. Benzhydryl 7α-vinyl-7-aminocephalosporanate 0.030 g of anhydrous cobaltous bromide is dissolved in 50 ml of absolute ethanol and treated with 0.065 g of α,α'-dipyridyl. 0.300 g of the benzhydryl 7α-vinyl-7-azidocephalosporanate is then added dissolved in 2 ml of EtOH, followed by 0.080 g of sodium borohydride. After the rapid evolution of gas ceases (~15 minutes) the reaction mixture is poured into pH 7 phosphate buffer and extracted with methylene chloride, washed once with water, dried and evaporated. The residue is chromatographed on silica gel (10 g) to give benzhydryl 7α-vinyl-7-aminocephalosporanate.

C. Benzhydryl 7α-vinyl-7-(phenylacetamido)cephalosporanate 0.450 g of benzhydryl 7α-vinyl-7-aminocephalosporanate is dissolved in 25 ml of methylene chloride and cooled to 0°. 0.400 ml of phenylacetyl chloride is added followed by 0.400 ml of pyridine. The reaction mixture is stirred for 25 minutes at 0° C. and poured onto crushed ice. The mixture is agitated, the organic phase is separated and washed with pH 2 phosphate buffer and then with water. The organic phase is dried and evaporated. The residue is chromatographed on silica gel to give the purified product.

D. 7α-Vinyl-7-(phenylacetamido)cephalosphoranic acid 0.350 g of benzhydryl 7α-vinyl-7-(phenylacetamido)-cephalosporanate is dissolved in 3 ml of anisole and treated with 10 ml of trifluoroacetic acid at room temperature for 10 minutes. The trifluoroacetic acid and anisole are evaporated under reduced pressure below 40° C. The residue is taken up in methylene chloride (25 ml) and stirred for ½ hour with 20 ml of water containing 0.120 g of $NaHCO_3$. The organic phase is separated and washed once with water. The combined aqueous phase is taken to pH 2 and extracted with ethyl acetate. The ethyl acetate extract is dried and evaporated to give the crude product which is purified by crystallization from ethyl acetate/ether.

Reaction of benzhydryl 7β-vinyl-7-azidocephalosporanate in the above sequence gives 7β-vinyl-7-(phenylacetamido)cephalosporanic acid.

EXAMPLE 124

A. Benzhydryl 7α-aminomethyl-7-(2-benzhydryloxycarbonyl-phenylacetamido)-cephalosporanate 0.800 g of benzhydryl 7α-cyano-7-(2-benzhydryloxycarbonylphenylacetamido)cephalosporanate (prepared as described in Example 108C) is dissolved in 10 ml of tetrahydrofuran and cooled to 0° C. 1 ml of a 1 M solution of $BH_3$.THF in THF is added dropwise over 5 minutes and the mixture is stirred at 0° for ½ hour.

The reaction mixture is poured into pH 7 phosphate buffer and extracted with methylene chloride. The methylene chloride extract is dried and evaporated to give crude product which is purified by chromatography on silica gel.

B. Disodium 7α-aminomethyl-7-(2-carboxyphenylacetamido)cephalosporanate 0.450 g of benzhydryl 7α-(aminomethyl)-7-(2-benzhydryloxycarbonylphenylacetamido)cephalosporanate is dissolved in 3 ml of anisole, 10 ml of $CF_3COOH$ is added and the reaction mixture is allowed to stand at room temperature for 10 minutes. The anisole and CF₃COOH are removed under reduced pressure below 40° C. The residue is taken up in 25 ml ethyl acetate and treated with 15 ml of H₂O containing 0.200 g of NaHCO₃. The mixture is stirred 15 minutes. The organic phase is evaporated and washed once with water. The combined aqueous phase is washed once with methylene chloride and then freeze dried. The product so obtained is purified by crystallization from methanol-isopropanol mixtures.

Reaction of the benzhydryl 7β-cyano-7-(2-benzhydryloxycarbonylphenylacetamido)cephalosporanate in the above sequence gives the 7β-aminomethyl-7-(2-carbonylphenylacetamido)cephalosporanate.

EXAMPLE 125

Sodium 7-hydroxymethyl-7-(2-thienylacetamido)cephalosporanate

A. Benzhydryl 7-(4-nitrobenzilidinamino)cephalosporanate

An equimolar mixture of benzhydryl 7-aminocephalosporanate and 4-nitrobenzaldehyde is heated under nitrogen in 200 ml of benzene per gram aldehyde, and the water azeotropically removed over a one hour period. The solution is evaporated under reduced pressure to give a foam. The ir (CHCl₃) shows bands at 5.60 (β-lactam) and 5.75μ (esters), while the NMR (60 Hz) shows peaks at (numbers are in Hz from internal TMS in CDCl₃) 518,516 (1H), 596, 587, 575, 566 (AB quartet; 4H), 439 (10H), 416 (1H), 330, 328, 325, 323 (doublet of doublets; 1H), 311, 306 (1H), 308, 295, 288, 274 (AB quartet; 2H), 227, 209, 206, 187 (AB quartet; 2H), and 119 (3H). Thin layer chromatography on 250μ silica plates with 10% ethyl acetate in chloroform shows essentially one spot at Rf≃0.58; only traces of the starting materials can be detected.

B. Benzhydryl 7-hydroxymethyl-7-(4-nitrobenzilidinamino) cephalosporanate

A gentle stream of nitrogen is passed into a half-dram vial containing 60 mg of benzhydryl 7-(4-nitrobenzilidinamino)cephalosporanate and after a few minutes 0.3 ml of N,N-dimethylformamide is added. The nitrogen stream is continued, bubbling through the greenish brown solution for ca 30 seconds, and then a stream of formaldehyde gas in nitrogen, generated by heating ~15 mg of paraformaldehyde in a nitrogen stream, is passed through. The color is discharged and the resultant solution is evaporated to a gum under high vacuum. The gum is flushed by dissolving it in a small volume of chloroform and again evaporating to a gum under high vacuum. The product exhibits an ir (neat) spectrum with hydroxy, β-lactam, and ester absorption. The nmr spectrum in CDCl₃ shows the expected singlet for the benzilidine proton, and new absorption associated with the hydroxymethyl group.

C. Benzhydryl 7-hydroxymethyl-7-aminocephalosporanate tosylate salt

A mixture of 100 mg of powdered 2,4-dinitrophenylhydrazine, 85.5 mg of p-toluene sulfonic acid monohydrate, and 3 ml of absolute ethanol are stirred for 30 minutes. To this is added a solution of 304 mg of benzhydryl 7-hydroxymethyl-7-(4-nitrobenzilidinamino) cephalosporanate in 3 ml of ethanol and 0.5 ml of methylene chloride. The mixture is stirred for 30 minutes, filtered, and after the filter cake has been thoroughly washed with ethanol, the filtrates are evaporated under reduced pressure at or below ambient temperature. The resultant solid is washed several times with ether and dried in a nitrogen stream. The ir and nmr of the product are consistent with the assigned structure.

D. Benzhydryl 7-hydroxymethyl-7-aminocephalosporanate

A mixture of 3.5 ml of ether, 0.5 ml of ethyl acetate, 2 ml of water and 22 mg of dipotassium hydrogen phosphate is prepared. To this is added 100 mg of benzhydryl 7-hydroxymethyl-7-aminocephalosporanate tosylate salt and the mixture is shaken vigorously for several minutes. After phase separation the aqueous phase is again extracted with ether, the combined organic phases are dried with anhydrous magnesium sulfate, and evaporated to a gum under reduced pressure. The product is flushed several times by dissolving it in a small volume of chloroform and again evaporating to a gum under high vacuum. The product so obtained exhibits ir and nmr spectra consistent with the assigned structure.

E. Benzhydryl 7-(2-thienylacetoxymethyl)-7-(4-nitrobenzilidinamino)-cephalosporanate A solution of 90 mg of benzhydryl 7-hydroxymethyl-7-(4-nitrobenzilidinamino)-cephalosporanate in 0.3 ml of dry methylene chloride is cooled to 0° and treated with 0.5 ml of dry methylene chloride containing 100 mg of pyridine, also cooled to 0°. To this is added with cooling and stirring over ten minutes a cooled solution of 25 mg of 2-thienylacetyl chloride in 0.25 ml of dry methylene chloride, and held for 2 hours at 0°. The mixture is then shaken with a solution of 55 mg of dipotassium hydrogen phosphate in 3 ml of water, the organic phase is removed, dried with anhydrous magnesium sulfate and taken to a gum under high vacuum. The gum is flushed by dissolving it in a small volume of chloroform and again evaporating it to a gum under reduced pressure. The product is purified by preparative tlc on 1000μ silica plates with fluoroscent indicator. After development with 5% ethyl acetate in chloroform, the desired band is located with the aid of both short and long wave uv light, removed, and eluted with ethyl acetate. The product exhibits ir and nmr spectra consistent with the proposed structure.

F. Benzhydryl 7-(2-thienylacetoxymethyl)-7-aminocephalosporanate

A mixture of 15.9 mg of powdered 2,4-dinitrophenylhydrazine, 13.5 mg of p-toluene sulfonic acid, and 2 ml of absolute ethanol is stirred for 30 minutes. To this is added a solution of 58 mg of benzhydryl 7-(2-thienylacetoxymethyl)-7-(4-nitrobenzilidinamino)cephalosporanate in 1.5 ml of ethanol and 0.2 ml of methylene chloride. After stirring for 30 minutes the mixture is filtered, and the cake washed thoroughly with ethanol. The filtrate is evaporated under reduced pressure at or below ambient temperature and the resultant solids washed several times with ether. The solids are shaken with a mixture of 28 mg of dipotassium hydrogen phosphate, 2 ml of water and 4 ml of ether, the phases are separated, and the aqueous phase is again extracted with ether. The combined organic phases are dried with anhydrous magnesium sulfate, and evaporated to a gum under high vacuum. The product is purified by preparative tlc on 1000μ silica plates with fluorescent indicator using 30% ethyl acetate in benzene as eluent. After locating the desired band with the help of both short and long wave length uv light, it is removed and eluted with ethyl acetate. The product exhibits the desired ir and nmr absorptions, and is essentially homogeneous by tlc.

G. Benzhydryl 7-hydroxymethyl-7-(2-thienylacetamido)cephalosporanate

I—By O→N acyl migration

Benzhydryl 7-(2-thienylacetoxymethyl)-7-aminocephalosporanate undergoes spontaneous O to N acyl migration. When the migration has proceeded to a satisfactory extent as judged by tlc, the substantially more polar product, benzhydryl 7-hydroxymethyl-7-(2-thienylacetamido)cephalosporanate, may be isolated by preparative tlc or chromatography on silica. It exhibits all of the desired characteristics in the ir and nmr spectra and is essentially homogeneous by tlc.

II—By Direct Acylation with Anhydride

A mixture of 100 mg of benzhydryl 7-hydroxy-methyl-7-aminocephalosporanate tosylate salt and 43 mg of 2-thienylacetic anhydride is shaken vigorously with a mixture of 2 ml of water, 3.5 ml of ether, 0.5 ml of ethyl acetate and 30 mg of dipotassium hydrogen phosphate. The phases are separated and the aqueous phase extracted again with ether, the organic phases are combined, dried with magnesium sulfate, and concentrated to ca 0.5 ml. After adding 0.1 ml of pyridine the reation mixture is allowed to stand for 18 hours at room temperature and evaporated to an oil under high vacuum. The oil is taken up in 5 ml of ether and shaken with a mixture of 25 mg of dipotassium hydrogen phosphate in 2 ml of water. After phase separation and reextraction of the aqueous phase with 3 ml of ether, the combined organic phases are dried with anhydrous magnesium sulfate and evaporated to an oil under high vacuum. The crude product is flushed twice by dissolving it in a small volume of chloroform and again evaporating under high vacuum, after which it is purified by preparative tlc. The material so obtained is identical in all respects to that obtained by the rearrangement procedure.

III—By Direct Acylation with Acid Chloride

A solution of benzyl 7-hydroxymethyl-7-aminocephalosporanate (prepared from 114 mg of tosylate salt) in 0.2 ml of sieve dried methylene chloride is cooled to 0°. To this is added dropwise with stirring, 33 mg of 2-thienylacetyl chloride in 0.2 ml of sieve dried methylene chloride over 30 seconds, followed by dropwise addition of 16 mg of pyridine also in 0.2 ml of sieve dried methylene chloride. The mixture is stirred for 1 hour at 0°, then evaporated to a gum under a stream of dry nitrogen. The gum is shaken vigorously with a mixture of 77 mg of dipotassium hydrogen phosphate, 3.5 of ether, 0.5 ml of ethyl acetate, and 2 ml of water. After phase separation the aqueous layer is again extracted with ether and the combined organic phases dried with anhydrous magnesium sulfate, filtered and evaporated under reduced pressure. The resultant gum is purified by preparative tlc on 1000μ silica plates with fluorescent indicator. The desired band is located by means of short wave length uv light, removed and eluted with ethyl acetate. The product exhibits all the physical and spectral properties expected for the desired compound.

H. Sodium 7-hydroxymethyl-7-(2-thienylacetamido)cephalosporanate

A mixture of 59 mg of benzhydryl 7-hydroxymethyl-7-(2-thienylacetamido)cephalosporanate, 0.5 ml of anisole, and 1.0 ml of trifluoroacetic acid is allowed to stand at room temperature for 10 minutes, after which the mixture is concentrated under reduced pressure to an oil. The product is dissolved in 5 ml of chloroform and shaken with a mixture of 5 ml of water and 8.4 mg of sodium bicarbonate. The phases are separated and the organic phase again washed with water. The combined aqueous phases are washed with methylene chloride and then lyophyllyzed to give 42 mg of solid, exhibiting ir and nmr spectral features consistent with the desired product.

EXAMPLE 126

Sodium 7-methoxymethyl-7-(2-furylacetamido)-cephalosporanate

A. Benzhydryl 7-hydroxymethyl-7-[2-(2-furyl)acetamido]cephalosporanate

To an ice cold, stirring solution of 0.350 g of benzhydryl 7-hydroxymethyl-7-aminocephalosporanate in 1.0 ml of dry methylene chloride is added dropwise over a period of 30 seconds 0.119 g of (2-furyl)acetyl chloride in 1.0 ml of dry methylene chloride, followed by 0.065 g of pyridine in 0.5 ml of dry methylene chloride. The reaction mixture is stirred for 60 minutes at 0°, then poured into 10 ml of methylene chloride layered with 10 ml of ice water and agitated. The organic phase is separated, washed with dilute aqueous dipotassium hydrogen phosphate solution, water, and saturated brine, and dried over anhydrous magnesium sulfate. Evaporation of the methylene chloride under reduced pressure yields a gum which is purified by preparative tlc on 1000μ silica gel GF plates. The desired band is visualized by short wavelength uv light, removed, and eluted with ethyl acetate. Evaporation of the ethyl acetate under reduced pressure gives benzhydryl 7-hydroxymethyl-7-[2-(2-furyl)acetamido]cephalosporanate.

B. Benzhydryl 7-methoxymethyl-7-[2-(2-furyl)acetamido]cephalosporanate

A stirring solution of 0.334 g of benzhydryl 7-hydroxymethyl-7-[2-(2-furyl)acetamido]cephalosporanate in 2 ml of methylene chloride is kept at −5° while 7.5μ of boron trifluoride etherate is added. A solution of diazomethane in methylene chloride is then added slowly at the same temperature. A vigorous reaction occurs with the formation of a white solid (polymethylene), and the addition is stopped when a faint yellow color persists in the solution for a short time. After 30 minutes at −5°, the solid is filtered off and the filtrate is diluted with 10 ml of methylene chloride and washed with dilute sodium bicarbonate and water, and dried over anhydrous magnesium sulfate. Evaporation of the solvent under reduced pressure yields an oil which is chromatographed on silica gel using chloroform as eluant to afford benzhydryl 7-methoxymethyl-7-[2-(2-furyl)acetamido]cephalosporanate.

C. Sodium 7-methoxymethyl-7-(2-furylacetamido)cephalosporanate

A solution of 0.295 g of benzhydryl 7-methoxymethyl-7-[2-(2-furyl)acetamido]cephalosporanate in 2.5 ml of anisole is treated with 7.5 ml of trifluoroacetic acid and then kept at room temperature for 10 minutes. Excess reagents are removed under reduced pressure at ambient temperature. The residue is dissolved in 20 ml of methylene chloride and stirred with a solution of 0.075 g of sodium bicarbonate in 10 ml of water. After phase separation, the methylene chloride layer is extracted with 5 ml of water. The combined aqueous solutions are washed with three 5 ml portions of methylene chloride and lyophilized to give sodium 7-methoxymethyl-7-[2-(2-furyl)acetamido]cephalosporanate as a powder.

The acetoxymethyl group of sodium 7-methoxymethyl-7-[2-(2-furyl)-acetamido]cephalosporanate can be converted to other 3-substituted cephalosporins. The acetoxy group can be displaced by reaction with nitrogen bases and other compounds of greater nucleophility than the oxygen nucleophile. Further, the 3-acetoxymethyl can be catalytically reduced in the presence of hydrogen to produce the 3-methyl cephalosporin. Other 3-substituted compounds, such as 3-hydroxymethyl, can also be made and converted to other valuable compounds.

EXAMPLE 127

Disodium 7-carboxymethyl-7-(2-thienylacetamido)cephalosporanate

A. 2,2,2-Trichloroethyl-7-(4-nitrobenzaldimino)cephalosporanate 0.800 g of 2,2,2-trichloroethyl-7-aminocephalosporanate is dissolved in 200 ml $C_6H_6$, 0.300 g of p-nitrobenzaldehyde is added. The mixture is refluxed with azeotropic removal of the water formed. After 1 hour the benzene solution is evaporated under reduced pressure to give a foam.

B. 2,2,2-Trichloroethyl-7-(2,2,2-trichloroethoxycarbonylhydroxymethyl)-7-(4-nitrobenzaldimino)cephalosporanate 0.550 g of 2,2,2-trichloroethyl-7-(4-nitrobenzaldimino)cephalosporanate is dissolved in 5 ml of DMF under $N_2$. 0.205 g of 2,2,2-trichloroethylglyoxalate in 2 ml of DMF is added dropwise over 15 minutes. The reaction mixture is stirred for ½ hour and the DMF is removed under reduced pressure to give the product.

C. 2,2,2-Trichloroethyl-7-(2,2,2-trichloroethoxycarbonylhydroxymethyl)-7-aminocephalosporanate A mixture of 0.200 g of 2,4-dinitrophenylhydrazine, 0.171 g of p-toluene sulfonic acid monohydrate and 6 ml of absolute ethanol is stirred for 30 minutes. To this is added a solution of 0.600 g of 2,2,2-trichloroethyl-7-(2,2,2-trichloroethoxycarbonylhydroxymethyl)-7-(4-nitrobenzaldimino)cephalosporanate in 6 ml of ethanol and 0.5 ml of $CH_2Cl_2$. The mixture is stirred for 30 minutes, filtered and after the filter cake has been thoroughly washed with ethanol, the filtrate and washings are evaporated under reduced pressure to give a solid.

The solid is suspended in 15 ml of water containing 155 mg of $K_2HPO_4$ and extracted thrice with methylene chloride (20 ml). The combined organic phase is dried over $MgSO_4$ and evaporated to a gum under reduced pressure to give the product.

D. 2,2,2-Trichloroethyl-7-(2,2,2-trichloroethoxycarbonylhydroxymethyl)-7-(2-thienylacetamido)cephalosporanate 0.620 g of 2,2,2-trichloroethyl-7-(2,2,2-trichloroethoxycarbonylhydroxymethyl)-7-aminocephalosporanate is dissolved in 100 ml of $CH_2Cl_2$, cooled to 0° and treated with 0.160 g of 2-thienylacetyl chloride, followed by dropwise addition of 0.100 g pyridine in 2 ml of $CH_2Cl_2$. The mixture is stirred for 1 hour at 0° and poured onto crushed ice. After agitation the organic phase is separated and washed once with pH 2 phosphate buffer and once with water. After drying over $MgSO_4$ the solvent is removed to give the crude product, which is purified by chromatography over silica gel.

E. 2,2,2-Trichloroethyl-7-(2,2,2-trichloroethoxycarbonylmethylsulfonyloxymethyl)-7-(2-thienylacetamido)cephalosporanate 0.350 g of 2,2,2-trichloroethyl-7-(2,2,2-trichloroethoxycarbonylhydroxymethyl)-7-(2-thienylacetamido)-cephalosporanate is dissolved in 10 ml of $CH_2Cl_2$ and and cooled to 0°, 0.115 g methane sulfonylchloride is added and then 0.080 g of pyridine. The reaction mixture is stirred at 0° for 1½ hours. The reaction mixture is poured onto crushed ice and agitated. The organic phase is separated and washed with pH 2 phosphate buffer, and water and is dried and evaporated. The crude product is purified by chromatography on silica gel.

F. 2,2,2-Trichloroethyl-7-(2,2,2-trichloroethoxycarbonyliodomethyl)-7-(2-thienylacetamidocephalosporanate)

0.300 g of 2,2,2-trichloroethyl-7-(2,2,2-trichloroethoxycarbonylmethylsulfonyloxymethyl)-7-(2-thienylacetamido)cephalosporanate is dissolved in 10 ml of DMSO. Sodium iodide 0.100 g is added and the mixture stirred at room temperature overnight. The dimethyl sulfoxide is removed under reduced pressure. The residue is partitioned between 10 ml of $H_2O$ and 10 ml $CH_2Cl_2$. The organic phase is washed once with water dried and evaporated to give the crude product which is purified by preparative tlc on silica gel plates.

G. 2,2,2-Trichloroethyl-7-(2,2,2-trichloroethoxycarbonylmethyl)-7-(2-thiophenacetamido)cephalosporanate 0.200 g 2,2,2-trichloroethyl-7-(2,2,2-trichloroethoxycarbonyliodomethyl)-7-(2-thiophenacetamido)cephalosporanate is dissolved in 20 ml ethanol, 0.100 g of sodium acetate and 0.100 g of 5% Pd on calcium carbonate are added and the mixture is treated with $H_2$ at 40 psig for 2 hours. The catalyst is filtered off. The filtrate is evaporated under reduced pressure and the residue is chromatographed on silica gel to give the product.

H. Disodium 7-carbomethoxy-7-(2-thienylacetamido)cephalosporanate 0.300 g of 2,2,2-trichloroethyl-7-(2,2,2-trichloroethoxycarbonylmethyl)-7-(2-thiophenacetamido)cephalosporanate is dissolved in 15 ml of 95% acetic acid. 0.300 g of Zn dust is added in 5 equal amounts over 20 minutes while the mixture is vigorously stirred at room temperature. The reaction mixture is carefully poured into ice cold pH 2 phosphate buffer and extracted with ethyl acetate. The ethyl acetate extract is washed once with water dried and evaporated. The residue is taken up in methyl isobutyl ketone 10 ml and extracted with 15 ml of $H_2O$ containing 0.120 g of $NaHCO_3$. The organic phase is separated and washed once with water. The combined aqueous phase is washed twice with methylene chloride and then freeze dried to give the crude product. Crystallization from MeOH/iPrOH gives the pure product.

EXAMPLE 128

A. Benzhydryl 7-azido-7-trifluoromethylcephalosporanate

A degassed solution of benzhydryl 7-diazocephalosporanate, 45 mg, and 144 mg $CF_3I$ in 15 ml benzene saturated with triethylammonium azide is irradiated with uv light >300 nm is a pyrex flask until the diazo band at 4.8μ in the ir spectrum is consumed. The resulting solution is washed with water, dried with $MgSO_4$, evaporated and carefully chromatographed on silica gel, eluting with chloroform, to afford both epimers of benzhydryl 7-azido-7-trifluoromethylcephalosporanate.

B. Benzhydryl 7β-amino-7α-trifluoromethylcephalosporanate Benzhydryl 7β-(2-thienylacetamido)-7α-trifluoromethylcephalosporanate Benzhydryl 7β-azido-7α-trifluoromethylcephalosporanate, 542 mg, is hydrogenated at 40 psi for three hours using 1 g $PtO_2$ in 50 ml dioxane containing 500 mg thienylacetic anhydride. The 7β-amino compound is formed during the hydrogenation and acylated in situ. After filtration of the catalyst, the solution is treated for 15 minutes with 0.5 ml water to hydrolyze excess anhyride, then vacuum stripped. The crude product is taken up in 25 ml ethyl acetate, washed with aqueous bicarbonate, dried with $MgSO_4$, filtered, evaporated, and chromatographed on silica gel, using 4:1 chloroform:ethyl acetate, to afford benzhydryl 7β-(2-thienylacetamido)-7α-trifluoromethylcephalosporanate. The other epimer affords the epimeric compound by the same procedure.

C. Sodium 7β-(2-thienylacetamido)-7α-trifluoromethylcephalosporanate

Benzhydryl 7β-(2-thienylacetamido)-7α-trifluoromethylcephalosporanate, 640 mg, is dissolved in 0.8 g anisole and cooled to 0° C. Trifluoroacetic acid, 4 ml, precooled to 0° C., is added and the reaction allowed to proceed for two minutes at 0° C. Vacuum of 0.1 mm is immediately applied and the reaction mixture allowed to warm to room temperature without external heating. Anisole is then distilled out at 30° C./0.1 mm. A few ml anisole is added to the residue and pulled off at 30° C./0.1 mm to insure total removal of trifluoroacetic acid. The product is treated with 5 ml water containing 84 mg $NaHCO_3$ and lyophilized. The resulting powder is washed thoroughly with ether and dried, affording the desired sodium salt. The other epimer affords the epimeric sodium salt by the same procedure.

EXAMPLE 129

Sodium 7α-difluoromethyl-7-(2-thienylacetamido)cephalosporanate

A. Benzhydryl 7β-(p-nitrobenzylideneamino)-7α-difluoromethylcephalosporanate Benzhydryl 7-(p-nitrobenzylideneamino)cephalosporanate 571 mg, is dissolved in 20 ml of 1,2-dimethoxyethane (DME) containing 1 ml of chlorodifluoromethane. With vigorous stirring under nitrogen, 112 mg potassium t-butoxide is slowly introduced as a slurry in DME over about one hour.

After stirring an additional hour, KCl is filtered off and the volatiles removed in vacuo to afford benzhydryl 7β-(p-nitrobenzylideneamino)-7α-difluoromethylcephalosporanate. It can be purified, if desired, by chromatography on silica gel, eluting with 2% ethyl acetate in chloroform.

B. Sodium 7α-difluoromethyl-7-(2-thienylacetamido)cephalosporanate

Removal of the Schiff base functionality with aniline hydrochloride, acylation of the resulting 7-aminocephalosporin with thienylacetyl chloride (or other acid chloride or anhydride), and deblocking of the 4-carboxy group with trifluoroacetic acid are all accomplished in the same manner as that described in previous examples to afford sodium 7α-difluoromethyl-7-(2-thienylacetamido)cephalosporanate.

EXAMPLE 130

7-(2-Thienylacetamido)-7-aminocephalosporanic acid

Step A: Benzhydryl 7,7-diazidocephalosporanate

Benzhydryl 7-bromo-7-azidocephalosporanate (10 mm.) is dissolved in 0.5 M lithium azide (20 ml.) in dimethylformamide and heated at 68° C. for three minutes under nitrogen. The solution is diluted with water (100 ml.) and extracted with chloroform (20 ml.). The chloroform layer is washed with two 60 ml. portions of water and dried over sodium sulfate. Evaporation of the solvent in vacuo yields crude benzhydryl 7,7-diazidocephalosporanate.

Step B: Benzhydryl 7-amino-7-azidocephalosporanate

Benzhydryl 7,7-diazidocephalosporanate (10 mm.) are dissolved in ethyl acetate and 3 g. 10% palladium-on-carbon are added. The mixture is hydrogenated at atmospheric pressure at 45° C. for one hour. There is thus obtained a crude isomeric mixture of benzhydryl 7-amino-7-azidocephalosporanate.

Step C: Benzhydryl 7-(2-thienylacetamido)-7-Azidocephalosporanate

The isomeric mixture of benzhydryl 7-amino-7-azidocephalosporanates (5 mm.) obtained in Step B is dissolved in methylene chloride (50 ml.) and cooled to 0° C. Collidine (5 mm.) and 2-thienylacetyl chloride (5mm.) are added and the solution is let stand at 0° C. for one hour. The methylene chloride solution is washed with saturated sodium bicarbonate solution, two 50 ml. portions of 1 N hydrochloric acid, a 1% sodium bicarbonate solution (50 ml.) and water (50 ml.). The solvent is dried over sodium sulfate and evaporated to afford benzhydryl 7-(2-thienylacetamido)-7-azidocephalosporanate in the form of a gum.

Step D: Benzhydryl 7-(2-thienylacetamido)-7-aminocephalosporanate

The benzhydryl 7-(2-thienylacetamido)-7-azidocephalosporanate (10 mm.) obtained in Step C is dissolved in ethyl acetate (50 ml.) and 3 g. of a palladium-on-charcoal catalyst is added. Hydrogenation is carried out at room temperature at 40 psi for one hour. The catalyst is removed by filtration and the solvent is evaporated in vacuo to afford crude benzhydryl 7-(2-thienylacetamido)-7-aminocephalosporanate.

Step E: 7-(2-thienylacetamido)-7-aminocephalosporanic Acid

Benzhydryl 7-(2-thienylacetamido)-7-aminocephalosporanate is dissolved in anisole (10 ml.) at 0° C. To this solution is added trifluoroacetic acid (15 ml.) cooled to 0° C. and the mixture is aged at room temperature for one hour. The excess trifluoroacetic acid-anisole is removed by evaporation and the residue flushed twice with chloroform and evaporated to dryness. The crude product thus obtained is 7-(2-thienylacetamido)-7-aminocephalosporanic acid.

EXAMPLE 131

7-(2-Thienylacetamido)-7-Azidocephalosporanic Acid 7-(2-Thienylacetamido)-7-azidocephalosporanate (1 mm.) is dissolved in anisole (10 ml.) at 0° C. To this solution is added trifluoroacetic acid (15 ml.) cooled to 0° C. and the mixture is aged at room temperature for one hour. Excess trifluoroacetic acid and anisole are removed by evaporation and the residue is flushed twice with chloroform and evaporated to dryness. The crude product thus obtained is 7-(2-thienylacetamido)-7-azidocephalosporanic acid.

EXAMPLE 132

7-(2-Thienyl acetamido)-7-Guanidinocephalosporanic Acid 7-(2-Thienyl acetamido)-7-aminocephalosporanic acid (10 mm.) are dissolved in methanol (50 ml.) at room temperature. 3,5-Dimethylamidinopyrazole (10 mm.) is added and the mixture is stirred for 16 hours at room temperature. The solution is diluted with 100 ml. of water and extracted three times with ether. The ether layer is then discarded and the water layer is lyophilized to afford crude 7-(2-thienyl acetamido)-7-guanidinocephalosporanic acid.

EXAMPLE 133

7-(2-Thienyl acetamido)-7-Ureidocephalosporanic Acid 7-(2-Thienyl acetamido)-7-aminocephalosporanic acid (10 mm.) are dissolved in dry pyridine (20 ml.) and the solution is cooled to −10° C. Carbamoyl chloride (10 mm.) dissolved in 20 ml. dry pyridine is added slowly and the mixture is stirred for one hour at −10° C. and then quenched with ice cold saturated sodium bicarbonate solution (100 ml.). The aqueous solution is extracted with ether to remove pyridine and the water layer is lyophilized. The salt cake is slurried with methanol and filtered and the methanol solution is evaporated to dryness to afford crude 7-(2-thienyl acetamido)-7-ureidocephalosporanic acid.

EXAMPLE 134

7-(2-Thienyl acetamido)-7-(N,N-Dimethylureido)cephalosporanic Acid

In a like manner N,N-dimethylcarbamoyl chloride is substituted for carbamoyl chloride to give 7-(2-thienyl acetamido)-7-(N,N-dimethylureido)cephalosporanic acid. Upon substituting an equivalent amount of N,N-dimethylcarbamoyl chloride for the carbamoyl chloride of Example 133 and following the procedure described therein there is thus obtained 7-(2-thienyl acetamido)7(N,N-dimethylureido)cephalosporanic acid.

EXAMPLE 135

7-(2-Thienyl acetamido)-7-(N-Amidinoureido)cephalosporanic Acid 7-(2-Thienyl acetamido)-7-aminocephalosporanic acid (10 mm.) is dissolved in a solution of dimethylformamide (50 ml.) and pyridine (20 ml.) and cooled to 0° C. The solution is treated with a 100 ml. solution of toluene containing 17% phosgene (large excess). The reaction is allowed to stand for two hours and evaporated under vacuum to remove toluene and excess phosgene. The resulting solution containing 7-(2-thienyl acetamido)-7-(chloroformamido)cephalosporanic acid is then cooled to 0° C. and guanidine (10 ml.) is added. The solution is aged at 0° C. for two hours and quenched by the addition of a saturated sodium bicarbonate solution. The mixture is extracted with ether to remove pyridine and the water is removed by evaporation in vacuo and the salt cake extracted with dry methanol. Evaporation of the methanol yields crude 7-(2-thienyl acetamido)-7-(N-amidinoureido)cephalosporanic acid.

EXAMPLE 136

7-(2-Thienyl acetamido)-7-Sulfonamidocephalosporanic Acid 7-(2-Thienyl acetamido)-7-aminocephalosporanic acid (10 mmoles) is dissolved in pyridine (50 ml.) and cooled to 0° C. To this solution is added pyridine-sulfur trioxide complex (10 mmoles). The mixture is aged for three hours at 0° C. and the pyridine is removed in vacuo to afford crude 7-(2-thienyl acetamido)-7-sulfonamidocephalosporanic acid.

EXAMPLE 137

7-(2-Thienyl acetamido)-7-Acetamidocephalosporanic Acid 7-(2-Thienyl acetamido)-7-aminocephalosporanic acid (1 mmole) is dissolved in 10 ml. of water at 0° C. containing one millimole of sodium bicarbonate at 0° C. The mixture is treated with acetic anhydride (2 mmoles), stirred at 0° C. for one hour and acidified with dilute hydrochloric acid (1 mmole). The precipitated product is filtered, washed with water and dried in vacuo to afford crude 7-(2-thienyl acetamido)-7-acetamidocephalosporanic acid.

EXAMPLE 138

7-(2-Thienyl acetamido)-7-Methanesulfonamidocephalosporanic acid

Upon substituting an equivalent amount of methanesulfonyl chloride for the acetic anhydride of Example 137 and otherwise following the procedure described therein there is obtained 7-(2-thienyl acetamido)-7-methanesulfonamidocephalosporanic acid.

EXAMPLE 139

7-(2-Thienylacetamido)-7-(Ethoxycarbonylamino)-Cephalosporanic Acid

Step A: Benzhydryl 7-azido-7-(ethoxycarbonylamino)cephalosporanate

Ethyl urethane (25.0 g.) is melted at 48° C. and benzhydryl 7-bromo-7-azidocephalosporanate (5 mm.) is then added. To this solution is also added in one portion molten ethyl urethane (15 g.) containing silver tetrafluoroborate (15 mm.). The temperature is maintained at 50° C. for five minutes and the reaction is then quenched by adding to a large volume of ether. The silver bromide formed is removed by filtration through diatomaceous earth and the ether solution is washed successively with water (400 ml.), a saturated sodium bicarbonate solution (400 ml.) and two 400 ml. portions of water. The organic layer is dried with sodium sulfate, the solvent evaporated in vacuo and the gummy residue triturated several times with water to remove excess ethyl urethane. There is thus obtained benzhydryl 7-azido-7-(ethoxycarbonylamino)cephalosporanate.

Step B: Benzhydryl 7-(2-thienylacetamido)-7-(ethoxycarbonylamino)cephalosporanate 2-Thienylacetic anhydride (5 mm.), pyridine (0.1 ml.) and 10% palladium-on-carbon (3.0 g.) are added to a solution of benzhydryl 7-azido-7-(ethoxycarbonylamino)cephalosporanate (5 mm.) dissolved in ethyl acetate (25 ml.). The mixture is hydrogenated at room temperature for one hour. The catalyst is then removed by filtration and the residue evaporated to a glass under vacuum. There is thus obtained crude benzhydryl 7-(2-thienylacetamido)-7-(ethoxycarbonylamino)cephalosporanate.

Step C: 7-(2-Thienylacetamido)-7-(ethoxycarbonylamino)cephalosporanate acid The benzhydryl 7-(2-thienylacetamido)-7-(ethoxycarbonylamino)cephalosporanate (1.0 mm.) obtained in Step B is dissolved in 10 ml. of anisole at 0° C. To this solution is added trifluoroacetic acid (15 ml.) cooled to 0° C. and the mixture is aged at room temperature for one hour. The excess trifluoroacetic acid-anisole is removed by evaporation and the residue is flushed twice with chloroform and evaporated to dryness. The crude product thus obtained is 7-(2-thienylacetamido)-7-(ethoxycarbonylamino)cephalosporanic acid.

EXAMPLE 140

7-(2-Thienylacetamido)-7-Methylaminocephalosporanic Acid

Step A: Benzhydryl 7-azido-7-nitrocephalosporanate

Benzhydryl 7-bromo-7-azidocephalosporanate (10 mm.) is heated for four minutes at 68° C. in dimethylformamide (60 ml.) containing lithium nitrite (10 mm.). The solution is diluted with water (300 ml.) and extracted with two 50 ml. portions of chloroform. The chloroform layer is washed with three 100 ml. portions of water and dried over anhydrous sodium sulfate. The crude product thus obtained is benzhydryl 7-azido-7-nitrocephalosporanate.

Step B: Benzhydryl 7-(2-thienylacetamido)-7-nitrocephalosporanate

Benzhydryl 7-azido-7-nitrocephalosporanate (10 mm.) is dissolved in isopropanol (25 ml.) at 0° C. and to this solution sodium borohydride (5 mm.) dissolved in isopropanol (25 ml.) is added slowly. The solution is aged for one hour at 0° C. and then quenched in ice water. The solution is extracted with three 50 ml. portions of methylene chloride and the organic layer is dried over sodium sulfate. To the dried methylene chloride solution is added ten millimoles of 2-thienylacetic anhydride (10 mm.) and collidine (10 mm.) at 0° C. After standing for 30 minutes at 0° C. the methylene chloride layer is extracted with two 50 ml. portions of 0.1 N hydrochloric acid and two 50 ml. portions of sodium bicarbonate and, finally, with two 50 ml. portions of water. The methylene chloride solution is then dried over sodium sulfate and evaporated in vacuo to afford a gum. The crude product thus obtained is benzhydryl 7-(2-thienylacetamido)-7-nitrocephalosporanate.

Step C: 7-(2-Thienylacetamido)-7-nitrocephalosporanic acid

Upon substituting an equivalent amount of benzhydryl 7-(2-thienylacetamido)-7-nitrocephalosporanate for the 7-(2-thienylacetamido)-7-(ethoxycarbonylamino)-cephalosporanate of Example 139, Step C, and following the procedure described therein there is thus obtained 7-(2-thienylacetamido)-7-nitrocephalosporanic acid.

Step D: 7-(2-Thienylacetamido)-7-aminocephalosporanic acid 7-(2-Thienylacetamido)-7-nitrocephalosporanic acid (10 mmoles) is reduced in methanol (50 ml.) using a palladium-on-charcoal catalyst (1.0 g.) at 40 psi at room temperature for one hour. The catalyst is removed by filtration. The solvent is then removed by evaporation to afford crude 7-(2-thienylacetamido)-7-aminocephalosporanic acid.

Step E: 7-(2-Thienylacetamido)-7-Methylaminocephalosporanic Acid 7-(2-Thienylacetamido)-7-aminocephalosporanic acid (10 mmoles) is dissolved in ethanol (100 ml.). To this solution is added platinum oxide catalyst (0.1 g.) and formaldehyde (13 mm.). Hydrogenation is accomplished at room temperature with two atmospheres hydrogen pressure over a 5 to 10 minute period. The catalyst is filtered off and the solvent removed in vacuo to afford crude 7-(2-thienylacetamido)-7-methylaminocephalosporanic acid.

EXAMPLE 141

By following the procedure described in Example 140 Steps A through E, all of the 7-amido-7-(alkylamino)cephalosporanate products of this invention may be obtained. Thus, for example, by substituting an equivalent amount of aralkanoic anhydride or heterocyclic anhydride for the 2-thienylacetic anhydride recited in Step B and, upon substituting an equivalent amount of alkaldehyde or aralkaldehyde for the formaldehyde recited in Step E therein, the corresponding 7-amido-7-(N-alkylamino- and N-aralkylamino)cephalosporanic acids of this invention may be synthesized. The following equation and accompanying Table illustrate this process and the products obtained thereby:

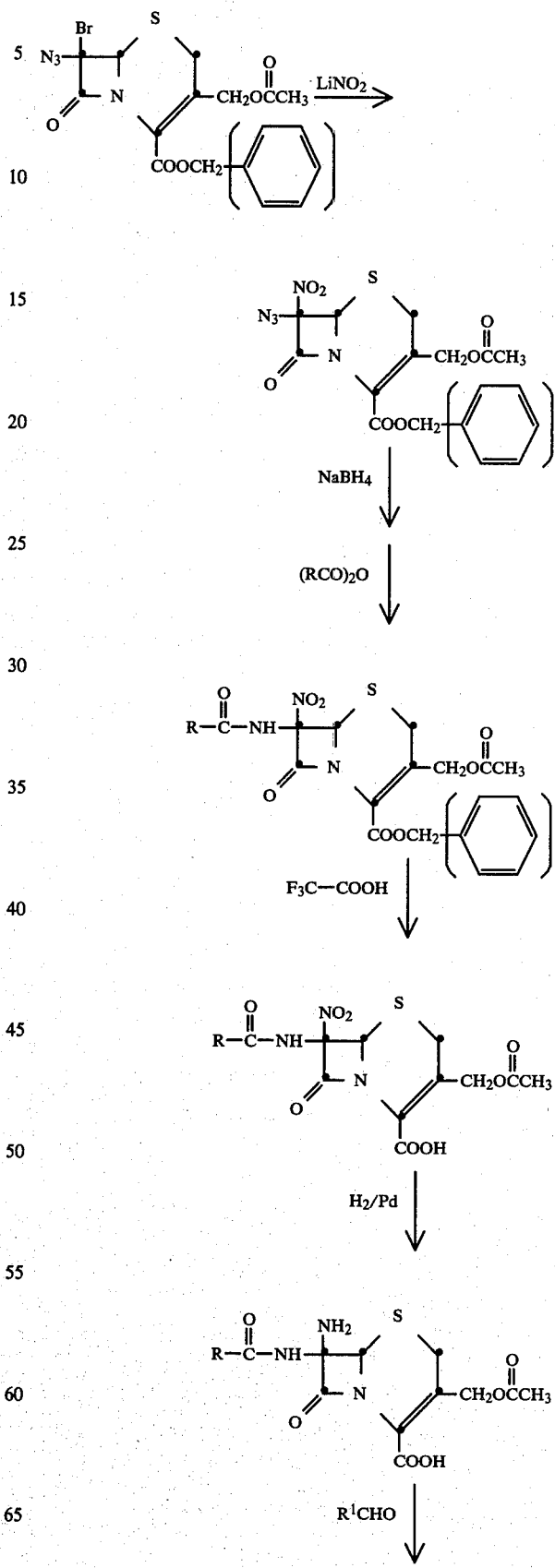

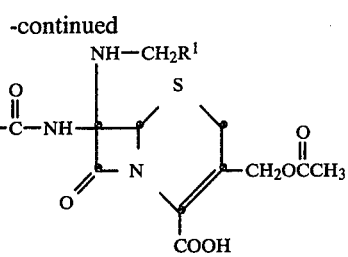

TABLE I

| R | CH₂R¹ |
|---|---|
| HOOC—CH—(C₆H₄)— | —CH₃ |
| (thienyl)-CH₂— | —C₂H₅ |
| (thienyl)-CH₂— | —(CH₂)₂CH₃ |
| (furyl)-CH₂— | (furyl) |
| (furyl)-CH₂— | —CH(CH₃)₂ |
| (pyridyl)-CH₂— | —CH₂-(furyl) |
| (pyridyl)-CH₂— | (furyl)-Cl |
| (pyridyl)-CH₂— | —(CH₂)₂CH₃ |
| (furyl)-CH₂— | (furyl)-CH₃ |

EXAMPLE 142

7-(2-Thienylacetamido)-7-(N,N-Dimethylamino)Cephalosporanic acid 7-(2-Thienylacetamido)-7-aminocephalosporanic acid (10 mm.) is dissolved in acetic acid (100 ml.) containing formaldehyde (40 mm.). To this solution is added platinum oxide catalyst (0.2 g.) and the hydrogenation is carried out at 4–6 atmospheres of hydrogen at 35° C. for eight hours. The catalyst is then filtered off and the solvent is removed by evaporation in vacuo to afford crude 7-(2-thienylacetamido)-7-(N,N-dimethylamino)cephalosporanic acid.

EXAMPLE 143

7-Phenylacetamido-7-(Ethoxycarbonylamino)cephalosporanic Acid

Step A: Benzhydryl 7-phenylacetamido-7-(ethoxycarbonylamino)cephalosporanate

Phenylacetic anhydride (5 mm.), pyridine (0.1 ml.) and Bolhoffer catalyst (3.0 g.) are added to a solution of benzhydryl 7-azido-7-(ethoxycarbonylamino)cephalosporanate (5 mm.) dissolved in ethyl acetate (25 ml.). The mixture is hydrogenated at room temperature for one hour. The catalyst is then removed by filtration and the residue evaporated under vacuum to afford crude benzhydryl 7-phenylacetamido-7-(ethoxy-carbonylamino)-cephalosporanate.

Step B: 7-Phenylacetamido-7-(ethoxycarbonylamino)cephalosporanic acid

Benzhydryl 7-phenylacetamido-7-(ethoxycarbonylamino)cephalosporanate (1.0 mm.) is dissolved in anisole (10 ml.) at 0° C. and to this solution is added trifluoroacetic acid (15 ml.) cooled to 0° C. The mixture is then aged at room temperature for one hour. Excess trifluoroacetic acid-anisole is removed by evaporation and the residue is flushed twice with chloroform and evaporated to dryness to afford crude 7-phenylacetamido-7-(ethoxycarbonylamino)cephalosporanic acid.

EXAMPLE 144

By following the procedure described in Example 142 for the preparation of 7-(2-thienylacetamido)-7-(N,N-dimethylamino)cephalosporanic acid all of the 7-amido-7-(N,N-dialkylamino)cephalosporanic acids of this invention may be obtained. Thus, for example, by substituting an equivalent amount of alkaldehyde for the formaldehyde recited in Example 142 and following the procedure described therein, the corresponding 7-(2-thienylacetamido)-7-(N,N-dialkylamino)cephalosporanic acid products may be obtained. The following equation and Table II illustrate this process and the products obtained thereby:

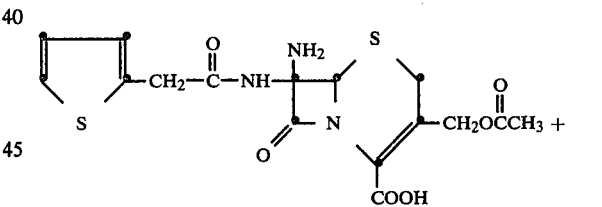

OCHR² ⟶

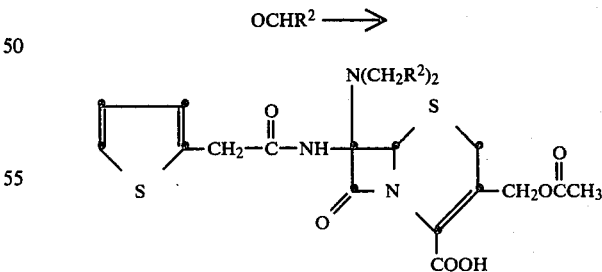

TABLE II

| R² | OCHR² |
|---|---|
| —C₂H₅ | OCHCH₃ |
| —(CH₂)₂CH₃ | OCHCH₂CH₃ |
| —CH₂—(C₆H₅) | OCH—(C₆H₅) |

TABLE II-continued

| R² | OCHR² |
|---|---|
| —CH₂—CH₂—⌬ | OCH—CH₂—⌬ 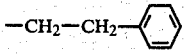 |
| —(CH₂)₃CH₃ | OCH(CH₂)₂CH₃ |
| —(CH₂)₄CH₃ | OCH(CH₂)₃CH₃ |

EXAMPLE 145

Sodium 7-Ethoxycarbonylamino-7-(2-Thienylacetamido)cephalosporanate

Step A: Benzhydryl 7-Azido-7-(Ethoxycarbonylamino)cephalosporanate cephalosporanate Benzhydryl 7-azido-7-bromocephalosporanate (3.9 g.) is added to ethylcarbamate (36 g.) maintained at 65° C. To the resulting mixture is added portionwise as a melt silver tetrafluoroborate (3.6 g.) dissolved in ethylcarbamate (18 g.) and the reaction mixture is maintained at 67°-70° C. for five minutes. The mixture is then poured into ether with stirring and the resulting slurry is filtered through celite to remove the silver bromide. The ether is extracted successively with water (100 ml.) saturated aqueous sodium bicarbonate (100 ml.) solution (100 ml.) and two portions of water (100 ml.). The extracted ether solution is dried over sodium sulfate and then evaporated under diminished pressure. The resulting residue is triturated three times with a small amount of water and then dissolved in chloroform. The chloroform solution is dried over sodium sulfate and evaporated to dryness to afford 2.1 g. of benzhydryl 7-azido-7-(ethoxycarbonylamino)cephalosporanate.

Step B: Benzhydryl 7-Amino-7-(Ethoxycarbonylamino)cephalosporanate

Benzhydryl 7-azido-7-(ethoxycarbonylamino)cephalosporanate (1.0 g.) is dissolved in dioxane (100 ml.). Platinum oxide (1.0 g.) is added and the reaction mixture is stirred under hydrogen at atmospheric pressure for one hour. Another 1.0 g. quantity of platinum oxide is added and the reaction mixture is again placed under hydrogen and stirred for three hours until the azide is completely reacted as determined by an infrared analysis of aliquots. The solvent is removed under reduced pressure and the residue taken up in chloroform (50 ml.) and filtered through silica gel G in chloroform in a 60 ml. sintered glass funnel. The resulting material is eluted with chlorofrom until 200 ml. of chloroform has been collected. The chloroform is then removed under reduced pressure to afford benzhydryl 7-amino-7-(ethoxycarbonylamino)cephalosporanate (0.6 g.).

Step C: Benzhydryl 7-Ethoxycarbonylamino-7-(2-Thienylacetamido)cephalosporanate The benzhydryl 7-amino-7-(ethoxycarbonylamino)-cephalosporanate (0.6 g.) obtained in Step B is taken up in methylene chloride (25 ml.) and cooled to 0° C. 2-Thienylacetyl chloride (0.6 ml., 0.038 mole) is added dropwise over 30 seconds followed by the addition of pyridine (0.6 ml., 0.01 mole) 60 seconds later. The reaction mixture is stirred at 0° C. for 15 minutes and poured into crushed ice. The mixture is agitated and the organic layer separated and washed once with water (20 ml.), once with 5% sodium bicarbonate (20 ml.) and once again with water (20 ml.). The methylene chloride mixture is then dried and evaporated to dryness to afford 1.42 g. of crude benzhydryl 7-ethoxycarbonylamino-7-(2-thienylacetamido)cephalosporanate. This material is placed on a column of 60 g. of silica gel under benzene and the column is eluted with benzene, taking 100 ml. fractions followed by 300 ml. of methylene chloride benzene (1:1) in three fractions and 500 ml. of methylene chloride in five fractions. The product is removed from the column by eluting with chloroform (400 ml.) in four fractions, affording 0.55 g. of benzhydryl 7-ethoxycarbonylamino-7-(2-thienylacetamido)cephalosporanate. This material is taken up in methylene chloride (25 ml.) and stirred at room temperature with 20 ml. of a solution of sodium bicarbonate (0.120 g.) in water for 0.5 hour. The resulting layers are then separated and the organic layer is washed with water, dried and evaporated to dryness to afford 0.4 g. of benzhydryl 7-ethoxycarbonylamino-7-(2-thienylacetamido)cephalosporanate.

Step D. Sodium 7-Ethoxycarbonylamino-7-(2-Thienylacetamido)cephalosporanate Benzhydryl 7-ethoxycarbonylamino-7-(2-thienylacetamido)cephalosporanate (0.4 g.) is dissolved in anisole (2.5 ml.) and treated with trifluoroacetic acid (10 ml.) at room temperature for 10 minutes. The trifluoroacetic acid and anisole are removed under reduced pressure while maintaining the temperature below 40° C., and the residue is taken up in chloroform (25 ml.) and treated with 20 ml. of water containing 0.120 g. of sodium bicarbonate. The mixture is stirred for 0.5 hour at room temperature and the organic phase is separated and washed with water. The combined aqueous phase is then washed twice with methylene chloride and lyophilized to afford 0.32 g. of sodium 7-ethoxycarbonylamino-7-(2-thienylacetamido)cephalosporanate as a brownish solid.

EXAMPLE 146

7-Ethoxycarbonylamino-7-(2-Thienylacetamido)-3-Pyridiniumdecephalosporanic Acid

Sodium 7-ethoxycarbonylamino-7-(2-thienylacetamido)cephalosporanate (1.3 g.) is dissolved in 3 cc. of a buffer solution made up by dissolving potassium iodide (30 g.) in water (20 ml.) containing 5 ml. of pyridine and adjusting the pH to 6.5 with dilute acetic acid. The resulting reaction mixture is stirred at 80° C. for two hours and then cooled to room temperature. The solution is then freeze dried, dissolved in 25% acetic acid (40 ml.), filtered and the filtered solution subjected to electrophoresis to obtain 7-ethoxycarbonylamino-7-(2-thienylacetamido)-3-pyridinium-decephalosporanic acid.

EXAMPLE 147

Sodium 7-ethoxycarbonylamino-7-phenylacetamidocephalosporanate

When benzhydryl 7-amino-7-ethoxycarbonylaminocephalosporanate is reacted with phenylacetyl chloride in place of thienylacetyl chloride as described in Example 145 above, benzhydryl 7-ethoxycarbonylamino-7-phenylacetamidocephalosporanate is obtained. Using the procedures described in Example 145, this ester is converted to the sodium salt.

EXAMPLE 148

Sodium 7-ethoxycarbonylamino-7-thiophenoxyacetamidocephalosporanate

When benzhydryl 7-amino-7-ethoxycarbonylaminocephalosporanate is reacted with an equivalent amount of phenylthioacetyl chloride in place of thienylacetyl chloride as described in Example 145 above, benzhydryl 7-ethoxycarbonylamino-7-thiophenoxyacetamidocephalosporanate is obtained. Using the procedures described in Example 145 above, this ester is converted to the sodium salt.

EXAMPLE 149

Sodium 7-ethoxycarbonylamino-7-(2-furylacetamido)cephalosporanate

The sodium salt of 7-ethoxycarbonylamino-7-(2-furylacetamido)cephalosporanic acid is prepared by reacting the 7-amino-7-ethoxycarbonylaminocephalosporanate ester with furylacetyl chloride and then converting the ester to the sodium salt as described in Example 145.

EXAMPLE 150

Sodium 7-amino-7-(2-thienylacetamido)cephalosporanate

When benzhydryl 7-azido-7-bromocephalosporanate is reacted with t-butylcarbamate in place of ethylcarbamate as described in Example 145 above, the 7-t-butylcarbonylamino-7-aminocephalosporanate ester is obtained. Treatment of this product as described in Example 145 above affords sodium 7-amino-7-(2-thienylacetamido)cephalosporanate.

EXAMPLE 151

Sodium 7-hydrazino-7-(2-thienylacetamido)cephalosporanate

When benzhydryl 7-azido-7-bromocephalosporanate is reacted with t-butylcarbazate in place of ethylcarbamate as described in Example 145 above, the resulting product is reacted as described in Example 145 and sodium 7-hydrazino-7-(2-thienylacetamido)cephalosporanate is obtained.

EXAMPLE 152

Sodium 7-azido-7-(2-thienylacetamido)cephalosporanate

Step A: Benzhydryl 7-azido-7-(2-thienylacetamido)cephalosporanate

Benzhydryl 7-azido-7-bromocephalosporanate (3.6 g.) is added to 2-thienylacetamide (30 g.) and the mixture is warmed to 65°–70° C. To this reaction mixture is added silver tetrafluoroborate (3.6 g.) and 2-thienylacetamide (15 g.) and the mixture heated to 65°–70° C. for 10 minutes. The reaction mixture is poured into ether (200 ml.) with stirring and the resulting slurry is filtered through diatomaceous earth to remove the silver bromide. The ether solution is extracted with water (100 ml.), saturated aqueous sodium bicarbonate solution (100 ml.) and two 100 ml. portions of water. The ether layer is then dried over sodium sulfate and evaporated under diminished pressure. The resulting residue is triturated twice with a small amount of water and then dissolved in chloroform (25 ml.). After drying the chloroform solution over sodium sulfate, it is evaporated under diminished pressure to afford 2.4 g. of benzhydryl 7-azido-7-(2-thienylacetamido)cephalosporanate.

Step B: Sodium 7-azido-7-(2-thienylacetamido)cephalosporanate

The benzhydryl 7-azido-7-(2-thienylacetamido)cephalosporanate obtained in Step B is deblocked by reaction with trifluoroacetic acid and anisole and the product recovered as the sodium salt following the procedure described in Example 145.

EXAMPLE 153

When the process of Example 130, step A is carried out starting with benzhydryl 7-chloro-7-azidocephalosporanate using an equivalent amount of potassium azide or sodium azide in place of the lithium azide, benzhydryl-7,7-diazocephalosporanate is obtained. Reduction of this product, acylation of the 7-amino compound with phenylacetyl chloride and furylacetyl chloride, and cleavage of the benzhydryl group following the procedures described in the foregoing examples affords 7-benzylacetamido-7-aminocephalosporanic acid and 7-(2-furylacetamido)-7-aminocephalosporanic acid, respectively.

EXAMPLE 154

Sodium 7-Bromo-7-Phenylacetamidocephalosporanate

Step A: Benzhydryl 7-Aminocephalosporanate

P-toluenesulfonic acid monohydrate (4.3 g., 0.22 mole) is added with stirring at room temperature, to a slurry of 7-aminocephalosporanic acid (6.8 g., 0.25 mole) in peroxide-free dioxane (300 ml.). The clear solution is concentrated in vacuo and flushed twice with dioxane. The residue is then dissolved in dioxane (300 ml.) at room temperature and a solution of diphenyldiazomethane (10 g., 0.05 mole) in dioxane (25 ml.) is added dropwise over 15 minutes. The resulting wine-colored solution is stirred for an additional 30 minutes and methanol (25 ml.) is then added to destroy the excess diphenyldiazomethane. The mixture is concentrated in vacuo and the residue is layered between methylene chloride (200 ml.) and water (200 ml.) containing dipotassium phosphate (10 g., pH 8.5). The organic phase is washed with water, dried over sodium sulfate and concentrated in vacuo to yield an oil. The oil is stirred with ether (100 ml.) for one hour and the resulting precipitate is filtered, washed with ether and dried to constant weight 4.7 g. (43% yield). The compound thus obtained is benzhydryl 7-aminocephalosporanate, m.p. 126°–128° C.

Analysis: Calc.: C, 63.0; H, 5.01; N, 6.37. Found: C, 62.7; H, 5.18; N, 5.18.

Infrared in chloroform: 5.6μ (β-lactam C=O) and 5.8μ (ester C=O).

Nuclear Magnetic Resonance in deuterated chloroform:

1.85 tau (s), (NH$_2$); 2.0 tau (s), (CH$_3$C̈);

3.45 tau (d), (CH$_2$S); 4.8 tau (s), (CH$_2$OAC);
4.7 tau (d), (C$_6$H); 4.9 tau (d), (C$_7$H);

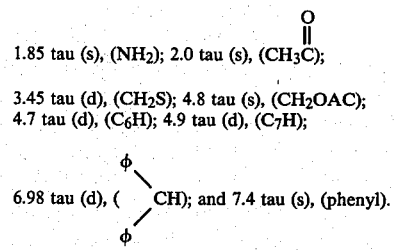

6.98 tau (d), (φ$_2$CH); and 7.4 tau (s), (phenyl).

Step B: Benzhydryl 7-Diazocephalosporanate

To a mixture of sodium nitrite (1.6 g.), water (30 ml.) and methylene chloride (40 ml.) is added benzhydryl 7-aminocephalosporanate (880 mg., 0.002 mole) with stirring at 0° C. A solution of para-toluenesulfonic acid (760 mg., 0.004 mole) in water (5 ml.) is then added over a few minutes and the mixture is stirred at 0° C. for 20 minutes. The organic phase is then cut away, washed with ice water (10 cc.), dried over sodium sulfate at 0° C., filtered and concentrated in vacuo at room temperature to yield 900 mg. of benzhydryl 7-diazocephalosporanate in the form of a glass. Infrared is 4.8μ (strong N=N), 5.6μ (β-lactam C=O) and 5.8μ (ester C=O).

Nuclear Magnetic Resonance in deuterated chloroform:

2.0 tau (s), (CH$_3$C̈); 3.4 tau (d), (CH$_2$S);

4.8 tau (s), (CH$_2$OAC); 5.6 tau (s), (C$_6$H);

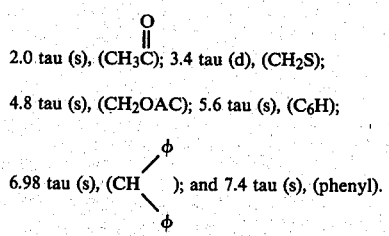

6.98 tau (s), (φ$_2$CH); and 7.4 tau (s), (phenyl).

Step C: Benzhydryl 7-Bromo-7-Azidocephalosporanate

Preparation of Triethylammonium Azide

To a slurry of sodium azide (1.5 g.) in water (5 ml.) and methylene chloride (10 ml.) maintained at −10° C. is added 50% sulfuric acid (4 ml.) dropwise over a five minute period. The mixture is stirred an additional five minutes and the organic phase is poured off from the aqueous paste and the aqueous extract is washed with methylene chloride (5 cc.). The combined organic phase is dried over calcium chloride and the decanted azide solution is brought to pH 7 with triethylamine. The triethylammonium azide thus obtained is stored at −10° C.

Preparation of Bromineazide

To methylene chloride (8 ml.) maintained at 0° C. is added sodium azide (2.66 g., 0.04 mole) followed by the addition of bromine (0.65 g., 0.0042 mole). To this mixture is added dropwise, with stirring, at 0° C. concentrated hydrochloric acid (2 ml.) and stirring is continued for an additional three hours at 0° C. The organic layer is decanted and the aqueous layer is extracted with methylene chloride (5 ml.). The extracted bromineazide is stored at −10° C.

To a solution of benzhydryl 7-diazocephalosporanate (900 mg.) in methylene chloride (20 ml.) and nitro methane (10 ml.) maintained at 0°–10° C. is added the triethylammonium azide solution (as prepared above) followed by the addition of the bromineazide solution (as prepared above). Water (50 ml.) is then added followed by the addition of sufficient solid sodium bicarbonate to bring the pH of the solution to 8. The organic layer is separated and extracted with two 20 ml. portions of water, dried over sodium sulfate and concentrated in vacuo to yield 900 mg. (83%) of benzhydryl 7-bromo-7-azidocephalosporanate.

Thin layer chromatography on silica gel with chloroform shows a major spot for this product at R$_f$ 0.2. Chromatography of the 900 mg. of product on 25 gms. of silica gel with chloroform gives 400 mg. (39%) single spot material as an oil.

Infrared in chloroform: 4.7μ (N$_3$), 5.56μ (β-lactam C=O) and 5.75μ (ester C=O).

Nuclear Magnetic Reasonance: in deuterated chloroform:

2.0 tau(s), CH$_3$C̈; 3.38 tau (s), (CH$_2$S);

4.7 tau (s), (CH$_2$O); 4.9 tau (s), (C$_6$H);

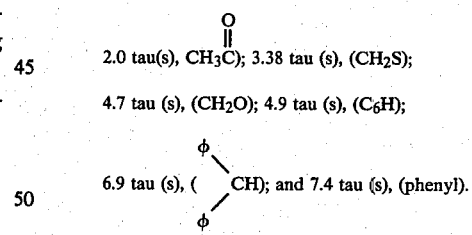

6.9 tau (s), (φ$_2$CH); and 7.4 tau (s), (phenyl).

Step D: Benzhydryl 7-Bromo-7-Phenylacetamidocephalosporanate

Sodium borohydride (0.1 g.) is added to a solution of benzhydryl 7-azido-7-bromocephalosporanate (0.5 g.) in bis-(2-methoxyethyl)ether (10 ml.) and the resulting mixture is stirred overnight under nitrogen. The mixture is then poured into ice water, adjusted to pH 8, extracted with methylene chloride, dried and evaporated to afford benzhydryl 7-amino-7-bromocephalosporanate.

The benzhydryl 7-amino-7-bromocephalosporanate is then treated with two equivalents of phenylacetic acid anhydride in methylene chloride solution and the resulting mixture is stirred for 0.5 hour and then poured into ice cold water. The resulting aqueous solution is extracted into methylene chloride and the solvent is dried over sodium sulfate and evaporated under reduced pressure to obtain benzhydryl 7-bromo-7-phenylacetamidocephalosporanate. This product is purified further by chromatography over silica gel to obtain pure benzhydryl 7-bromo-7-phenylacetamidocephalosporanate.

Step E: Sodium 7-Bromo-7-Phenylacetamidocephalosporanate

Benzhydryl 7-bromo-7-phenylacetamidocephalosporanate (0.4 g.) is dissolved in anisole (3.5 ml.) and treated with trifluoroacetic acid (10 ml.) at room temperature for 10 minutes. The trifluoroacetic acid and anisole are removed under reduced pressure while maintaining the temperature below 40° C. The residue is then taken up in chloroform (25 ml.) and treated with water (20 ml.) containing sodium bicarbonate (0.120 g.). The resulting mixture is stirred for 0.5 hour at room temperature and the organic phase is separated and washed with water. The combined aqueous phase is then washed twice with methylene chloride and lyophilized to afford sodium 7-bromo-7-phenylacetamidocephalosporanate as a brownish solid.

EXAMPLE 155

Sodium-7-Chloro-7-(2-Thienylacetamido)cephalosporanate

Step A: Benzhydryl 7-Azido-7-Chlorocephalosporanate

To a solution of benzhydryl 7-diazocephalosporanate (900 mg.) in methylene chloride (20 ml.) and nitromethane (10 ml.) at 0°–10° C. is added triethylammonium azide (prepared as described in Example 154, Step C) followed by the addition of the chlorineazide (prepared as described below). To this reaction mixture is added 50 ml. of water and sufficient solid sodium bicarbonate to bring the pH of the mixture to 8. The organic layer is separated and extracted with two 20 ml. portions of water, dried over sodium sulfate and concentrated under reduced pressure to yield benzhydryl 7-azido-7-chlorocephhalosporanate.

Preparation of Chlorineazide

A 5.25% solution (100 ml.) of sodium hypochlorite in water is mixed with chlorine (50 ml.) and cooled to −10° C. To this mixture is added sodium azide (4.3 g.) followed by the addition of aqueous acetic acid (10 ml.) prepared by diluting 4 ml. of glacial acetic acid to 10 ml. The addition of the acetic acid is made over a period of 15 minutes and the reaction mixture is stirred for an additional 15 minutes at −10° C. The aqueous phase is then separated, frozen by cooling in a solid carbon dioxide acetone bath and the organic phase is decanted and dried over anhydrous sodium sulfate. This methylene chloride solution is then used in the reaction described above.

Step B: Sodium 7-Chloro-7-(2-Thienylacetamido)cephalosporanate

The benzhydryl 7-azido-7-chlorocephalosporanate obtained in Step A is reduced with sodium borohydride as in Example 154, Step D to obtain benzhydryl 7-amino-7-chlorocephalosporanate and this product is then acylated by reaction with 2-thienylacetic acid anhydride to afford benzhydryl 7-chloro-7-(2-thienylacetamido)-cephalosporanate. Upon substituting benzhydryl 7-chloro-7-(2-thienylacetamido) cephalosporanate for the benzhydryl 7-bromo-7-phenylacetamidocephalosporanate of Example 154, Step E, and following the procedure described therein there is thus obtained sodium-7-chloro-7-(2-thienylacetamido)-cephalosporanate.

EXAMPLE 156

Sodium 7-Fluoro-7-(2-Furylacetamido)cephalosporanate

Step A: Benzhydryl 7-Azido-7-Fluorocephalosporanate

To a solution of benzhydryl 7-azido-7-bromocephalosporanate (0.5 g.) in anhydrous acetonitrile (50 ml.) is added tetraethylammonium fluoride (3.0 g.). The resulting mixture is stirred overnight at room temperature and then poured into water and extracted into methylene chloride to afford benzhydryl 7-azido-7-fluorocephalosporanate.

Step B: Sodium 7-Fluoro-7-(2-Furylacetamido)cephalosporanate

The benzhydryl 7-azido-7-fluorocephalosporanate obtained in Step A is reduced with sodium borohydride to obtain benzhydryl 7-amino-7-fluorocephalosporanate and this product is then acylated by reaction with 2-furylacetic acid anhydride and the resulting benzhydryl 7-fluoro-7-(2-furylacetamido)-cephalosporanate is converted to the sodium salt following the procedure described in Example 154, Step E.

EXAMPLE 157

Sodium 7-(2-Thienylacetamido)-7-Chlorocephalosporanate

Step A: Benzhydryl 7-Aminocephalosporanate

7-Aminocephalosporanic acid (272 mg.) is slurried for five minutes at 250° C. in dioxane (7 ml.) with p-toluenesulfonic acid monohydrate (170 mg.). Methanol (2 ml.) is added, the solvents are removed under vacuum and dioxane is twice added and evaporated in vacuo. Dioxane (8 ml.) is then added followed by the addition of diphenyldiazomethane (290 mg.). After the evolution of nitrogen is complete, the solvent is distilled under vacuum and the residue is stirred with methylene chloride (10 ml.) and water (10 ml.) containing sufficient dibasic potassium phosphate to bring the pH of the mixture to 8. The layers are separated and the aqueous portion is extracted twice more with methylene chloride. The combined organic layers are dried with sodium sulfate, filtered and then evaporated to yield an oily crystalline material. Washing with ether affords 150 mg. (35% yield) of the benzhydryl 7-aminocephalosporanate in the form of a dry solid, m.p. 110°–115° C.

Step B: Benzhydryl 7-(p-Nitrobenzylideneamino)cephalosporanate

Benzhydryl 7-aminocephalosporanate (438 mg.) is refluxed for one hour in benzene (50 ml.) with p-nitrobenzaldehyde (151 mg.) in an azeotropic drying apparatus. The solvent is then eliminated by vacuum distillation to afford 571 mg. of crude benzhydryl 7-(p-nitrobenzylideneamino)cephalosporanate. This compound may be used directly in the next step or, if desired, may be purified by recrystallization from a mixture of one part benzene and two parts cyclohexane.

Step C: Benzhydryl 7-(p-Nitrobenzylideneamino)-7-Chlorocephalosporanate

Benzhydryl 7-(p-nitrobenzylideneamino)cephalosporanate (571 mg.) is stirred at 0° C. under nitrogen in dimethylformamide (5 ml.). A catalytic amount of potassium t-butoxide is added and then t-butyl hypochlorite (109 mg.) is added with rapid stirring over a one to two minute period.

The solvent is evaporated in vacuo and the resulting oily residue is taken up in benzene (25 ml.), washed four times with water (10 ml.), dried with magnesium sulfate and then filtered and evaporated to afford the benzhydryl 7-(p-nitrobenzylideneamino)-7-chlorocephalosporanate. The crude material thus obtained may be used directly in the next step or, if desired, may be purified by chromatography on neutral silica gel and elution with 2% ethyl acetate in chloroform.

Step D: Benzhydryl 7-Amino-7-Chlorocephalosporanate Hydrochloride

Benzhydryl 7-(p-nitrobenzylideneamino)-7-chlorocephalosporanate (606 mg.) and aniline hydrochloride (260 mg.) are stirred together for one hour at 25° C. in methanol (10 ml.). The methanol is removed at 0.1 mm. pressure and 30° C. and the residue is then covered with ether and allowed to stand for one hour to effect crystallization. The solid is triturated with ether, filtered and then washed with ether to afford the benzhydryl 7-amino-7-chlorocephalosporanate hydrochloride. This material contains some unreacted aniline hydrochloride but is of sufficient purity as to be useable directly (i.e., without further purification) in the next step.

Step E: Benzhydryl 7-(2-Thienylacetamido)-7-Chlorocephalosporanate

Benzhydryl 7-amino-7-chlorocephalosporanate hydrochloride, obtained in step D, is added to methylene chloride (25 ml.) and this mixture is sitrred vigorously at −10° C. Triethylamine (0.5 g.) is added slowly whereupon the free amine, i.e., the benzhydryl 7-amino-7-chlorocephalosporanate is obtained. 2-Thienylacetyl chloride (0.5 g.) is then added and the reaction mixture is allowed to warm to room temperature. Excess acid chloride is then hydrolyzed by shaking with water and the methylene chloride layer is washed successively with a dilute phosphoric acid solution buffered to pH 2, water and dilute sodium bicarbonate solution. After drying with magnesium sulfate the solution is filtered and evaporated to afford a mixture of benzhydryl 7-(2-thienylacetamido)-7-chlorocephalosporanate and N-phenyl-2-theinylacetamide. Pure benzhydryl 7-(2-thienylacetamido)-7-chlorocephalosporanate is obtained via silica gel chromatography by eluting the said mixture with four parts chloroform and one part ethyl acetate.

Step F: Sodium 7-(2-Thienylacetamido)-7-Chlorocephalosporanate

Benzhydryl 7-(2-thienylacetamido)-7-chlorocephalosporanate (597 mg.) is dissolved in anisole (0.8 g.) and cooled to 0° C. Trifluoroacetic acid (4 ml.) precooled to 0° C. is added and the reaction is allowed to proceed for two minutes at 0° C. A vacuum of 0.1 mm. of mercury is immediately applied and the reaction mixture is allowed to warm to room temperature without external heating. Anisole is then pushed over at 30° C. at 0.1 mm of mercury and a few ml. of anisole is added to the residue and pulled off at 30° C. at 0.1 mm. of mercury to insure total removal of trifluoroacetic acid. The product is treated with water (5 ml.) containing sodium bicarbonate (84 mg.) and then lyophilized. The resulting powder is washed thoroughly with ether and dried to afford pure sodium 7-(2-thienylacetamido)-7-chlorocephalosporanate.

EXAMPLE 158

Sodium 7-(2-Thienylacetamido)-7-Bromocephalosporanate

Step A: Benzhydryl 7-(2-Thienylacetamido)-7-Bromocephalosporanate

Benzhydryl 7-bromo-7-azidocephalosporanate (543 mg.) is added to 2-thienylacetic anhydride (500 mg.) and a platinum oxide catalyst (1.0 g.) in dioxane (50 ml.) and the said mixture is hydrogenated at atmospheric pressure for four hours. The resulting mixture is filtered to remove the platinum oxide catalyst, water (0.5 ml.) is added and the solution is allowed to stand for 15 minutes to effect an hydrolysis of any unreacted 2-thienylacetic anhydride. The solution is then distilled under vacuum and the crude benzhydryl ester of 7-(2-thienylacetamido)-7-bromocephalosporanate thus obtained is dissolved in ether (25 ml.), washed with aqueous sodium bicarbonate, dried over magnesium sulfate, filtered and evaporated. The product thus obtained is benzhydryl 7-(2-thienylacetamido)-7-bromocephalosporanate which, if desired, may be purified further by chromatography on silica gel by eluting with four parts chloroform and one part ethyl acetate.

Step B: Sodium 7-(2-Thienylacetamido)-7-Bromocephalosporanate

Benzyhydryl 7-(2-thienylacetamido)-7-bromocephalosporanate (641 mg.) is dissolved in anisole (0.8 mole) and cooled to 0° C. Trifluoroacetic acid (4 ml.) precooled to 0° C. is added and the mixture is allowed to proceed for two minutes at 0° C. The reaction mixture is then placed immediately under vacuum and allowed to warm to room temperature without external heating. The mixture is then subjected to vacuum distillation whereupon anisole distills over at 30° C./0.1 mm. mercury. The product thus obtained is treated with water (5 ml.) containing sodium bicarbonate (84 mg.) and lyphilized to a powder; this powder is washed thoroughly with ether and dried to afford sodium 7-(2-thienylacetamido)-7-bromocephalosporanate.

EXAMPLE 159

Sodium 7-(2-thienylacetamido)-7-chlorocephalosporanate

Step A: Benzhydryl 7-(2-thienylacetamido)-7-chlorocephalosporanate

By substituting benzhydryl 7-chloro-7-azidocephalosporanate (499 mg.) for the benzhydryl 7-bromo-7-chlorocephalosporanate recited in Example 158 and following the procedure described therein, there is thus obtained the benzhydryl 7-(2-thienylacetamido)-7-chlorocephalosporanate.

Step B: Sodium 7-(2-thienylacetamido)-7-chlorocephalosporanate

By substituting benzhydryl 7-(2-thienylacetamido)-7-chlorocephalosporanate for the benzhydryl 7-(2-thienylacetamido)-7-bromocephalosporanate in Example 158, Step B and following the procedure described therein, there is thus obtained the sodium 7-(2-thienylacetamido)-7-chlorocephalosporanate.

EXAMPLE 160

Sodium 7-[α-(α-Aminophenyl(Acetamido]-7-(Dimethylphosphono)cephalosporanate

Step A: Benzhydryl 7-Azido-7-(Dimethylphosphono)Cephalosporanate

To a solution of benzhydryl 7-azido-7-bromocephalosporanate (272 mg., 0.0005 mole) in dimethoxyethane (10 ml.) is added silver dimethylphosphite (120 mg., 0.00055 mole) (prepared by mixing equimolar amounts of dimethylphosphite and silver oxide in water and filtering the solid which slowly forms). The mixture is stirred overnight at room temperature protected from light, air, and moisture. The inorganic material is filtered and the filtrate is concentrated at a low temperature and pressure. The residue is dissolved in methylene chloride and the solution is washed with a cold, dilute, aqueous solution of sodium bicarbonate. It is dried and concentrated at reduced pressure. The residue is re-dissolved in a small amount of chloroform and the mixture is purified by chromatography on silica gel using chloroform as the elution solvent. The initial eluate contains a little recovered starting material. The second elution fraction is concentrated at reduced pressure to afford benzhydryl 7-azido-7-(dimethylphosphono)cephalosporanate.

Step B: Benzhydryl 7-Amino-7-(Dimethylphosphono)Cephalosporanate

Benzhydryl 7-azido-7-(dimethylphosphono)cephalosporanate (200 mg.) is dissolved in dioxane (20 ml.) and hydrogenated at room temperature and normal pressure for one hour using platinium oxide (200 mg.) as catalyst. A fresh 200 mg.-portion of catalyst is added and the hydrogenation is continued for an additional two hours. The solvent is removed at low temperature and pressure. The dry residue is dissolved in chloroform and the solution is filtered by suction through a layer of silica gel to remove the suspended, spent catalyst. The silica gel is washed copiously with chloroform to elute any adsorbed material. The filtrate is concentrated at reduced pressure to afford benzhydryl 7-amino-7-(dimethylphosphono)cephalosporanate suitable for use in the next step without further purification.

Step C: Benzhydryl 7-α-(α-Aminophenyl)Acetamido-7-(Dimethylphosphono)Cephalosporanate A solution of benzhydryl 7-amino-7-(dimethylphosphono)cephalosporanate (273 mg.) in methylene chloride (15 ml.) is stirred at 0° C. and α-amino-α-phenylacetyl chloride hydrochloride (220 mg.) is added. Immediately thereafter pyridine (0.5 ml.) is added, and the mixture is stirred at 0° C. for 15 minutes and then poured onto crushed ice containing a slight excess of hydrochloric acid. The layers are separated and the organic phase is washed with an excess of a cold, dilute, aqueous solution of sodium bicarbonate. It is dried and concentrated yielding benzhydryl 7-β-(α-aminophenyl)acetamido-7-(dimethylphosphono)cephalosporanate.
The crude material is purified by chromatography on silica gel with chloroform as the elution agent. A small amount of the isomer, benzhydryl 7-α-(α-aminophenyl)acetamido-7-(dimethylphosphono)cephalosporanate, is also isolated from the chromatographed mixture.

Step D: Sodium 7-β-(α-Aminophenyl)Acetamido-7-(Dimethylphsophono)Cephalosporanate A solution of benzhydryl 7-β-(α-aminophenyl)acetamido-7-(dimethylphosphono)cephalosporanate (70 mg.) and anisole (11 mg.) in methylene chloride (0.5 ml.) is stirred in an ice bath. A cold solution of trifluoroacetic acid (23 mg.) in methylene chloride (0.2 ml.) is added in increments over a period of five minutes. After an additional 30 minutes the mixture is concentrated by means of a high vacuum pump. The residue is taken up in benzene (5 ml.) and 3 ml. of an aqueous solution of sodium bicarbonate (8.4 ml.) is added. The mixture is then stirred well at room temperature for 15 minutes, the layers are separated and the organic phase is stirred once more with water (2 ml.), after which the layers are again separated. The combined aqueous extracts are washed once with ether and are lyophilized to yield sodium 7-β-(α-aminophenyl)acetamido-7-(dimethylphosphono)cephalosporanate.

EXAMPLE 161

Sodium 7-[(Dimethylamino)Methoxyphosphinyl]-7-(α-2-Furylacetamido)Cephalosporanate

Step A: Benzhydryl 7-Azido-7-[(Dimethylamino)Methoxyphosphinyl]-Cephalosporanate A mixture of benzhydryl 7-azido-7-bromocephalosporanate (545 mg.), N,N,O-trimethylphosphonamidic acid (246 mg.) and silver tetrafluoroborate (195 mg.) in dimethoxyethane (5 ml.) is stirred overnight at room temperature protected from air, light, and moisture. The solution is filtered from inorganic salts and concentrated to dryness at low temperature and pressure. The residue is dissolved in methylene chloride and the solution is washed with cold, aqueous sodium bicarbonate solution, then with water and is dried and concentrated. The residue is redissolved in chloroform and the solution is charged onto a column of silica gel suspended in chloroform. Elution of the column with chloroform and concentration of the eluate yields benzhydryl 7-azido-7-[(dimethylamino)methoxyphosphinyl]cephalosporanate.

Step B: Benzhydryl 7-Amino-7-[(Dimethylamino)Methoxyphosphinyl]-Cephalosporanate Benzhydryl 7-azido-7-[(dimethylamino)methoxyphosphinyl]cephalosporanate (250 mg.) in dioxane (25 ml.) is hydrogenated at room temperature and under normal pressure using a platinum oxide catalyst (500 mg.) added in two equal portions with an interval of one hour. The hydrogenation is continued for 2-3 hours after the second addition, or until the azide is absent as determined by infrared spectroscopy. The solvent is completely removed at low temperature and pressure. The residue is dissolved in chloroform and the spent catalyst is removed by filtration through a layer of silica gel, which adsorbent is thoroughly washed with chloroform. The filtrate is then concentrated at reduced pressure to yield benzhydryl 7-amino-7-[(dimethylamino)methoxyphosphinyl]cephalosporanate.

Step C: Benzhydryl 7-[(Dimethylamino)Methoxyphosphinyl]-7-α-(2-Furylacetamido)Cephalosporanate A solution of benzhydryl 7-[(dimethylamino)methoxyphosphinyl]cephalosporanate (280 mg.) in methylene chloride (15 ml.) is stirred at 0° C. and 2-furylacetyl chloride (145 mg.) is added. Pyridine (0.5 ml.) is then added immediately and the stirring at 0° C. continued for 15 minutes. The reaction mixture is poured onto crushed ice which contains a slight excess of hydrochloric acid. The layers are separated and the organic phase is washed with an excess of cold, dilute aqueous sodium bicarbonate; it is then washed once more with water, dried and concentrated. The crude product is purified by chromatography on silica gel with chloroform as the elution solvent. Concentration of the eluate yields benzhydryl 7-[(dimethylamino)methoxyphosphinyl]-7-β-(2-furylacetamido)cephalosporanate together with a small amount of the isomer benzhydryl 7-[(dimethylamino)methoxyphosphinyl]-7-α-(2-furylacetamido)cephalosporanate.

Step D: Sodium 7-[(Dimethylamino)Methoxyphosphinyl]-7-β-(2-Furylacetamido)Cephalosporanate A solution of benzhydryl 7-[(dimethylamino)methoxyphosphinyl]-7-β-(2-furylacetamido)cephalosporanate (65 mg.) and anisole (11 mg.) in methylene chloride (0.5 ml.) is stirred at 0° C. A cold solution of 23 mg. of trifluoroacetic acid (23 mg.) in methylene chloride (0.2 ml.) is added over a period of 3-4 minutes. After an additional 30 minutes at 0° C. the mixture is concentrated to dryness at greatly reduced pressure and the residue is taken up in benzene (5 ml.) and 3 ml. of an aqueous solution of sodium bicarbonate (8.4 mg.) is added. The mixture is well stirred at room temperature for about 15 minutes and the layers are separated. The organic phase is extracted once with water and the combined aqueous phases are washed once with ether and are lyophilized to yield sodium 7-[(dimethylamino)methoxyphosphinyl]-7-β-(2-furylacetamido)cephalosporanate.

EXAMPLE 162

Disodium 7-β-(α-Carboxyphenyl)Acetamido-7-(Bis(Dimethylamino)Phosphinyl]Cephalosporanate

Step A: Benzhydryl 7-Azido-7-[Bis(Dimethylamino)Phosphinyl]Cephalosporanate

A mixture of benzhydryl 7-Azido-7-bromocephalosporanate (545 mg.), tetramethyldiamidophosphorous acid (273 mg.) and silver tetrafluoroborate (195 mg.) in dimethoxyethane (5 ml.) is stirred overnight at room temperature protected from light, air, and moisture. The reaction mixture is filtered and the filtrate is concentrated to dryness at reduced pressure. The residue is redissolved in methylene chloride and the solution is washed with a cold, dilute solution of sodium bicarbonate and then dried and concentrated. The residue is dissolved in a little chloroform and charged onto a column of silica gel from which the product is eluted by chloroform. The eluate is concentrated at reduced pressure to yield benzhydryl 7-azido-7-[bis(dimethylamino)phosphinyl]cephalosporanate.

Step B: Benzhydryl 7-amino-7-[bis(dimethylamino)phosphinyl]cephalosporanate

Benzhydryl 7-azido-7-[bis(dimethylamino)phosphinyl]cephalosporanate (250 mg) is dissolved in dioxane (25 ml.) and hydrogenated at room temperature and normal pressure for ¾ hour using platinum oxide (250 mg) as a catalyst. A fresh portion of catalyst (250 mg) is added and the hydrogenation is continued for an additional 2-3 hours or until the azide has disappeared when examined in an infrared absorption spectrophotometer. The mixture is concentrated to dryness at reduced pressure and the residue is taken up in chloroform and filtered by suction through a layer of silica gel to remove the spent catalyst. The silica gel is then thoroughly washed with chloroform and the filtrate is concentrated at low temperature and pressure to afford benzhydryl 7-amino-7-[bis(dimethylamino)phosphinyl]cephalosporanate.

Step C: Benzhydryl 7-β-(α-tert. butoxy-carbonylphenyl)acetamido-7-[bis(dimethylamino)phosphinyl]cephalosporanate The benzhydryl 7-amino-7-[bis(dimethylamino)phosphinyl]cephalosporanate obtained in Step B is dissolved in methylene chloride (20 ml.) and α-(tert-butoxycarbonyl)phenylacetyl chloride (510 mg.) is added to the stirred solution at 0° C. The addition is immediately followed by the addition of pyridine (1 ml.). After 15 minutes the reaction is quenched by pouring onto crushed ice and the organic phase of the mixture is washed successively with cold dilute hydrochloric acid, with cold dilute potassium bicarbonate solution and then with water. The mixture is dried and concentrated at reduced pressure to yield benzhydryl 7-$\beta$-($\alpha$-tert-butoxycarbonylphenyl)acetamido-7-[bis(dimethylamino)phosphinyl]cephalosporanate. The product is purified by chromatography on silica gel, the purified material being eluted with chloroform. The isomer benzhydryl 7-$\alpha$-($\alpha$-tert-butoxycarbonylphenyl)acetamido-7-[bis(dimethylamino)phosphinyl]cephalosporanate is also obtained from this chromatographic purification.

Step D: Disodium
7-$\beta$-($\alpha$-carboxyphenyl)acetamido-7-[bis(dimethylamino)phosphinyl]-cephalosporanate A mixture of benzhydryl 7-$\beta$-($\alpha$-tert-butoxycarbonylphenyl)acetamido-7-[bis(dimethylamino)phosphinyl]-cephalosporanate (153 mg.), anisole (22 mg.) and methylene chloride (1 ml.) is stirred at 0° C. A cold solution of 46 mg. of trifluoroacetic acid (46 mg.) in methylene chloride (0.5 ml.) is added over a period of about 5 minutes and is concentrated to dryness at reduced pressure. The residue is taken up in a mixture of benzene (5 ml.) and ether (5 ml.) and 10 ml. of an aqueous solution of sodium bicarbonate (33.6 mg.) is added. After stirring at room temperature for 10 minutes the layers are separated and the organic phase is again stirred with water (5 ml.) for an additional 5 minutes. The combined aqueous extracts are washed once with ether (2 ml.) and are lyophilized to yield disodium 7-$\beta$-($\alpha$-carboxyphenyl)acetamido-7-[bis(dimethylamino)phosphinyl]cephalosporanate.

EXAMPLE 163

Trisodium
7-Phosphono-7-$\beta$-(2-Thienylacetamido)Cephalosporanate

Step A: Benzhydryl
7-Azido-7-(Di-Tert-Butylphosphono)Cephalosporanate

A mixture of benzhydryl 7-azido-7-bromocephalosporanate (545 mg.), di-tert-butylphosphite (388 mg.) and silver tetrafluoroborate (195 mg.) in dimethoxyethane (5 ml.) is stirred overnight at room temperature while protecting from air, light, and moisture. The mixture is then filtered from insoluble material and concentrated to dryness at low temperature and pressure. The residue is redissolved in methylene chloride and the solution is washed with a little ice water and then dried and concentrated. The residue is dissolved in a little chloroform and the solution is chromatographed on acid-washed alumina using a mixture of chloroform and ethanol as the eluting solvent. The eluate is concentrated at reduced pressure to afford benzhydryl 7-azido-7-(di-tert-butylphosphono)cephalosporanate.

Step B: Benzhydryl
7-Amino-7-Di-tert-Butylphosphono)Cephalosporanate

Benzhydryl 7-azido-7-(di-tert-butylphosphono)cephalosporanate (110 mg.) is dissolved in dioxane (10 ml.) and is hydrogenated at room temperature and under normal pressure for one hour using a platinum oxide catalyst (100 mg.). A second portion of catalyst (100 mg.) is added and the hydrogenation is continued for an additional 2-3 hours. The solvent is completely removed at reduced pressure and the residue in re-dissolved in chloroform. The spent catalyst is then removed by filtration through a layer of silica gel and the filter bed is washed thoroughly with chloroform. The filtrate is concentrated at reduced pressure to yield benzhydryl 7-amino-7-(di-t-butylphosphono)cephalosporanate, which is suitable for use in the next step without further purification.

Step C: Benzhydryl
7-Di-t-Butylphosphono-7-$\beta$-(2-Thienylacetamido)-Cephalosporanate The benzhydryl 7-amino-7-(di-t-butylphosphono)-cephalosporanate obtained in Step B is dissolved in methylene chloride (10 ml.) and the solution is stirred at 0° C. To this solution is added 2-thienylacetic acid (32 mg.) and dicyclohexylcarbodiimide (41 mg.). The reaction mixture is then allowed to warm slowly to room temperature and is stirred overnight. The dicyclohexylurea which forms is removed by filtration and the filtrate is concentrated at reduced pressure. The residue is dissolved in a little chloroform and the solution is charged onto a column of acid-washed alumina, from which benzhydryl 7-di-tert-butylphosphono-7-$\beta$-(2-thienylacetamido)cephalosporanate is obtained by elution with a dilute solution of methanol in chloroform. The product is recovered by concentration of the eluate. A small amount of the isomer benzhydryl 7-di-tert-butylphosphono-7-$\alpha$-(2-thienylacetamido)cephalosporanate is also obtained.

Step D: Trisodium
7-Phosphono-7-($\alpha$-2-Thienylacetamido)Cephalosporanate

A mixture of benzhydryl 7-di-tert-butylphosphono-7-$\beta$-(2-thienylacetamido)cephalosporanate (70 mg.), anisole (33 mg.) and methylene chloride (1 ml.) is stirred at 0° C. and a cold solution of trifluoroacetic acid (70 mg.) in methylene chloride (0.2 ml.) is added. After about 30 minutes the solution is concentrated to dryness at reduced pressure and the residue is suspended in a mixture of benzene (3 ml.) and ether (3 ml.) and 5 ml. of an aqueous solution of sodium bicarbonate (50 mg.) is added. The mixture is stirred well and the layers are separated. The organic phase is washed with 5 ml. of water and the combined aqueous solutions are washed with ether and lyophilized to yield trisodium 7-phosphono-7-$\beta$-(2-thienylacetamido)cephalosporanate.

EXAMPLE 164

By following the procedures described in Example 163, Steps A-D all of the 7-amido-7-phosphonocephalosporanic acid salts of this invention may be obtained. Thus, for example, by substituting an equivalent amount of the appropriate phosphite and acyl halide for the di-tertiarybutylphosphite and 2-thienylacetic acid reactants recited in Steps A and C of Example 163 and otherwise following the procedure described therein, the corresponding salts of 7-amido-7-phosphonocephalosporanic acid are obtained. The following equation and accompanying Table IV illustrate this method of preparation:

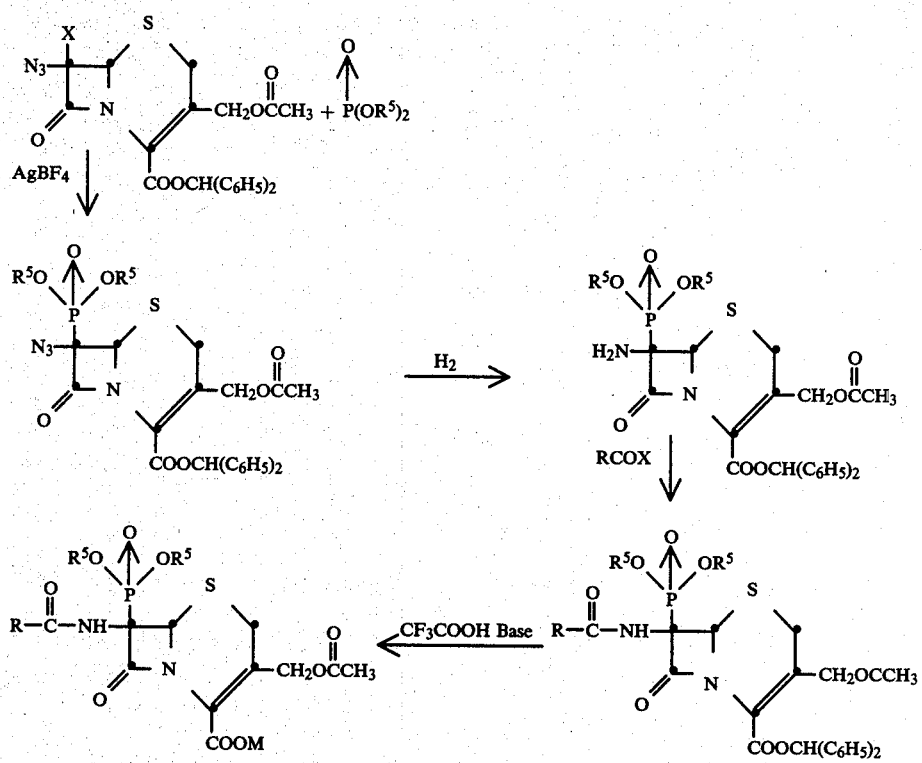

TABLE IV

| R | R⁵ | X | M | Base |
|---|---|---|---|---|
| ![thienyl]-CH₂— | —C₂H₅ | Br | Na | NaOH |
| HOOC—CH₂— | —(CH₂)₂CH₃ | Cl | K | KHCO₃ |
| ![furyl]-CH₂— | —CH₃ | Br | Na | NaHCO₃ |
| HOOC—CH(C₆H₅)— | —C₂H₅ | Cl | Li | LiOH |
| HOOC—CH(C₆H₅)— | —(CH₂)₃CH₃ | I | Na | Na₂CO₃ |

EXAMPLE 165

Sodium 7-(β-cyanoethyl)-7-(2-furylacetamido)cephalosporanate

A solution of 500 mg. of benzhydryl 7-(p-nitrobenzylideneamino)cephalosporanate prepared as in Example 43 in a mixture of 2.5 ml. of t-butyl alcohol and 2.5 ml. of acrylonitrile is treated with 20 μl. of N,N-diisopropylethylamine with stirring under nitrogen. The initially green solution turns yellow-orange after stirring 10 minutes. It is then concentrated under reduced pressure to 620 mg. of a yellow gummy residue. This residue is chromatographed on a mixture of 48 g. of active, powdered silica gel and 40 g. of powdered diatomaceous earth. Elution is carried out with 2 l ether in benzene. The desired non-crystalline cyanoethyl adduct is eluted after 2 liters of eluent has passed through the column. The product is identified as 7-(p-nitrobenzylideneamino)-7-(β-cyanoethyl)cephalosporanic acid benzhydryl ester.

Using the procedures described in the foregoing examples, the above product is converted to sodium 7-(β-cyanoethyl)-7-(2-furylacetamido)cephalosporanate.

EXAMPLE 166

Sodium 7-methyl-7-(2-thienylacetamido)cephalosporanate

Benzhydryl 7-(p-nitrobenzylideneamino)cephalosporanate (571 mg.) is dissolved in 10 ml. dry acetonitrile containing 0.950 ml. dimethyl sulfate. With vigorous stirring under nitrogen, a solution of diisopropylethylamine in 12 ml. acetonitrile is added over a 5 hour period. The reaction mixture is stirred overnight and the solvent removed in vacuo. The residue is taken up in 50 ml. benzene and washed successively with water, 1 M aqueous pH 2 phosphate buffer, water, and bicarbonate. After drying, filtering and removing the solvent, the residue is a crude compound suitable for further reaction without additional purification. It may be purified if desired by chromatography on silica gel, eluting with 25:1 chloroform-ethylacetate. It is identified as 7-(p-nitrobenzylideneamino)-7-methylcephalosporanic acid benzhydryl ester.

This product is converted to the title compound following procedures described in the foregoing examples.

EXAMPLE 167

Sodium 7-acetyl-7-(2-thienylacetamido)cephalosporanate

Benzhydryl 7-(p-nitrobenzylideneamino)cephalosporanate (571 mg.) is dissolved in 10 ml. dry acetonitrile containing 0.950 ml. acetyl chloride. With vigorous stirring under nitrogen, a solution of diisopropylethylamine in 12 ml. acetonitrile is added over a 5 hour period. The reaction mixture is stirred overnight and the solvent removed in vacuo. The residue is taken up in 50 ml. benzene and washed successively with water, 1 M aqueous pH 2 phosphate buffer, water and bicarbonate. After drying, filtering and removing the solvent, the residue is a crude compound suitable for further reaction without additional purification. It may be purified if desired by chromatography on silica gel eluting with 25:1 chloroform-ethylacetate. It is identified as 7-(p-nitrobenzylideneamino)-7-acetylcephalosporanic acid benzhydryl ester.

This product is converted to the title compound following procedures described in the foregoing examples.

EXAMPLE 168

3-Carbamoyloxymethyl-7-methoxy-7$\beta$-phenylacetamido-3-cephem-4-carboxylic Acid

Step A:
7$\beta$-(D-5-trichloroethoxycarbonylamino-5-carboxyvaleramido)-3-carbamoyloxymethyl-7-methoxy-3-cephem-4-carboxylic Acid The mono-sodium salt of 7$\beta$-(D-5-amino-5-carboxyvaleramido)-3-carbamoyloxymethyl-7-methoxy-3-cephem-4-carboxylic acid (20.5 gm.) is dissolved in the mixture of acetone (80 ml.) and aqueous 10% dipotassium hydrogen phosphate (240 ml.). To this solution is added dropwise trichloroethoxycarbonyl chloride (25 gm., 118 mmoles) in acetone (80 ml.). During the addition the pH of the solution is kept at 9.1 by gradual addition of 2.5 N sodium hydroxide solution. After 30 minutes the mixture is extracted with ethyl acetate, the ethyl acetate layer discarded, and the aqueous layer is acidified to pH 2.5 with concentrated hydrochloric acid. The precipitated product is extracted into ethyl acetate. After drying over sodium sulfate and removing the solvent in vacuo, the title compound is obtained as an oil.

UV: (CH$_3$OH) $\lambda$max. 262.5 $\epsilon$=5450
NMR: (Solvent—DMSO, d$_6$) $\delta$=3.43 (O—CH$_3$, s), 4.73 (2-H$_2$, partially visible), $$\overset{CCl_3}{4.81\ (CH_2-O,\ s),}$$

5.12 (6-H, s), ~4.74 (10-H$_2$, partially visible).

Step B: Di-benzhydryl ester of 7$\beta$-(D-5'-trichloroethoxycarbonylamino-5'-carboxyvaleramido)-3-carbamoyloxymethyl-7-methoxy-3-cephem-4-carboxylic Acid To the solution of the above 7$\beta$-(D-5-trichloroethoxycarbonylamino-5-carboxyvaleramido)-3-carbamoyloxymethyl-7-methoxy-3-cephem-4-carboxylic acid in ethyl acetate (500 ml.) is added diphenyldiazomethane (17 gm.) in 200 ml. of ether. After agitating the mixture overnight, it is extracted successively with sodium bicarbonate and sodium chloride solutions. The solvent is evaporated from the dried solution to afford a crude product which is purified by chromatography on silica gel. A 2:1 mixture of chloroform and ethyl acetate is used for elution. This material showed a single spot on TLC chromatography.

UV: (CH$_3$OH) $\lambda$max. 2650 $\mu$m $\epsilon$7000
NMR: (Solvent—CDCl$_3$) $\delta$=3.45 (O—CH$_3$, s), 3.35 (2-H$_2$, partially visible, $$\overset{CCl_3}{4.69\ (CH_2-O,\ s),}$$

5.03 (6-H, s), ~4.88 (10-H$_2$, partially visible).

Step C: Di-benzhydryl ester of 7$\beta$-[(D-5'-trichloroethoxycarbonylamino-5'-carboxyvaleryl)phenylacetylamino]-3-carbamoyloxymethyl-7-methoxy-3-cephem-4-carboxylic Acid A mixture of the di-benzhydryl ester of 7$\beta$-(D-5'-trichloroethoxycarbonylamino-5'-carboxyvaleramido)-3-carbamoyloxymethyl-7-methoxy-3-cephem-4-carboxylic acid (1.1 gm., 1.18 mmole), acetonitrile (5 ml.) and bis-trimethylsilyl trifluoroacetamide (3 ml.) is allowed to stand at room temperature for 6 hours. After this period, the volatile products are removed in high vacuum and the residue is dissolved in 3 ml. of methylene chloride. To this solution is added phenylacetyl chloride (0.23 ml., 1.79 mmole) and the mixture is allowed to stand at room temperature for 65 hours. After this, the solution is evaporated and the residue is dissolved in 5 ml. tetrahydrofuran and 0.7 ml. of 2.5 N hydrochloric acid. After 20 minutes reaction time the solvent is evaporated and the residue is partitioned between methylene chloride and sodium bicarbonate solution. The organic layer is washed with sodium chloride solution, dried and evaporated to dryness. The crude product thus obtained is purified by chromatography on silica gel, using chloroform ethyl acetate 95:5 as eluant. The title compound obtained appears homogenous on thin layer chromatography.

UV: (CH$_3$OH) $\lambda$max. 2640 $\mu$m $\epsilon$6650
NMR: (Solvent—CDCl$_3$) $\delta$=3.50 (O—CH$_3$, s), 3.31 (2-H$_2$, partially visible), $$\overset{CCl_3}{4.67\ (CH_2-O,\ s),}$$

5.04 (6-H, s), ~4.96 (10-H$_2$, partially visible), 3.95 (13-H$_2$, s).

Step D: Benzhydryl ester of 3-carbamoyloxymethyl-7-methoxy-7$\beta$-phenylacetamido-3-cephem-4-carboxylic Acid The solution of di-benzhydryl ester of 7$\beta$-[(D-5'-trichloroethoxycarbonylamino-5'-carboxyvaleryl)-phenylacetylamino]-3-carbamoyloxymethyl-7-methoxy-3-cephem-4-carboxylic acid (104 mg.) in 90% acetic acid-water (1 ml.) is agitated with 100 mg. of zinc dust for 5 hours. After this, the solution is filtered and the solvent is removed in vacuo. The residue is partitioned between methylene chloride and water, and the methylene chloride layer is extracted with sodium bicarbonate and sodium chloride solutions. After drying and evaporation a crude product is obtained which is purified by thin layer chromatography utilizing silica gel plates and a 3:2 mixture of chloroform and ethyl acetate. The product is characterized by its IR and NMR spectra.

IR: (CHCl$_3$) 1780, 1730 and 1680 cm$^{-1}$
UV: (CH$_3$OH) λmax. 2640 μm ε5870
NMR: (Solvent—CDCl$_3$) δ=3.40 (O—CH$_3$, s), 3.33 (2-H$_2$, partially visible), 5.01 (6-H, s), ~4.88 (10-H$_2$, partially visible), 3.60 (13-H$_2$, s).

Step E:
3-Carbamoyloxymethyl-7-methoxy-7β-phenylacetamido-3-cephem-4-carboxylic Acid Benzhydryl ester of 3-carbamoyloxymethyl-7-methoxy-7β-phenylacetamido-3-cephem-4-carboxylic acid (17 mg.) is dissolved in anisole (0.2 ml.) and treated with trifluoroacetic acid (0.5 ml.) for 5 minutes. After this period, the mixture is concentrated rapidly in high vacuum and diluted with ethyl acetate. The product is removed from the ethyl acetate solution by extraction with a pH 7.5 sodium phosphate buffer. The buffer solution is acidified to pH 2.5 with dilute hydrochloric acid and the title compound is removed by extraction with ethyl acetate. After drying and evaporating the solution, the product is obtained. An analytical sample is obtained by recrystallization from ethylacetate. MP: 159°-161° C.

UV: (pH 7 buffer) λmax. 2670 μm ε8650
IR: (CH$_3$CN) 1780, 1735 and 1700
NMR: (Solvent—CD$_3$CN+D$_2$O) δ=3.42 (O-CH$_3$, s), 3.35 (2-H$_2$, partially visible), 5.01 (6-H, s), 4.83 (10-H$_2$, d), 3.61 (13-H$_2$, s).
Elemental analysis for C$_{18}$H$_{19}$O$_7$N$_3$S: Calc: C, 51.29; H, 4.54; Found: C, 51.47; H, 4.73.

Two milligrams of the above acid is dissolved in one drop of methanol and treated with a solution of 2 mg. dibenzyl ethylenediamine diacetate in ethyl acetate. The dibenzyl ethylenediamine salt of the title compound precipitates after standing in the form of needle-like crystals. MP: 140°-143° C.

UV: (CH$_3$OH) λmax. 263 μm ε8600

Preparation of Monosodium Salt of 7β-(D-5-amino-5-carboxyvaleramido)-3-carbamoyloxymethyl-7-methoxy-3-cephem-4-carboxylic Acid

Modified Fermentation Process

Step 1: Slants

A lyophilized tube of *Streptomyces lactamdurans* culture (MA-2908) was opened asceptically and the organism transferred to a medium of the following composition:

Medium XI
1% Blackstrap Molasses
1% National Brewer's Yeast
2.5% Difco agar pH 7.0
Water to volume The slants are inoculated for seven days at 28° C. When stored in the cold, the slants are stable for more than 13 weeks.

Step 2: Seed Stages: Two Stage System

First Seed: The first seed is inoculated directly from the slant of Step 1 to 40 ml. of 1% Primary Dried Yeast N.F., pH 7.0 (obtained from the Yeast Product Corporation) in a 250 ml. baffled Erlenmeyer flask. The flasks were then shaken on a 220 rpm. rotary shaker with a 2 inch throw at 28° C. for a period of from two to three days.

Second Seed: A 2.5% inoculum from the first seed stage was added to a flask containing a 2% Fleischmann S-150 yeast autolysate, pH 7.0. The growth in this stage is characteristically light and the incubation, performed as in the first stage, was not extended beyond 48 hours.

Step 3: Production Medium

The production medium contains per liter of distilled water: 30 g. distiller's solubles; 7.5 g. of Primary Dried Yeast N.F. and 0.25% v/v Mobilpar-S defoamer. The medium is adjusted to pH 7.0 with a small amount of concentrated sodium hydroxide solution, dispensed into Erlenmeyer flasks and autoclaved for 15 or 20 minutes at 121° C. After cooling the medium received a 2.5% inoculum of the seed obtained in Step 2. The time of incubation can vary from about 50 hours to 100 hours but an incubation period of about 72 hours is preferred. The volume of media in each flask can vary from 30 to 50 ml. but 40 ml. was used routinely. The level of inoculum can vary from 1% to 5%; but, in practice, a 2.5% level is generally employed.

Step 4: Assay

When the fermentation was complete, the cells were removed by centrifugation and the broth was diluted with phosphate buffer, pH 7.0. The concentration of 7β-(D-5-amino-5-carboxyvaleramido)-3-(carbamoyloxymethyl)-7-methoxy-3-cephem-4-carboxylic acid in the fermentation broth was determined by the standard biological-disc assay method. The assay organism employed was *Vibrio percolans* (ATCC 8461). Filter paper discs are emersed into the diluted broths and placed on the surface of agar-containing Petri dishes that had been inoculated with the assay organism *Vibrio pecolans* (ATCC 8461). Also placed on these Petri dishes are discs that had been dipped previously in standard solutions containing known concentrations of 7β-(D-5-amino-5-carboxyvaleramido)-3-carbamoyloxymethyl)-7-methoxy-3-cephem-4-carboxylic acid. The discs were incubated overnight at 28° C. and the diameters of the zones of inhibition recorded. The concentration of product and the fermented broth is calculated by interpolation from the standard curve which relates zone diameter with the known concentrations of standard solutions of the product. By this procedure it was calculated that *Streptomyces lactamdurans* MB-2908 produced 78.6 μg./ml. of 7β-(D-5-amino-5-carboxyvaleramido)-3-carbamoyloxymethyl-7-methoxy-3-cephem-4-carboxylic acid in the modified fermentation process.

Step 5: Isolation

The filtered broth is adjusted to pH 7.0 with dilute hydrochloric acid and 2900 ml. is passed through a column containing a strongly basic anion exchange resin (100 g.) having a styrene-divinylbenzene matrix (Dowex 1×2 chloride cycle resin) at 10 ml./minute. The spent solvent is collected in 500 ml. fractions. The resin column is washed with water and eluted with 3% ammonium chloride in 90% methanol. The eluate is collected in 100 ml. fractions. The spent fractions are combined, the pH adjusted to pH 7.2 to 8.0 with dilute sodium hydroxide and adsorbed on a strongly basic anion exchange resin (100 g.) having a styrene-divinylbenzene matrix (Dowex 1×2 chloride cycle resin) at 14 ml./minute. The column is washed with water and eluted with 5% aqueous sodium chloride. The eluate is collected in 50 ml. fractions and concentrated. The concentrate is diluted to 500 ml., adjusted from pH 8.8 to pH 2.0 with dilute hydrochloric acid and adsorbed on 25 ml. of a strongly acidic cation exchange resin of the sulfonate type having a styrenedivinylbenzene matrix (Dowex 50×2 hydrogen cycle resin) at 2.5 ml./minute. The column is washed with 25 ml. of water then eluted with 2% pyridine until the pH of the column effluent rose to pH 7 (54 ml.). The eluate thus obtained is adjusted to pH 8.0 with dilute sodium hydroxide and concentrated under vacuum to remove the pyridine and afford the monosodium salt of 7β-(D-5-amino-5-carboxyvaleramido)-3-carbamoyloxymethyl-7-methoxy-3-cephem-4-carboxylic acid.

Elemental analysis for $C_{16}H_{21}N_4SO_9Na$: Calc.: C, 41.0%; H, 4.5%; N, 12.0%; S, 6.8%; Found: C, 39.31%; H, 4.76%; N, 11.16%; S, 6.46%.

EXAMPLE 169

3-Carbamoyloxymethyl-7-methoxy-7β-phenylacetamido-3-cephem-4-carboxylic Acid

Step A: Di-benzhydryl ester of 7β-[(D-5'-trichloroethoxycarbonylamino-5'-carboxyvaleryl)phenylacetylamino]-3-carbamoyloxymethyl-7-methoxy-3-cephem-4-carboxylic Acid A solution of the di-benzhydryl ester of 7β-(D-5-trichloroethoxycarbonylamino-5-carboxyvaleramido)-3-carbamoyloxymethyl-7-methoxy-3-cephem-4-carboxylic acid (9.3 gm., 10 mmoles), N-trimethylsilyl phthalimide (7.8 gm., 40 mmoles) and phenylacetyl chloride (5.3 ml., 40 mmoles) in 50 ml. of acetonitrile is heated to 40° C. for 20 hours. After this period the mixture is cooled to room temperature and filtered. The filtrate is evaporated to dryness and triturated with hexane. The insoluble residue, containing di-benzhydryl ester of 7β-[(D-5'-trichloroethoxycarbonylamino-5'-carboxyvaleryl)phenylacetylamino]-3-carbamoyloxymethyl-7-methoxy-3-cephem-4-carboxylic acid, is used without purification in the next step.

Step B: Benzhydryl ester of 3-carbamoyloxymethyl-7-methoxy-7β-phenylacetamido-3-cephem-4-carboxylic Acid The crude product from Step A is dissolved in a mixture of ethylacetate (50 ml.), acetic acid (45 ml.) and water (5 ml.). To this solution is added 20 gm. of zinc powder and the mixture is agitated at room temperature for 4 hours. After this, the excess zinc is removed by filtration and the filtrate partitioned between ethylacetate and water. The organic layer is washed with a sodium bicarbonate solution and water, dried and the solvent is evaporated. The crude product thus obtained is purified by chromatography on 1 kg. of silica gel, using a mixture of chloroform, hexane, and methanol (47:47:6) for elution. The product obtained has the physical characteristics described in Example 168, Step E.

Step C: 3-Carbamoyloxymethyl-7-methoxy-7-phenylacetamido-3-cephem-4-carboxylic Acid The title compound is prepared by the procedure described in Example 168 Step F, and has the same physical characteristics as the product of Example 168.

EXAMPLE 170

3-Carbamoyloxymethyl-7-methoxy-7β-(2-thienylacetamido)-3-cephem-4-carboxylic Acid Step A: Di-benzhydryl ester of 7β-[(D-5'-trichloroethoxycarbonylamino-5'-carboxyvaleryl)-2-thienylacetylamino]-3-carbamoyloxymethyl-7-methoxy-3-cephem-4-carboxylic Acid A mixture of 6.0 gm. (6.3 mmole) of the dibenzhydryl ester of 7β-(D-5'-trichloroethoxycarbonylamino-5'-carboxyvaleramido)-3-carbamoyloxymethyl-7-methoxy-3-cephem-4-carboxylic acid, 4.7 gm. (40 mmoles) N-trimethylsilyl trifluoroacetamide, 3.42 ml. (25 mmoles) 2-thienylacetylchloride, and 50 ml. of chloroform is warmed at 47° C. for 16 hours. After the solvent is removed by evaporation, the crude reaction mixture is extracted with hexane, and further purified by chromatography on 1 kg. of silica gel using 10% ethylacetate in chloroform as the eluant.

UV: ($CH_3OH$) λmax. 265 μm ε5810

NMR: (Solvent—$CDCl_3$) δ=3.53 (—$OCH_3$, s), ~3.4 (2-$H_2$, d),

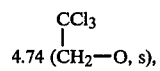
4.74 ($CH_2$—O, s), 5.05 (6-H, s), ~5.0 (10-$H_2$, partially visible), 4.15 (13-$H_2$, s).

Step B: Benzhydryl ester of 3-carbamoyloxymethyl-7-methoxy-7β-(2-thienylacetamido)-3-cephem-4-carboxylic Acid The di-benzhydryl ester of 7β-[(D-5'-trichloroethoxycarbonylamino-5'-carboxyvaleryl)-3-thienylacetylamino]-3-carbamoyloxymethyl-7-methoxy-3-cephem-4-carboxylic acid (4.2 gm., 3.8 mmoles) is dissolved in 30 ml. of ethylacetate and added to 30 ml. of 90% aqueous acetic acid and 12 gm. of zinc dust. The mixture is stirred vigorously for 5½ hours at room temperature. After the zinc is filtered off, excess acetic acid is removed by washing the ethylacetate solution with water. The title compound is isolated in the same manner as described in Example 1, Step E. It is characterized by TLC (7% CH3OH in 1:1 CHCl3:n-hexane) as a single spot material.

IR: (CHCl3) 1740, 1800 cm⁻¹;
UV: λmax. 263 μm ε5800
NMR: (Solvent—CDCl3) δ=3.45 (—OCH3, s), ~3.4 (2-H2, d), 5.02 (6-H, s), ~4.92 (10-H2, partially visible), 3.85 (13-H2, s).

Step C:
3-Carbamoyloxymethyl-7-methoxy-7β-(2-thienylacetamido)-3-cephem-4-carboxylic Acid A cold solution of the benzhydryl ester of 3-carbamoyloxymethyl-7-methoxy-7β-(2-thienylacetamido)-3-cephem-4-carboxylic acid (1.36 gm.) in 10.88 ml. of anisole is stirred with 5.44 ml. of trifluoroacetic acid at 0° C. for ½ hour. The volatiles are removed in high vacuum, and the product is recrystallized from ethyl acetate. MP: 165°–167° C.

UV: (pH 7 buffer) λmax. 263 μm ε8840
236μm ε14000
;[α]D (C = 1, CH3OH) = + 199°

NMR: (Solvent—CD3CN+D2O) δ=3.48 (—OCH3, s), ~3.4 (2-H2, partially visible), 5.05 (6-H, s), 4.91 (10-H2, d), 3.86 (13-H2, s).

Elemental analysis for C16H17N3O7S2: Calc.: C, 44.96; H, 4.01; N, 9.83 Found: C, 44.86; H, 3.99; N, 9.21, S, 15.00.

Step D: Sodium 3-carbamoyloxymethyl-7-methoxy-7β-(2-thienylacetamide)-3-cephem-4-carboxylate A suspension of 1 gram of 3-carbamoyloxymethyl-7-methoxy-7β-(2-thienylacetamide)-3-cephem-4-carboxylic acid in 100 ml. of distilled water is stirred at room temperature while gradually adding 0.2 gram of sodium bicarbonate. After solution is attained and pH is substantially neutral (pH 6–7), the batch is filtered into a lyophilization bottle. The filtrate is lyophilized.

There is obtained 1 gram of amorphous sodium 3-carbamoyloxymethyl-7-methoxy-7β-(2-thienylacetamide)-3-cephem-4-carboxylate, representing a recovery of 99%. UV (pH 7 buffer): E% 198 at 262 nm, 315 at 236 nm. ir (KBr): 1760 (lactam). [α]D=183.1° (C=1, pH 7 buffer).

EXAMPLE 171
3-Carbamoyloxymethyl-7β-(2-furylacetamido)-7-methoxy-3-cephem-4-carboxylic acid Step A: Di-benzhydryl ester of 7β-[(D-5'-trichloroethoxycarbonylamino-5'-carboxyvaleryl)-2-furylacetylamino]-3-carbamoyloxymethyl-7-methoxy-3-cephem-4-carboxylic Acid A mixture of the di-benzhydryl ester of 7β-(D-5'-trichloroethoxycarbonylamino-5'-carboxyvaleramido)-3-carbamoyloxymethyl-7-methoxy-3-cephem-4-carboxylic acid (9.3 gm.), bis-(trimethylsilyl)-trifluoroacetamide (7.0 ml.), 2-furylacetylchloride (4.7 ml.) and dichloromethane (50 ml.) is warmed at 47° C. for 16 hours. The solvent is removed by evaporation, the crude reaction mixture is extracted with hexane, and the residue is used without purification in the next step.

NMR: (Solvent-CDCl3) δ=3.48 (—OCH3, s), 3.08 (2-H2, d),

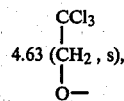

4.63 (CH2, s), 5.02 (6-H, s), ~4.88 (10-H2, d), 3.72 (13-H2, s).

Step B: Benzhydryl ester of 7β-(2-furylacetamido)-3-carbamoyloxymethyl-7-methoxy-3-cephem-4-carboxylic Acid The di-benzhydryl ester from Step A is reacted with zinc dust and acetic acid following the procedures described in Example 170 Step B. After crystallization from chloroformhexane, the pure product has the following physical characteristics:

MP: 168°–171° C.
IR: (CHCl3) 1800, 1720, 1700
UV: λmax. 265 μm ε7200
NMR: (Solvent —CD3CN) δ=3.43 (—OCH3, s), 3.39 (2-H2, partially visible), 5.0 (6-H, s), 4.75 (10-H2, d), 3.64 (13-H2, s).

Step C:
3-Carbamoyloxymethyl-7-methoxy-7β-(2-furylacetamido)-3-cephem-4-carboxylic Acid The 3-carbamoyloxymethyl-7-methoxy-7β-(2-furylacetamido)-3-cephem-4-carboxylic acid is prepared from the product of Step B following the procedure described in Example 170 Step C. The product, after recrystallization from ethyl acetate, has a melting point of 156°–161° C.

UV: (pH 7 buffer) λmax. 265 μm ε7200
IR is consistent with the structure.
NMR: (Solvent-CD3CN+D2O) δ=3.44 (—OCH3, s), ~3.38 (2-H2, partially visible), 5.02 (6-H, s), 4.82 (10-H2, d), 3.66 (13-H2, s).

EXAMPLE 172
3-Carbamoyloxymethyl-7-methoxy-7β-thiophenoxyacetamido-3-cephem-4-carboxylic Acid Step A: Di-benzhydryl ester of 7β-[(D-5-Trichloroethoxycarbonylamino-5-carboxyvaleryl)thiophenoxyamido]-3-carbamoyloxymethyl-7-methoxy-3-cephem-4-carboxylic Acid By following substantially the procedure described in Example 171 Step A, and by substituting for the 2-furylacetyl chloride an equimolar quantity of phenylthioacetyl chloride there is obtained di-benzhydryl ester of 7β-[(D-5-trichloroethoxycarbonylamino-5-carboxyvaleryl)thiophenoxyamido]-3-carbamoyloxymethyl-7-methoxy-3-cephem-4-carboxylic acid.

NMR: (Solvent-CDCl3) δ=3.33 (—OCH3, s), ~3.23 (2-H2, partially visible),

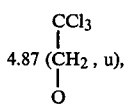

5.0 (6-H, s), 4.87 (10-H₂, u), 3.68 (13-H₂, s).

Step B: Benzhydryl ester of 3-carbamoyloxymethyl-7-methoxy-7β-thiophenoxyacetamido-3-cephem-4-carboxylic Acid By following substantially the procedure described in Example 171 Step B, and by substituting the di-benzhydryl ester of 7β-[(D-5-trichloroethoxycarbonylamino-5-carboxyvaleryl)thiophenoxyamido]-3-carbamoyloxymethyl-7-methoxy-3-cephem-4-carboxylic acid in place of the di-benzhydryl ester of 7β-[(D-5'-trichloroethoxycarbonylamino-5'-carboxyvaleryl)-2-furylacetylamino]-3-carbamoyloxymethyl-7-methoxy-3-cephem-4-carboxylic acid there is obtained, after chromatographic purification, substantially pure product which appears as a single spot on thin layer chromatography (TLC). The IR is in accord with the structure.

UV: λmax. 274 μm ε11350

NMR: (Solvent-CDCl₃) δ=3.34 (—OCH₃, s), 3.24 (2-H₂, partially visible), 5.0 (6-H, s), 4.88 (10-H₂, d), 3.68 (13-H₂, s).

Step C: 3-Carbamoyloxymethyl-7-methoxy-7β-thiophenoxyacetamido-3-cephem-4-carboxylic Acid The title compoun is prepared from the product of Step B above following the procedure of Example 170 Step C. The product exhibits a single spot on TLC. MP: 119°–123° C.

UV: (pH 7 buffer) λmax. 247 μm ε10400

NMR: (Solvent-CD₃CN+D₂O) δ=3.38 (—OCH₃, s), 3.34 (2-H₂, partially visible), 5.0 (6-H, s), 4.82 (10-H₂, s), 3.71 (13-H₂, s).

EXAMPLE 173

7β-(D,L-α-azidophenylacetylamido)-3-carbamoyloxymethyl-7-methoxy-3-cephem-4-carboxylic Acid

Step A: 7β-(D-5-tert-butoxycarbonylamino-5-carboxyvaleramido)-3-carbamoyloxymethyl-7-methoxy-3-cephem-4-carboxylic Acid 7β-(D-5-amino-5-carboxyvaleramido)-3-carbamoyloxymethyl-7-methoxy-3-cephem-4-carboxylic acid (50.0 g.) is dissolved in a mixture of 1500 ml. aqueous 5% dipotassium hydrogen phosphate and 1000 ml. acetone and adjusted to pH 9.5 with 2.5 N sodium hydroxide solution. To this stirred solution is added tert-butoxycarbonyl azide (50 ml.) and the pH maintained at 9.5 over a 20 hour period. The reaction mixture is then extracted with ethyl acetate, the ethyl acetate layer discarded, and the aqueous layer is cooled to 0° C., stirred with 1200 ml. of ethylacetate, and acidified to pH 2.5 with concentrated hydrochloric acid. The ethyl acetate layer is separated, dried over sodium sulfate and concentrated in vacuo, and the solid so obtained may be used without further purification.

IR: 1790 (β-Lactam), 1700

UV: (pH 7 buffer) λmax. 263 ε6820

NMR: (Solvent-DMSO, d₆) δ=3.30 (—OCH₃, s), 3.42 (2-H₂, partially visible), 5.06 (6-H, s), 4.78 (10-H, d), 1.38 (t-Bu, s).

Step B: Di-benzhydryl ester of 7β-(D-5-tert-butoxycarbonylamino-5-carboxyvaleramido)-3-carbamoyloxymethyl-7-methoxy-3-cephem-4-carboxylic Acid To a solution of 7β-(D-5-butoxycarbonylamino-5-carboxyvaleramido)-3-carbamoyloxymethyl-7-methoxy-3-cephem-4-carboxylic acid (15.0 g.) in ethyl acetate (500 ml.) is added diphenyldiazomethane (5.5 g.) in 70 ml. of ether. The reaction mixture is warmed to 40° C. with stirring and after 30 minutes is treated with additional diphenyldiazomethane (5.5 g.) in ether (70 ml.). After 3 hours, the solvent is removed in vacuo and replaced by a mixture of methanol (500 ml.) and water (20 ml.). The methanol-water solution is extracted four times with hexane and then evaporated in vacuo. The residue is dissolved in ethyl acetate, dried over sodium sulfate and evaporated in vacuo to yield the title compound which is used without purification in the next step.

NMR: (Solvent-CDCl₃) δ=3.60 (—OCH₃, s), 3.4 (2-H₂, partially visible), 5.10 (6-H, s), 4.95 (10-H, partially visible).

Step C: Di-benzhydryl ester of 7β-[(D-5'-tert-butoxycarbonylamino-5'-carboxyvaleryl)-D,L-α-azidophenylacetylamino]-3-carbamoyloxymethyl-7-methoxy-3-cephem-4-carboxylic Acid A mixture of the di-benzhydryl ester of 7β-(D-5'-tert-butoxycarbonylamino-5'-carboxyvaleramido)-3-carbamoyloxymethyl-7-methoxy-3-cephem-4-carboxylic acid (10.8 g.), chloroform (100 ml.), bis-(trimethylsilyl)-trifluoroacetamide (16.2 g.) and D,L-α-azido-phenylacetyl chloride is warmed at 45° C. for 16 hours. The mixture is diluted with chloroform (300 ml.), washed with 2% aqueous bicarbonate and saturated aqueous sodium chloride, dried over sodium sulfate and evaporated to an oil which is purified by precipitating the product from a chloroform solution with hexane. The light yellow solid is used in the next step without further purification.

IR: 1790 (β-Lactam, 1, 1735, 2100 (—N₃)

NMR: (Solvent-CDCl₃) δ=3.70 (—OCH₃, s), 3.2 (2-H₂, partially visible).

Step D: 7β-(D,L-α-azidophenylacetylamido)-3-carbamoyloxymethyl-7-methoxy-3-cephem-4-carboxylic Acid A solution of the di-benzhydryl ester of 7β-[(D-5'-tert-butoxycarbonylamino-5'-carboxyvaleryl)-D,L-α-azidophenylacetylamino]-3-carbamoyloxymethyl-7-methoxy-3-cephem-4-carboxylic acid (13.0 g.) in anisole (13 ml.) is poured into 65 ml. of cold (0° C.) trifluoroacetic acid. After 5 minutes the solution is poured into 1800 ml. of stirred, cold (0° C.) ether. The precipitated solid is collected and distributed between 10% aqueous disodium acid phosphate and ethyl acetate. The ethyl acetate layer is discarded and the aqueous layer is layered with fresh ethyl acetate and the stirred mixture brought to pH 2 in the cold with 60% aqueous phosphoric acid. The ethyl acetate layer is collected, washed with saturated aqueous sodium chloride and then dried over sodium sulfate. Volatiles are removed in vacuo to afford the title compound.

| UV: λmax. 264μm | ε7537 | (pH 7 buffer) |
|---|---|---|
| 231 μm | ε13567 | |

IR: 1760 (β-Lactam) 1705, 2105 (—N$_3$)
NMR: (Solvent-CD$_3$CN) δ=3.36 (—OCH$_3$, s), 3.50 (—OCH$_3$, s), 3.40 (2-H$_2$, partially visible), 5.06 (6-H, s), 4.86 (10-H, s), 5.15 (13-H, s).

EXAMPLE 174

7β-(D,L-α-aminophenylacetylamido)-3-carbamoyloxymethyl-7-methoxy-3-cephem-4-carboxylic Acid A slurry of 1.0 g. of 7β-(D,L-α-azidophenylacetylamido)-3-carbamoyloxymethyl-7-methoxy-3-cephem-4-carboxylic acid in acetic acid (10 ml.) and water (90 ml.) at 0° C. is stirred with zinc dust (5.0 g.) for 10 minutes and filtered. The filtrate is sparged with hydrogen sulfide, filtered, and the filtrate freeze dried to afford a white solid which is washed with ether and dried in vacuo to afford the title compound as a white powder.

UV: (pH 7 buffer) λmax. 264 μm ε6525
IR: 1770 (β-Lactam) 2650, 1550 (HN$_3$+)
NMR: (Solvent-D$_2$O+HCO$_3$-) δ=3.78 (—OCH$_3$, s), 3.84 (—OCH$_3$, s), 3.90 (2-H$_2$, partially visible).

EXAMPLE 175

3-Acetoxymethyl-7β-(2-thionylacetamido)-3-cephem-4-carboxylic Acid

Step A:
7β-(D-5-Trichloroethoxycarbonylamino-5-carboxyvaleramido)-3-acetylmethyl-3-cephem-4-carboxylic Acid To a solution of 7β-(D-5-amino-5-carboxyvaleramido)-3-acetoxymethyl-3-cephem-4-carboxylic acid (2.5 g., 0.53 mole) in acetone (13 ml.) and aqueous 10% dipotassium hydrogen phosphate (40 ml.) is added dropwise trichloroethoxycarbonyl chloride (3.35 g., 0.159 mole). During the addition the pH of the solution is kept in the range of from 8.5 to 9 by the gradual addition of a 17% aqueous solution of sodium hydroxide. After 30 minutes the mixture is washed with ethyl acetate and the aqueous layer is acidified to pH 2.5 with concentrated hydrochloric acid. The precipitated product is extracted into ethyl acetate, the solution is dried over sodium sulfate, filtered and the solvent removed to afford 2.7 g. of 7β-(D-5-trichloroethoxycarbonylamino-5-carboxyvaleramido)-3-acetylmethyl-3-cephem-4-carboxylic acid.

Step B: Dibenzhydryl ester of 7-(D-5-trichloroethoxycarbonylamino-5-carboxyvaleramido)-3-acetoxymethyl-3-cephem-4-carboxylic Acid To a solution of 7β-(D-5-trichloroethoxycarbonylamino-5-carboxyvaleramido)-3-acetylmethyl-3-cephem-4-carboxylic acid in ethyl acetate (30 ml.) is added diphenyl diazomethane (2.0 g.) in ether (25 ml.). The mixture is stirred overnight and the solvent removed to afford 4.0 g. of crude product. The crude product is purified by chromatography on silica gel using chloroform as the eluant to afford 2.3 g. of substantially pure dibenzhydryl ester of 7-(D-5-trichloroethoxycarbonylamino-5-carboxyvaleramido)-3-acetylmethyl-3-cephem-4-carboxylic acid.

NMR: (Solvent-CDCl$_3$) δ=2.0 (methyl, s), 4.9 (10-H$_2$, quartet), 3.2 (2-H$_2$, quartet), 4.95 (6-H, d), 5.92 (7-H), 7.0 (benzhydryl protons, 2 s).

Step C: Dibenzhydryl ester of 7-[(D-5-trichloroethoxycarbonylamino-5-carboxyvaleryl)-2-thienylacetylamino]-3-acetoxymethyl-3-cephem-4-carboxylic Acid A mixture of the dibenzhydryl ester of 7β-(D-5-trichloroethoxycarbonylamino-5-carboxyvaleramido)-3-acetoxymethyl-3-cephem-4-carboxylic acid (2.0 g., 0.02 mole), N-trimethylsilyl trifluoroacetamide (1.65 g., 0.09 mole), 2-thienylacetyl chloride (1.31 g., 0.0815 mole) and methylene chloride (6 ml.) is warmed at 40°–45° C. in an oil bath under a nitrogen atmosphere for 20 hours. The reaction mixture is poured into hexane (100 ml.) and filtered through diatomaceous earth. Removal of the solvent affords the dibenzhydryl ester of 7-[D-5-trichloroethoxycarbonylamino-5-carboxyvaleryl)-2-thienylacetylamino]-3-acetoxymethyl-3-cephem-4-carboxylic acid.

Step D: Benzhydryl ester of 3-acetoxymethyl-7-(2-thienylacetamido)-3-cephem-4-carboxylic Acid The dibenzhydryl ester of 7-[(D-5-trichloroethoxycarbonylamino-5-carboxyvaleryl)-2-thienylacetylamino]-3-acetoxymethyl-3-cephem-4-carboxylic acid is dissolved in ethyl acetate (10 ml.) and added to a mixture of 90% aqueous acetic acid (10 ml.) and zinc dust (1.0 g.). The mixture is stirred for two hours at room temperature. The reaction mixture is filtered to remove the zinc. The reaction mixture is washed successively with 2 portions of water, a cold sodium bicarbonate solution and then with a saturated sodium chloride solution (15.0 ml.). The ethyl acetate solution is dried over sodium sulfate, filtered and the solvent removed to afford 1.9 g. of crude product which is chromatographed on silica gel using a mixture of chloroform and ethyl acetate (50:1) as the eluant to afford 0.380 g. of product which, after recrystallization from ethyl acetate, has a melting point of 141.5°–143° C.

UV: (CH$_3$OH) λmax. 263 δ7580
Elemental analysis for C$_{29}$H$_{26}$N$_2$O$_6$S$_2$: Calc.: C, 61.91; H, 4.66; N, 4.98; Found: C, 62.14; H, 4.84; N, 4.91.

Step E:
3-(Acetoxymethyl)-7-(2-thienylacetamido)-3-cephem-4-carboxylic Acid

A cold solution of benzhydryl ester of 3-acetoxymethyl-7-(2-thienylacetamido)-3-cephem-4-carboxylic acid (100 mg.) in anisole (1.0 ml.) and trifluoroacetic acid (0.5 ml.) is stirred at 0° C. for 35 minutes. Carbon tetrachloride (50 ml.) is added and the reaction mixture is concentrated to dryness. The residue is triturated with hexane. The hexane is removed by decantation and this residue is dissolved in ethyl acetate (10 ml.), concentrated to 1 ml. and diethyl ether added to afford precipitate. This precipitate is recrystallized from a mixture of diethyl ether and ethyl acetate to afford 0.025 g. of 3-(acetoxymethyl)-7-(2-thienylacetamido)-3-cephem-4-carboxylic acid, m.p. 164° C. Mixed melting point with an authentic sample was 163° C.

EXAMPLE 176

Dibenzylethylenediamine salt of 3-methyl-7-methoxy-7β-(2-thienylacetamido-3-cephem-4-carboxylic Acid

Step A: 7β-(D-5-Amino-5-carboxyvaleramido)-3-methyl-7-methoxy-3-cephem-4-carboxylic Acid A 10% palladium on charcoal catalyst is suspended in water (80 ml.) and treated with hydrogen. The catalyst is filtered and suspended again in water (50 ml.) and to this mixture (2.67 g.) is added the sodium salt of 7β-(D-5-amino-5-carboxyvaleramido)-3-carbamoyloxymethyl-7-methoxy-3-cephem-4-carboxylic acid (1.0 g.) in water (10 ml.). The resulting mixture is shaken for twenty-two hours at room temperature. The catalyst is removed by filtration and washed with water (50 ml.). The combined wash and filtrate is concentrated to dryness to afford a 52.8% yield of 7β-(D-5-amino-5-carboxyvaleramido)-3-methyl-7-methoxy-3-cephem-4-carboxylic acid (528 mg.).

UV: λmax. 265 μm; $E_{1\ cm}^{1\%}$ is 100

Step B: Dibenzylethylenediamine salt of 7β-(D-5-tert-butoxycarbonylamino-5-carboxyvaleramido)-7-methoxy-3-methyl-3-cephem-4-carboxylic Acid A solution of the disodium salt of 7β-(D-5-amino-5-carboxyvaleramido)-7-methoxy-3-methyl-3-cephem-4-carboxylic acid (11.5 g.) is dissolved in water (150 ml.) and acetone (50 ml.). The pH is adjusted to 9–9.1 with sodium hydroxide and 10 ml. of tert-butyl azidoformate is added. The reaction mixture is stirred for 16 hours at room temperature with additional sodium hydroxide being added to maintain the pH at 9–9.1. The reaction mixture is extracted with ethyl acetate (100 ml.) and the organic layer discarded. The product is precipitated by lowering the pH to 2.5 with dilute hydrochloric acid. The precipitate is collected by centrifugation and converted to its dibenzylethylenediamine salt which is crystallized from ethyl acetate. There is obtained 4.3 g. of the dibenzylethylenediamine salt of 7β-(D-5-tert-butoxycarbonylamino-5-carboxyvaleramido)-7-methoxy-3-methyl-3-cephem-4-carboxylic acid, m.p. 177°–179° C. (dec.).

UV: λmax. 263 μm, 238 $E_{1\ cm}^{1\%}$ = 98.2, 81.1

Elemental analysis for $C_{36}H_{49}N_5O_9S$: Calc.: C, 59.42; H, 6.74; N, 9.63; Found: C, 60.02; H, 6.80; N, 9.79.

Step C: Dibenzylethylenediamine salt of 3-methyl-7-methoxy-7β-(2-thienylacetamido-3-cephem-4-carboxylic Acid The 7β-(D-5-tert-butoxycarbonylamino-5-carboxyvaleramido)-3-methyl-7-methoxy-3-cephem-4-carboxylic acid is treated with aqueous dilute hydrochloric acid (200 ml., 0.1 N) and ethyl acetate (100 ml.) in order to extract the free acid. To a solution of 1.33 g. (2.74 mmoles) of the free acid in methylene chloride (10 ml.) is added bis-trimethylsilyl trifluoroacetamide (2.2 ml.) and mono-trimethylsilyl trifluoroacetamide (0.5 ml.). 2-Thienylacetyl chloride (1.1 ml.) is then added and the reaction mixture stirred for 18 hours under a nitrogen atmosphere at 43° C. The solvent is removed in vacuo, and the residue partitioned between ethyl acetate and aqueous phosphate buffer (pH 7.5). The aqueous layer is acidified with dilute hydrochloric acid and the precipitated product extracted with ethyl acetate. Addition of dibenzethylenediamine results in crystallization of 250 mg. of the desired product as a salt in the proportion of 2 equivalents of product to one mole of dibenzylethylenediamine. Recrystallization of the salt from ethanol affords substantially pure product, m.p. 153°–155° C. (dec.) with previous darkening.

Elemental analysis for $C_{46}H_{52}S_4N_6O_{10}$: Calc.: C, 56.54; H, 5.36; N, 8.60; S, 13.12; Found: C, 55.75; H, 5.16; N, 8.37; S, 12.16.

EXAMPLE 177

7-(Phenylacetyl-2-thienylacetyl)amino-3-acetoxymethyl-3-cephem-4-carboxylic Acid A suspension of sodium cephalothin (3.36 g.) in anhydrous alcohol-free chloroform (20 ml.) is silylated by the addition of trimethylchlorosilane (2.2 ml.). After stirring for 30 minutes, monosilyltrifluoroacetamide (5.0 ml.) and phenylacetyl chloride (4.0 ml.) are added and the mixture is then heated to 45° C. for two days under a condenser fitted with a drying tube. The volatiles are evaporated to afford a residue which is dissolved in 100 ml. of ethyl acetate and washed three times with water. The ethyl acetate layer is dried over magnesium sulfate, filtered and the solution evaporated in vacuo to a residue. The residue is triturated with chloroform, any insolubles are removed by filtration and the product precipitated from the filtrate with hexane. This procedure is followed two more times. The 7-(phenylacetyl-2-thienylacetyl)amino-3-acetoxymethyl-3-cephem-4-carboxylic acid is obtained in a solvent-free form by freeze drying from a solution in benzene.

IR: (CHCl₃) 1780μ 1720μ

NMR: (CDCl₃) Consistent with structure; φCH₂C(=O)—(4.03 ppm), 2-thienyl-CH₂—C(=O)—(4.3 ppm)

TLC: 1 major spot, $R_f$=0.69 (EtOAC:62, $C_5H_5N$:21, HOAC:6, $H_2O$:11) on silica gel.

EXAMPLE 178

7-(Di-2-thienylacetyl)amino-3-acetoxymethyl-3-cephem-4-carboxylic Acid

A suspension of sodium cephalothin (1.18 g.) in anhydrous alcohol-free chloroform (10 ml.) is silylated by the addition of trimethylchlorosilane (1.1 ml.). After stirring for 30 minutes, monosilyltrifluoroacetamide (2.5 ml.) and 2-thienylacetyl chloride (2.0 ml.) are added to the suspension which is then heated to 45° C. The mixture is allowed to remain at this temperature for two days and then evaporated in vacuo to a residue which is dissolved in ethyl acetate (50 ml.) and washed three times with water. The ethyl acetate layer is dried over magnesium sulfate, filtered and the filtrate evaporated in vacuo to obtained a residue. The residue is dissolved in chloroform and precipitated with hexane three times, each time discarding the supernatent liquid. The 7-(di-2-thienylacetyl)amino-3-acetoxymethyl-3-cephem-4-carboxylic acid is obtained in a solvent-free form by freeze-drying from a solution in benzene.

NMR: (Solvent-CDCl$_3$)-Consistent with structure;

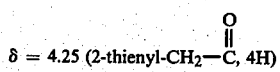

$\delta = 4.25$ (2-thienyl-CH$_2$—C, 4H)

TLC: 1 major spot, R$_f$=0.67 (EtOAC:62, C$_5$H$_5$N:21, HOAC:6, H$_2$O:11) on silica gel.

EXAMPLE 179

7-(2-Thienylacetyl)amino-3-acetoxymethyl-3-cephem-4-carboxylic Acid 7-(Phenylacetyl-2-thienylacetyl)amino-3-acetoxymethyl-3-cephem-4-carboxylic acid (250 mg.) is dissolved in tetrahydrofuran (10 ml.) and water (10ml.). The pH of the solution is adjusted to 9 and the mixture is allowed to stand for one hour. After this the solution is extracted with ethyl acetate and the extracts are washed with a disodium hydrogen phosphate solution. After drying the solvent is evaporated to afford a mixture of the 7-(2-thienylacetyl)amino-3-acetoxymethyl-3-cephem-4-carboxylic acid and the starting material. The product is separated from the starting material by chromatography to afford substantially pure 7-(2-thienylacetyl)amino-3-acetoxymethyl-3-cephem-4-carboxylic acid. The ratio of these two products is 7:3.

EXAMPLE 180

By following substantially the procedure described in Example 170 Step A, and by substituting for the thienylacetyl chloride described therein an equimolar quantity of an appropriate acylating agent there is obtained the corresponding diester of 7-diacylamino-3-carbamoyloxymethyl-7-methoxy(or hydro)-3-cephem-4-carboxylic acid which upon removal of the N-protecting group by following the procedure of Example 170, Step B, and subsequent treatment by the procedure of Step C affords the desired 7-acylamino-3-carbamoyloxymethyl-7-methoxy(or hydro)-3-cephem-4-carboxylic acid.

The following equation, taken together with Table I, illustrates the starting materials, intermediates and novel final products which can be prepared by this novel process. It should be noted that in the following equation and table that those compounds having a 7-hydro substituent instead of the 7-methoxy substituent would undergo the same reaction to afford those compounds of Table I having a 7-hydro substituent in place of the 7-methoxy substituent.

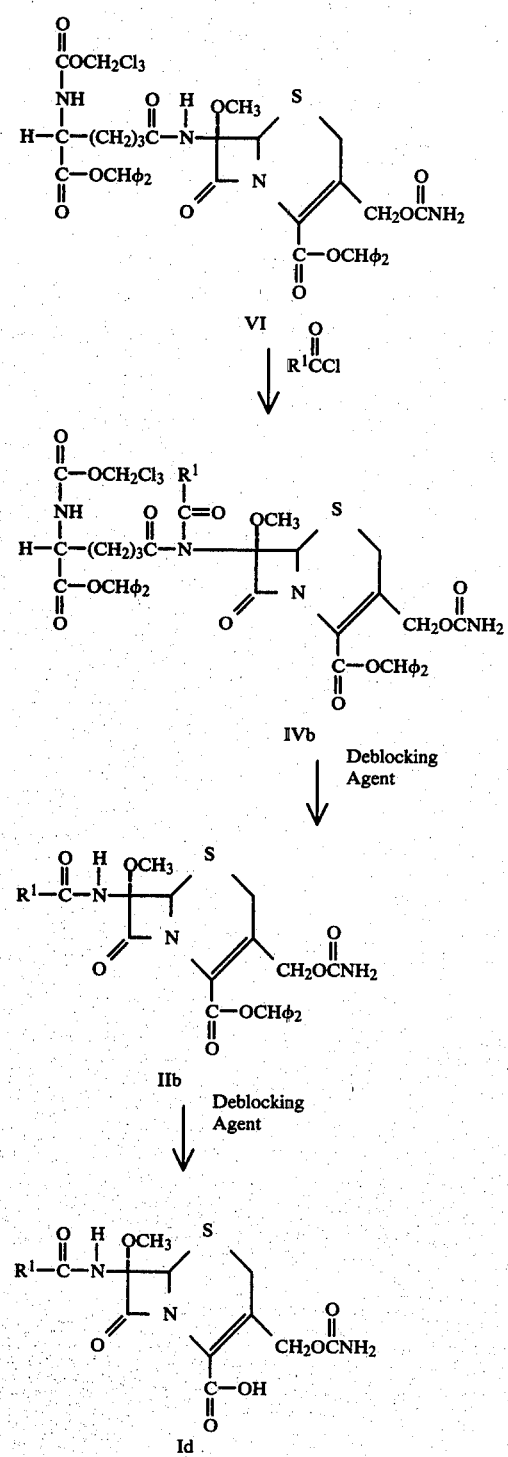

TABLE I

| R¹ |
|---|

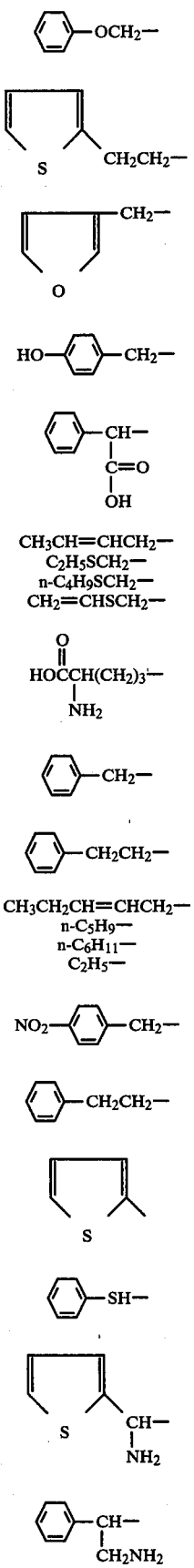

CH₃CH=CHCH₂—
C₂H₅SCH₂—
n-C₄H₉SCH₂—
CH₂=CHSCH₂—

CH₃CH₂CH=CHCH₂—
n-C₅H₉—
n-C₆H₁₁—
C₂H₅—

TABLE I-continued

| R¹ |
|---|

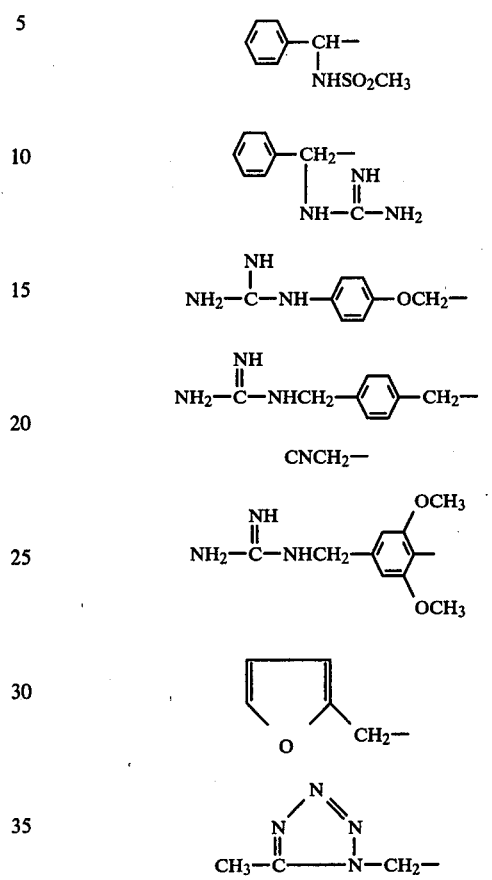

CNCH₂—

EXAMPLE 181

7-Amino-7-Allyl-Cephalosporanic Acid Benzhydryl Ester

7-Amino-7-Benzyl-Cephalosporanic Acid Benzhydryl Ester

The benzhydryl ester of 7-(p-nitrobenzylideneamino)-cephalosporanic acid is reacted with allyl chloride, following the procedure of Example 166, to form benzhydryl 7-(p-nitrobenzylideneamino)-7-allyl-cephalosporanate. This is then regenerated to the benzhydryl 7-amino-7-allyl-cephalosporanate using aniline hydrochloride.

The benzhydryl 7-amino-7-benzyl-cephalosporanate is prepared in the same manner using benzyl chloride.

EXAMPLE 182

7-Amino-7-Carboxy-Cephalosporanic Acid Benzhydryl Ester

7-Amino-7-Dithiocarboxy-Cephalosporanic Acid Benzhydryl Ester

A solution of 0.5 g. of benzhydryl 7-(p-nitrobenzylideneamino)-cephalosporanate in 5 ml. of tetrahydrofuran is prepared under a nitrogen atmosphere. Carbon dioxide gas is bubbled through the solution until the color disappears. Benzene, 50 ml., is added and the solution washed with aqueous pH 2 phosphate buffer.

The benzene solution is dried with MgSO₄, filtered, and evaporated to afford the product, benzhydryl 7-(p-nitrobenzylideneamino)-7-carboxy-cephalosporanate.

Using carbon disulfide gas or dry ice (solid $CO_2$) in the above reaction, the compounds 7-(p-nitrobenzylideneamino)-7-dithiocarboxy-cephalosporanate or 7-(p-nitrobenzylideneamino)-7-carboxy-cephalosporanate are prepared, respectively.

The amino moiety is regenerated using aniline hydrochloride, thereby yielding the compounds 7-amino-7-carboxy-cephalosporanic acid benzhydryl ester or 7-amino-7-dithiocarboxy-cephalosporanic acid benzhydryl ester.

EXAMPLE 183

7-Amino-7-Nitro-Cephalosporanic Acid Benzhydryl Ester

Benzhydryl 7-(p-nitrobenzylideneamino)-cephalosporanate, 571 mg., is dissolved in 10 ml. dry acetonitrile containing 4 mg. acetone cyanhydrin nitrate. The latter has the formula:

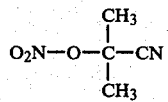

With vigorous stirring under nitrogen, a solution of diisopropylethylamine in 12 ml. acetonitrile is added over a five hour period. The reaction mixture is stirred overnight and the solvent removed in vacuo. The residue is taken up in 50 ml. benzene and washed successively with water, 1 M aqueous pH 2 phosphate buffer, water and bicarbonate. After drying, filtering and removing the solvent, the residue is a crude compound suitable for further reaction without additional purification. It may be purified if desired by chromatography on silica gel, eluting with 25:1 chloroform-ethyl acetate. It is identified as 7-(p-nitrobenzylideneamino)-7-nitro-cephalosporanic acid benzhydryl ester.

The compounds 7-(p-nitrobenzylideneamino)-7-nitroso-cephalosporanic acid benzhydryl ester; 7-(p-nitrobenzylideneamino)-7-carbamoyl-cephalosporanic acid benzhydryl ester; 7-(p-nitrobenzylideneamino)-7-carboethoxy-cephalosporanic acid benzhydryl ester; 7-(p-nitrobenzylideneamino)-7-sulfo-cephalosporanic acid benzhydryl ester; 7-(p-nitrobenzylideneamino)-7-sulfamoyl-cephalosporanic acid benzhydryl ester; 7-(p-nitrobenzylideneamino)-7-methylsulfo-cephalosporanic acid benzhydryl ester; or 7-(p-nitrobenzylideneamino)-7-phospho-cephalosporanic acid benzhydryl ester can be prepared using the reagents nitrosyl chloride, carbamoyl chloride, ethylchloroformate, sulfamoyl chloride, methanesulfonyl chloride, or phosphorous oxychloride, respectively.

The above imino derivatives can all be regenerated to the amino functionality using either aniline hydrochloride or 2,4-dinitrophenylhydrazine, as described infra. The products thereby obtained are 7-amino-7-nitro-cephalosporanic acid, 7-amino-7-nitrosocephalosporanic acid, 7-amino-7-carbamoyl-cephalosporanic acid, 7-amino-7-carboethoxy-cephalosporanic acid, 7-amino-7-sulfo-cephalosporanic acid, 7-amino- b 7-sulfamoyl-cephalosporanic acid, 7-amino-7-methylsulfo-cephalosporanic acid and 7-amino-7-phospho-cephalosporanic acid, respectively. In all cases, the benzhydryl ester is the ester made.

EXAMPLE 184

Benzhydryl 7-aminocephalosporanate-S-oxide 0.500 g. of benzhydryl 7-aminocephalosporanate is dissolved in 10 ml. of $CH_2Cl_2$ cooled to 0° C. and treated with m-chloroperbenzoic acid (0.172 g.) for 1 hour, during which the reaction mixture is allowed to come to room temperature.

The reaction mixture is diluted with $CH_2Cl_2$ and washed with 5% $NaHCO_3$ solution three times and then with water, dried and evaporated to give the crude product. This is stirred with 10 ml. of ether for 1 hour. The precipitate is filtered and washed with ether to give the title product.

In like manner other 7-aminodecephalosporanic acid esters described herein can be converted to the S-oxides. These oxides can be used as intermediates in the preparation of the sulfoxides set forth in formula I above. Alternatively, the various intermediates and final products described herein can be converted to the corresponding S-oxides following the procedure described above. The various S-oxide derivatives can be converted to the corresponding cephem compounds in accordance with the process of the example which follows.

EXAMPLE 185

Benzhydryl 3-methoxymethyl-7-methoxy-7-(2-thienylacetamido))cephalosporanate-S-oxide prepared by the oxidation of the corresponding cephalosporanate compound with m-chloroperbenzoic acid (1.0 g.) is dissolved in 10 ml. of acetonitrile and 10 ml. of dimethylformamide. An equivalent of stannous chloride and ½ equivalent of acetyl chloride is added at 0° C. The mixture is stirred at 0° C. for 1 hour and then at room temperature for 1 hour. The solvent is removed in vacuo and water is added. The mixture is extracted with ethylacetate and the extract washed with 0.1 N HCl, saturated sodium bicarbonate and water. After drying the solvent is removed in vacuo to afford benzhydryl 3-methoxymethyl-7-methoxy-7-(2-thienylacetamido)-cephalosporanate.

The new cephalosporins of formula I are valuable antibiotics active against various gram-positive and gram-negative bacteria. Although, in general, their biological spectrums are similar to those of the known cephalosporins, these new cephalosporins possess some new and unexpected properties. Thus, in general, they are active against many microorganisms which are resistant to the known cephalosporins such as cephaloridine and cephalothin and are resistant to the β-lactamase produced by cephalosporin resistant clinical isolates of pathogens such as *E. coli* and *A. cloacae*. Also, they are generally more active against strains of Proteus such as *mirabilis*, and are active against strains of *Proteus morganii* which are resistant to the unsubstituted cephalosporins. They are useful in separating microorganisms in remaining susceptible microorganisms from pharmaceutical, medical and dental equipment and as bactericides in industrial applications, for example in water-based paints and in the white water of paper mills to inhibit the growth of harmful bacteria.

Thus, the 7-methoxycephalosporins produced in accordance with the processes of this invention are generally more active than the 7-(D-5'-amino-5'-carboxyvaleramido)-7-methoxycephalosporins against various gram-negative organisms and possess increased activity against gram-positive organisms. For example, these 7-methoxycephalosporins are active against gram-positive pathogens such as Staphylococcus aureus at Minimum Inhibitory Concentrations (MIC) as low as about 1.5 mcg./ml., Streptococcus pyogenes at MIC of about 0.7 mcg./ml., and Diplococcus pneumoniae at MIC of about 0.7 mcg./ml.; and against gram-negative organisms such as Aerobacter aerogenes at MIC of about 3 mcg./ml., Proteus vulgaris at MIC of about 1.5 mcg./ml. and Proteus morganii at about 6 mcg./ml. Thus, activities of specific products of the foregoing examples that might be mentioned are: 3-carbamoyloxymethyl-7-methoxy-7-phenylacetamido-3-cephem-4-carboxylic acid, S. pyogenes MIC 1.56 mcg./ml. and P. vulgaris MIC 1.56 mcg./ml.; 3-carbamoyloxymethyl-7-methoxy-7-(2-thienylacetamido)-3-cephem-4-carboxylic acid, S. pyogenes MIC 0.78 mcg./ml. and P. morganii MIC 12.5 mcg./ml.; 3-carbamoyloxymethyl-7-methoxy-7-(2-furylacetamido)-3-cephem-4-carboxylic acid, S. aureus MIC 6.25 mcg./ml. and P. vulgaris MIC 1.56 mcg./ml.; 3-carbamoyloxymethyl-7-methoxy-7-thiophenoxyacetamido-3-cephem-4-carboxylic acid, S. pyrogenes MIC 0.78 mcg./ml. and D. pneumoniae MIC 0.78 mcg./ml.; 3-acetoxymethyl-7-methoxy-7-(2-thienylacetamido)-3-cephem-4-carboxylic acid, S. pyogenes MIC 1.56 mcg./ml. and P. vulgaris MIC 0.78 mcg./ml; and 3-pyridiummethyl-7-methoxy-7-(2-thienylacetamido)-3-cephem-4-carboxylic acid Serratia MIC 25 mcg./ml. and S. aureus MIC 156 mcg./ml.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly. Suitable carriers which may be used in the composition include, for example, mannitol, sucrose, glucose or sterile liquids such as water, saline, glycols and oils of a petroleum, animal, vegetable or synthetic origin as, for example, peanut oil, mineral oil or sesame oil. Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

The dosage to be administered depends to a large extent upon the condition of the subject being treated and the weight of the host, the parenteral route being preferred for generalized infections and the oral route for intestinal infections. In general, a daily dosage consists of from about 15 to about 600 mg. of active ingredient per kg. of body weight of the subject in one or more applications per day. A preferred daily dosage lies in the range of from about 80 to 120 mg. of active ingredient per kg. of body weight. The preferred daily dosage for the compound sodium 3-carbamoyloxymethyl-7-methoxy-7-(2-thienylacetamido)decephalosporanate is in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid, will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Typical formulations of specific products are described below.

One such unit dosage form consists in mixing 120 mg. of 3-carbamoyloxymethyl-7-methoxy-7-(D-α-aminophenylacetamido)decephalosporanic acid sodium salt with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative:

| Tablet Containing 125 mg. of 7-Methoxy-7-(D-α-carboxy-Phenylacetamido)cephalosporanic Acid | |
|---|---|
| | Per Tablet |
| 7-Methoxy-7-(D-α-Amino-Phenylacetamido)cephalosporanic Acid | 125. mg. |
| Cornstarch, U.S.P. | 6. mg. |
| Dicalcium Phosphate | 192. mg. |
| Lactose, U.S.P. | 190. mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| Parenteral Solution Containing 500 mg. of 3-Carbamoyl-oxymethyl-7-Methoxy-7-(2-Thienylacetamido)decephalosporanate Ampoule: | |
|---|---|
| Sodium 3-Carbamoyloxymethyl-7-Methoxy-7-(2-Thienylacetamido)decephalosporanate | 500 mg. |
| Diluent: Sterile Water for Injection | 2 cc. |

By substituting an equivalent amount of 7-methoxy-7-(α-carboxy-phenylacetamido)cephalosporanic acid for the 500 mg. of sodium salt of 3-carbamoyloxymethyl-7-methoxy-7-(2-thienylacetamido)decephalosporanate recited in the foregoing example there is also obtained a formulation suitable for parenteral administration.

| Opthalmic Solution Containing 100 mg. of Sodium 3-Carbamoyloxymethyl-7-Methoxy-7-(2-Thienylacetamido) decephalosporanate | |
|---|---|
| Sodium 3-Carbamoyloxy-7-Methoxy-7-(2-Thienylacetamido)decephalosporanate | 100 mg. |
| Hydroxypropylmethyl Cellulose | 5 mg. |
| Sterile Water | to 1 ml. |

| Otic Solution Containing 100 mg. of Sodium 3-Carbamoyloxymethyl-7-Methoxy-7-(2-Thienylacetamido)decephalosporanate | |
|---|---|
| Sodium 3-Carbamoyloxy-7-Methoxy-7-(2-Thienylacetamido)decephalosporanate | 100 mg. |
| Benzalkonium Chloride | 0.1 mg. |
| Sterile Water | to 1 ml. |

| Topical Ointment Containing 100 mg. of Sodium 3-Carbamoyloxymethyl-7-Methoxy-7-(2-Thienylacetamido)decephalosporanate | |
|---|---|
| Sodium 3-Carbamoyloxy-7-Methoxy-7-(2-Thienylacetamido)decephalosporanate | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

The new cephalosporins of this invention can be used in the form of the free acid, as salts such as alkali metal, alkaline earth metal or ammonium salts, for example, sodium, potassium, calcium, triethylammonium, procaine, and the like, as esters, particularly labile esters such as acetoxymethyl or pivaloyloxy and the like, or as amides.

The 7-(D-5'-amino-5'-carboxyvaleramido)-3-carbamoyloxymethyl-7-methoxy-3-cephem-4-carboxylic acid and the derivatives thereof having various substituents at the 3-position of the general formula —CH$_2$A as defined above are disclosed and claimed in the following United States applications of Edward O. Stapley and Justo M. Mata:

Ser. No. 19,496 filed Mar. 13, 1970
Ser. No. 51,319 filed June 30, 1970
Ser. No. 96,594 filed Dec. 9, 1970 and
Ser. No. 115,779 filed Feb. 16, 1971.

These products are therefore not within the scope of this invention.

What is claimed is:

1. An antibacterial composition comprising an antibacterially effective amount of a 3-A-7-methoxy-7-acylamido-3-cephem-4-carboxylic acid wherein A is methyl, hydroxymethyl, chloromethyl, bromomethyl, or fluoromethyl, mercaptomethyl, methoxymethyl, n-propoxymethyl, methylthiomethyl, acetoxymethyl, propionyloxymethyl, benzoyloxymethyl, (p-chlorobenzoyl)oxymethyl, (p-methylbenzoyl)oxymethyl, pivaloyloxymethyl, (1-adamantyl)carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, N-p-sulfophenylcarbamoyl)oxymethyl, p-carboxymethylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, N,N-diethylthiocarbamoylthiomethyl, N-methylpiperazinium-1-thiocarbonylthiomethyl, N,N-dimethylpiperzinium-1-thiocarbonylthiomethyl, 2-furoylthiomethyl, isothiouroniummethyl, (5-methyl-1,3,4-thiadiazol-2-yl)-thiomethyl, p-tolylsulfonylthiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl, or pyridinium methyl; and acylamido is

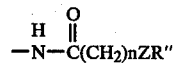

wherein n is 0–4, Z is oxygen or sulfur, and R'' is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)-methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-quanidinomethylbenzyl, 4-guanidinobenzyl, 4-quanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl), difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)methyl, 2- or 3-(sulfothienyl)methyl, 2-or 3-(5-carboxythienyl)-methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl; and the pharmaceutically acceptable salts thereof, or the carboxylic acid protecting derivatives thereof wherein the derivative group is methyl, t-butyl, trichloroethyl, allyl, propargyl, benzyl, diphenylmethyl, o-nitrobenzyl, 3,5-dinitrobenzyl, p-methoxybenzyl, acetoxymethyl, pivaloyloxymethyl, phenacyl, trichloroethoxy carbonyl, trimethylsilyl or tributyltin in a pharmaceutically acceptable carrier vehicle.

2. The composition of claim 1 wherein the cephem-4-carboxylic acid is 3-carbamoyloxymethyl-7-methoxy-7-(2-thienylacetamido)-3-cephem-4-carboxylic acid or a salt thereof.

3. The composition of claim 2 wherein the salt is the sodium salt.

* * * * *